US008894563B2

(12) United States Patent
Connors et al.

(10) Patent No.: US 8,894,563 B2
(45) Date of Patent: Nov. 25, 2014

(54) METHODS AND SYSTEMS FOR PERFORMING A MEDICAL PROCEDURE

(71) Applicant: Attenuex Technologies, Inc., Newton, MA (US)

(72) Inventors: Kevin G. Connors, Wellesley, MA (US); Ryan J. Cahill, Newton, MA (US); Peter Dayton, Brookline, MA (US); John Gillespie, Jr., Dover, MA (US)

(73) Assignee: AttenueX Technologies, Inc., Newton, MA (US)

( * ) Notice: Subject to any disclaimer, the term of this patent is extended or adjusted under 35 U.S.C. 154(b) by 0 days.

(21) Appl. No.: 13/843,621

(22) Filed: Mar. 15, 2013

(65) Prior Publication Data

US 2014/0046123 A1    Feb. 13, 2014

Related U.S. Application Data

(60) Provisional application No. 61/682,184, filed on Aug. 10, 2012, provisional application No. 61/769,719, filed on Feb. 26, 2013.

(51) Int. Cl.
*A61F 2/00* (2006.01)
*A61B 17/34* (2006.01)
(Continued)

(52) U.S. Cl.
CPC ............ *A61B 17/3468* (2013.01); *A61F 2/0027* (2013.01); *A61F 2/004* (2013.01); *A61B*
(Continued)

(58) Field of Classification Search
CPC ......... A61F 2/0027; A61F 2/06; A61F 2/042; A61M 25/10; A61M 25/1002; A61M 2210/1078; A61M 2210/1085; A61M 2025/0076; A61B 5/205

USPC .......................... 600/37, 28–32; 606/191–199
See application file for complete search history.

(56) References Cited

U.S. PATENT DOCUMENTS 2,849,001 A    8/1958  Oddo
3,834,394 A *  9/1974  Hunter et al. ................. 606/195
(Continued)

FOREIGN PATENT DOCUMENTS

DE    19819432    11/1999
EP     1813303     8/2007
(Continued)

OTHER PUBLICATIONS

A New Technique for Dynamic Analysis of Bladder Compliance, Robert F. Gilmore et al., The Journal of Urology, vol. 150, pp. 1200-1203, Oct. 1993.

(Continued)

*Primary Examiner* — Samuel Gilbert
(74) *Attorney, Agent, or Firm* — Knobbe Martens Olson & Bear LLP

(57) ABSTRACT

Method and system for treating a patient using a compressible, pressure-attenuating device. According to one embodiment, the system is used to treat urinary tract disorders and comprises an access device, a delivery device, a pressure-attenuating device, and a removal device. The access device may be used to create a passageway to an anatomical structure, such as the patient's bladder. The delivery device may be inserted through the passageway created by the access device and may be used to deliver the pressure-attenuating device to the anatomical structure. The removal device may be inserted through the passageway created by the access device and may be used to view the bladder and/or to capture, to deflate and to remove the pressure-attenuating device.

39 Claims, 138 Drawing Sheets

(51) Int. Cl.
*A61B 1/00* (2006.01)
*A61B 1/12* (2006.01)
*A61B 1/307* (2006.01)
*A61M 1/00* (2006.01)
*A61M 25/10* (2013.01)
*A61B 17/295* (2006.01)
*A61B 5/20* (2006.01)
*A61M 39/22* (2006.01)
*A61M 39/28* (2006.01)
*A61B 17/00* (2006.01)
*A61M 39/00* (2006.01)
*A61B 17/29* (2006.01)
*A61M 25/00* (2006.01)
*A61M 25/06* (2006.01)

(52) U.S. Cl.
CPC ...... *1/00068* (2013.01); *A61B 1/12* (2013.01); *A61B 1/307* (2013.01); *A61M 1/0064* (2013.01); *A61M 25/10* (2013.01); *A61M 25/1002* (2013.01); *A61B 17/295* (2013.01); *A61B 5/205* (2013.01); *A61M 39/22* (2013.01); *A61M 39/223* (2013.01); *A61M 39/28* (2013.01); *A61B 2017/00805* (2013.01); *A61M 2025/1054* (2013.01); *A61M 2039/0009* (2013.01); *A61B 2017/2926* (2013.01); *A61M 25/007* (2013.01); *A61M 25/0074* (2013.01); *A61B 2017/345* (2013.01); *A61M 2025/0681* (2013.01); *A61M 2210/1078* (2013.01)
USPC .......................................................... 600/30

(56) References Cited

U.S. PATENT DOCUMENTS

| | | | |
|---|---|---|---|
| 3,841,304 A | 10/1974 | Jones | |
| 3,964,484 A | 6/1976 | Reynolds et al. | |
| 4,044,401 A | 8/1977 | Guiset | |
| 4,213,461 A * | 7/1980 | Pevsner | 604/103.01 |
| 4,246,893 A | 1/1981 | Berson | |
| 4,300,557 A * | 11/1981 | Refojo et al. | 424/424 |
| 4,311,146 A | 1/1982 | Wonder | |
| 4,341,218 A | 7/1982 | U | |
| 4,346,712 A | 8/1982 | Handa et al. | |
| 4,364,392 A | 12/1982 | Strother et al. | |
| 4,416,267 A | 11/1983 | Garren et al. | |
| 4,416,663 A | 11/1983 | Hall | |
| 4,441,495 A | 4/1984 | Hicswa | |
| 4,517,979 A * | 5/1985 | Pecenka | 606/195 |
| 4,545,367 A | 10/1985 | Tucci | |
| 4,567,880 A | 2/1986 | Goodman | |
| 4,607,618 A | 8/1986 | Angelchik | |
| 4,694,827 A | 9/1987 | Weiner et al. | |
| 4,723,547 A | 2/1988 | Kullas et al. | |
| 4,773,393 A | 9/1988 | Haber et al. | |
| 4,802,479 A | 2/1989 | Haber et al. | |
| 4,819,637 A | 4/1989 | Dormandy, Jr. et al. | |
| 4,832,680 A * | 5/1989 | Haber et al. | 600/31 |
| 4,850,963 A | 7/1989 | Sparks et al. | |
| 4,899,747 A | 2/1990 | Garren et al. | |
| 4,925,446 A | 5/1990 | Garay et al. | |
| 4,929,214 A | 5/1990 | Liebermann | |
| 4,930,535 A | 6/1990 | Rinehold | |
| 4,938,766 A | 7/1990 | Jarvik | |
| 5,019,032 A | 5/1991 | Robertson | |
| 5,084,061 A | 1/1992 | Gau et al. | |
| 5,144,708 A | 9/1992 | Pekar | |
| 5,181,921 A | 1/1993 | Makita et al. | |
| 5,222,970 A | 6/1993 | Reeves | |
| 5,248,275 A * | 9/1993 | McGrath et al. | 446/224 |
| 5,295,956 A | 3/1994 | Bales et al. | |
| 5,295,960 A | 3/1994 | Aliahmad et al. | |
| 5,304,123 A | 4/1994 | Atala et al. | |
| 5,308,327 A | 5/1994 | Heaven et al. | |
| 5,347,992 A | 9/1994 | Pearlman et al. | |
| 5,356,430 A | 10/1994 | Nadol, Jr. | |
| 5,389,217 A | 2/1995 | Singer | |
| 5,403,123 A | 4/1995 | Walters | |
| 5,411,475 A | 5/1995 | Atala et al. | |
| 5,433,216 A | 7/1995 | Sugrue et al. | |
| 5,437,603 A | 8/1995 | Cerny et al. | |
| 5,479,945 A | 1/1996 | Simon | |
| 5,501,669 A | 3/1996 | Conway et al. | |
| 5,513,659 A | 5/1996 | Buuck et al. | |
| 5,564,143 A | 10/1996 | Pekar et al. | |
| 5,588,438 A | 12/1996 | McKnown et al. | |
| 5,588,556 A | 12/1996 | Sancoff et al. | |
| 5,603,685 A | 2/1997 | Tutrone, Jr. | |
| 5,617,876 A | 4/1997 | Van Duyl | |
| 5,667,520 A | 9/1997 | Bonutti | |
| 5,695,741 A | 12/1997 | Schutt et al. | |
| 5,720,938 A | 2/1998 | Schutt et al. | |
| 5,755,239 A | 5/1998 | Baltierra | |
| 5,779,672 A | 7/1998 | Dormandy, Jr. | |
| 5,782,812 A | 7/1998 | Hart et al. | |
| 5,830,228 A | 11/1998 | Knapp et al. | |
| 5,830,780 A | 11/1998 | Dennison et al. | |
| 5,868,141 A | 2/1999 | Ellias | |
| 5,916,198 A | 6/1999 | Dillow | |
| 5,964,806 A | 10/1999 | Cook et al. | |
| 5,989,180 A | 11/1999 | Norton | |
| 5,992,419 A | 11/1999 | Sterzer et al. | |
| 5,992,700 A | 11/1999 | McGlothlin et al. | |
| 6,021,781 A | 2/2000 | Thompson et al. | |
| 6,027,442 A | 2/2000 | Von Iderstein | |
| 6,045,498 A | 4/2000 | Burton et al. | |
| 6,095,969 A | 8/2000 | Karram et al. | |
| 6,102,848 A | 8/2000 | Porter | |
| 6,119,697 A | 9/2000 | Engel et al. | |
| 6,127,010 A | 10/2000 | Rudy | |
| 6,171,298 B1 | 1/2001 | Matsuura et al. | |
| 6,240,968 B1 | 6/2001 | Bigonzi-Jaker et al. | |
| 6,251,138 B1 | 6/2001 | Nadol et al. | |
| 6,293,923 B1 * | 9/2001 | Yachia et al. | 604/96.01 |
| 6,311,689 B1 | 11/2001 | Tihon | |
| 6,358,200 B1 | 3/2002 | Grossi | |
| 6,372,195 B1 | 4/2002 | Schutt et al. | |
| 6,398,718 B1 | 6/2002 | Yachia et al. | |
| 6,398,738 B1 | 6/2002 | Millar | |
| 6,443,947 B1 | 9/2002 | Marko et al. | |
| 6,463,332 B1 | 10/2002 | Aldrich | |
| 6,544,224 B1 * | 4/2003 | Steese-Bradley | 604/103.06 |
| 6,544,287 B1 | 4/2003 | Johnson et al. | |
| 6,547,804 B2 | 4/2003 | Porter et al. | |
| 6,682,473 B1 | 1/2004 | Matsuura et al. | |
| 6,736,793 B2 * | 5/2004 | Meyer et al. | 604/96.01 |
| 6,746,421 B2 | 6/2004 | Yachia et al. | |
| 6,849,061 B2 | 2/2005 | Wagner | |
| 6,852,095 B1 | 2/2005 | Ray | |
| 6,976,950 B2 | 12/2005 | Connors et al. | |
| 6,976,951 B2 | 12/2005 | Connors et al. | |
| 6,988,983 B2 | 1/2006 | Connors et al. | |
| 7,074,178 B2 | 7/2006 | Connors et al. | |
| 7,083,626 B2 | 8/2006 | Hart et al. | |
| 7,112,185 B2 | 9/2006 | Hart et al. | |
| 7,150,853 B2 | 12/2006 | Lee et al. | |
| 7,374,532 B2 | 5/2008 | Connors et al. | |
| 7,390,317 B2 | 6/2008 | Taylor et al. | |
| 7,470,228 B2 | 12/2008 | Connors et al. | |
| 7,484,510 B2 | 2/2009 | Connors et al. | |
| 7,540,876 B2 | 6/2009 | Connors et al. | |
| 7,691,051 B2 | 4/2010 | Connors et al. | |
| 7,766,814 B2 | 8/2010 | Walsh | |
| 7,771,395 B2 | 8/2010 | Hart et al. | |
| 7,811,221 B2 | 10/2010 | Gross | |
| 8,016,740 B2 | 9/2011 | Connors et al. | |
| 8,025,064 B2 | 9/2011 | Connors et al. | |
| 2002/0026226 A1 | 2/2002 | Ein | |
| 2002/0055730 A1 | 5/2002 | Yachia et al. | |
| 2002/0082551 A1 | 6/2002 | Yachia et al. | |
| 2002/0107490 A1 | 8/2002 | Butterfield et al. | |
| 2002/0165427 A1 | 11/2002 | Yachia et al. | |
| 2004/0111006 A1 | 6/2004 | Yachia et al. | |

(56) References Cited

U.S. PATENT DOCUMENTS

| | | |
|---|---|---|
| 2004/0143319 A1 | 7/2004 | Schwartz et al. |
| 2004/0260272 A1 | 12/2004 | Friedman et al. |
| 2005/0070995 A1 | 3/2005 | Zilla et al. |
| 2006/0264697 A1 | 11/2006 | Timm et al. |
| 2007/0202151 A1 | 8/2007 | Lee et al. |
| 2008/0086082 A1 | 4/2008 | Brooks |
| 2008/0086149 A1 | 4/2008 | Diamant et al. |
| 2008/0275428 A1 | 11/2008 | Tegg et al. |
| 2009/0105527 A1 | 4/2009 | Connors et al. |
| 2009/0240277 A1 | 9/2009 | Connors et al. |
| 2010/0152654 A1 | 6/2010 | Tilson et al. |
| 2010/0222802 A1 | 9/2010 | Gillespie, Jr. et al. |
| 2014/0046124 A1 | 2/2014 | Cahill et al. |
| 2014/0046125 A1 | 2/2014 | Gillespie, Jr. et al. |

FOREIGN PATENT DOCUMENTS

| | | |
|---|---|---|
| FR | 2774579 | 8/1999 |
| FR | 2788224 | 7/2000 |
| GB | 2023405 | 1/1980 |
| JP | 1285263 | 11/1989 |
| JP | 5049690 | 3/1993 |
| JP | 2000-325328 | 11/2000 |
| JP | 2007-190430 | 8/2007 |
| WO | WO 90/13321 | 11/1990 |
| WO | WO 91/03267 | 3/1991 |
| WO | WO 99/24106 | 5/1999 |
| WO | WO 00/27405 | 5/2000 |
| WO | WO 00/54701 | 9/2000 |
| WO | WO 00/54702 | 9/2000 |
| WO | WO 01/02042 | 1/2001 |
| WO | WO 01/57093 | 8/2001 |
| WO | WO 01/64145 | 9/2001 |
| WO | WO 01/66052 | 9/2001 |
| WO | WO 01/78576 | 10/2001 |
| WO | WO 02/38038 | 5/2002 |
| WO | WO 02/065894 | 8/2002 |
| WO | WO 02/100300 | 12/2002 |
| WO | WO 03/015673 | 2/2003 |
| WO | WO 03/022164 | 3/2003 |
| WO | WO 2004/091592 | 10/2004 |
| WO | WO 2004/096071 | 11/2004 |
| WO | WO 2005/058203 | 6/2005 |
| WO | WO 2006/086627 | 8/2006 |
| WO | WO 2007/050546 | 5/2007 |
| WO | WO 2007/059160 | 5/2007 |
| WO | WO 2007/103809 | 9/2007 |

OTHER PUBLICATIONS

The Effect of Urinary Bladder Shape on its Mechanics During Filling, Margot S. Damasar et al., Pergamon, vol. 6, pp. 725-732, 1995.
Difference in Bladder Compliance with Time and Associations of Bladder Management with Compliance in Spinal Cord Injured Patients, Kyle J. Weld et al., The Journal of Urology, vol. 163, pp. 1228-1233, Apr. 2000.
Visco-elastic Properties of Isolated Detrusor Smooth Muscle, A. Wagg et al., Scandinavian Journal of Urology Nephoral, Suppl. 201, pp. 12-18, 1999.
Decreased Elastin Gene Expression in Noncompliant Human Bladder Tissue: A Competitive Reverse Transcriptase-Polymerase Chain Reaction Analysis, Bob Djavan et al., Journal of Urology, vol. 160, pp. 1658-1662, Nov. 1998.
Molecular, Cellular and Experimental Morphology, Narinder Dass et al., Journal of Anatomy, vol. 195, Part 3, pp. 447-453, Oct. 1999.
Design of Miniaturized Ultrasonic Bladder Volume Monitor and Subsequent Preliminary Evaluation on 41 Enuretic Patients, IEEE Transactions on Rehabilitation Engineering, vol. 6, No. 1, pp. 66-74, Mar. 1998.
Temporal Expression of Elastic Fiber Components in Bladder Development, H.P. Koo et al., Connective Tissue Research, vol. 3701-20, pp. 1-11, 1998.
Voiding Dysfunction in Ileal Neobladder, Naohito Mikuma et al., The Journal of Urology, vol. 158 pp. 1365-1367, Oct. 1997.
Interstital Cystitus: Bladder Training with Intravesical Oxybutynin, George A. Barballas et al., The Journal of Urology, vol. 163, pp. 1818-1822, Jun. 2000.
Noninvasive Evaluation of Bladder Compliance in Children Using Ultrasound Estimated Bladder Weight, Osamu Ukimura et al., The Journal of Urology, vol. 160 pp. 1459-1462, Oct. 1998.
Surgical Complications of Bladder Augmentation: Comparison Between Various Enterocystoplasties in 133 Patients, Bijan Shekarriz et al., Elsevier Science Inc., Pediatric Urology 55, pp. 123-128, 2000.
Elastic Fibers and Their Role in Bladder Extracellular Matrix, Joel Rosenbloom et al., Muscle, Matrix and Bladder Function, vol. 385, pp. 161-184, 1995.
Effect of Spinal Versus General Anesthesia on Bladder Compliance and Intraabdominal Pressure During Transurethral Procedures, David Olsfanger et al., Journal of Clinical Anesthesia, vol. 11, pp. 328-331, 1999.
Structure of the Lymphatic Microcirculation in the Human Urinary Bladder with Different Intraluminal Pressure and Distension, R. Scelsi et al., Lymphologyu, pp. 60-66, 1996.
Boston Scientific Target Detachable Silicone Balloon, Product Information (Part No. ES-05827 Rev. A); published by Boston Scientific and Target Therapeutics at Fremont, CA or Natick,MA; relevant pages consist of the entire document (total of 24 pages); print-out in 2 pages from the USPTO's Trademark Electronic Search System identifying the date of first used in commerce of on or about Aug. 1998.
Urge Incontinence and the Unstable Bladder, Practical Urogynecology, Chapter 8—Incontinence and the Unstable Bladder, pp. 191-214, Oct. 1, 1993.
Abstract, Surgical treatment for stress urinary incontinence associated with valsalva induced detrusor instability., S.R. Serets et al. Website PubMed, Mar. 2000.
Abstract, Identifying patients who require urodynamic testing before surgery for stress incontinence based on questionnaire information and surgical history., G.E. Lemack et al., Website PubMed, Apr. 2000.
Abstract, Ambulatory urodynamics: do they help clinical management?, E. Gorton et al., Website PubMed, Mar. 2000.
Abstract, The effect of bladder filling on changes in ultrasonography parameters of the lower urinary tract in women with urinary stress incontinence., A. Martan et al., Website PubMed, Jan. 2000.
Abstract, Urodynamic protocol and central review of data for clinical trials in lower urinary tract dysfunction., P. Lewis et al., Website PubMed, Mar. 2000.
Abstract, New data on the diagnosis and treatment of urinary stress incontinence in women., J. Colin et al., Website PubMed, Feb. 2000.
Abstract, Office evaluation of the patient with an overactive urinary bladder., J. Kowalcyzk, Website PubMed, Mar. 2000.
Abstract, Surgical and medical treatment options for urge incontinence., J.M. Lonsway, Website PubMed, Mar. 2000.
Abstract, Experimental development of a fixed volume, gravity draining, prosthetic urinary bladder., M.J. Gleeson et al., Website PubMed, Jul. 1990.
Abstract, Urodynamics of normal and disordered miction., U. Jonas, Website PubMed, Oct. 1979.
Abstract, Whole bladder mechanics during filling., M.S. Damaser, Website PubMed, Oct. 1999.
Abstract, A mathematical micturition to restore simple flow recordings in healthy and symptomatic individuals and enhance uroflow interpretation., F.A. Valentini et al., Website PubMed, 2000.
Abstract, Barometers and bladders: a primer on pressures., D.A. Bloom et al., Website PubMed, Mar. 2000.
Die Detrusormyektomie (Autoaugmentation) in der Behandlung der Hyperreflexiven Low-compliance-Blasé, M. Stohrer et al., Der Urologe [A], pp. 30-37, 1999.
Effect of aging on bladder function and the response to outlet obstruction in female rats, A.D. Kohan et al., Urol Res. 2000, 28: pp. 33-37.
European Search Report for European Patent Application No. EP 01 92 7115 dated Nov. 2, 2004 in 3 pages.

(56) References Cited

OTHER PUBLICATIONS

Fluid Transients in Systems by Wylie et al., Prentice Hall (1993) pp. 59-70.
PCT Search Report and Written Opinion dated Aug. 16, 2007 in 6 pages.
Supplementary European Search Report for European Application No. 03770516.7 dated Aug. 6, 2007 in 3 pages.
Extended European Search Report for European Application No. 07015011.5 dated Sep. 4, 2007 in 6 pages.
International Search Report and Written Opinion for International Application No. PCT/US2009/065815, Notification mailed Jan. 26, 2010.
International Search Report and Written Opinion for International Application No. PCT/US2013/054185, Notification mailed Jan. 20, 2014.
Brash et al., "Development of Block Copolyether-Urethane Intra-Aortic Balloons and Other Medical Devices," Journal of Biomedical Materials Research, vol. 7, pp. 313-334, Jul. 1973.

* cited by examiner

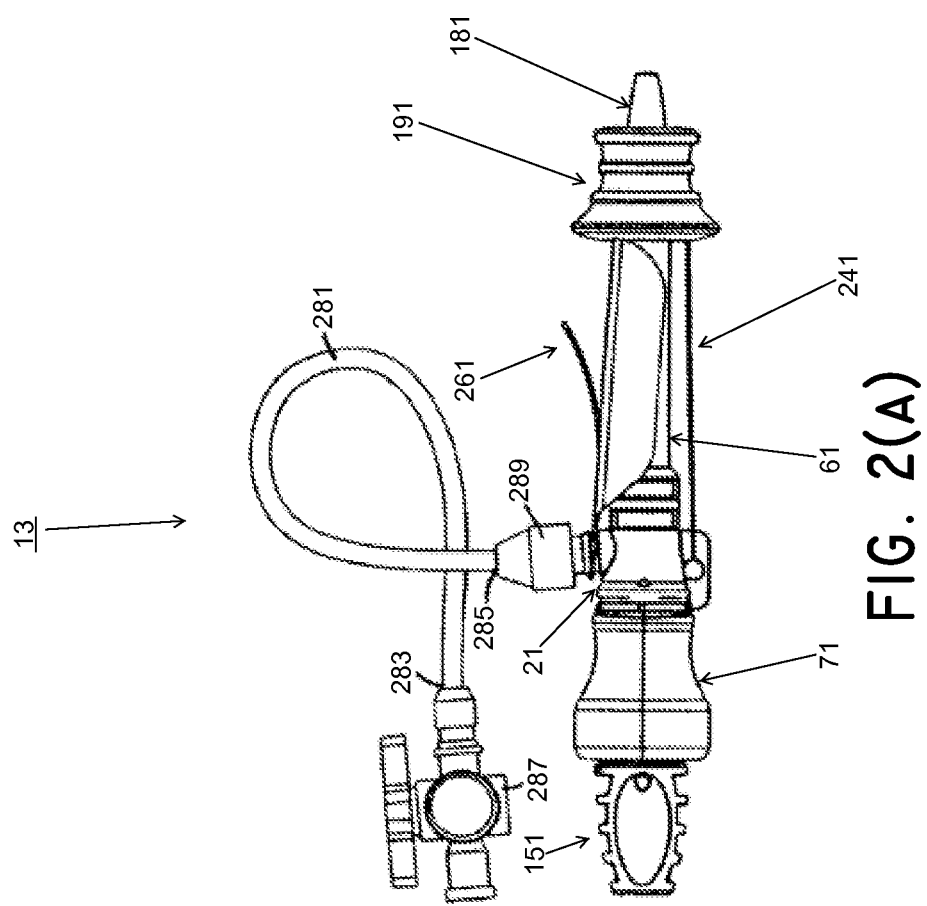

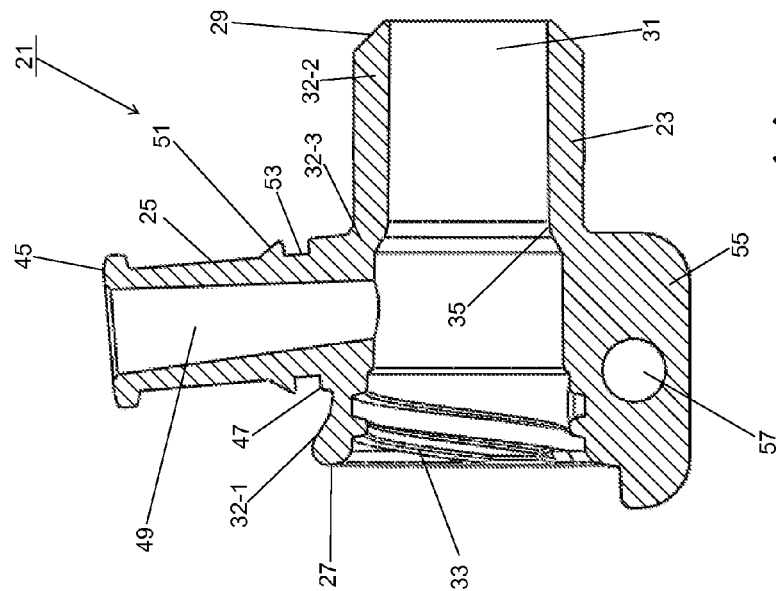
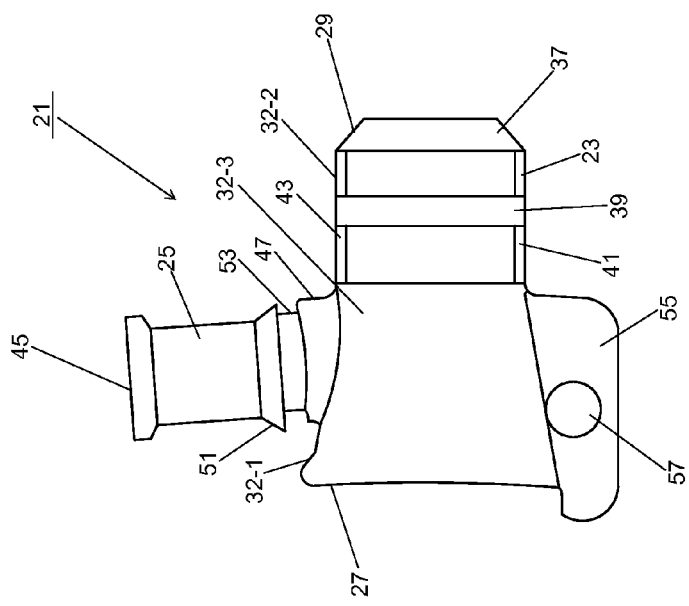

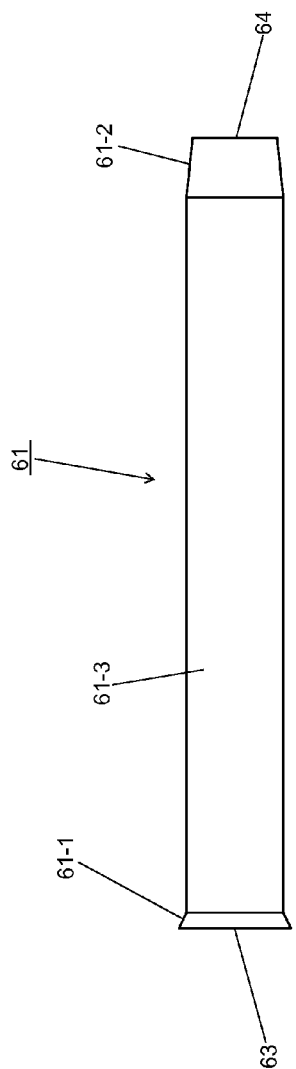
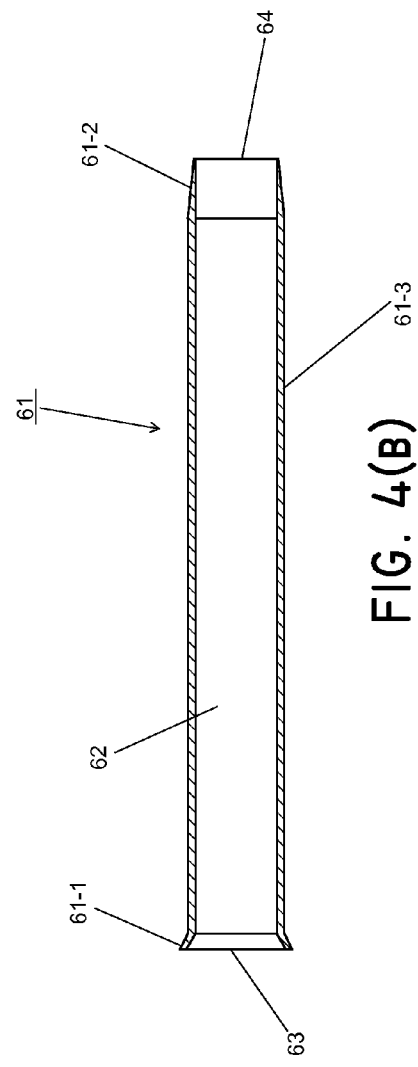
FIG. 4(A)
FIG. 4(B)

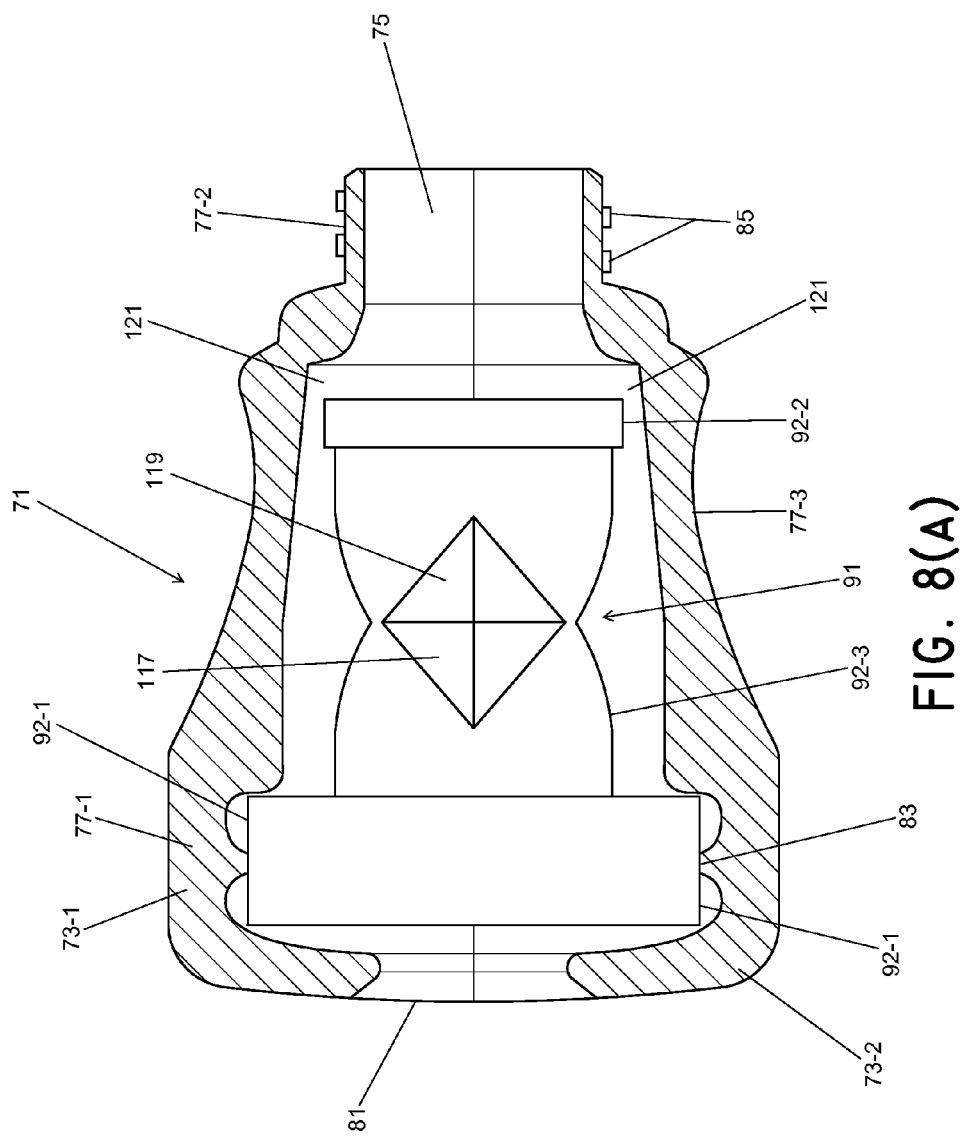

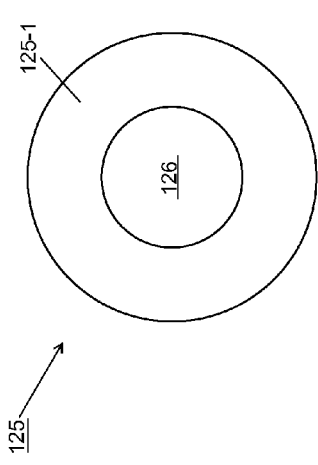
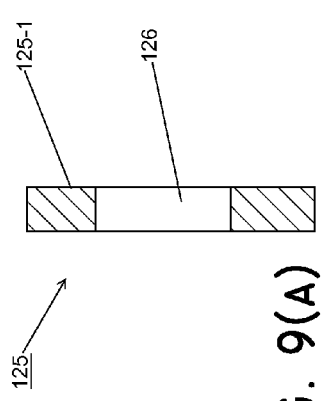
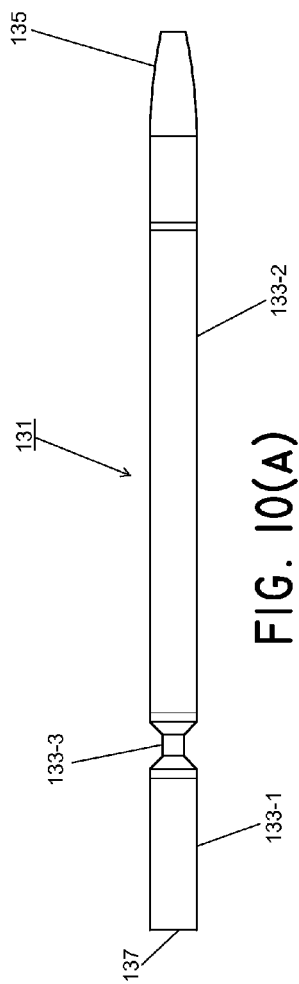
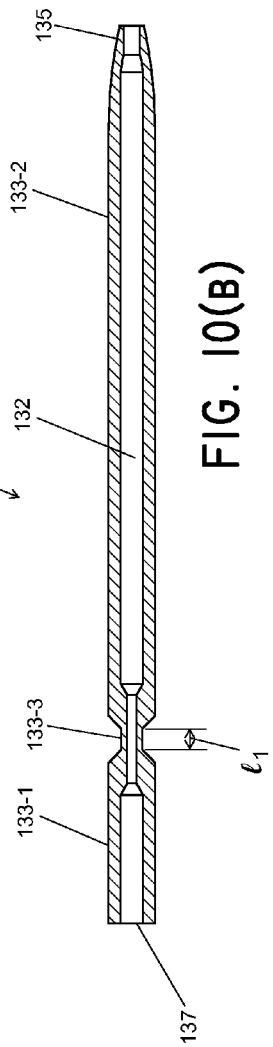

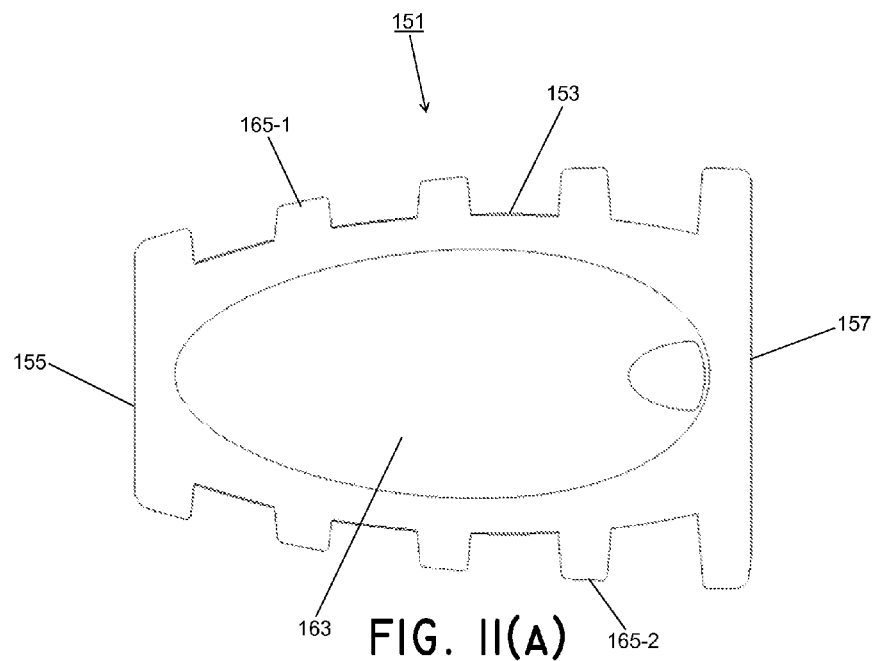
FIG. II(A)
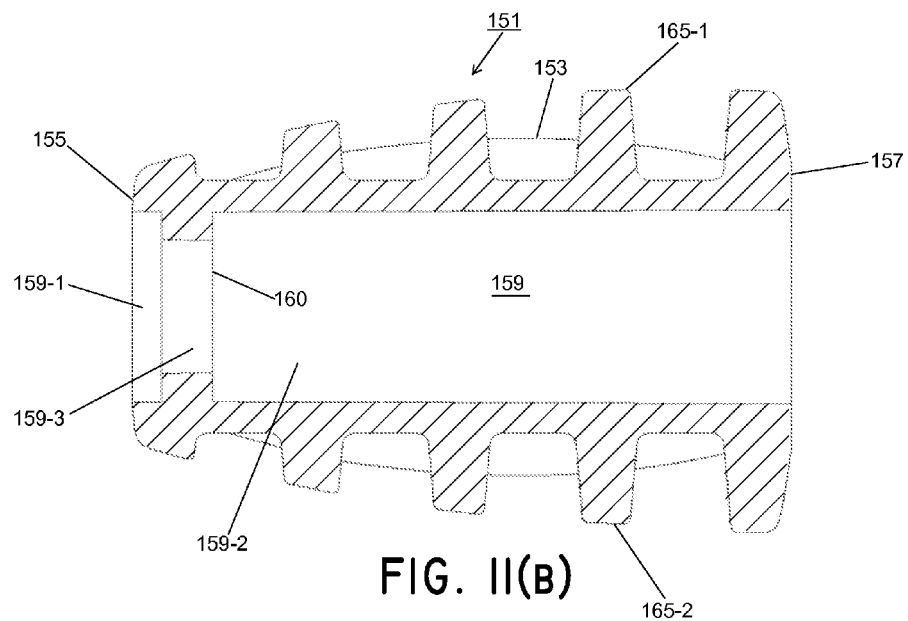
FIG. II(B)

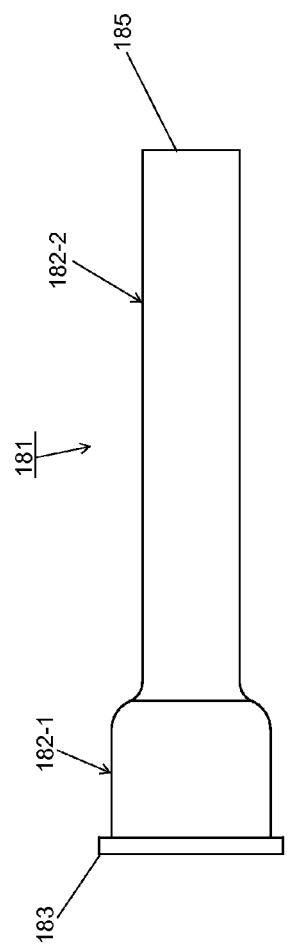
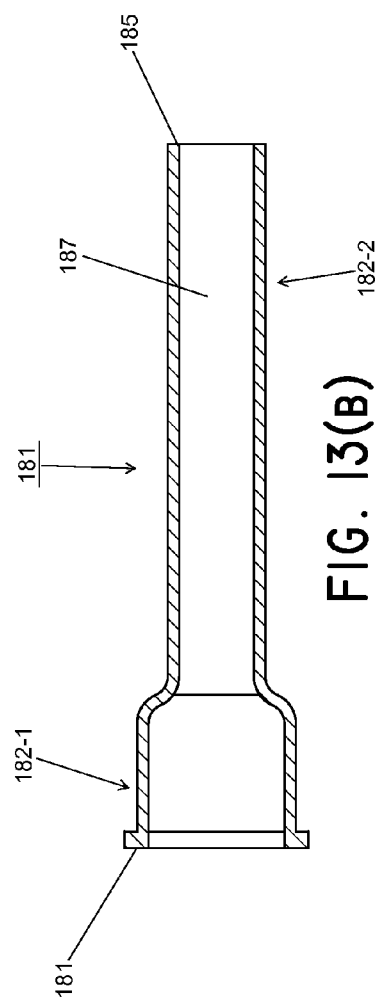
FIG. 13(A)
FIG. 13(B)

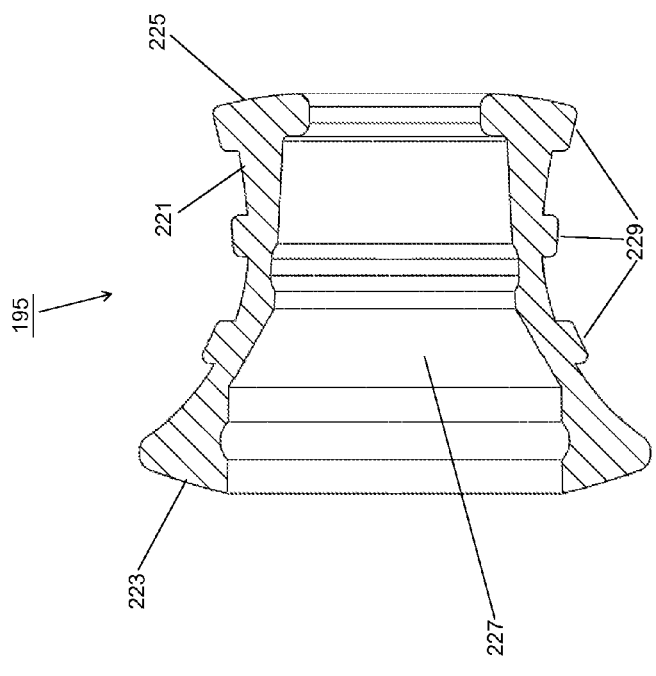
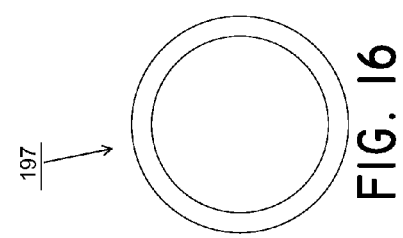
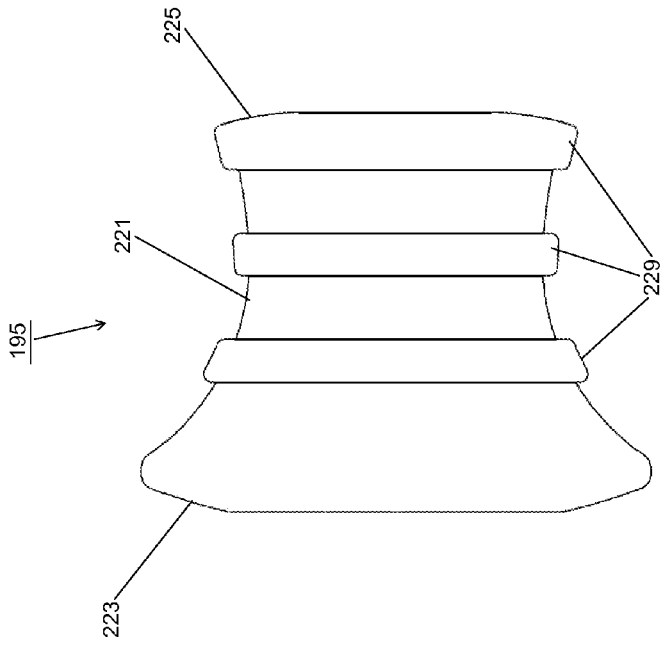
FIG. 15(A)
FIG. 15(B)
FIG. 16

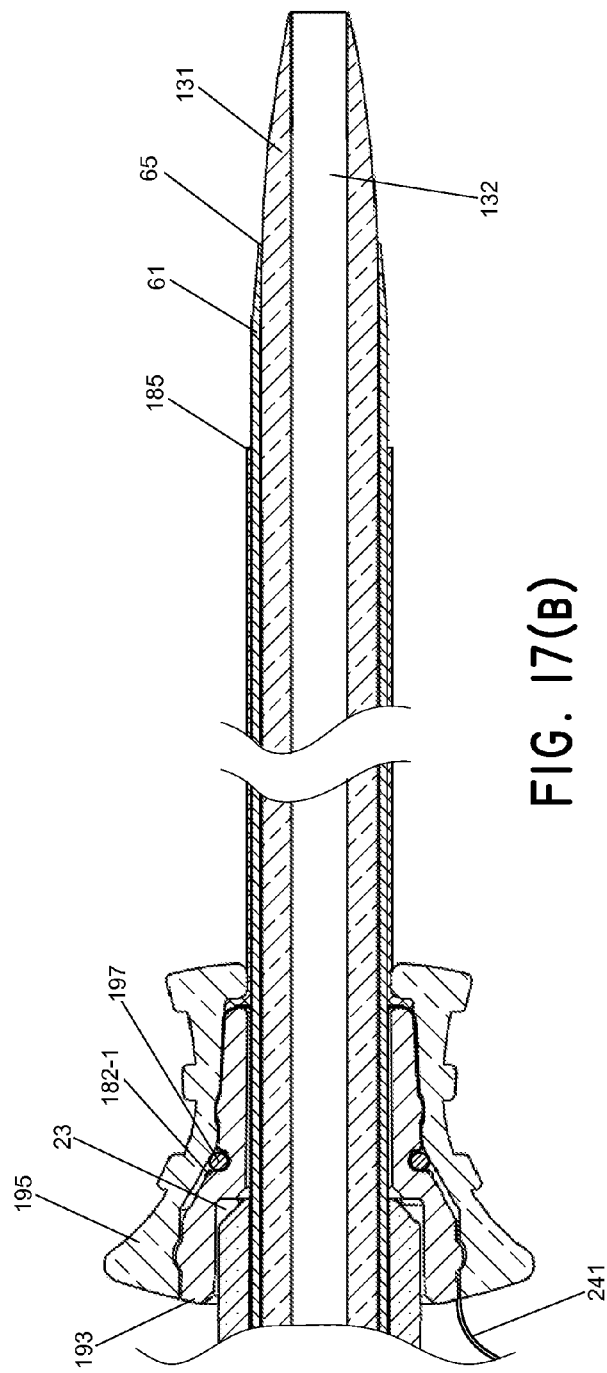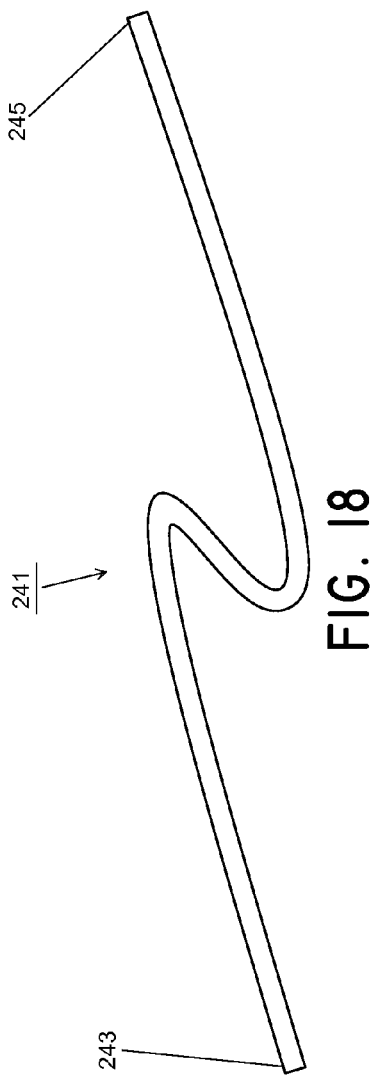

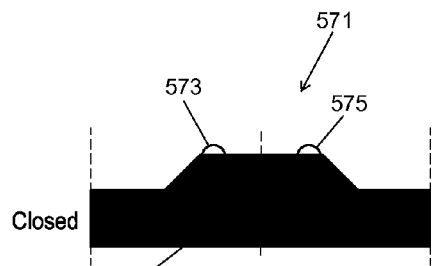
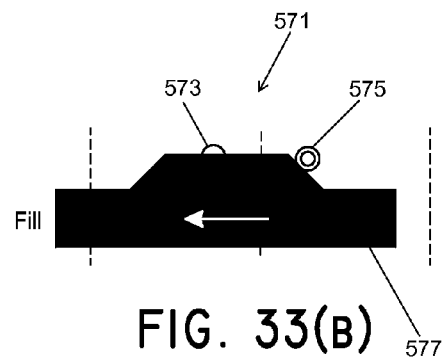
FIG. 33(A)    FIG. 33(B)
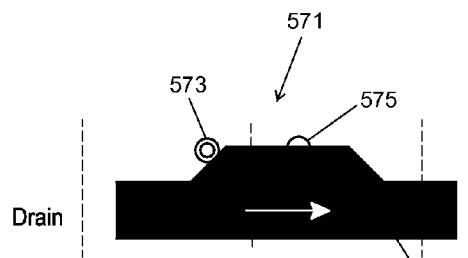
FIG. 33(C)
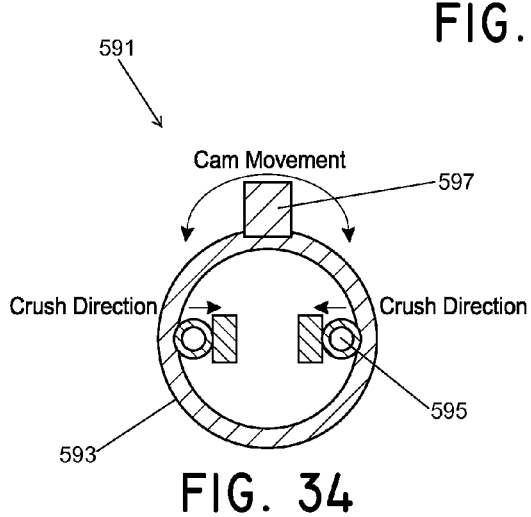
FIG. 34
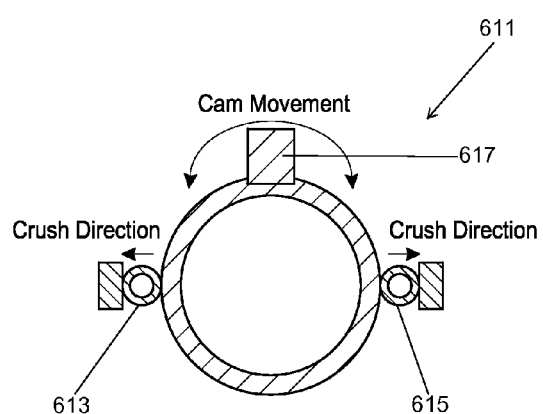
FIG. 35

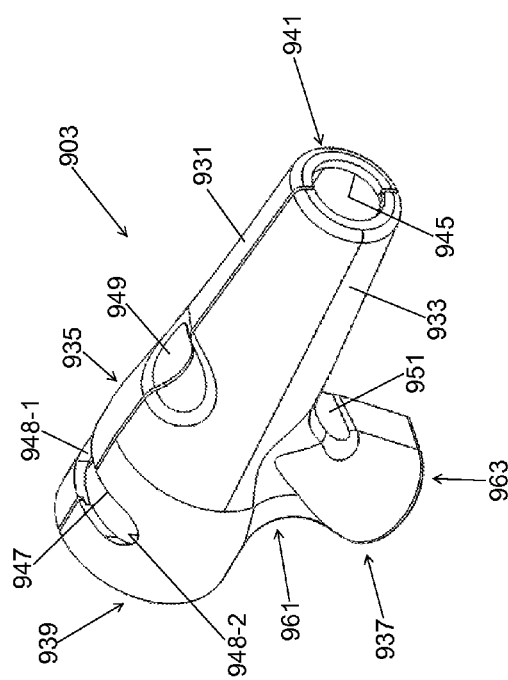
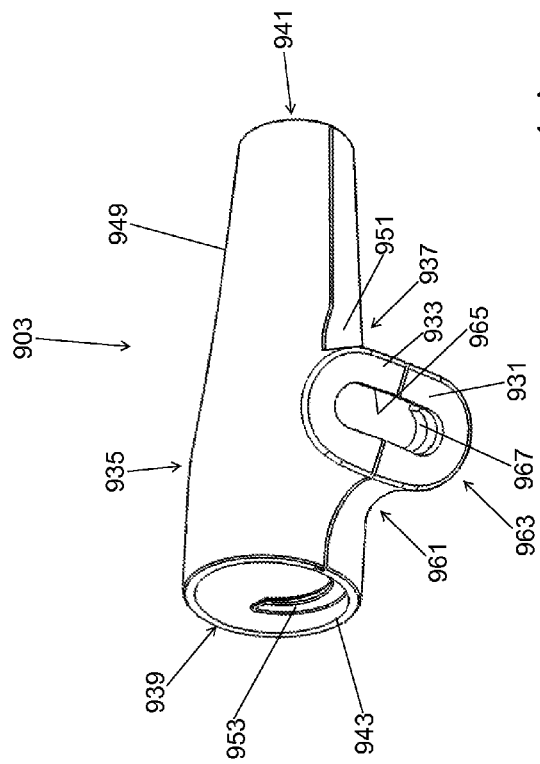
FIG. 42(A)
FIG. 42(B)

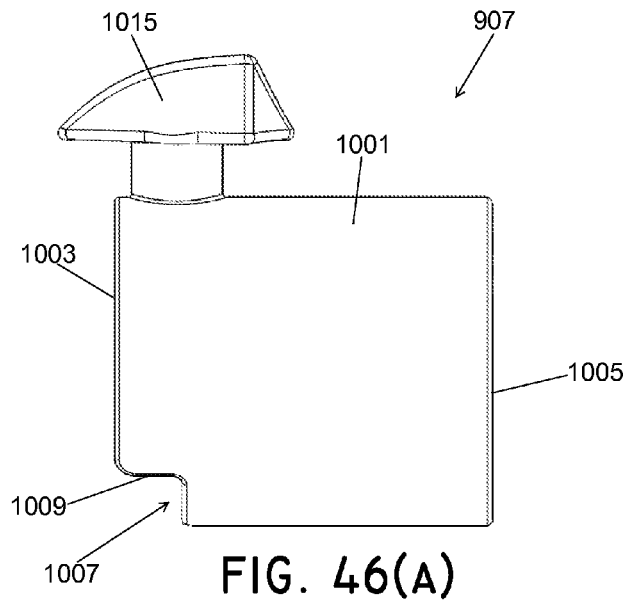
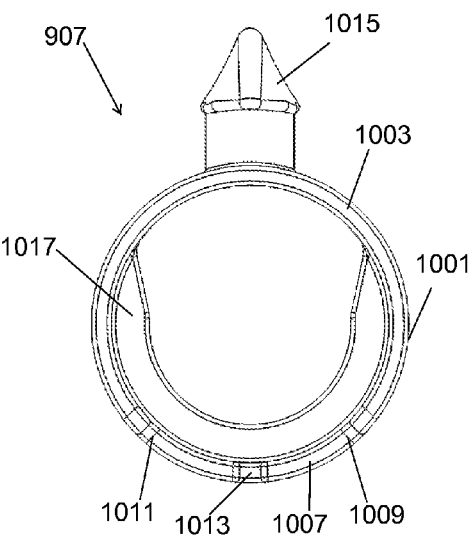
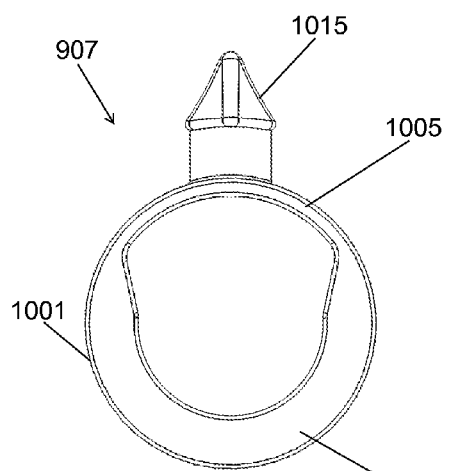
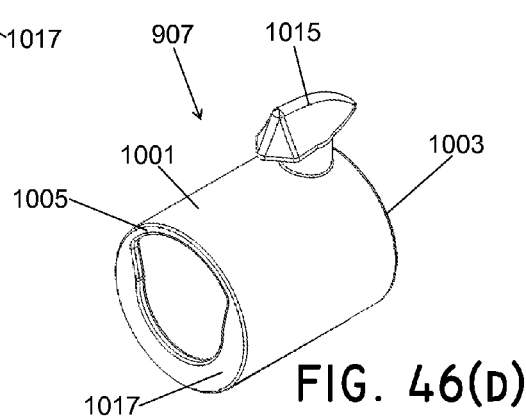
FIG. 46(A)
FIG. 46(B)
FIG. 46(C)
FIG. 46(D)

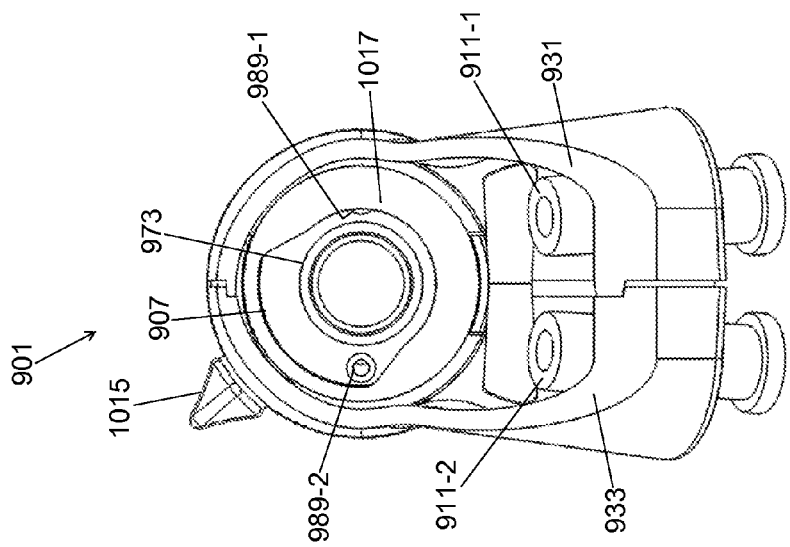
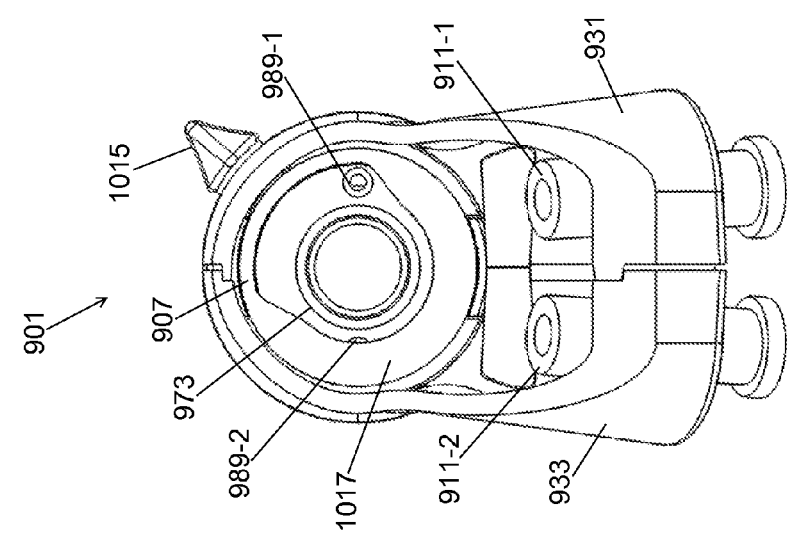
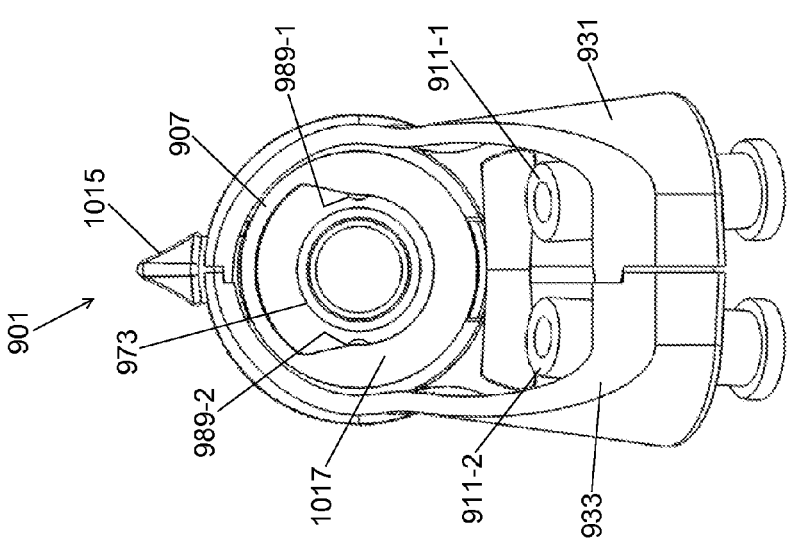

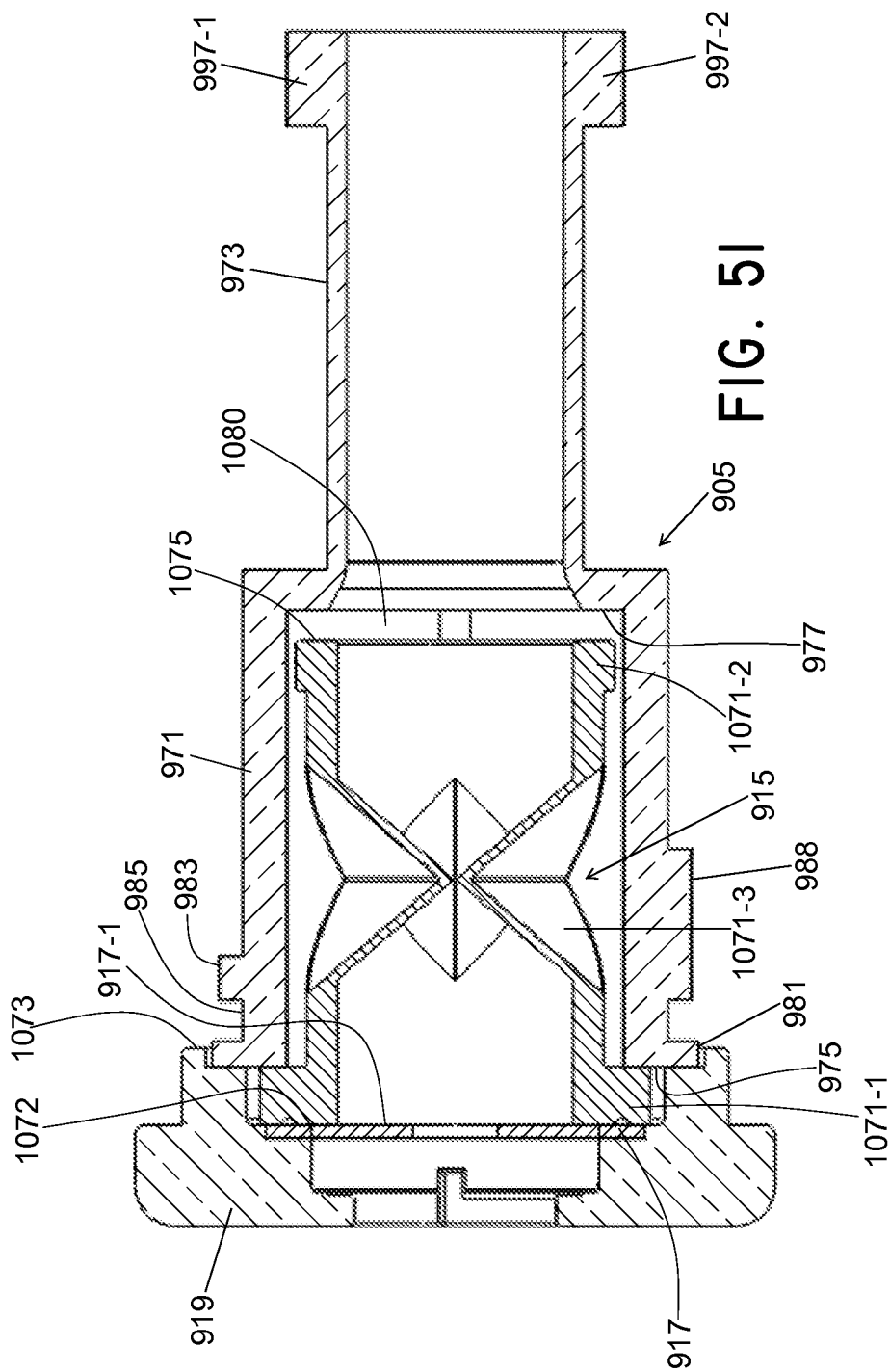

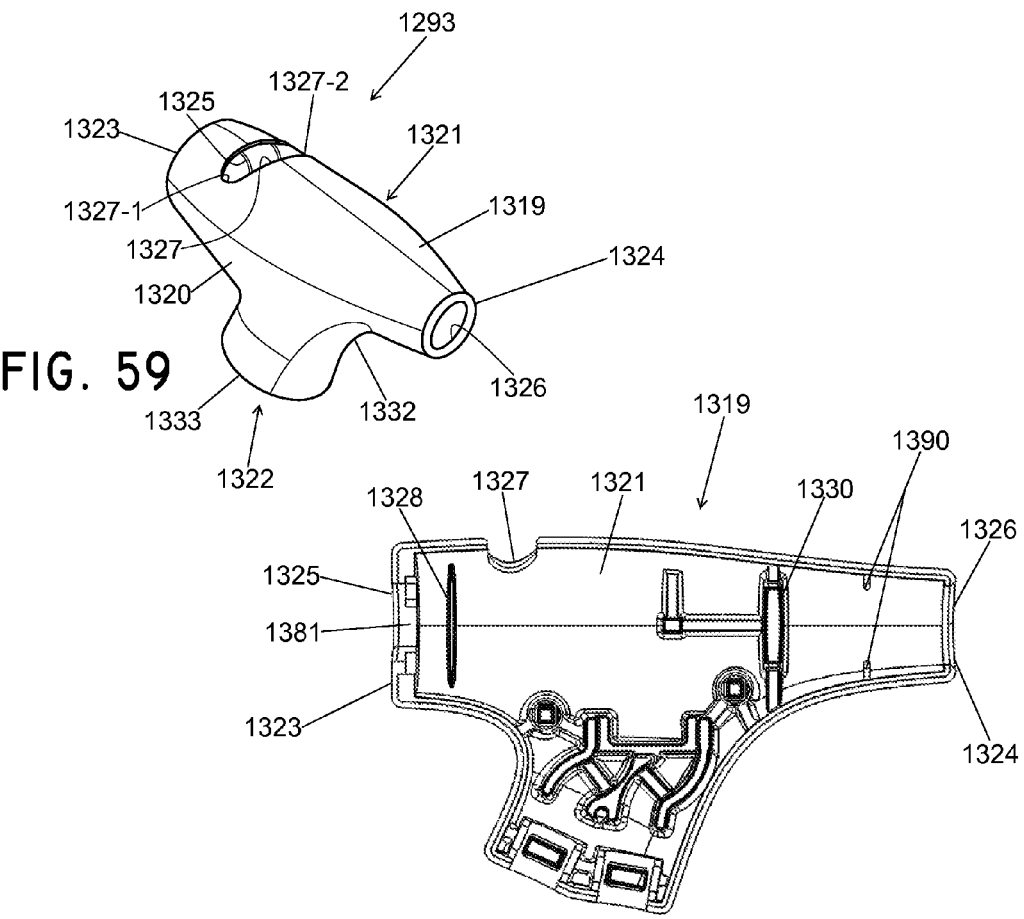
FIG. 59
FIG. 60(A)
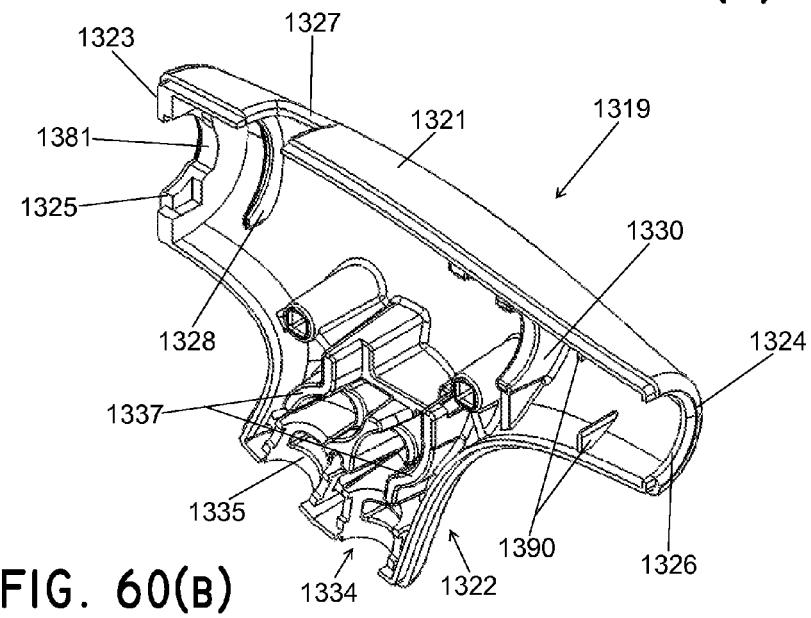
FIG. 60(B)

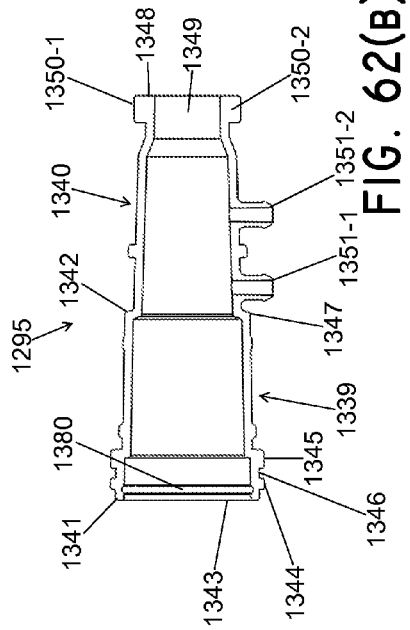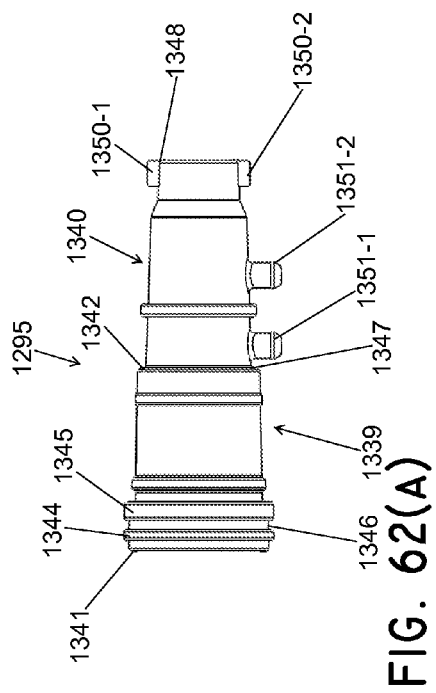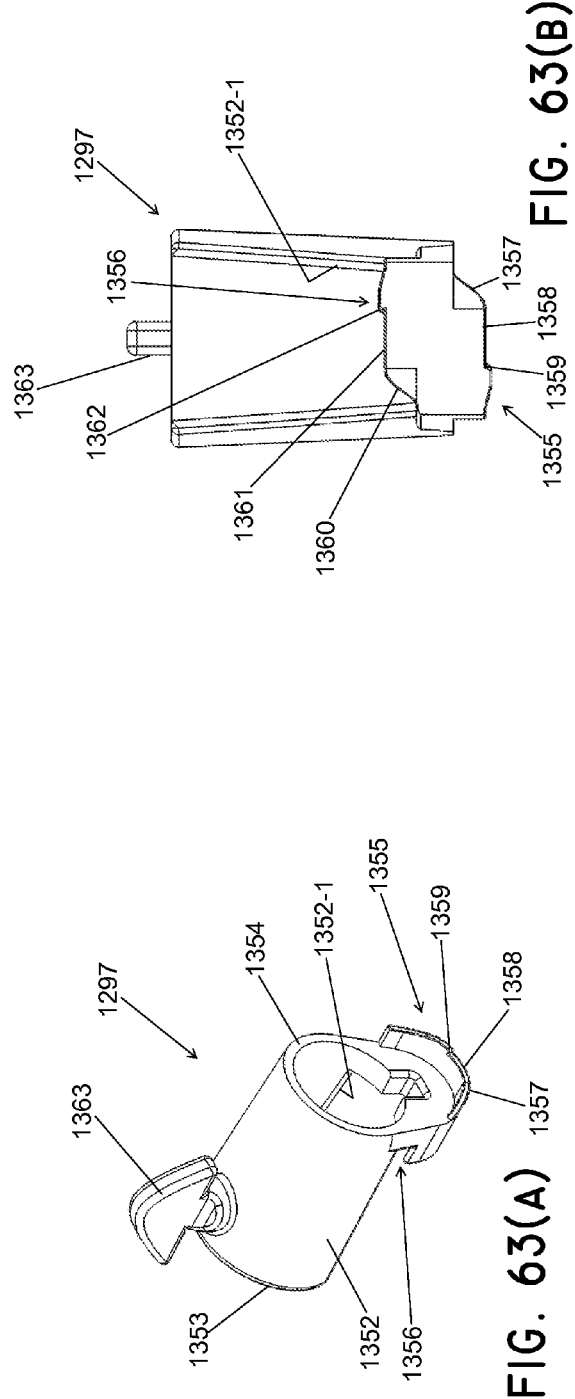

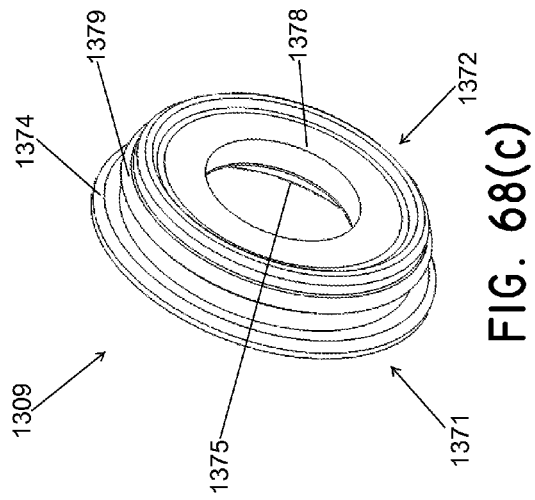
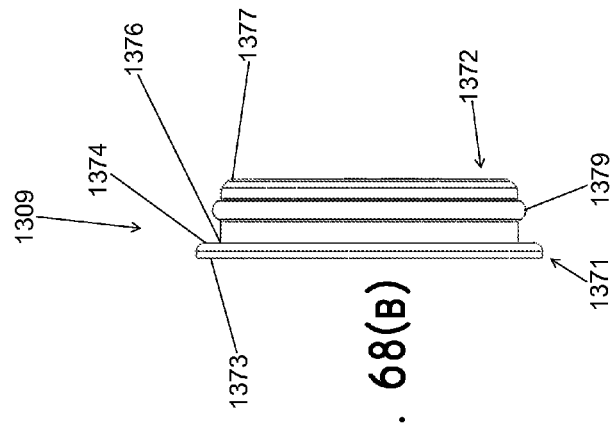
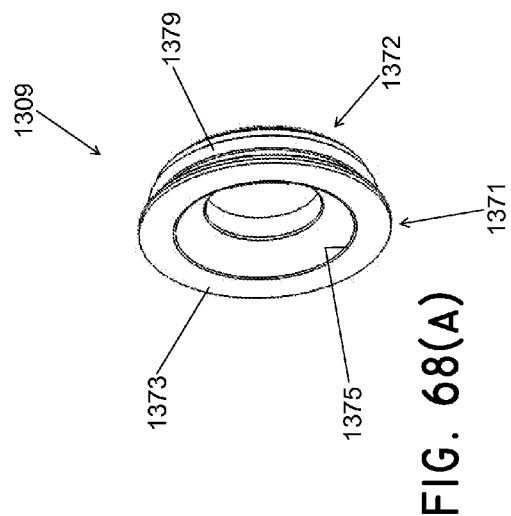
FIG. 68(C)
FIG. 68(B)
FIG. 68(A)

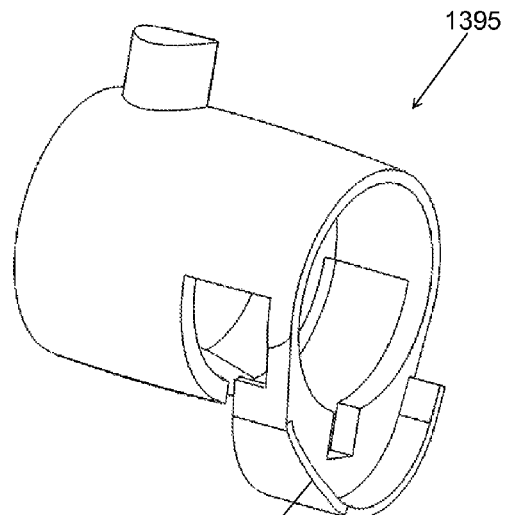
FIG. 76
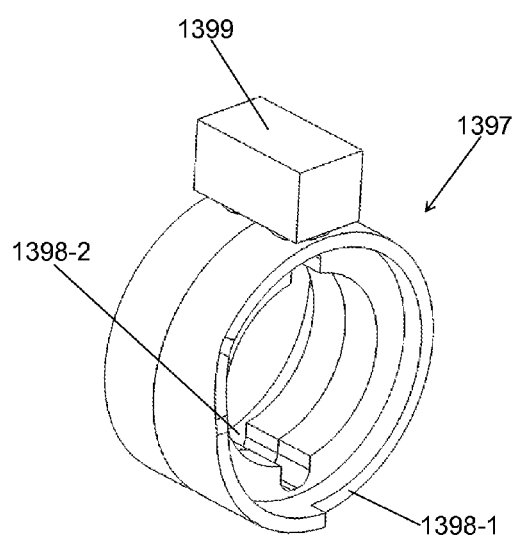
FIG. 77(A)
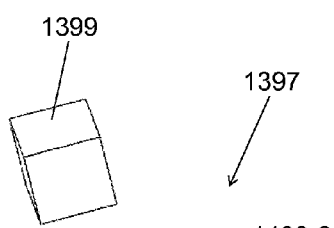
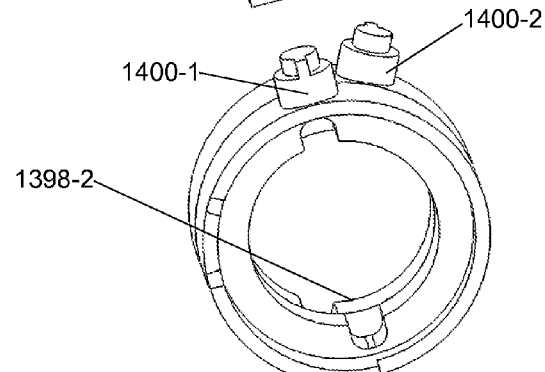
FIG. 77(B)

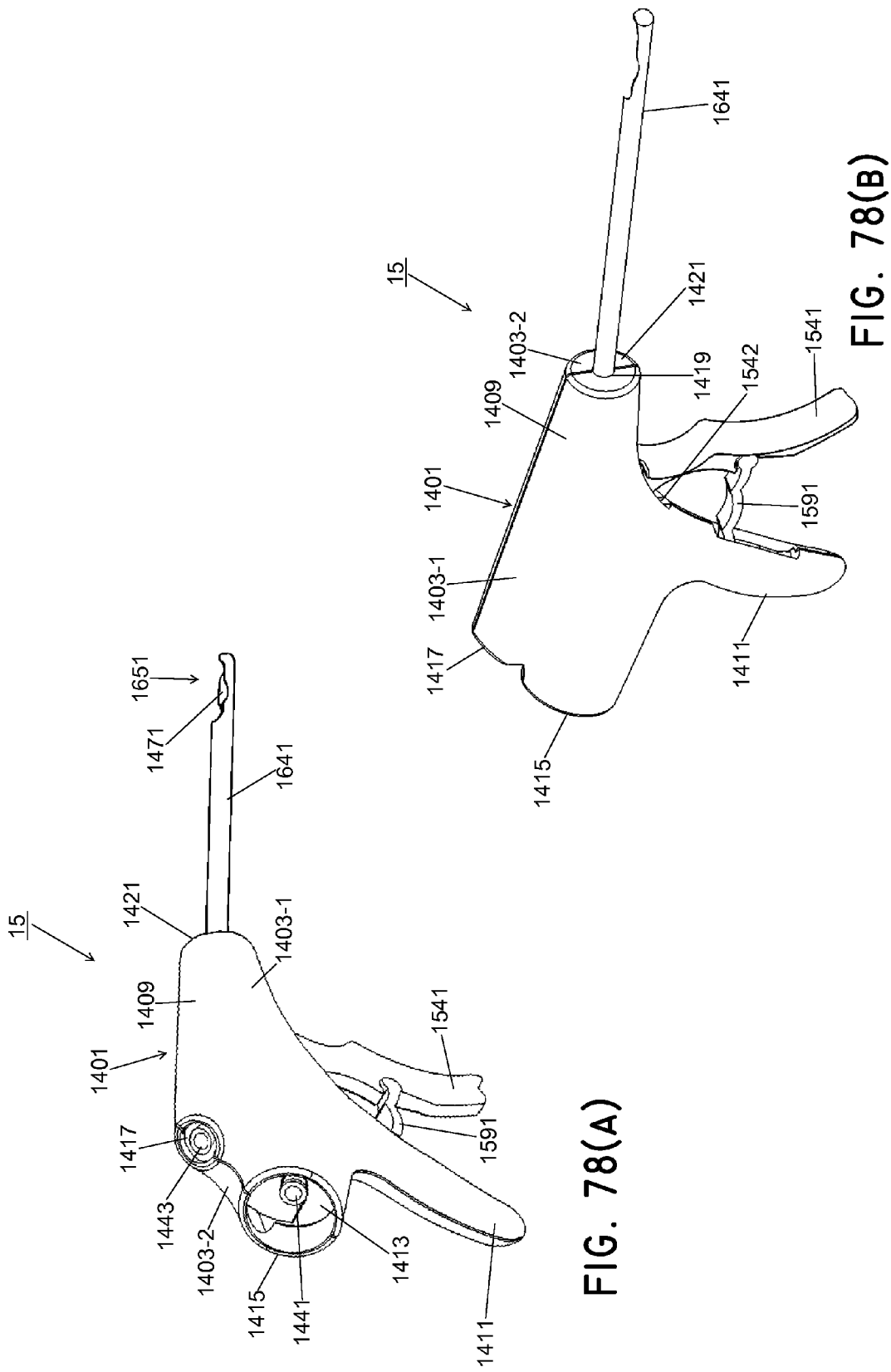

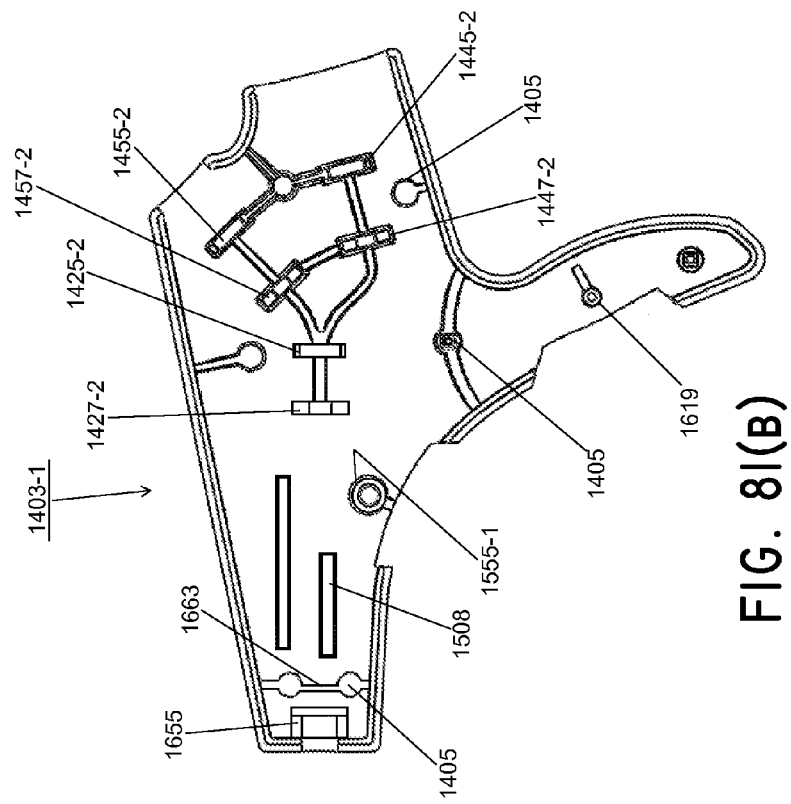
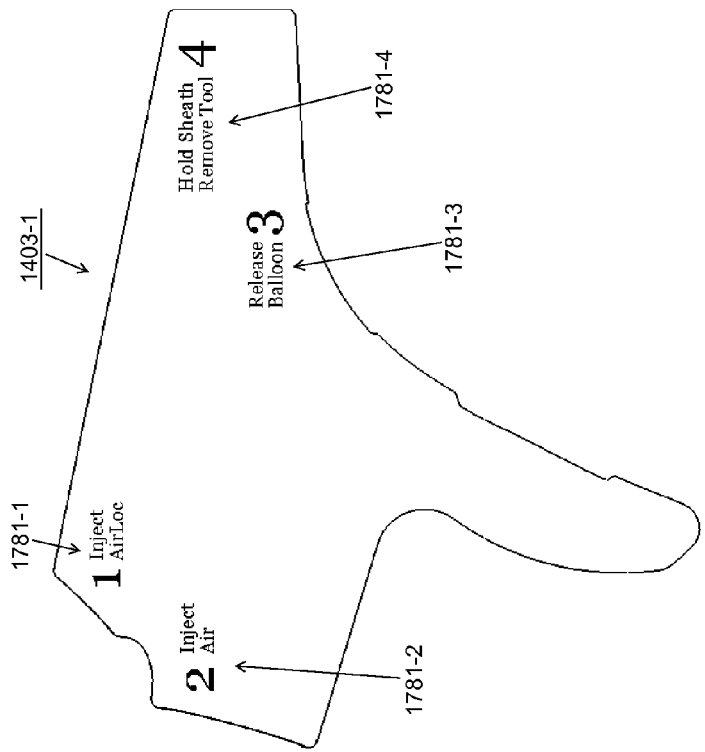
FIG. 8I(B)
FIG. 8I(A)

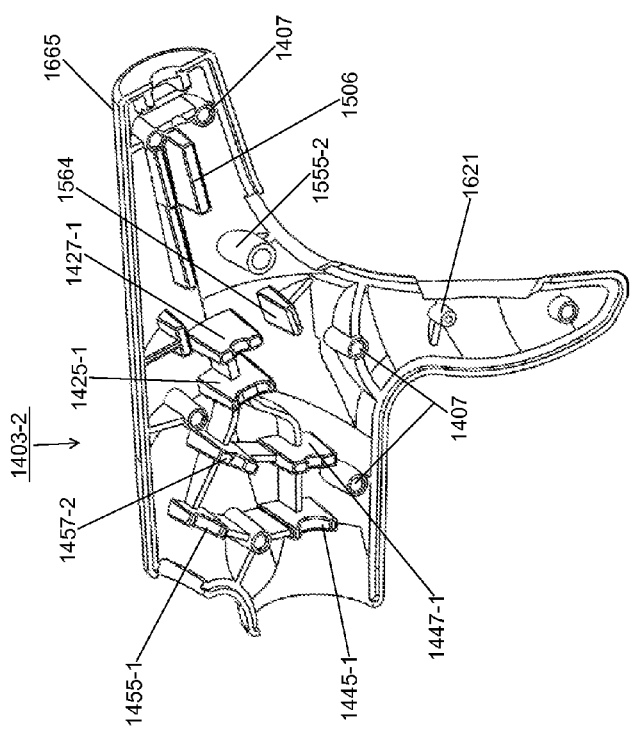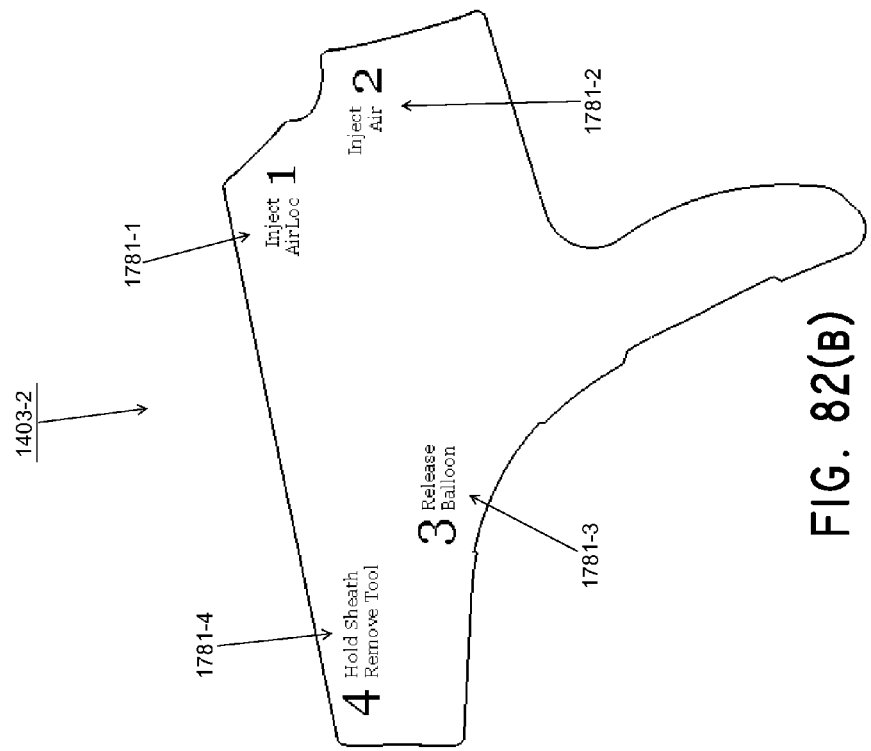
FIG. 82(A)
FIG. 82(B)

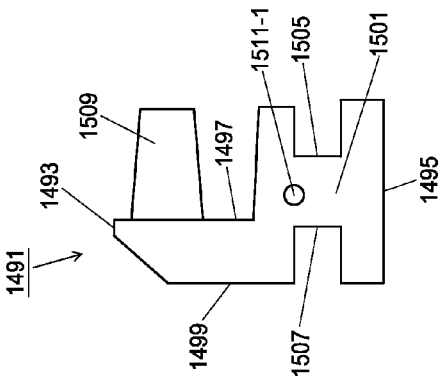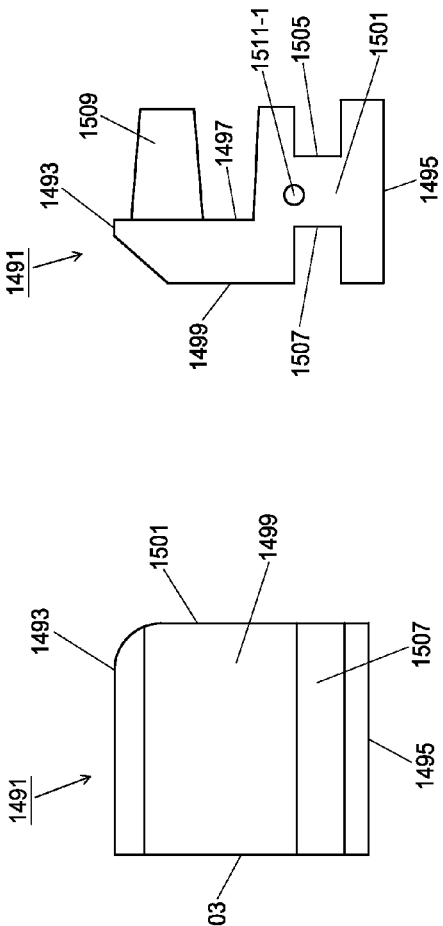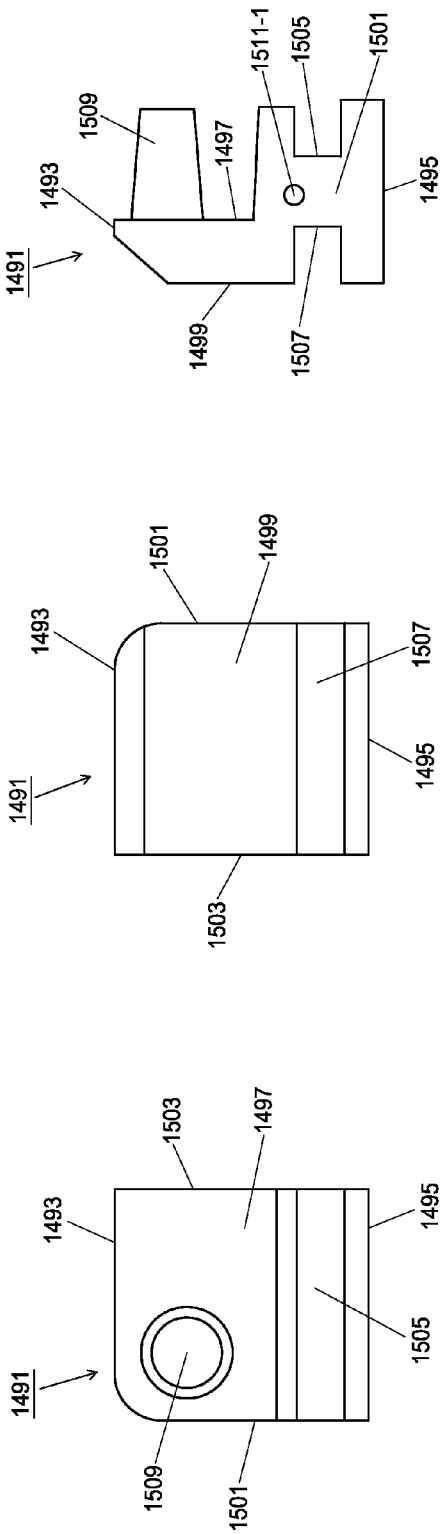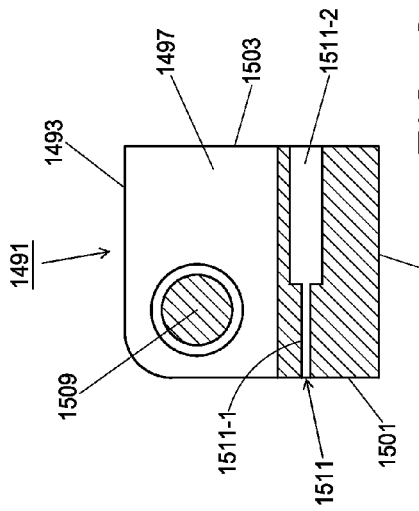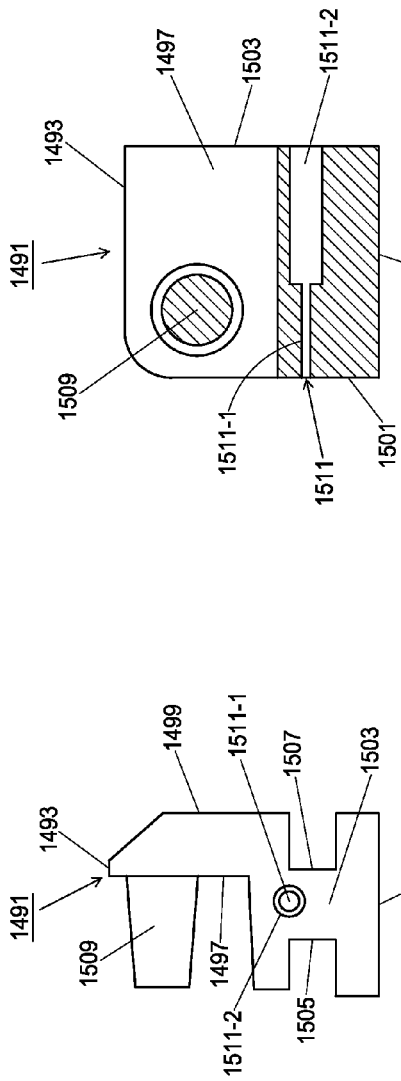

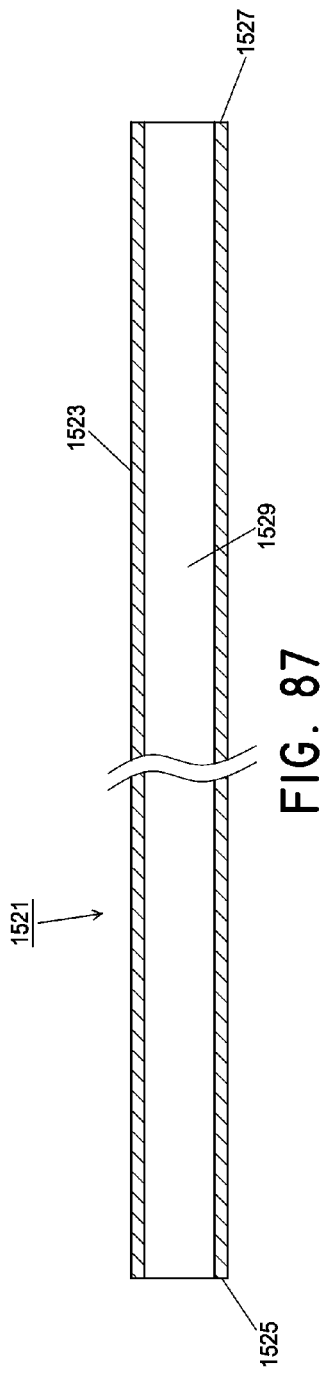
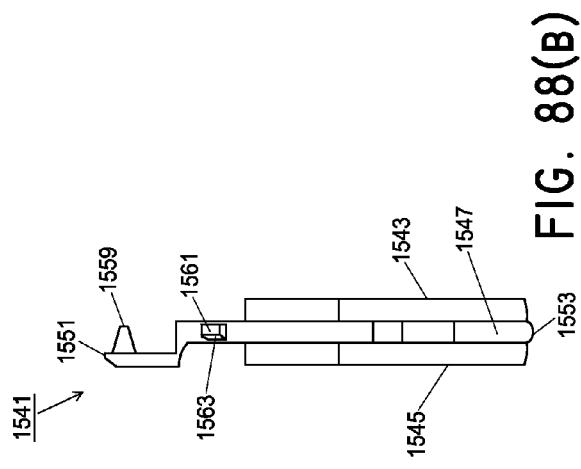
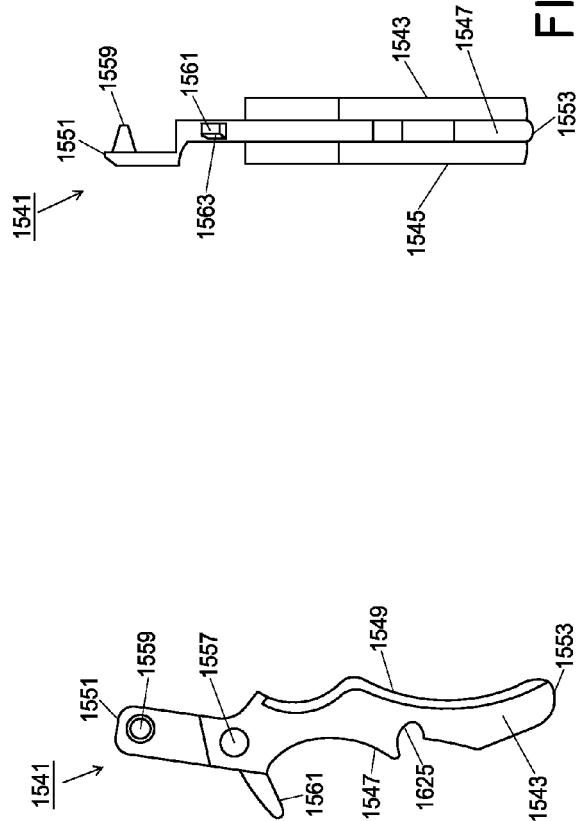

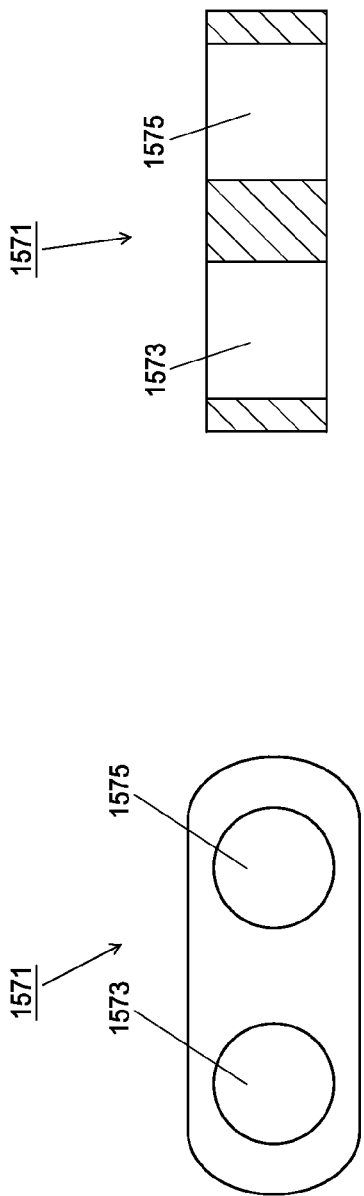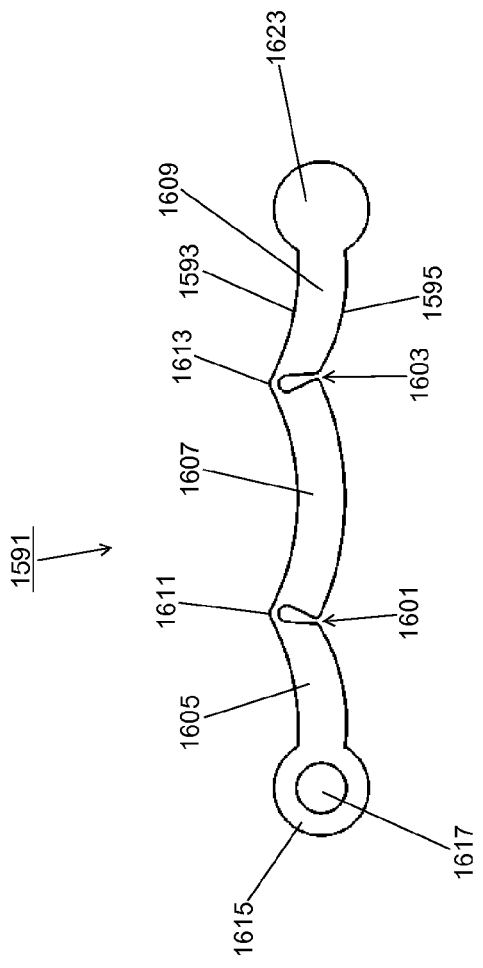

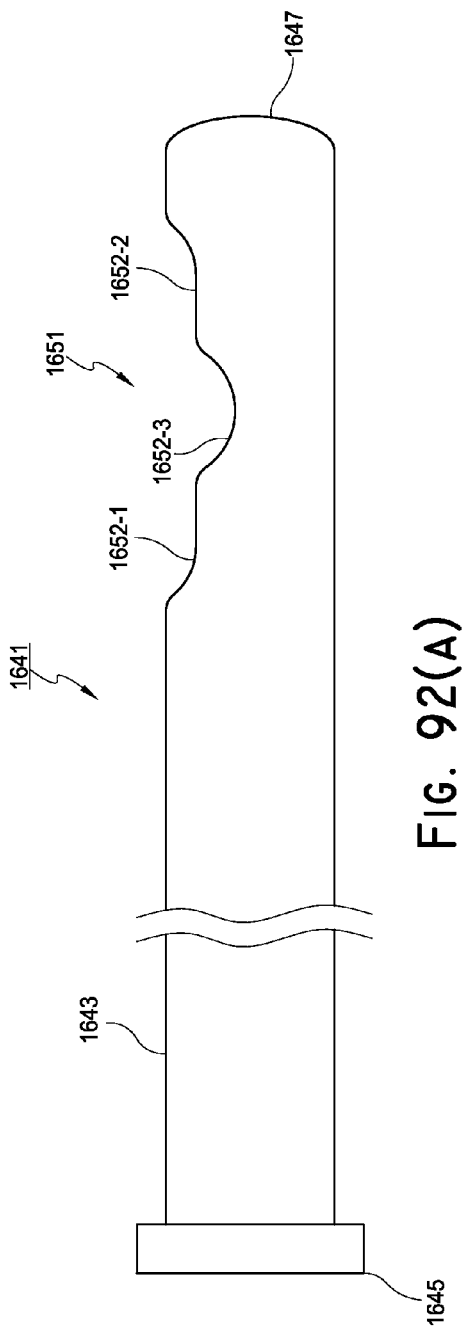
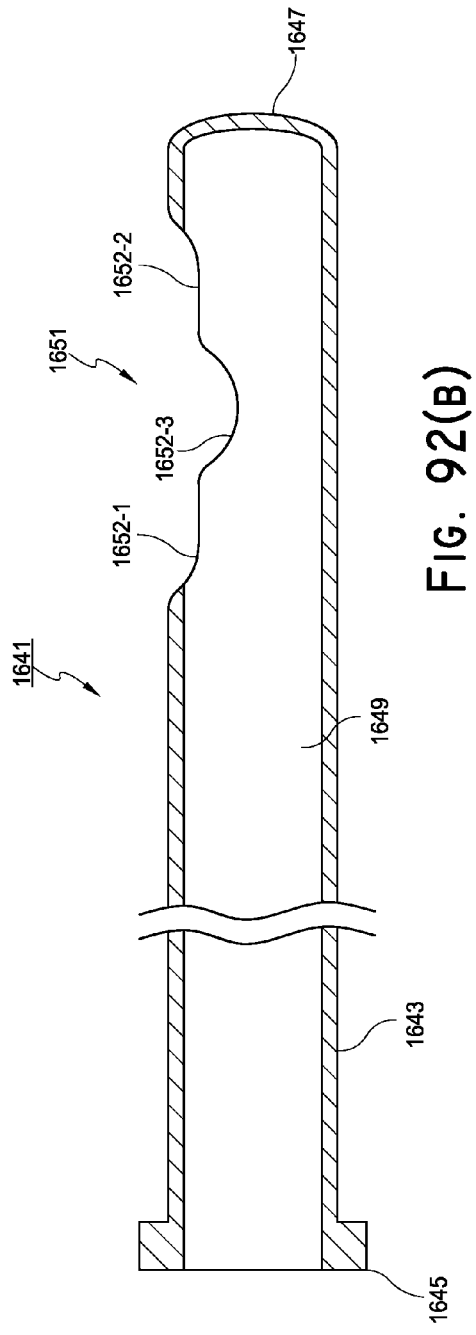
FIG. 92(A)
FIG. 92(B)

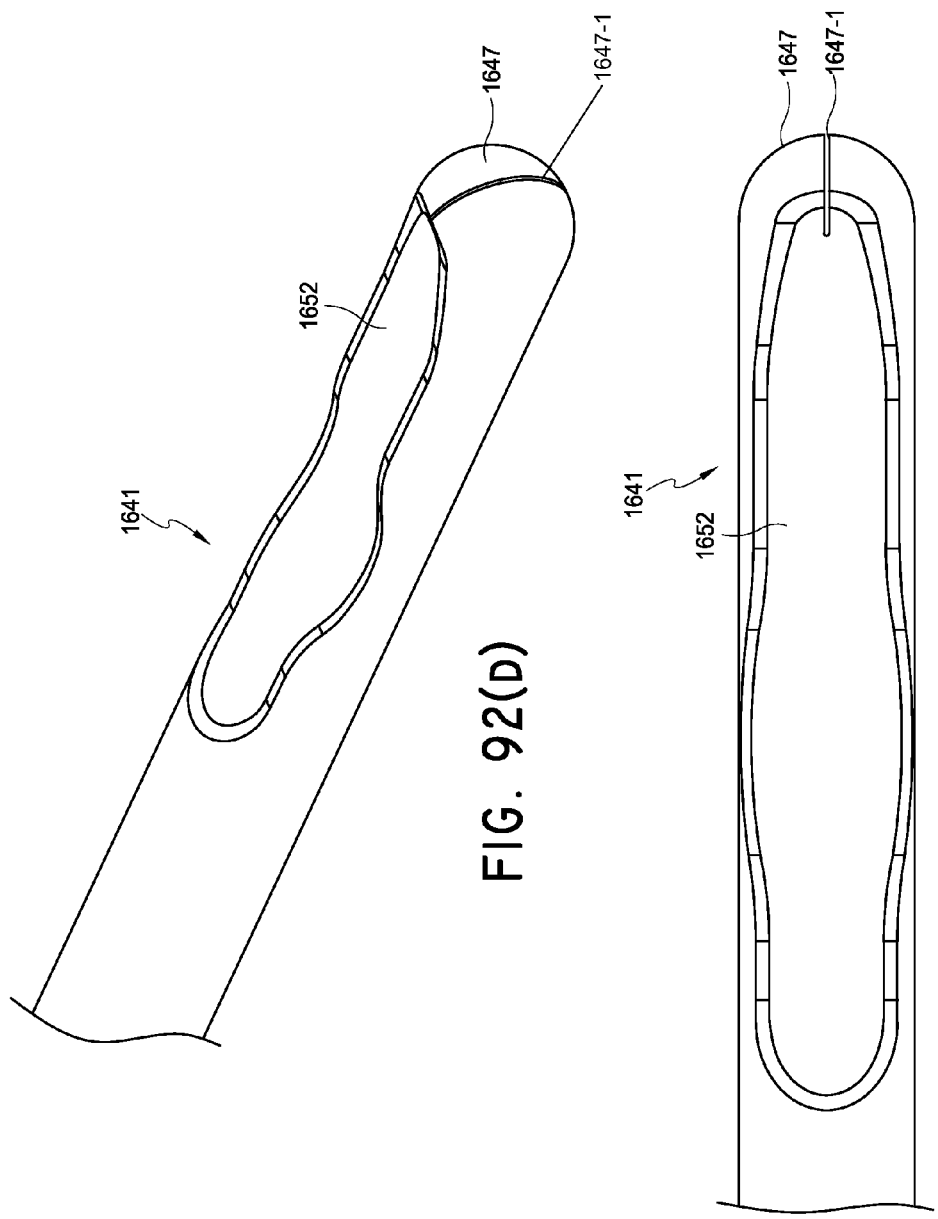

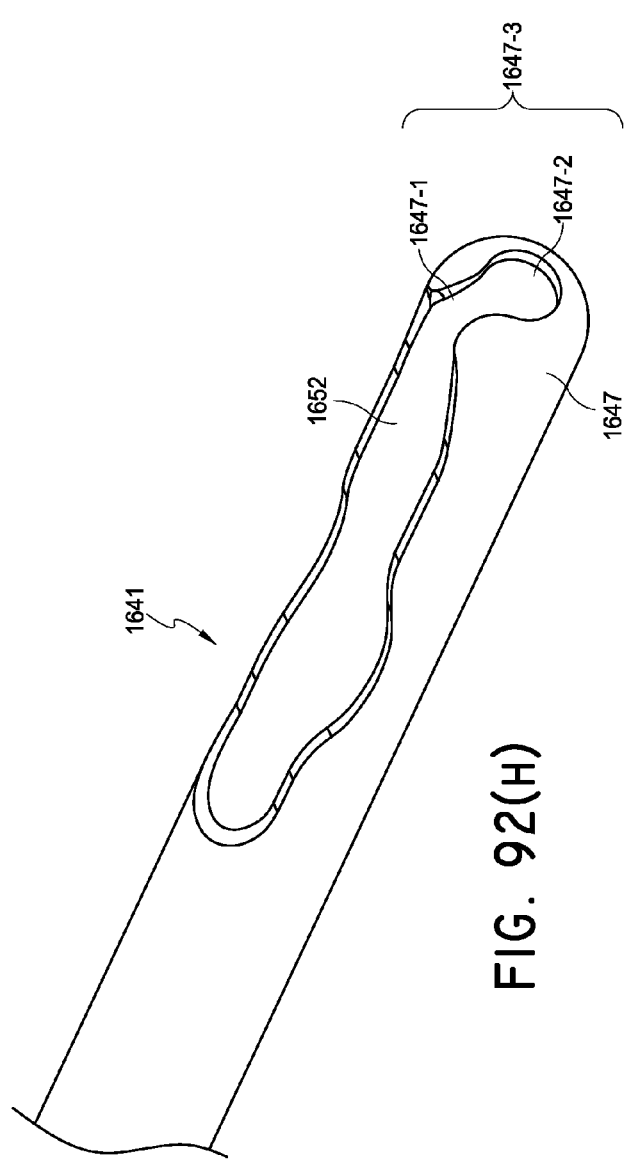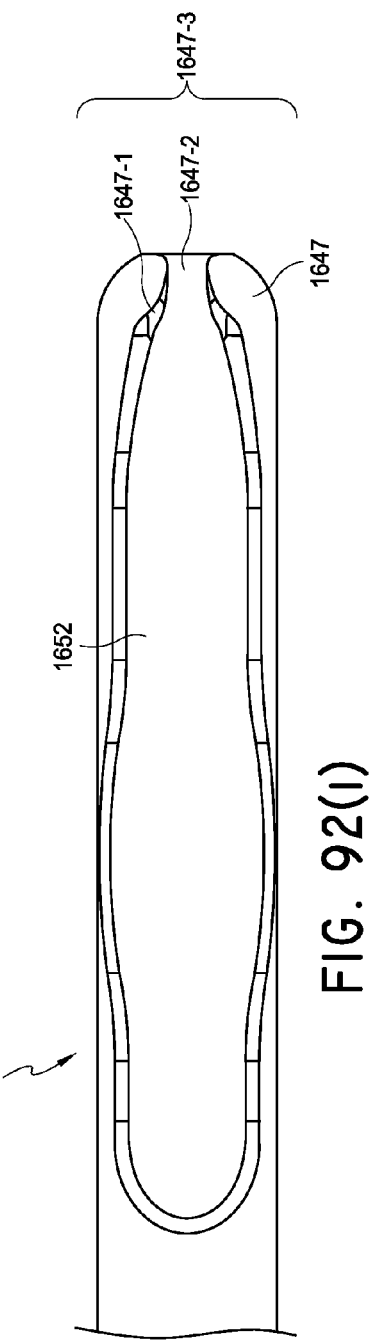

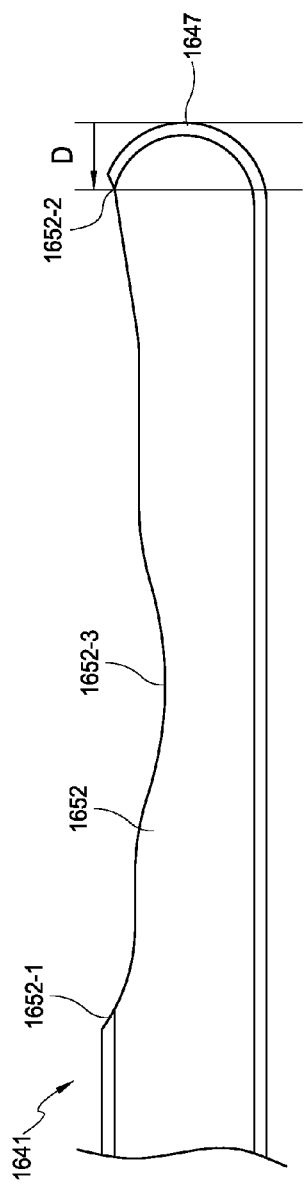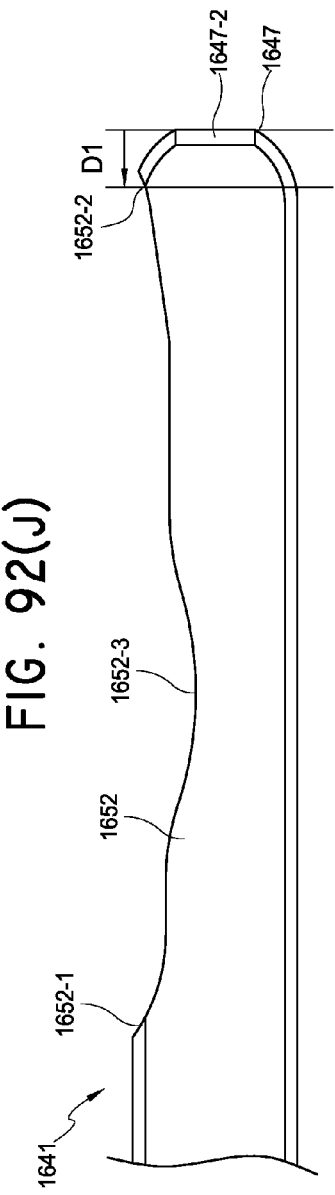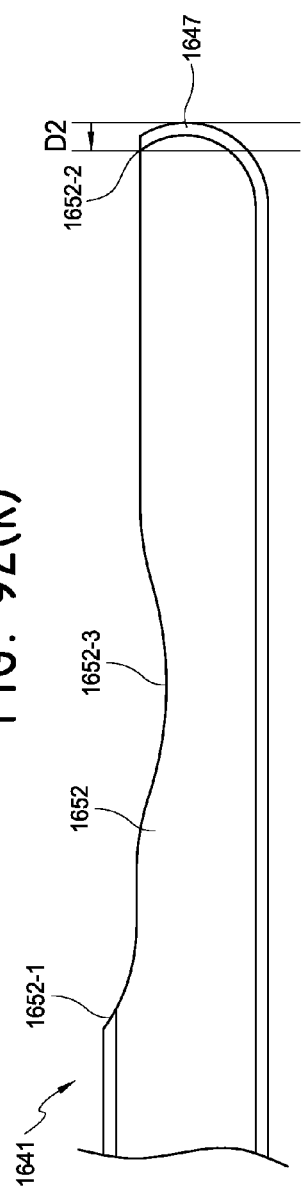

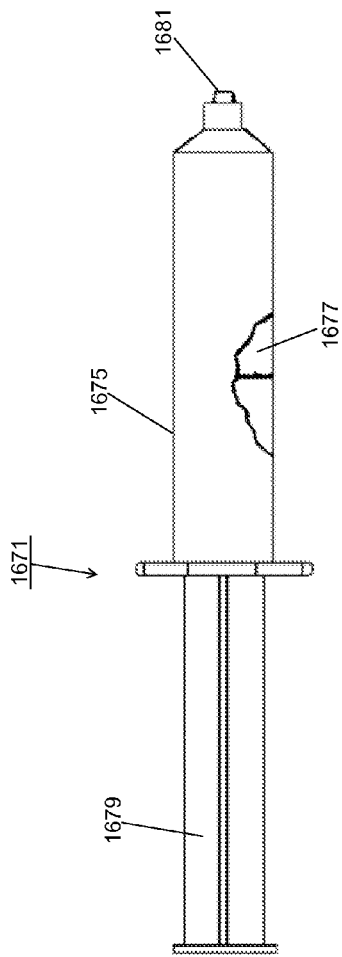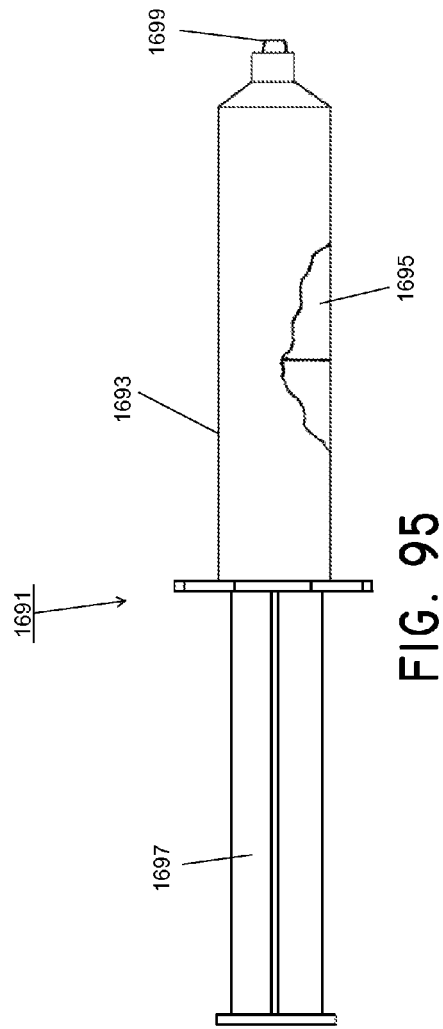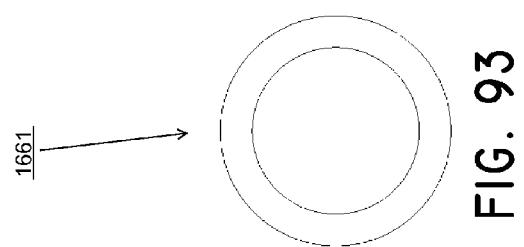

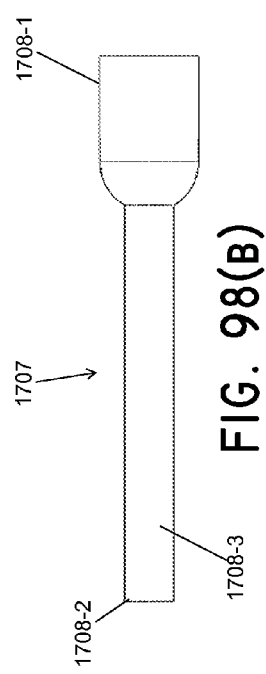
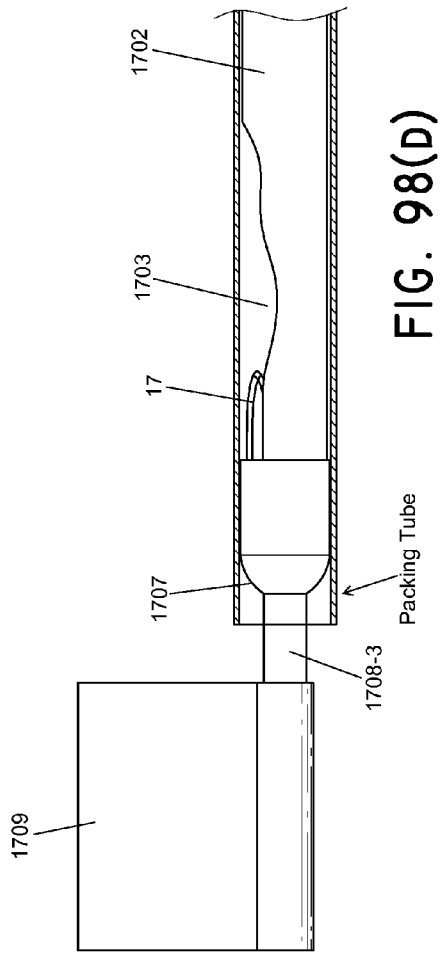
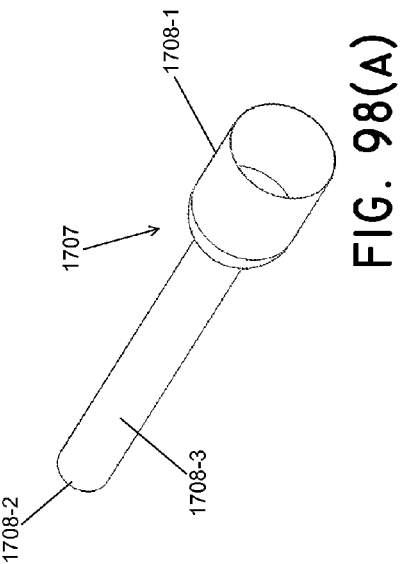
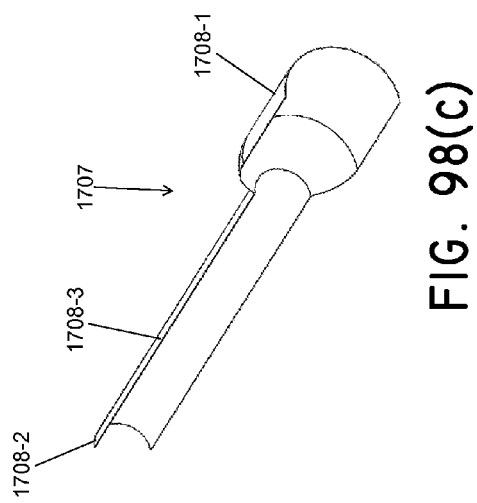

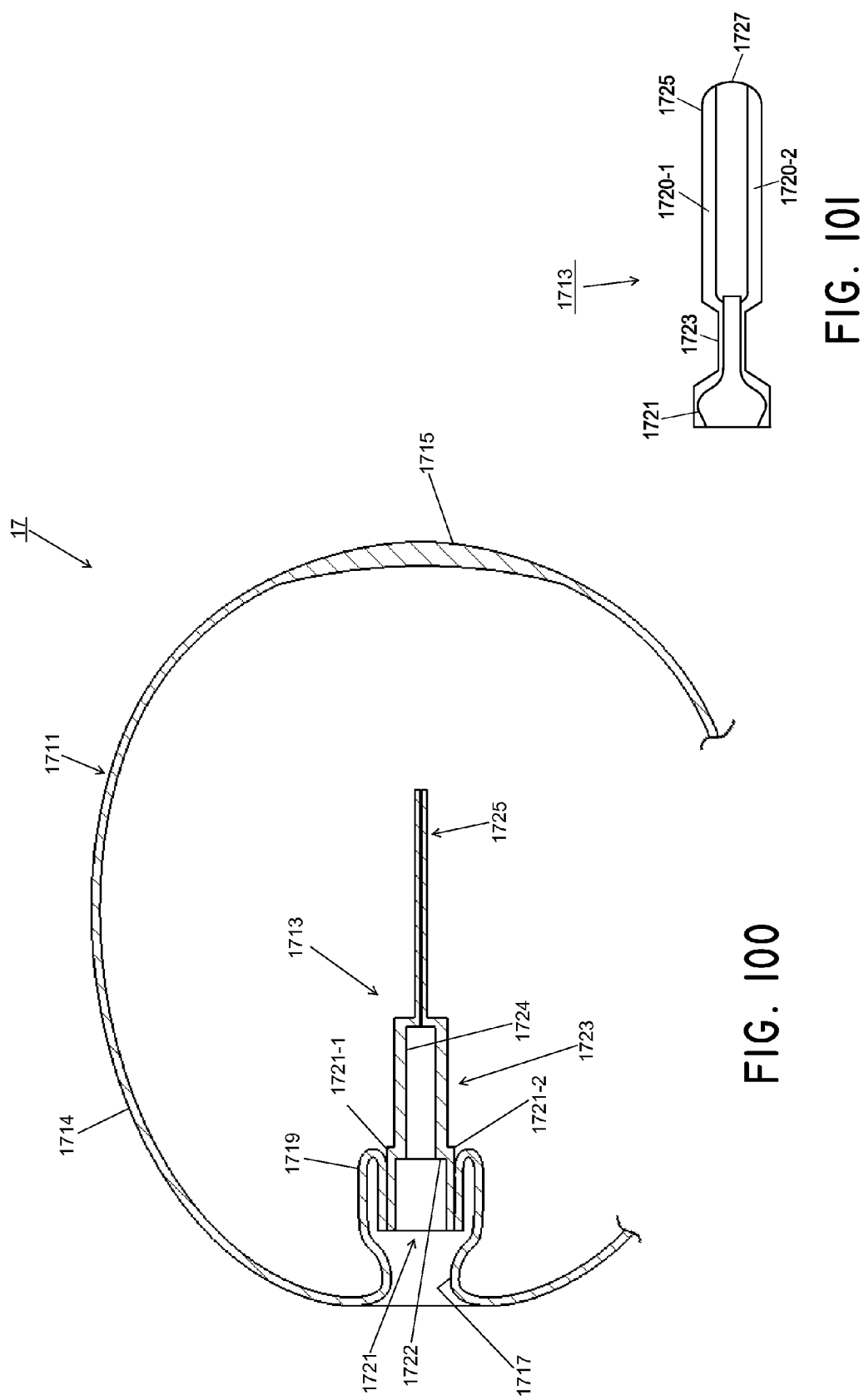

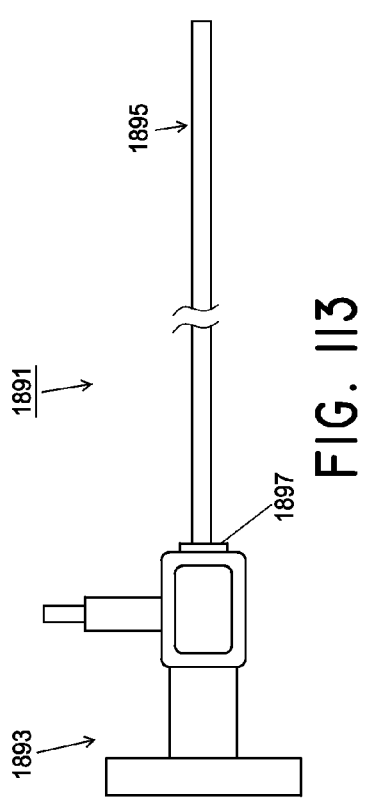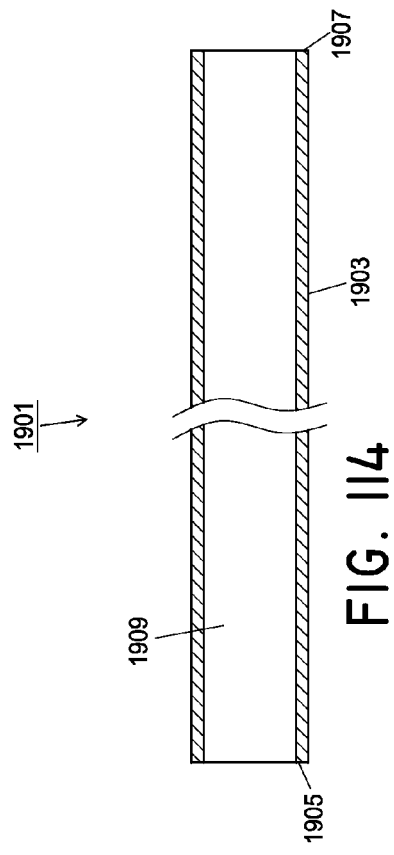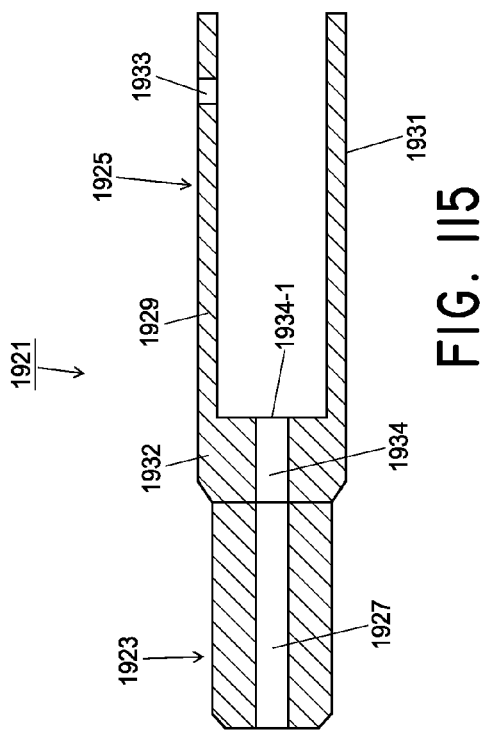

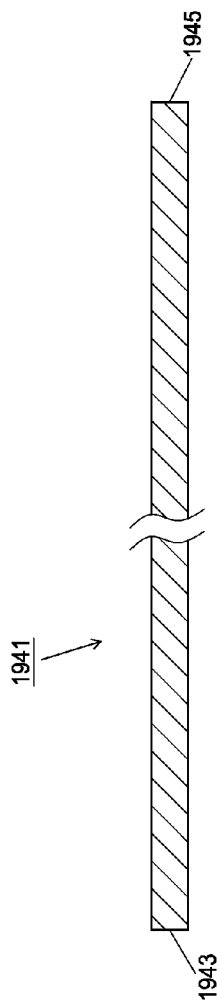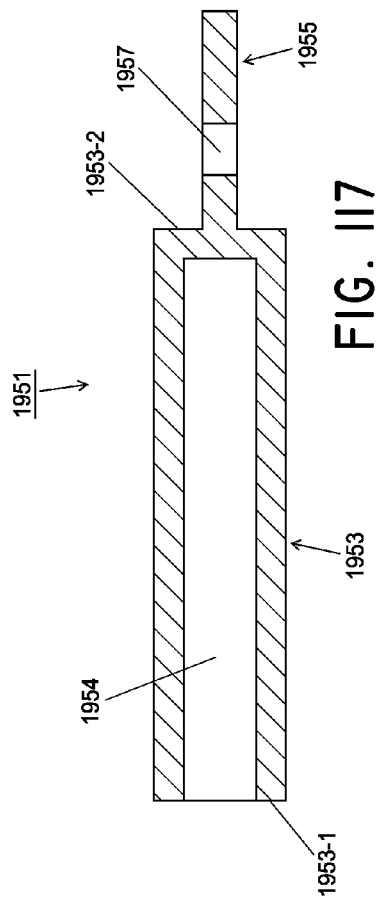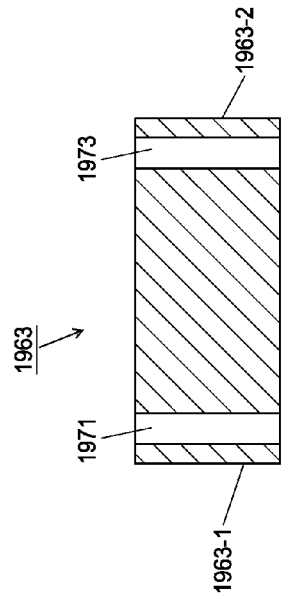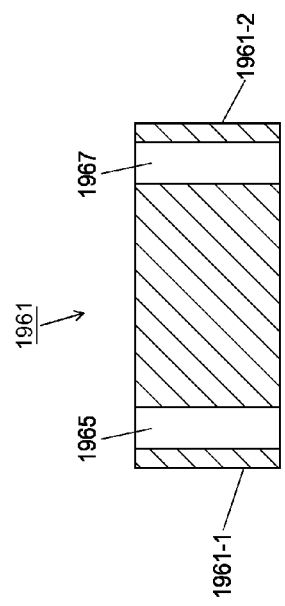

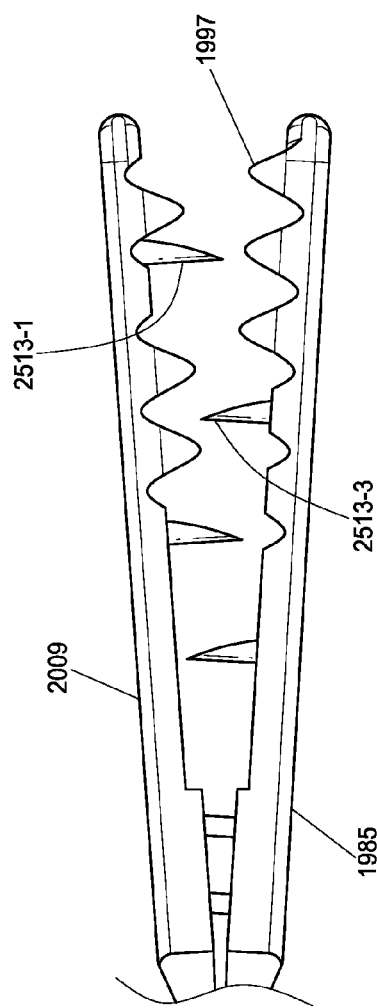
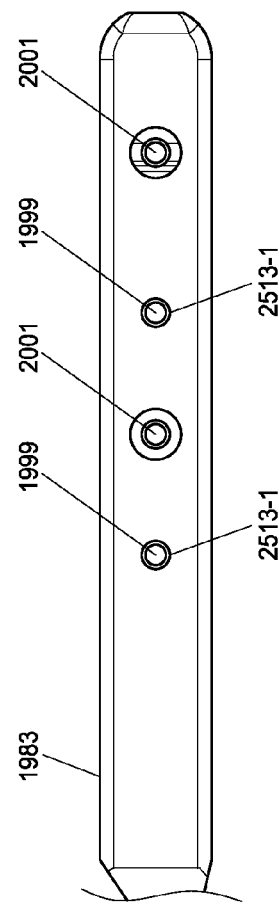
FIG. 120(E)
FIG. 120(F)

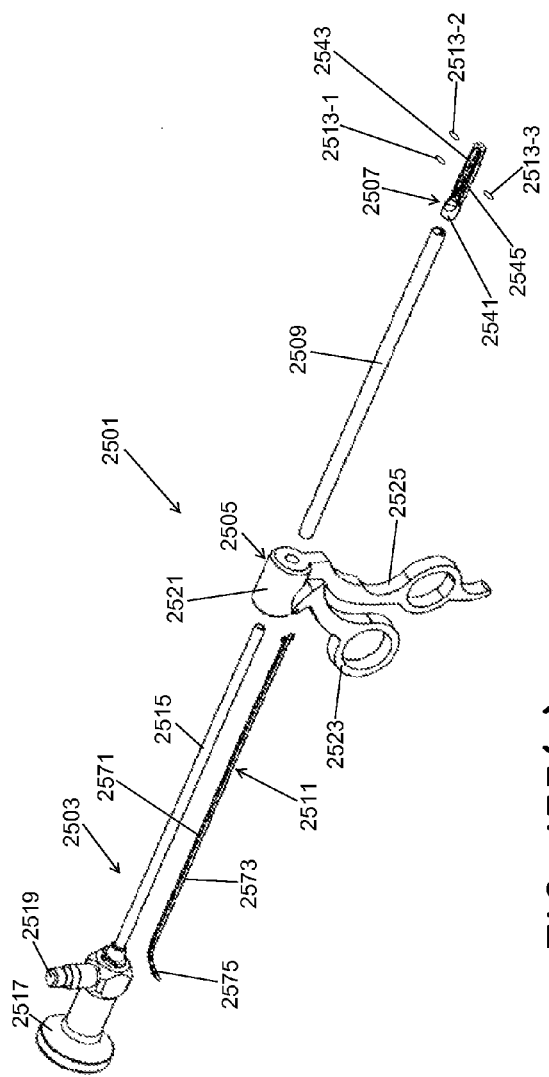
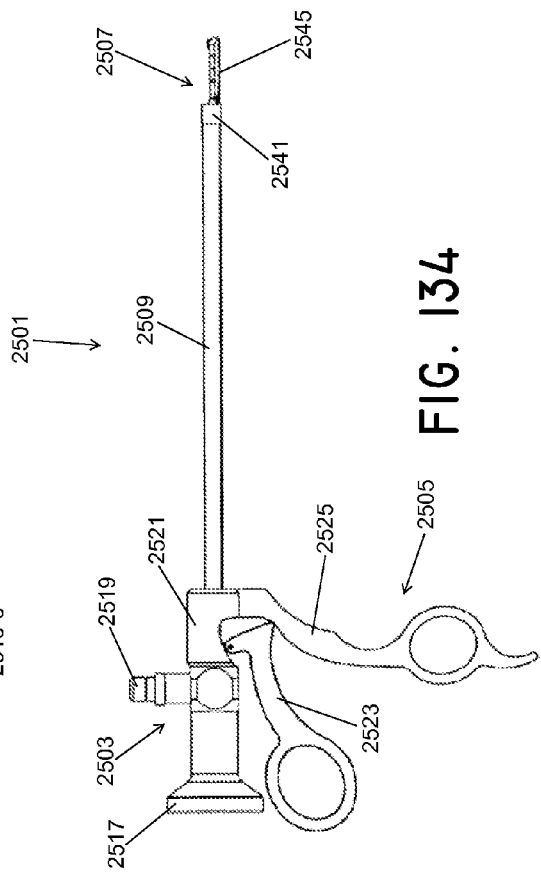
FIG. 133(c)
FIG. 134

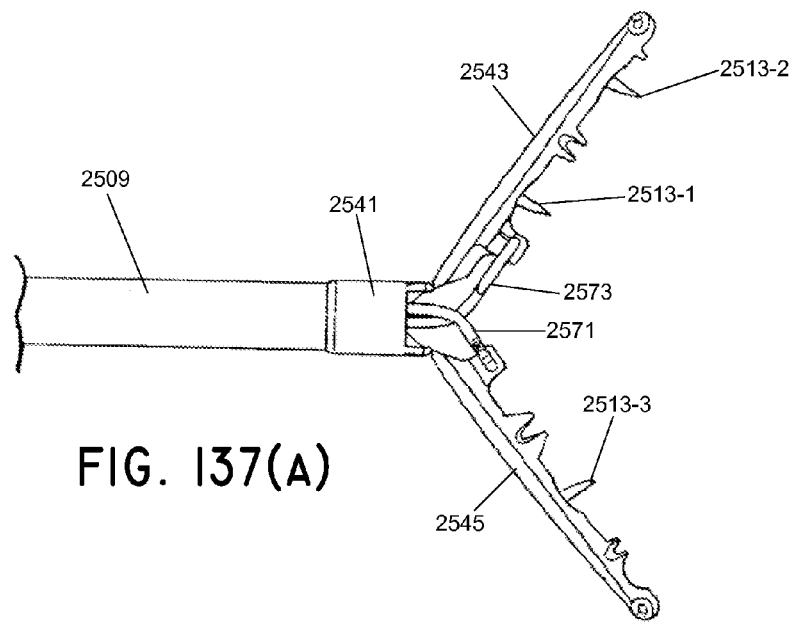
FIG. 137(A)
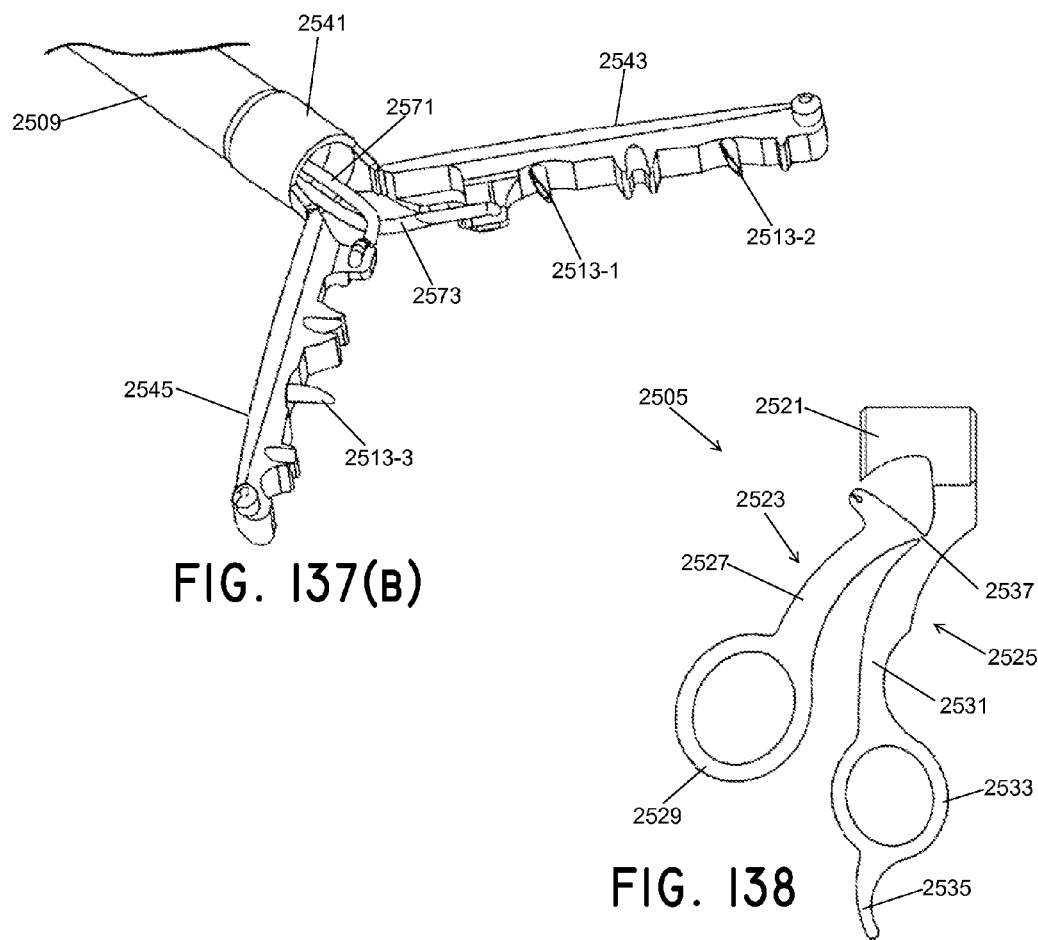
FIG. 137(B)
FIG. 138

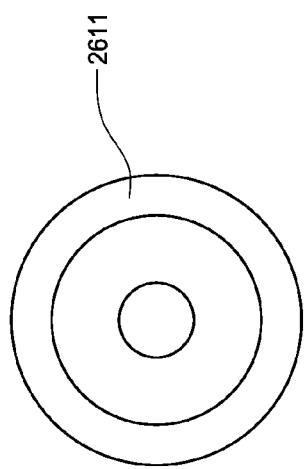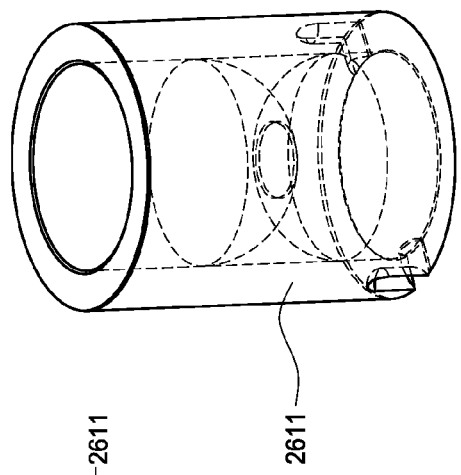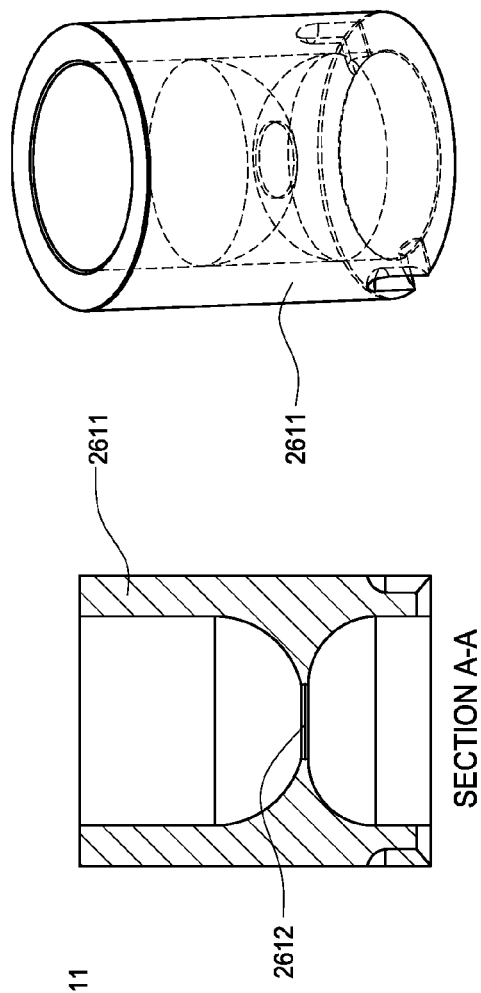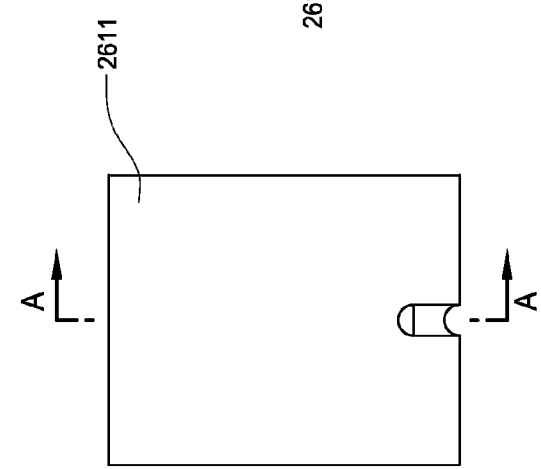

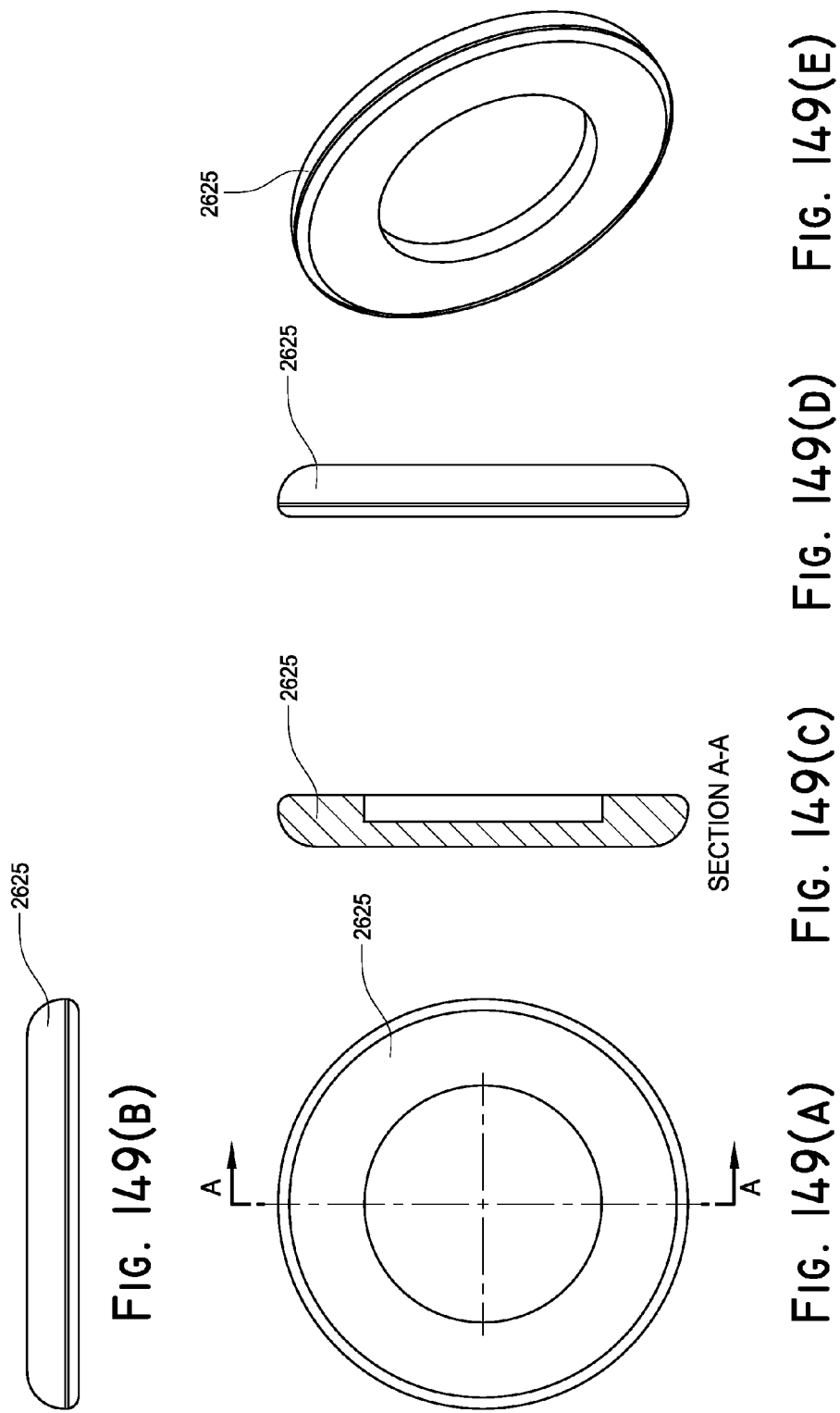

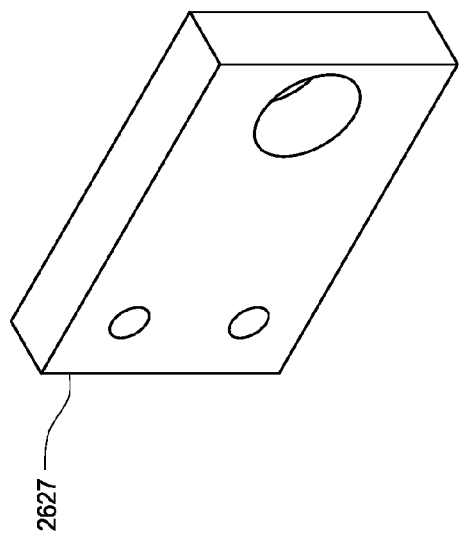
Fig. 152(D)
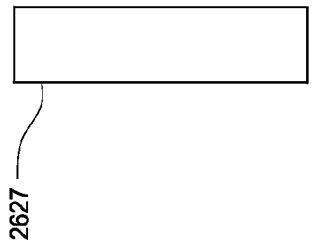
Fig. 152(C)
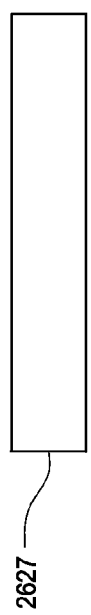 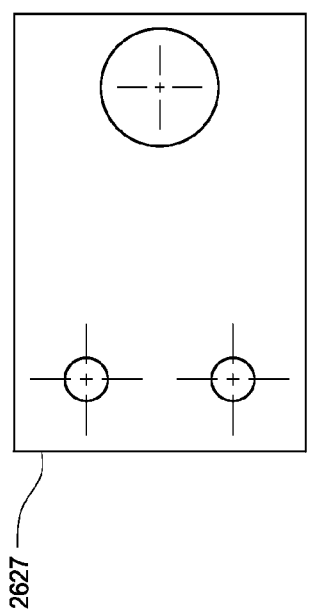
Fig. 152(B)  Fig. 152(A)

| Configuration | Silicone | Pellethane | Estane 18 | Estane T0 | Estane T1 | Estane T2 | Estane Gen 1 |
|---|---|---|---|---|---|---|---|
| Material | Silicone | Pellethane | Estane | Estane | Estane | Estane | Estane |
| Process | Dip molded | blow molded | blow molded | blow molded | blow molded | blow molded | Welded sheets |
| Size | 18ml | 30ml | 18ml | 30ml | 30ml | 30ml | 18ml |
| Single Wall Thickness (inches) | 0.00500 | 0.00045 | 0.00055 | 0.00035 | 0.00090 | 0.00108 | 0.00150 |
| Constrained Results: | | | | | | | |
| Deformation | | | | | | | |
| d (mm) @ 4.25lbs | 18 | 6 | 6.2 | 10.6 | 6.4 | 6.2 | 5 |
| Burst | | | | | | | |
| Force at Burst | N/A | 10.1 | N/A | 4.9 | 10.08 | 12.5 | 9 |
| d at Burst | N/A | 18.6 | N/A | 15.8 | 18.8 | 21.9 | 12 |
| Cycle | | | | | | | |
| # at 4.25lb cycle (50max) | N/A | 100%@50 | 100%@50 | 0% | 100%@50 | 100%@50 | 100%@50 |

| P/V Characteristics | | | | | | | |
|---|---|---|---|---|---|---|---|
| Base Volume | 15 | 25 | 18 | 25 | 25 | 25 | 18 |
| Volume at 30 cmH2O | 22 | 36 | 24 | 43 | 33 | 31 | 23 |
| Delta (% increase) | 47% | 44% | 33% | 72% | 32% | 24% | 28% |
| Volume at 15 cmH2O | 18 | 30 | 22 | 32 | 29 | 28 | 20.5 |
| Delta (% increase) | 20% | 20% | 22% | 28% | 16% | 12% | 14% |

FIG. 154

METHODS AND SYSTEMS FOR PERFORMING A MEDICAL PROCEDURE

CROSS REFERENCE TO RELATED APPLICATIONS

This application claims priority to U.S. Application No. 61/682,184, filed Aug. 10, 2012, titled METHODS AND SYSTEMS FOR PERFORMING A MEDICAL PROCEDURE, and U.S. Application No. 61/769,719, filed Feb. 26, 2013, titled METHODS AND SYSTEMS FOR PERFORMING A MEDICAL PROCEDURE, the entire contents of which are incorporated by reference herein and made a part of this specification.

BACKGROUND OF THE INVENTION

1. Field of the Invention

The present invention relates to methods and systems for performing medical procedures on anatomical structures of the body. Such medical procedures may involve, for example, attenuating transient pressure waves in anatomical structures of the body, for example, by implanting a compressible pressure-attenuating device in an anatomical structure of the body that is subjected to such pressure waves.

2. Description of the Related Art

Pressure waves are known to propagate through incompressible fluids in various anatomical structures of the body. These pressure waves may be caused by normally-occurring events within the body, such as a beating heart, breathing in the lungs, peristalsis actions in the GI tract, and movement of the muscles of the body. Alternatively, these pressure waves may be caused by sudden events, such as coughing, laughing, external trauma to the body, and movement of the body relative to gravity. As the elasticity of the surrounding tissues and organs, sometimes referred to as compliance, decreases, the propagation of these pressure waves increases. These pressure waves have many undesirable effects ranging from discomfort to stress on the organs and tissue to fluid leakage to renal failure to stroke to heart attack to blindness.

Urinary tract disorders, such as frequency, urgency, incontinence, and cystitis, are a widespread problem in the United States and throughout the world, affecting people of all ages, both physiologically and psychologically. Urine is primarily composed of water and is a virtually incompressible fluid in the typical pressure ranges that are present within the human bladder. The relationship between the maximum urethral pressure and the intravesical pressure for normal voiding of the bladder is well-defined. During normal voiding, relaxation of the urethra occurs before the detrusor muscle contracts to cause the intravesical pressure to exceed the urethral pressure.

Intravesical pressure spikes often result from volumetric tissue displacement in response to gravity, muscular activity or rapid acceleration. The lack of compliance of the bladder and the urine contained in the bladder with respect to events of high frequency, high intensity and short wavelength results in minimal fluidic pressure attenuation of the higher frequency pressure wave(s) and results in high intravesical pressures that are directly transmitted to the bladder neck and urethra, which may or may not cause detrusor contractions. Under these conditions, the urethra may act as a volumetric pressure relief mechanism, allowing a proportional volume of fluid to escape the bladder, thereby lowering the intravesical pressure to a tolerable level. The urethra has a maximum urethral pressure value, and when the intravesical pressure exceeds the maximum urethral pressure, fluid will escape the bladder. Under these conditions, nerve receptors in the bladder and/or bladder neck and/or trigone trigger a detrusor contraction that may lead to matriculation (frequency) or may subside without matriculation (urgency) or may lead to the intravesical pressure exceeding the maximum urethral pressure resulting in fluid escaping the bladder (stress incontinence).

For the vast majority of patients suffering from problems of urinary tract disorders, such as frequency, urgency, stress and urge incontinence and cystitis, the cause and/or contributor to bladder dysfunction is a reduction of overall dynamic bladder compliance, as opposed to a reduction of steady-state bladder compliance. These patients may often have bladders that are compliant in steady-state conditions but that become non-dynamically compliant when subjected to external pressure events having a short duration of, for example, less than 5 seconds or, in some cases, less than 0.5 seconds. Reduction in dynamic compliance of the bladder is often caused by aging, use, distention, childbirth and trauma. In addition, the anatomical structure of the bladder in relation to the diaphragm, stomach, and uterus (for women) causes external pressure to be exerted on the bladder during physical activities, such as talking, walking, laughing, sitting, moving, turning, and rolling over. For a patient suffering from stress incontinence due to lack of dynamic compliance in the bladder, when the intravesical pressure exceeds the maximum urethral pressure, leakage occurs.

In light of the foregoing, a number of attempts have been made to combat urinary tract disorders. One such attempt involves the use of an indwelling catheter connected to a collection bag with a clamping device on the catheter. Indwelling catheters, however, have a number of drawbacks. For instance, there is an infection risk associated with indwelling catheters, which provide a direct passage for bacteria or other microorganisms into the bladder. Thus, indwelling catheters can only be used for relatively short-term situations. In addition, indwelling catheters and associated collection bags are not cosmetically appealing to most patients.

An approach that has been taken to address urinary incontinence involves the use of prosthetic urethral valves. One known prosthetic urethral valve utilizes an inflatable cuff that is inserted around the outside of the urethra. Prosthetic urethral valves also have numerous disadvantages. One disadvantage of these valves is that they typically require surgery for installation, and some of these valves must be operated externally and, therefore, are dependent on manual intervention.

The use of intra-urethral valves to address urinary tract disorders is also known. Typical intra-urethral valves also generally require manual intervention. Another problem associated with typical intra-urethral valves is that the valves may be displaced into the bladder or expelled from the urethra. There is also an infection risk associated with many such valves since they often extend into the meatus and/or have portions of the device external to the urethra providing a passage for microorganisms into the bladder.

Electrical stimulation therapy, including rectal, intra-vaginal, and external varieties, has been used to tone the muscles and to stimulate nerves supporting the bladder and urethra. However, this type of therapy requires lengthy and numerous treatments, and any benefits derived from the therapy typically diminish when the treatments are stopped.

Current surgical incontinence procedures typically focus on the augmentation of urethral flow resistance. Such surgical interventions typically include bladder neck suspensions and bulk (collagen) injections. Although these procedures can be clinically effective with certain patients, problems include widely variable clinical outcomes, relatively high costs to perform, and potential complications related to surgery. Moreover, the effects of such surgical procedures may be short-lived.

Drug therapy also exists for a number of urinary tract conditions, including overactive bladder. These drugs include oral medications (systemic) and drugs delivered directly into the bladder. Unfortunately, these drugs typically suffer from side effects, lack of efficacy and high morbidity. In particular, oral medications typically do not provide immediate relief of symptoms and include side effects, such as dry mouth and constipation. Drugs delivered directly into the bladder often require continuous or intermittent catheterization for introduction of the therapeutic agents at the clinically appropriate time.

As can be appreciated, the treatment methods described above either focus on the augmentation of urethral flow resistance, the temporary stoppage or absorption of all urethral flow, or the relaxing of the detrusor muscles to minimize unwanted contractions. The disadvantages and limitations of these treatment methods are numerous and include: an excessively high level of patient interaction required to operate and/or to maintain the devices, especially for elderly patients and for physically or mentally challenged patients; limited clinical efficacy; restricted urine outflow; patient discomfort and side effects; urethral and bladder infections related to the devices used; and relatively great expense as compared to non-clinical solutions (diapers, pads, etc.).

Accordingly, an alternative approach to those described above has been to implant a compressible, pressure-attenuating device in the bladder in order to lower the intravesical pressure. This approach is disclosed, for example, in the following documents, all of which are incorporated herein by reference: U.S. Pat. No. 6,682,473, Matsuura et al., issued Jan. 27, 2004; U.S. Pat. No. 7,074,178, Connors et al., issued Jul. 11, 2006; and U.S. Patent Application Publication No. 2010/0222802, Gillespie, Jr. et al., published Sep. 2, 2010. According to one aspect of the foregoing approach, a compressible device is inserted, in a compacted state, into the bladder of a patient through the patient's urethra, and, then, once in the bladder, the compressible device is expanded, for example, by inflation with atmospheric air. A delivery system may be used to deliver the compressible device through the urethra and into the bladder and also may be used to expand the compressible device from its compacted state to its expanded state and to deploy the compressible device, once expanded, from the delivery system. If removal or replacement of the compressible device is desired, a removal system may be used to remove the compressible device from the bladder through the urethra.

Although the above-described implantable, compressible, pressure-attenuating device has had some success in treating urinary tract disorders, the present inventors have identified certain areas of improvement relating to the device, its introduction into a patient, its expansion and deployment within a patient, and its removal from a patient.

SUMMARY OF THE INVENTION

It is an object of the disclosure to provide a method and system for performing a medical procedure on an anatomical structure of a body. The medical procedure may be performed, for example, to attenuate transient pressure waves in the anatomical structure and may involve, for example, implanting a compressible pressure-attenuating device in the anatomical structure subject to such pressure waves. Such a method and system may be used in, but is not limited to use in, treating urinary tract disorders.

A system may comprise one or more of the following: an access device, a therapeutic or diagnostic object, a delivery device, and a removal device. The access device may be used to create a passageway to the anatomical structure, such as, for example, a trans-urethral passageway to a patient's bladder. The therapeutic or diagnostic object may be an inflatable device and may be, for example, a pressure-attenuating device. The delivery device may be used to deliver a therapeutic or diagnostic object to the anatomical structure. Such an object may be, for example, a pressure-attenuating device, which may be delivered to the anatomical structure in a compacted or deflated state and then inflated and released from the delivery device. The removal device may be used to view the anatomical structure. In addition, where an object delivered to the anatomical structure is an inflatable pressure-attenuating device, the removal device may also be used to capture, to deflate, and to remove the pressure-attenuating device from the anatomical structure.

In some embodiments, an access device can provide access to an anatomical structure within a patient. The access device can comprise an elongated sheath or cannula, the elongated sheath comprising a proximal end, a distal end, and a longitudinal channel. The access device may also include an obturator that can be removably mounted within the longitudinal channel of the elongated sheath.

In some embodiments, an access device can comprise one or more of a housing assembly, a sheath assembly, and a fluid control system. The housing assembly can comprise one or more housing structures that define a body for the access device.

According to one aspect, there is provided an access device for use in providing access to an anatomical structure within a patient. The access device can comprise (a) an elongated sheath, the elongated sheath comprising a channel; (b) an obturator, the obturator being insertable into the channel of the elongated sheath; and (c) a locking mechanism for selectively locking the obturator within the channel of the elongated sheath.

According to another aspect, there is provided an access device for use in providing access to an anatomical structure within a patient. The access device can comprise (a) an elongated sheath, the elongated sheath comprising a sheath channel; (b) an obturator, the obturator being insertable into the sheath channel of the elongated sheath, the obturator comprising an obturator channel; and (c) an obturator handle, the obturator handle being secured to a proximal end of the obturator, the obturator handle comprising a handle channel, the handle channel being in fluid communication with the obturator channel.

In some embodiments, the access device can include a system for positioning a flexible sleeve in an access channel. The flexible sleeve can be used to protect the access channel and/or body tissue in the patient. For example, in some embodiments, the obturator can include a cavity, and the sleeve can be positionable in the cavity in a first position and positionable outside of the cavity in a second position. The distal end of the obturator may also be positionable distally beyond the distal end of an elongated sheath. In some embodiments, a slide ring can be connected to the sleeve to move the sleeve between the first and second positions.

According to one aspect, there is provided an access device for use in providing access to an anatomical structure within a patient. The access device can comprise (a) an elongated sheath, the elongated sheath comprising a proximal end, a distal end, and a longitudinal channel; (b) an obturator, the obturator being removably mounted within the longitudinal channel of the elongated sheath, the obturator comprising a proximal end, a distal end, and a cavity, the distal end of the obturator being positionable distally beyond the distal end of the elongated sheath; (c) a slide ring, the slide ring being slidably mounted around the elongated sheath; and (d) a flexible sleeve, the flexible sleeve comprising a proximal end, a distal end, and a longitudinal channel, the proximal end of the flexible sleeve being coupled to the slide ring, the distal end of the flexible sleeve being positionable within the cavity of the obturator.

In some embodiments, the access device can include, in addition to the elongated sheath, a first fluid conduit, a second fluid conduit, and a valve mechanism for controlling fluid communication between the first fluid conduit and the elongated sheath and between the second fluid conduit and the elongated sheath. The first fluid conduit may be used to deliver fluid to the elongated sheath for delivery to the patient, and the second fluid conduit may be used to drain fluid from the patient through the elongated sheath. The valve mechanism may comprise a cam which may be positioned in a first position in which the first fluid conduit is pinched shut by the cam and the second fluid conduit is kept open, a second position in which the second fluid conduit is pinched shut by the cam and the first fluid conduit is kept open, and a third position in which both the first fluid conduit and the second fluid conduit are pinched shut by the cam. The cam may additionally be positioned in a fourth position in which the first fluid conduit and the second fluid conduit are simultaneously kept open. The cam may be constructed to provide more than merely a fully opened state and a fully closed state for each of the first and second fluid conduits. More specifically, the cam may be constructed to additionally include a finite number or an infinite number (i.e. continuously adjustable) of intermediate positions having flow rates varying by equal or unequal increments between the fully opened state and the fully closed state.

According to another aspect, there can be provided a delivery device for use in delivering a therapeutic and/or diagnostic object, such as an inflatable pressure-attenuating device, to an anatomical structure within a patient. The delivery device can include a delivery tube, an inflation tube, and a release mechanism, among other features. In some embodiments, the delivery device can comprise (a) a housing; (b) a tube extending from a distal end of the housing, the tube having a proximal end, a distal end, and at least one longitudinal channel; (c) a first fluid supply, the first fluid supply comprising a volume of a first fluid; (d) a second fluid supply, the second fluid supply comprising a volume of a second fluid; and (e) a connection system, the connection system connecting each of the first fluid supply and the second fluid supply to the at least one longitudinal channel of the tube.

According to another aspect, there can be provided a delivery device for use in delivering an inflatable medical device, such as an inflatable pressure-attenuating device, to an anatomical structure within a patient. The delivery device can comprise (a) a housing; (b) an inflation tube extending from a distal end of the housing, the inflation tube having a proximal end, a distal end, and a longitudinal channel, the distal end of the inflation tube being insertable into an inflatable medical device for use in delivering at least one inflation medium to the inflatable medical device; and (c) a push-off member slidably mounted relative to the inflation tube, the push-off member comprising a distal end slidable distally past the distal end of the inflation tube to decouple the inflation tube from the inflatable medical device.

According to another aspect, there can be provided a delivery device for use in delivering an inflatable medical device, such as an inflatable pressure-attenuating device, to an anatomical structure within a patient. The delivery device can comprise (a) a housing, (b) an inflation tube extending from the housing, the inflation tube comprising a distal end adapted for coupling to an inflatable medical device, and (c) a decoupling member for decoupling the distal end of the inflation tube from the inflatable medical device, (d) wherein the housing is marked with markings communicating a sequence of steps for operation of the delivery device.

According to another aspect, there can be provided a delivery device for use in delivering an inflatable medical device, such as a pressure-attenuating device, to an anatomical structure within a patient. The delivery device can comprise (a) a housing, the housing comprising a first opening, a second opening and a third opening; (b) a trigger, the trigger being pivotally mounted on the housing; (c) an inflation tube extending through the second opening of the housing, the inflation tube having a proximal end, a distal end, and at least one longitudinal channel, the distal end of the inflation tube extending distally from the second opening of the housing and being insertable into a medical device for use in delivering at least one inflation medium to the medical device; (d) a push-off member coupled to the trigger and slidably mounted relative to the inflation tube, the push-off member comprising a distal end slidable distally past the distal end of the inflation tube to decouple the inflation tube from the medical device; (e) a first syringe, the first syringe being mounted within the first opening of the housing and comprising a volume of a first inflation medium, the first inflation medium being, for example, air, the first syringe being adapted for connection to the at least one longitudinal channel of the inflation tube; and (f) a second syringe, the second syringe being mounted within the third opening of the housing and comprising a volume of a second inflation medium, the second inflation medium being, for example, at least one high vapor pressure medium, such as at least one liquid perfluorocarbon, the second syringe being adapted for connection to the at least one longitudinal channel of the inflation tube. The housing may also be marked with markings communicating a sequence of steps for operation of the delivery device.

According to another aspect, there can be provided a delivery device for use in delivering a medical device to an anatomical structure within a patient. The delivery device can comprise (a) a catheter, the catheter having a channel and a window, the channel being dimensioned to receive the medical device, the window communicating with the channel and being dimensioned for passage of the medical device therethrough; and (b) a cover slidably mounted over the catheter for selectively covering and uncovering the window.

According to another aspect, a kit can be provided. The kit can comprise (a) a sealed compartment; (b) a support disposed within the sealed compartment; (c) a delivery device disposed within the sealed compartment and mounted on the support, the delivery device comprising (i) a housing, (ii) an inflation tube extending from a distal end of the housing, the inflation tube comprising a distal end, (iii) a push-off member slidably mounted relative to the inflation tube, the push-off member comprising a distal end slidable distally past the distal end of the inflation tube, and (iv) a catheter extending from the distal end of the housing, the catheter mounted around the push-off member and extending distally beyond the distal end of the inflation tube, the catheter comprising a window in the proximity of the distal end of the inflation tube; (d) an inflatable medical device, the inflatable medical device being disposed within the catheter in a deflated and folded state and being mounted on the distal end of the inflation tube to receive fluid therefrom; and (e) a syringe disposed within the sealed compartment and mounted on the support separate from the delivery device, the syringe containing a volume of an inflation medium, such as air, to be injected into the inflatable medical device; (f) wherein all of the sealed compartment, the support, the delivery device, the inflatable medical device, and the syringe are sterilizable by the same sterilization technique, which may be, for example, gamma radiation sterilization, ethylene oxide sterilization, or electron beam sterilization.

According to another aspect, there can be provided the combination of a delivery device and an inflatable medical device. The delivery device can comprise a housing, an inflation tube, a push-off member, and a catheter. The inflation tube can extend from a distal end of the housing. The inflation tube can comprise a distal end. The push-off member can be slidably mounted relative to the inflation tube, and the push-off member can comprise a distal end slidable distally past the distal end of the inflation tube. The catheter can extend from the distal end of the housing, and the catheter can be positioned around the push-off member and can extend distally beyond the distal end of the inflation tube. The catheter can comprise a window aligned with the distal end of the inflation tube. The inflatable medical device can be disposed within the catheter in a deflated and folded state and can be mounted on the distal end of the inflation tube to receive fluid therefrom.

According to another aspect, there can be provided an inflatable medical device. The inflatable medical device can comprise (a) an inflatable cell, the inflatable cell comprising an opening, wherein the inflatable cell is seamless; and (b) a fluid valve mounted in the opening of the inflatable cell.

According to another aspect, there can be provided an inflatable medical device. The inflatable medical device can comprise (a) an inflatable cell, the inflatable cell comprising an opening; and (b) a fluid valve mounted in the opening of the inflatable cell, wherein the fluid valve comprises a proximal portion, an intermediate portion, and a distal portion, the intermediate portion being generally cylindrical in shape, and the distal portion being generally flat.

According to another aspect, there can be provided a medical device. The medical device can comprise an inflatable cell, wherein over 95% of the external surface of the inflatable cell is continuously arcuate and less than 5% of the surface area of the inflatable cell is not continuously arcuate.

According to another aspect, there can be provided a medical device. The medical device can comprise an inflatable cell, wherein the ratio of continuously arcuate surface area to non-arcuate surface area for the inflatable cell is between about 100:1 to 1500:1.

According to another aspect, there can be provided a medical device. The medical device can comprise an inflatable cell, the inflatable cell comprising a bulb portion and a tail portion, wherein the ratio of the diameter of the bulb portion to the tail portion is between about 6:1 and 20:1.

According to another aspect, there can be provided a removal device. The removal device can include at least one manually-actuable member; and at least one movable arm or jaw, the at least one movable jaw being operable by actuation of the at least one manually-actuable member.

According to another aspect, there can be provided a removal device. The removal device can comprise (a) at least one manually-actuable member; (b) at least two jaws, at least one of the at least two jaws being moveable by actuation of the at least one manually-actuable member; (c) a cystoscope, the cystoscope being positioned to enable observation of the at least two jaws, wherein the cystoscope is a wide angle cystoscope.

According to another aspect, there can be provided a removal device. The removal device can comprise (a) at least one manually-actuable member; (b) at least two jaws, at least one of the at least two jaws being movable by actuating the at least one manually-actuable member, wherein at least one of the at least two jaws comprises a gripping member, such as teeth, to securely hold an object to be removed and wherein at least one of the at least two jaws comprises a puncturing member, such as a blade, scissor, pin, hook, or the like, to puncture the object to be removed.

According to another aspect, there can be provided a system for use in treating a patient. The system can comprise (a) an access device for use in providing access to an anatomical structure within the patient, the access device comprising an elongated sheath and an obturator removably mounted within the elongated sheath; (b) a pressure-attenuating device; and (c) a delivery device, the delivery device comprising a catheter removably insertable through the elongated sheath of the access device and into the anatomical structure, the pressure-attenuating device being disposed within the catheter of the delivery device.

According to another aspect, there can be provided a method of treating a patient. The method can comprise the steps of (a) providing an access device, the access device comprising an elongated sheath and an obturator removably mounted within the elongated sheath; (b) inserting a distal end of the access device into an anatomical structure within a patient, a proximal end of the access device remaining external to the patient; (c) withdrawing the obturator from the patient, thereby creating a passageway to the anatomical structure; and (d) delivering a pressure-attenuating device to the anatomical structure through the passageway.

BRIEF DESCRIPTION OF THE DRAWINGS

These and other features, aspects and advantages are described below with reference to the drawings, which are intended to illustrate but not to limit the invention. In the drawings, like reference characters denote corresponding features consistently throughout similar embodiments.

FIGS. 3(a) and 3(b) are side and section views, respectively, of the hub shown in FIG. 2(b);

FIG. 8(a) is a side view, partly in section, of the combination of the handle shown in FIGS. 5(a) through 5(c) and the valve assembly shown in FIGS. 7(a) and 7(b);

FIGS. 10(a) and 10(b) are side and section views, respectively, of the obturator shown in FIG. 2(b);

FIGS. 11(a) and 11(b) are side and section views, respectively, of the obturator handle shown in FIG. 2(b);

FIGS. 13(a) and 13(b) are side and section views, respectively, of the sleeve shown in FIG. 2(b);

FIGS. 15(a) and 15(b) are side and section views, respectively, of the slide ring assembly outer member shown in FIG. 2(b);

FIG. 16 is a distal view of the slide ring assembly O-ring shown in FIG. 2(b);

FIGS. 17(a) and 17(b) are fragmentary section views of the access device of FIG. 1, with the slide ring assembly being shown in a distal position and in a proximal position, respectively;

FIG. 18 is a side view of the tether shown in FIG. 2(b);

FIGS. 21(a) through 21(d) are side views, some partly in section and/or broken away in part, illustrating certain steps of the method shown in FIG. 20;

FIGS. 33(a) through 33(c) are simplified schematic representations of a third alternate embodiment to the cam-actuated valve mechanism shown in FIG. 30, the cam-actuated valve mechanism being shown in closed, fill, and drain positions, respectively;

FIG. 34 is a simplified schematic representation of a fourth alternate embodiment to the cam-actuated valve mechanism shown in FIG. 30, the cam-actuated valve mechanism being constructed to be radially inwardly-compressing;

FIG. 35 is a simplified schematic representation of a fifth alternate embodiment to the cam-actuated valve mechanism shown in FIG. 30, the cam-actuated valve mechanism being constructed to be radially outwardly-compressing;

FIGS. 41(a) through 41(d) are perspective, side, side partly in section, and partially exploded perspective views, respectively, of an eleventh alternate embodiment to the access device shown in FIG. 1, the access device being shown in FIGS. 41(a) through 41(c) with the cam-actuated switch in the closed position and with the slide ring assembly in its distal position;

FIGS. 42(a) and 42(b) are perspective views of the housing shown in FIGS. 41(a) through 41(d);

FIGS. 46(a) through 46(e) are side, front, rear, perspective and bottom views, respectively, of the cam shown in FIG. 41(d);

FIGS. 49(a) through 49(c) are fragmentary rear views of the access device shown in FIGS. 41(a) through 41(d), certain components of the access device not being shown for clarity, with the cam being shown in its closed position, in one of its two open positions, and in the other of its two open positions, respectively;

FIG. 51 is an enlarged side view, partly in section, of the combination of the hub, the valve assembly, the seal, and the cap shown in FIGS. 41(c) and 41(d);

FIG. 59 is a perspective view of the housing shown in FIGS. 58(a) through 58(c);

FIGS. 60(a) and 60(b) are side and perspective views, respectively, of the left housing half shown in FIG. 59;

FIGS. 62(a) and 62(b) are side and section views, respectively, of the hub shown in FIG. 58(d);

FIGS. 63(a) through 63(c) are perspective, bottom, and enlarged fragmentary perspective views, respectively, of the cam shown in FIG. 58(d);

FIGS. 68(a) through 68(c) are front, side, and rear views, respectively, of the cap shown in FIGS. 58(a) through 58(d);

FIGS. 71(a) and 71(b) are perspective and side views, respectively, of a first alternate obturator handle to the obturator handle shown in FIGS. 58(a) and 58(b);

FIG. 76 is a perspective view of a first alternate cam to the cam shown in FIGS. 63(a) through 63(c);

FIGS. 77(a) and 77(b) are perspective and partly exploded perspective views, respectively, of a second alternate cam to the cam shown in FIGS. 63(a) through 63(c);

FIGS. 78(a) and 78(b) are proximal perspective and distal perspective views, respectively, of the delivery device shown in FIG. 1, with the two syringes not being shown;

FIGS. 81(a) and 81(b) are left and right side views, respectively, of the left housing half of the delivery device shown in FIGS. 78(a) and 78(b);

FIGS. 82(a) and 82(b) are left and right side views, respectively, of the right housing half of the delivery device shown in FIGS. 78(a) and 78(b);

FIGS. 86(a) through 86(e) are left side, right side, proximal, distal, and section views, respectively, of the carriage shown in FIG. 79;

FIG. 87 is a section view of the push-off tube shown in FIG. 79;

FIGS. 88(a) and 88(b) are side and proximal views, respectively, of the trigger shown in FIG. 79;

FIGS. 89(a) and 89(b) are side and section views, respectively, of the linkage shown in FIG. 79;

FIG. 90 is a side view of the safety shown in FIG. 79;

FIGS. 91(a) and 91(b) are fragmentary side views, partly in section, of the delivery device shown in FIG. 79 with one of the housing halves and the syringes removed and with the safety being shown in a locked state and in an unlocked state, respectively;

FIGS. 92(a) through 92(c) are fragmentary side, fragmentary section, and fragmentary top views, respectively, of the window catheter shown in FIG. 79;

FIGS. 92(d) through 92(l) show embodiments of window catheter distal portion;

FIG. 93 is a distal view of the sealing ring shown in FIG. 79;

FIGS. 94 and 95 are side views, broken away in part, of the syringes shown in FIG. 79;

FIGS. 98(a) through 98(d) show additional embodiments of the retractable cover shown in FIGS. 96(a) and 96(b);

FIG. 100 is a fragmentary section view of the pressure-attenuating device of FIGS. 99(a) through 99(c);

FIG. 101 is a top view of the valve shown in FIGS. 99(a) through 99(c);

FIGS. 112, 113 and 114 are respective fragmentary section views of the scope guide, cystoscope, and support shown in FIG. 109(a);

FIG. 115 is a section view of the bracket shown in FIG. 109(a);

FIG. 116 is a fragmentary section view of the rod shown in FIG. 109(a);

FIG. 117 is a section view of the connector shown in FIG. 109(b);

FIG. 118 is a section view of the linking arm shown in FIG. 109(b);

FIG. 119 is a section view of the linking arm shown in FIG. 109(b);

FIGS. 120 (e) and 120(f) are right and top section views of an alternative design of the jaws shown in FIG. 109(b);

Figure 1:
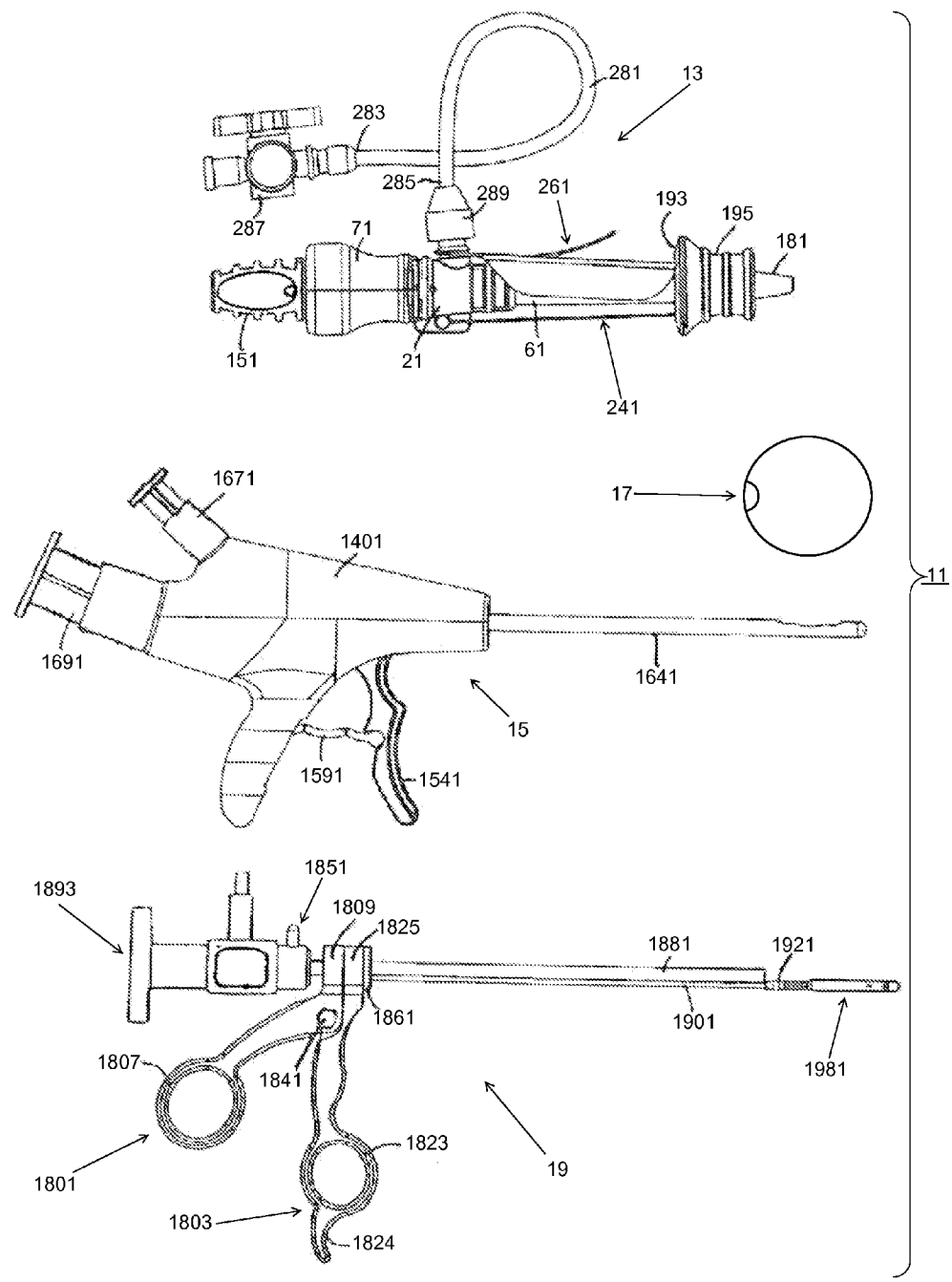
FIG. 1 is a side view of a first embodiment of some of the components of a system for treating a patient.
Figure 4I:
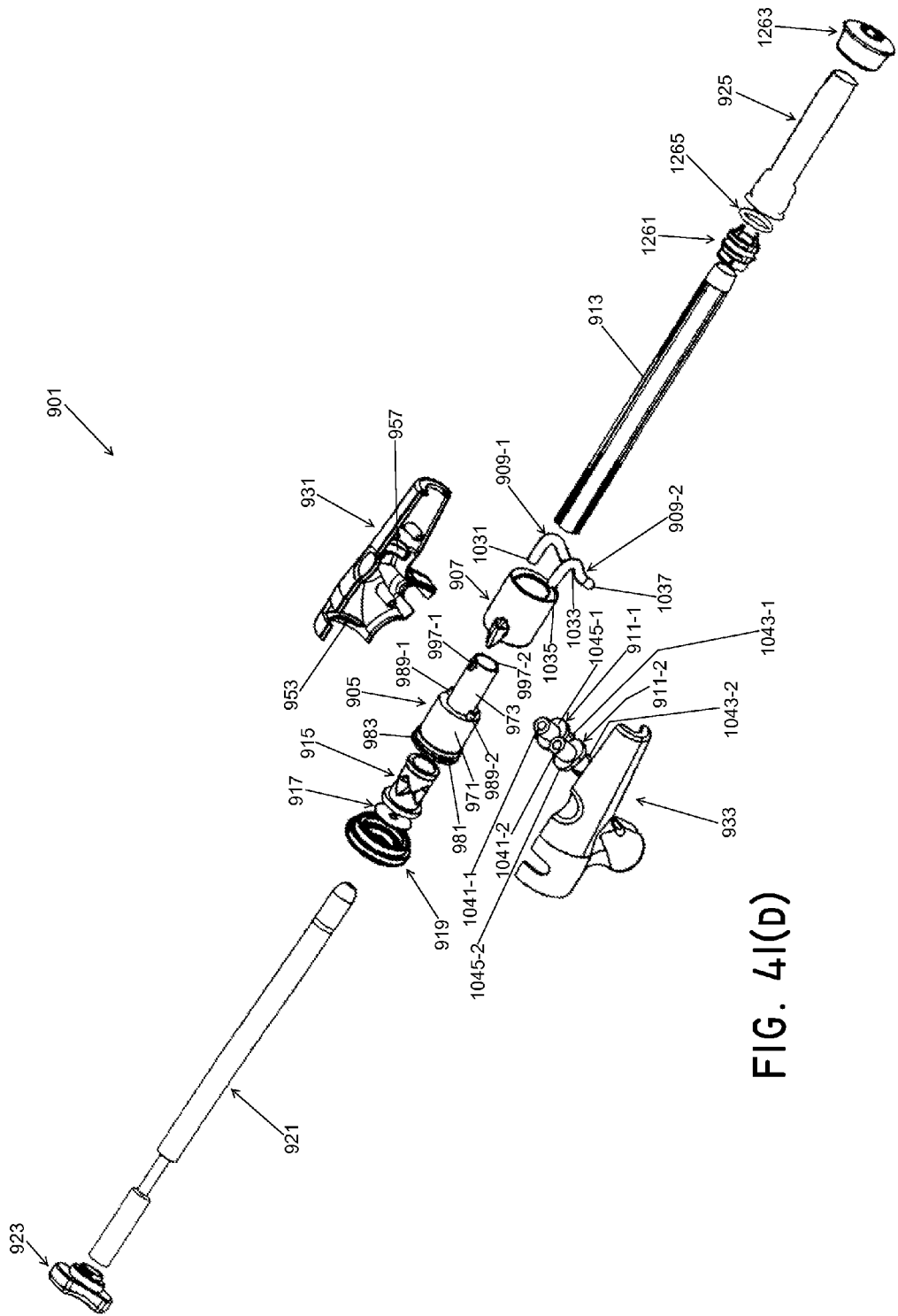
FIGS. 4(a) and 4(b) are side and section views, respectively, of the sheath shown in FIG. 2(b)
Figure 99A:
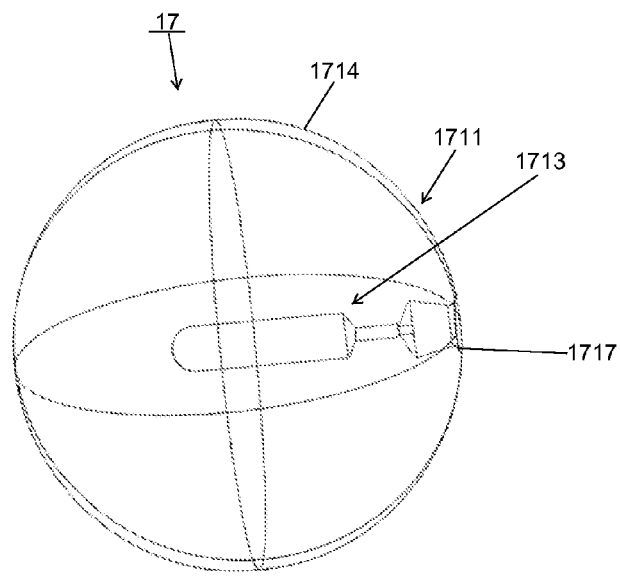
FIGS. 99(a) through 99(c) are perspective views of the pressure-attenuating device shown in FIG. 1 in an inflated state, the fluids within the inflated device not being shown.
Figure 109A:
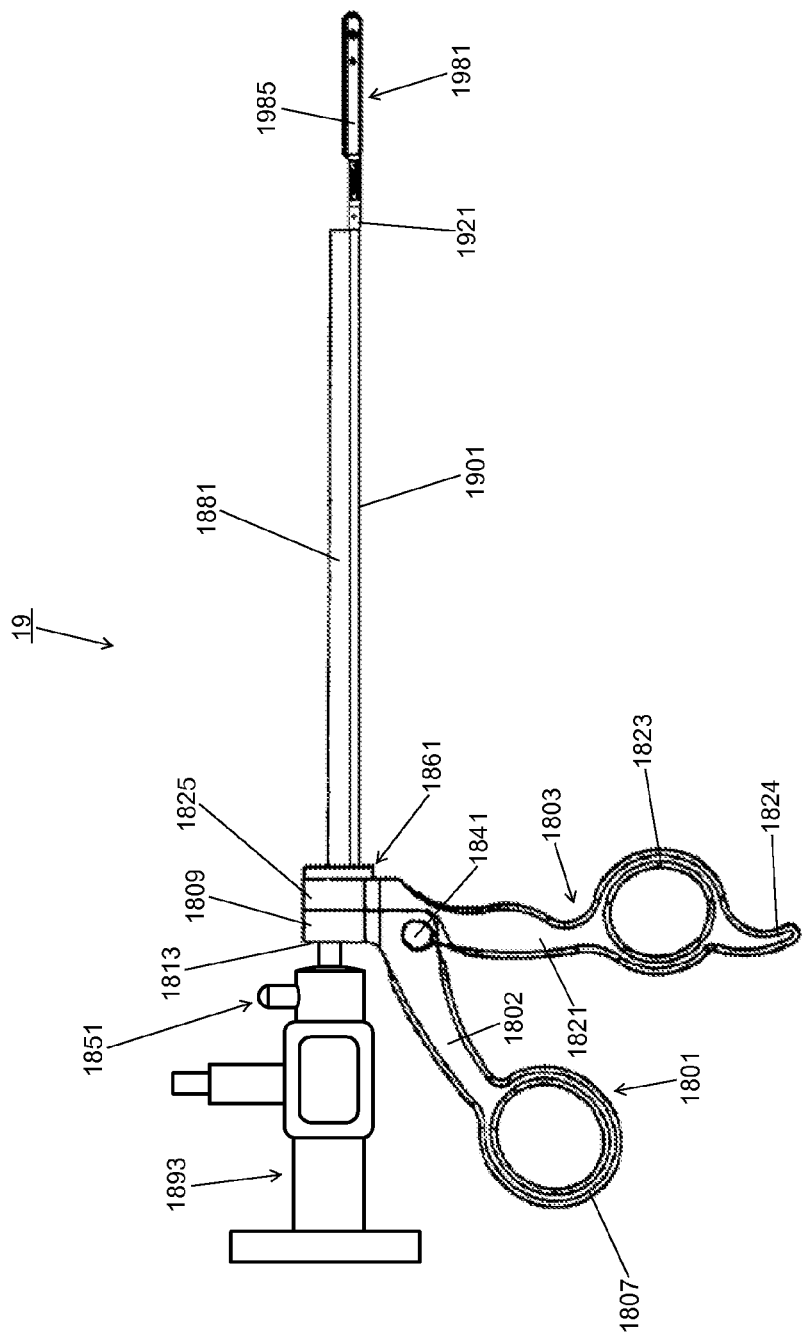
FIGS. 109(a) through 109(d) are side, partially exploded fragmentary perspective, fragmentary top, and fragmentary top, broken away in part, views, respectively, of the removal device shown in FIG. 1.
Figure 109B:
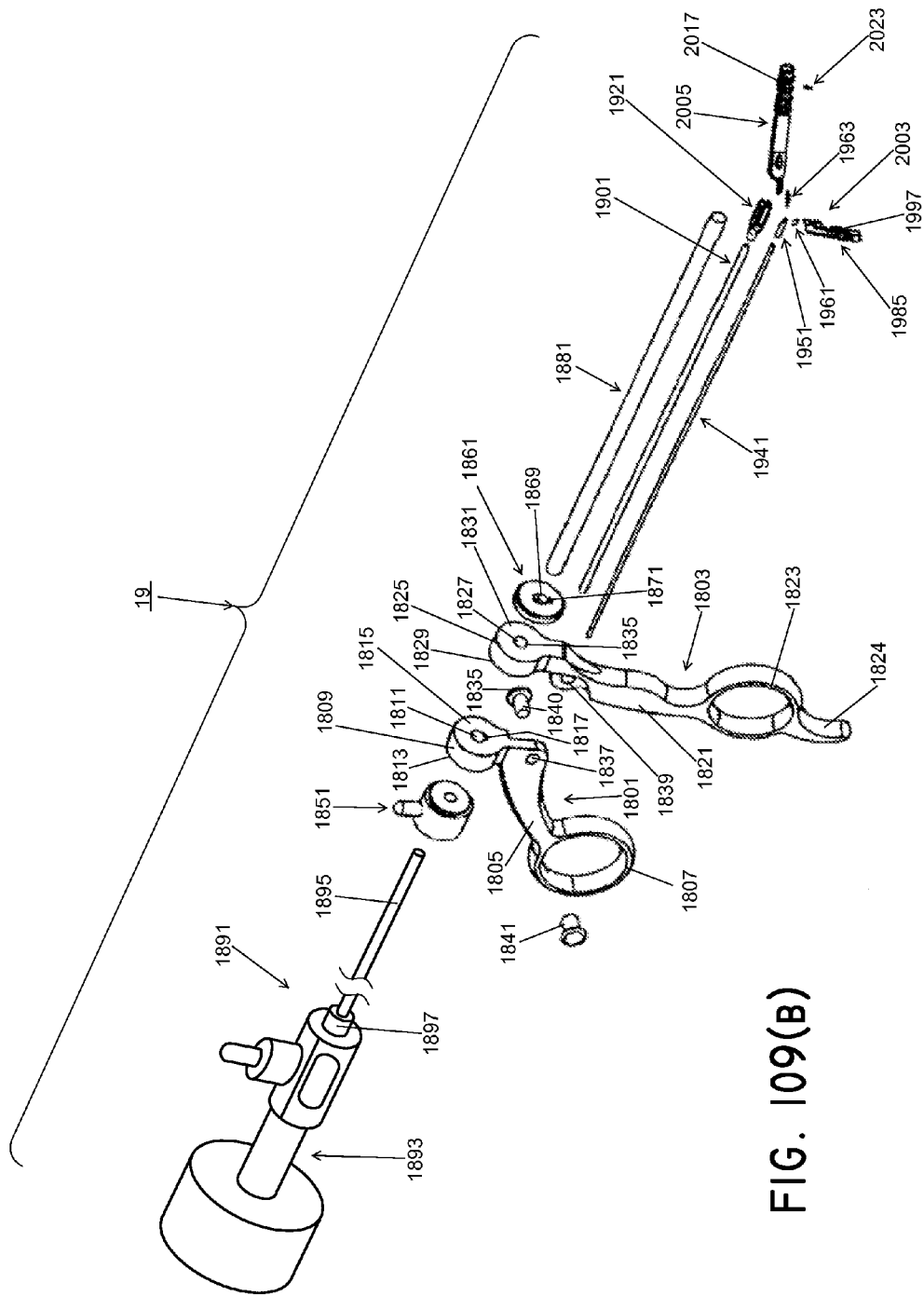
Figure 122:
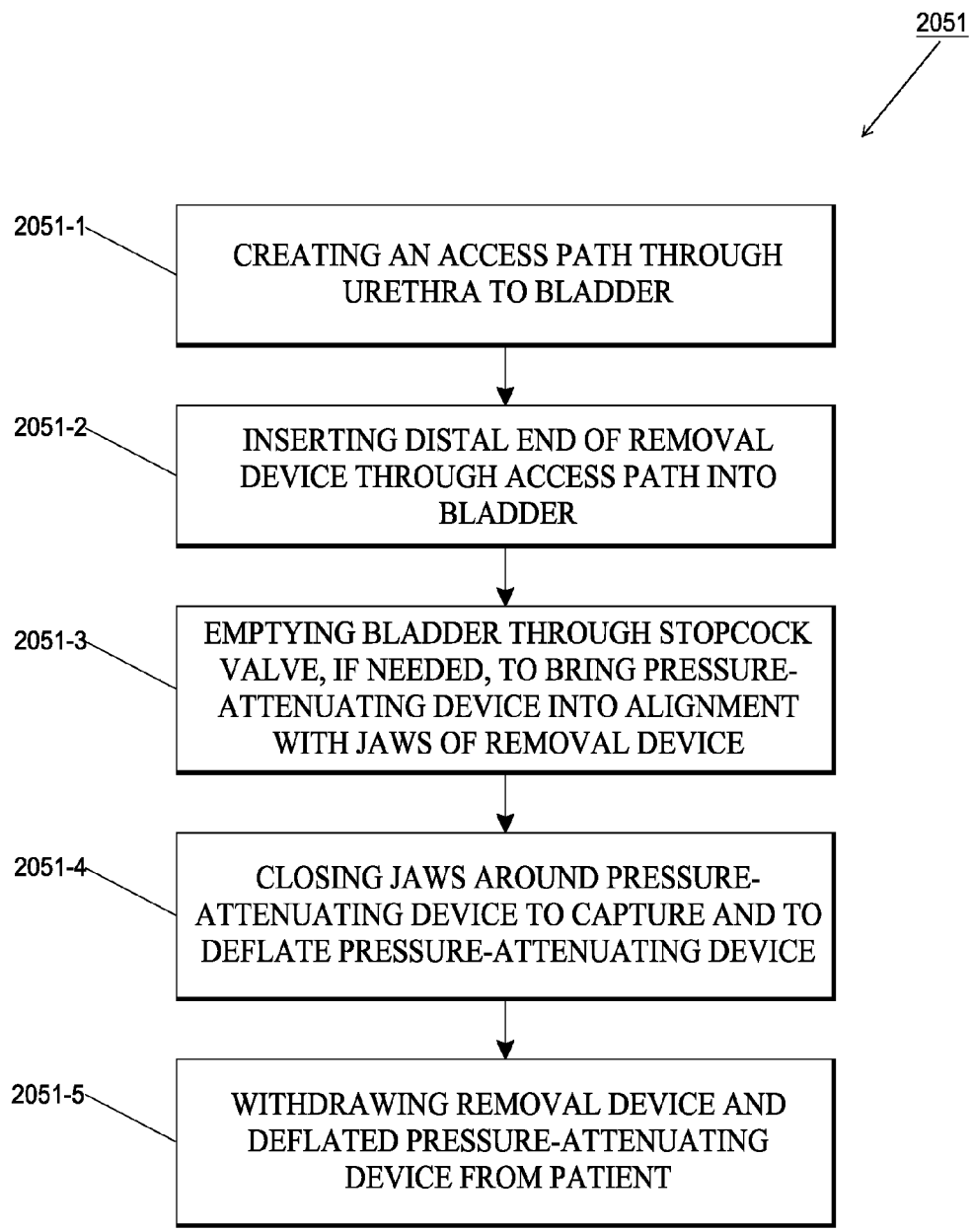
Figure 123A:
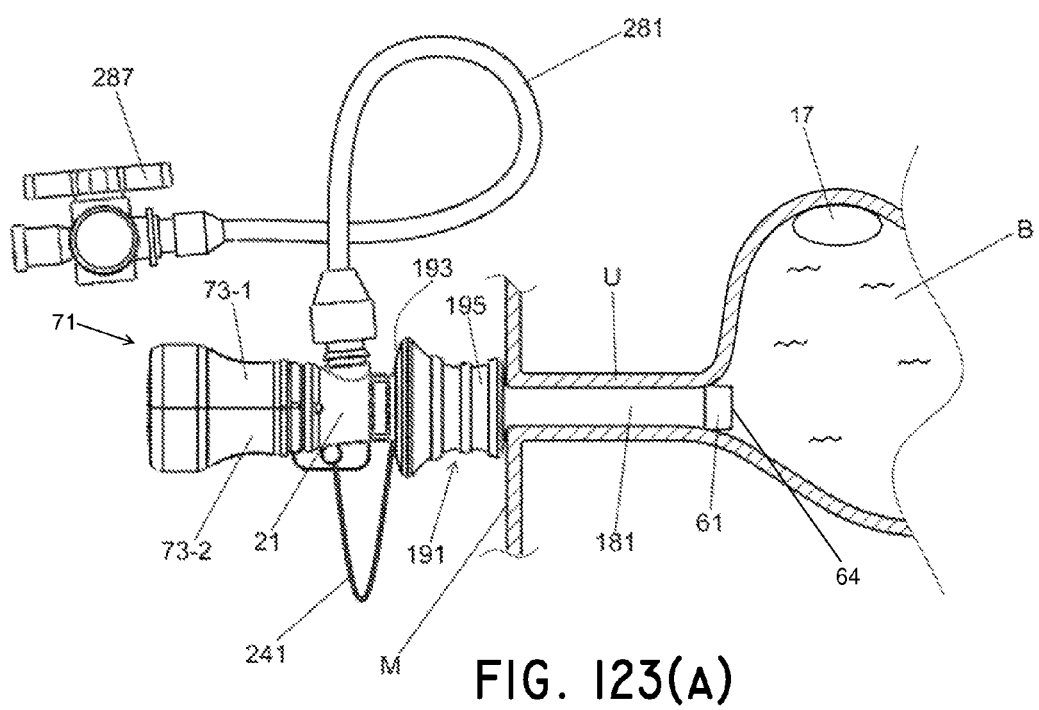
Figure 123B:
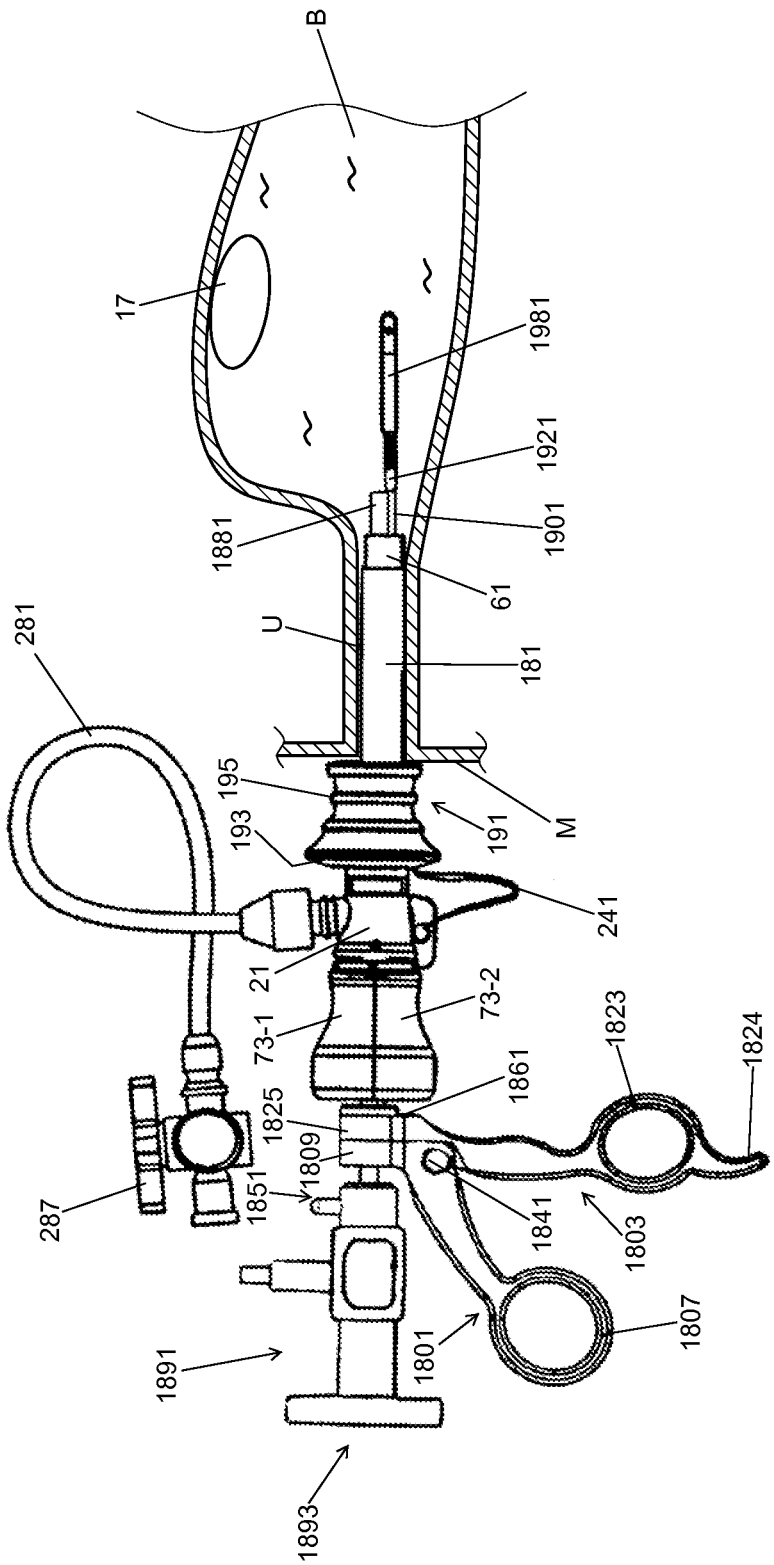
Figure 123C:
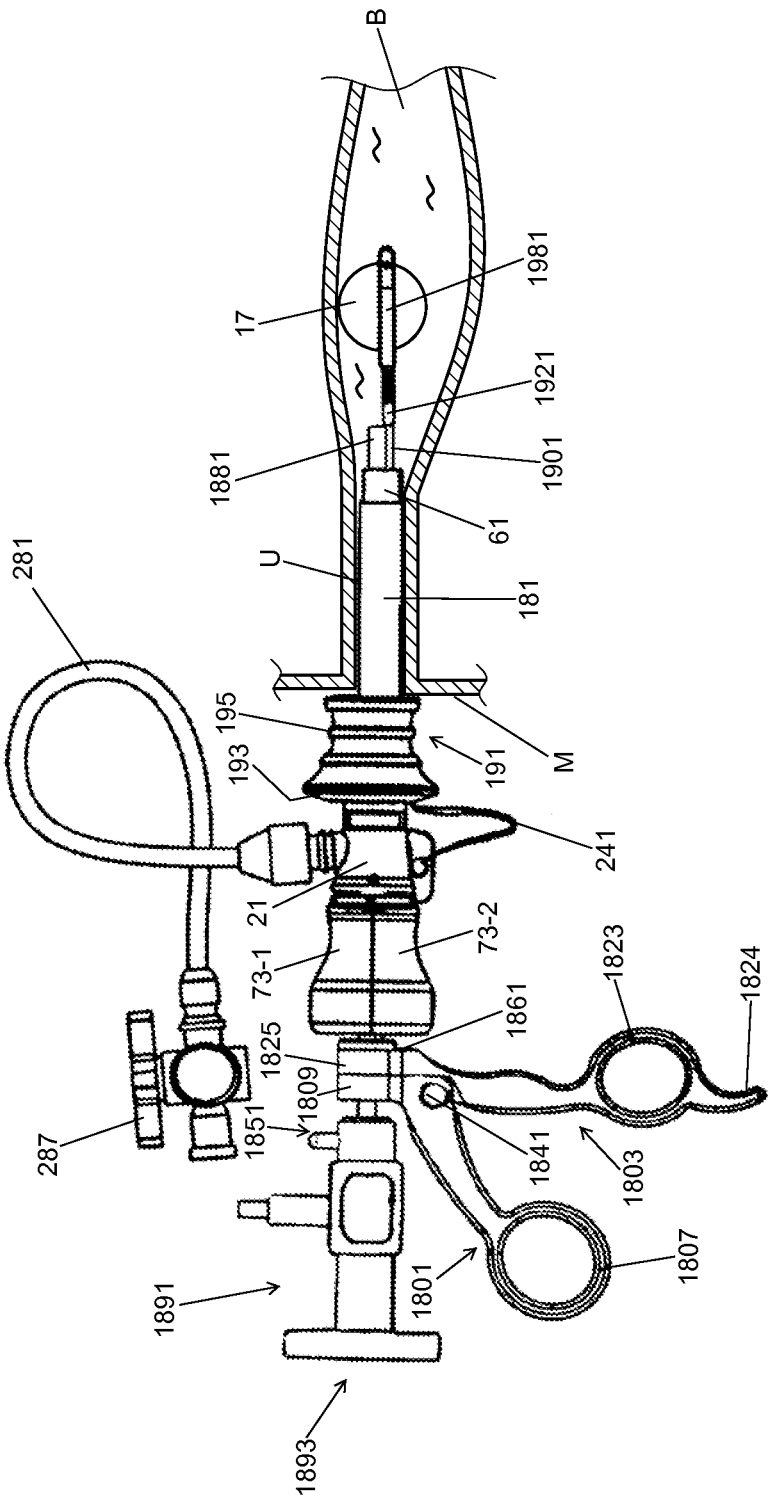
Figure 123D:
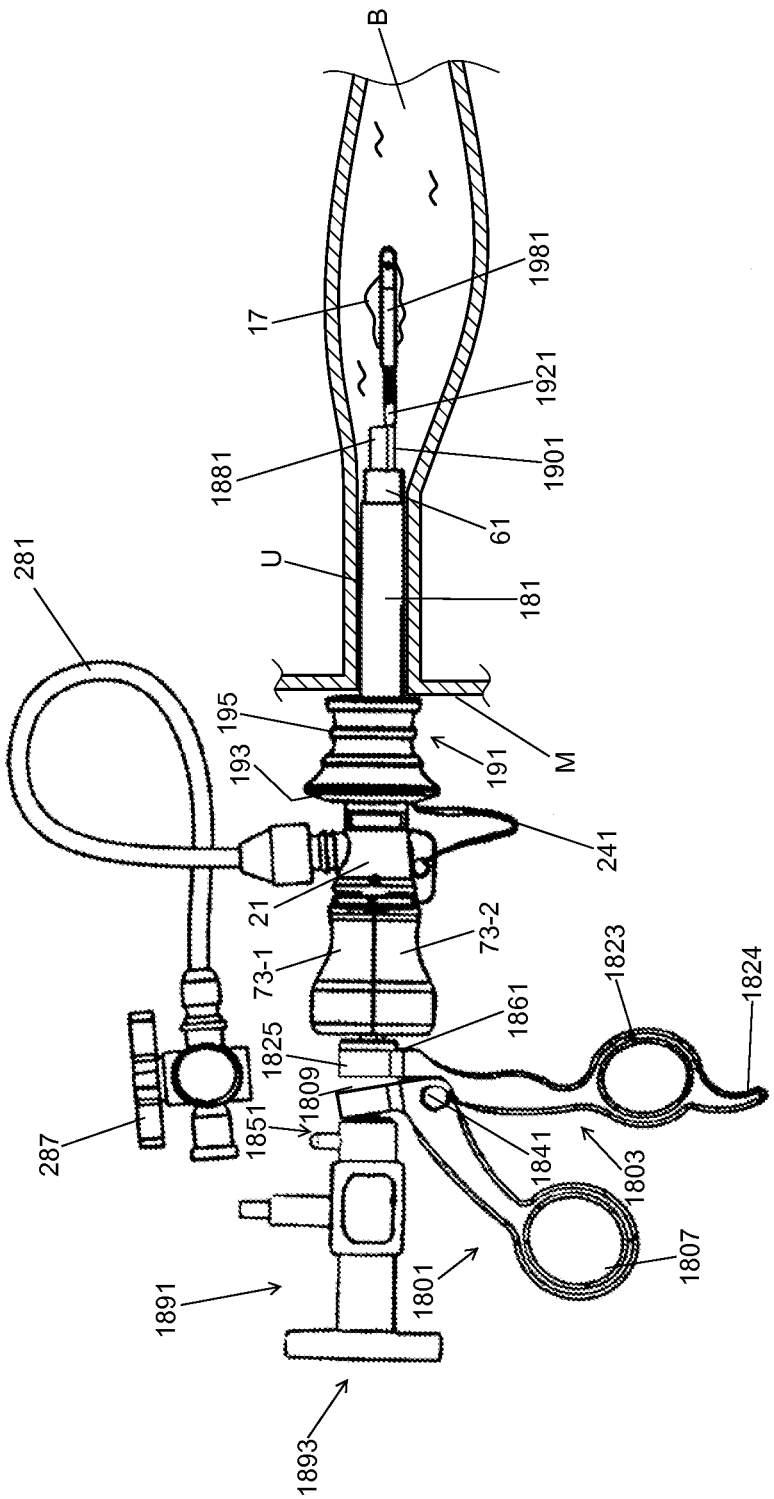
Figure 124:
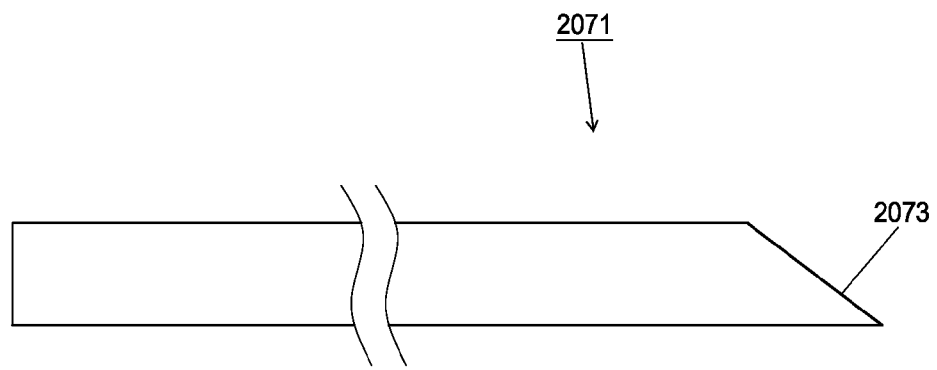
Figure 125:
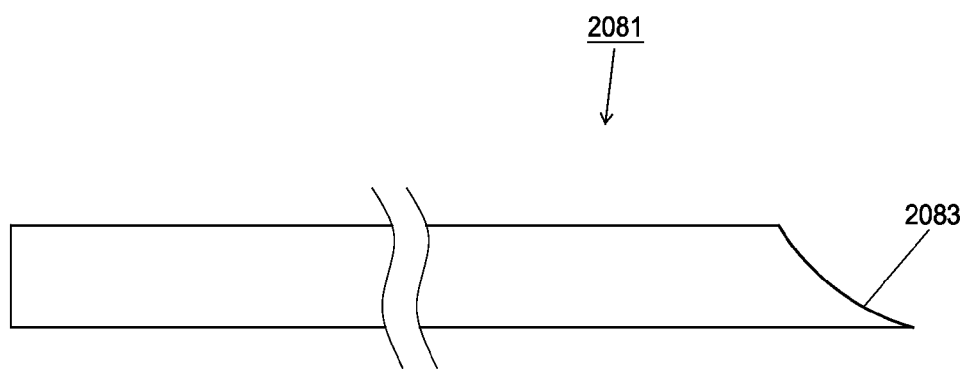
Figure 126A:
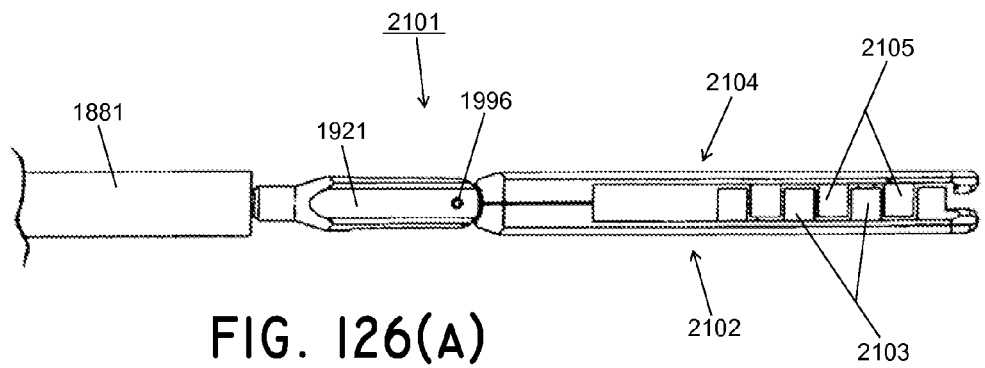
Figure 126B:
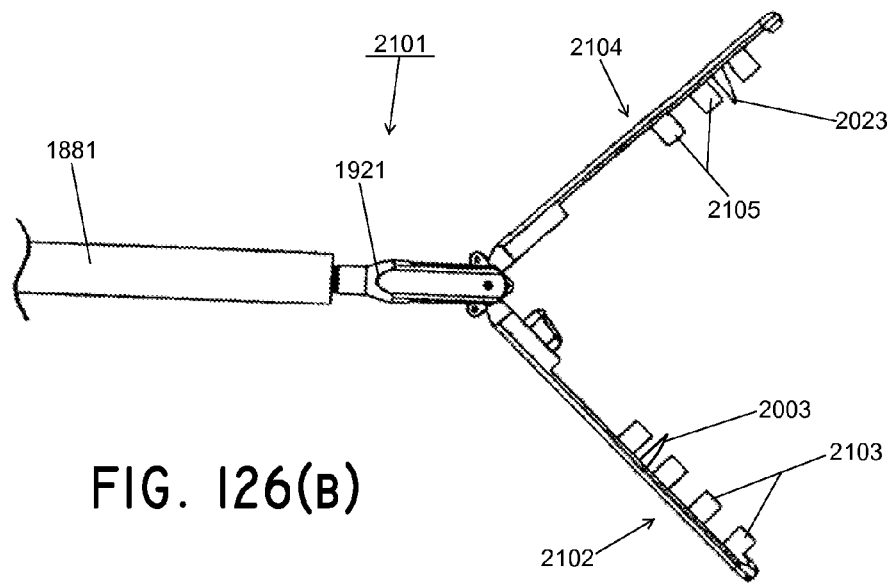
Figure 127:
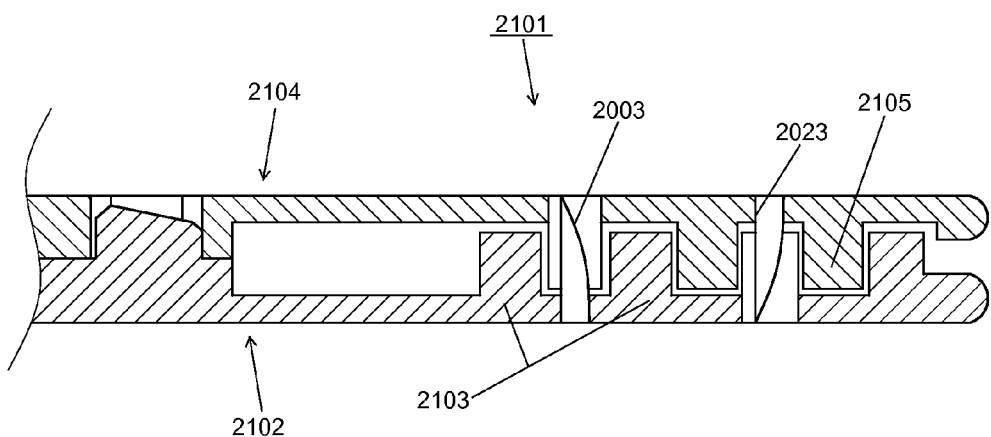
Figure 128A:
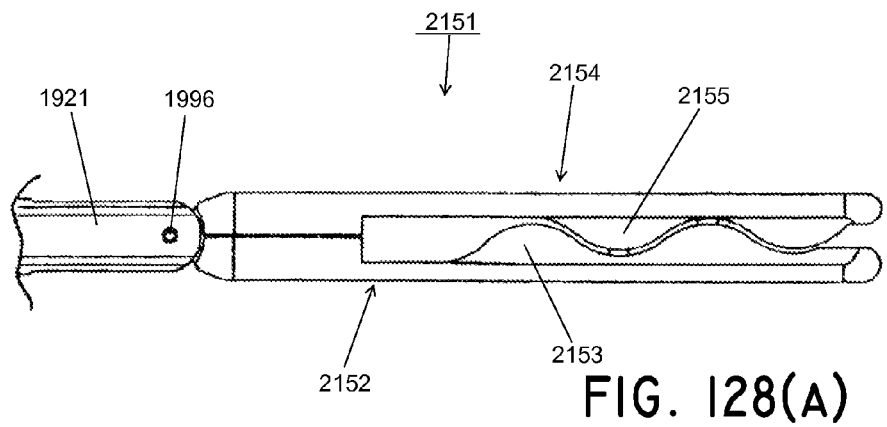
Figure 128B:
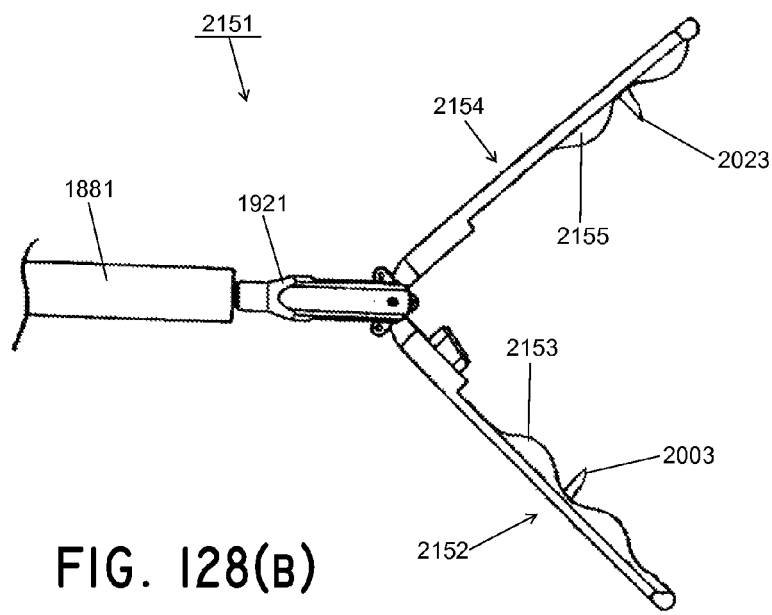
Figure 129:
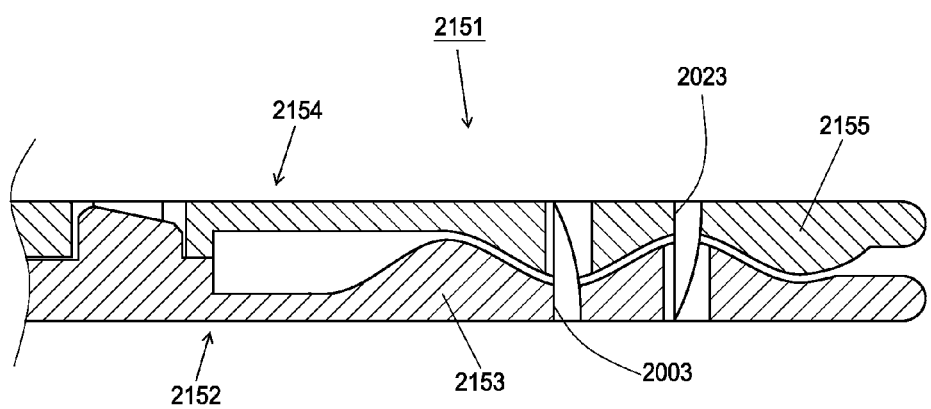
Figure 130:
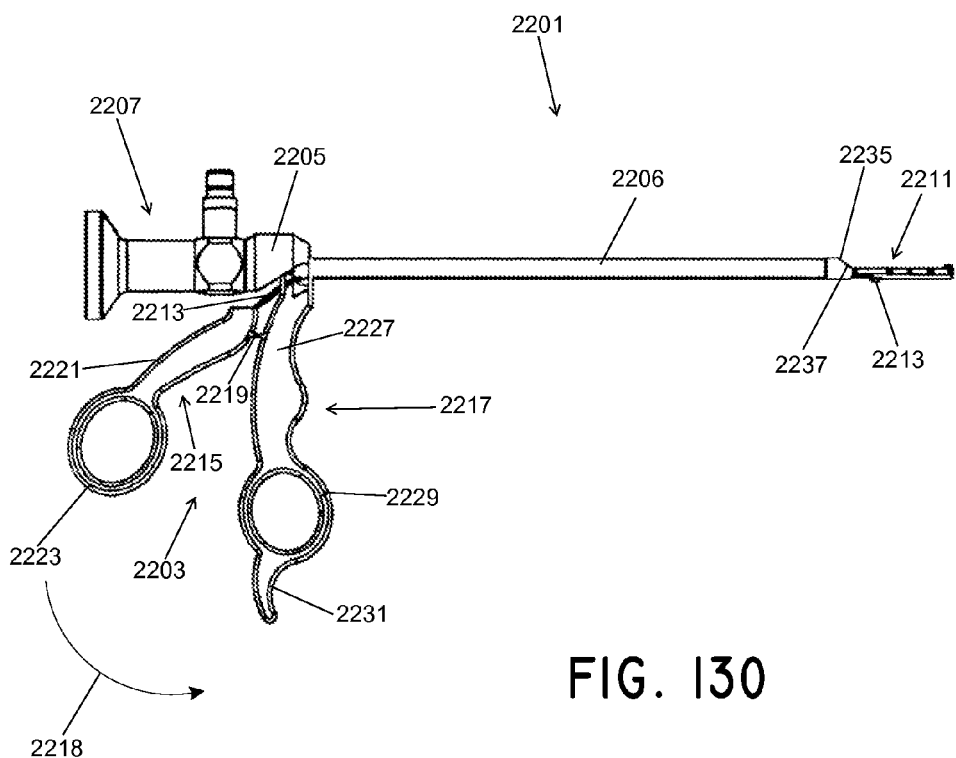
Figure 131:
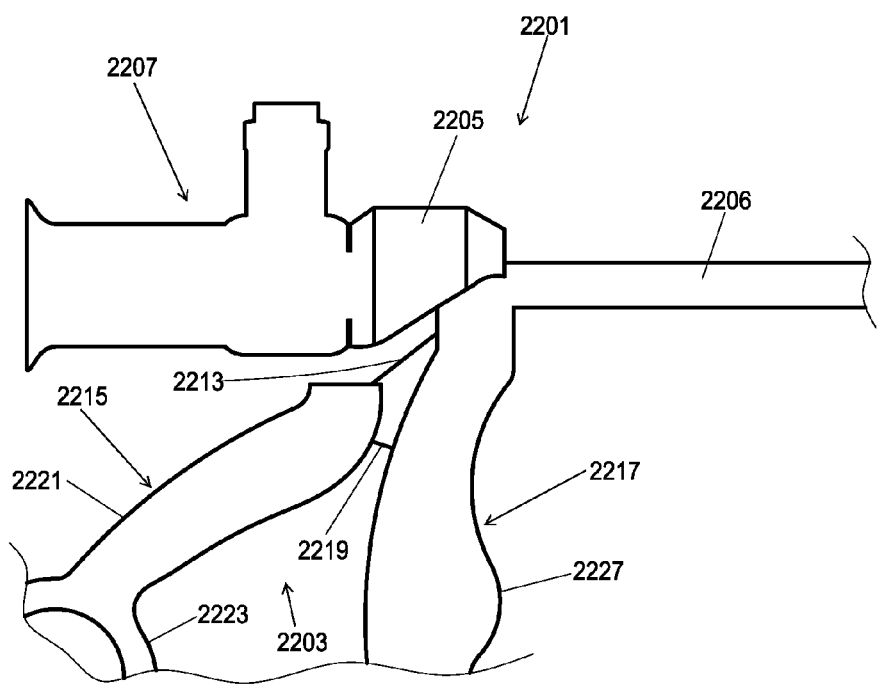
Figure 132A:
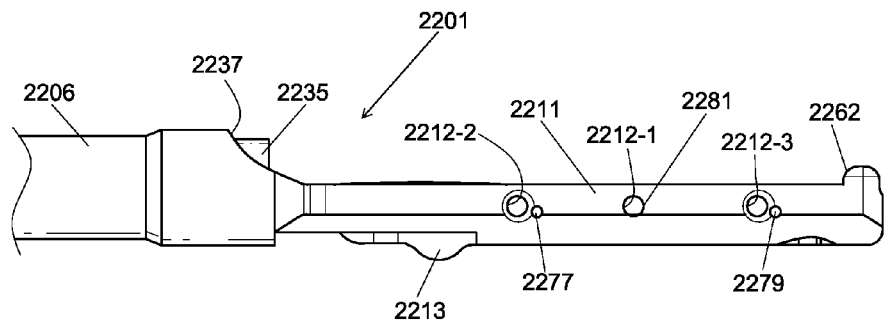
Figure 132B:
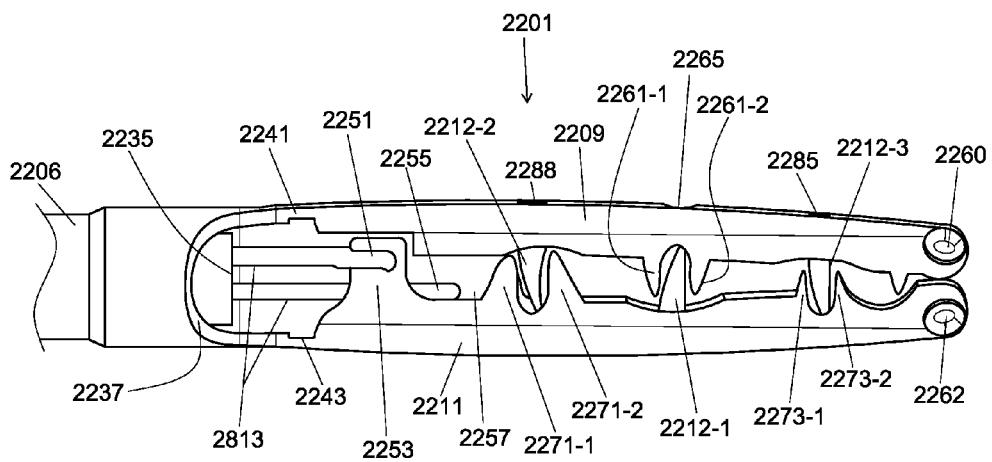
Figure 132C:
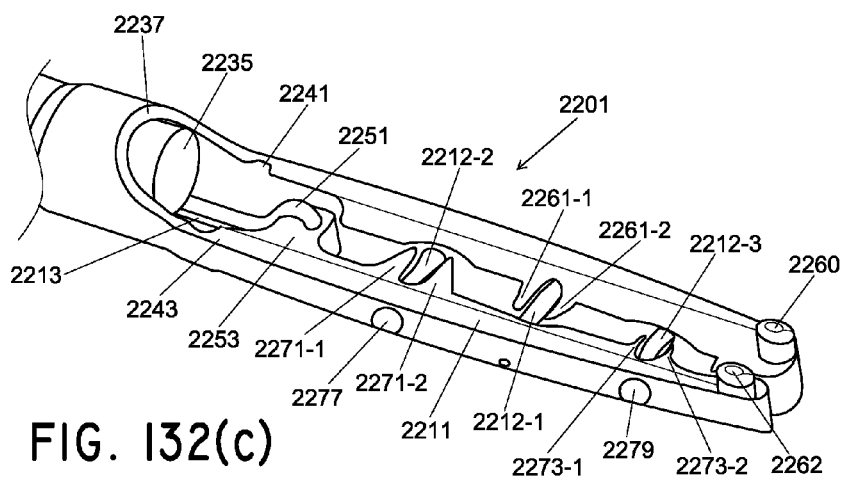
Figure 133A:
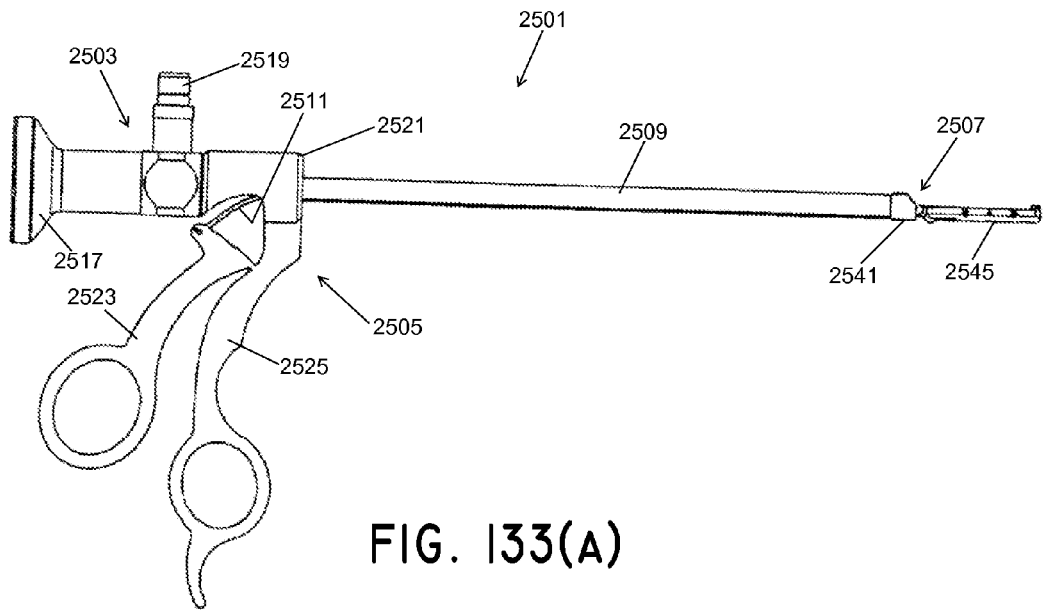
Figure 133B:
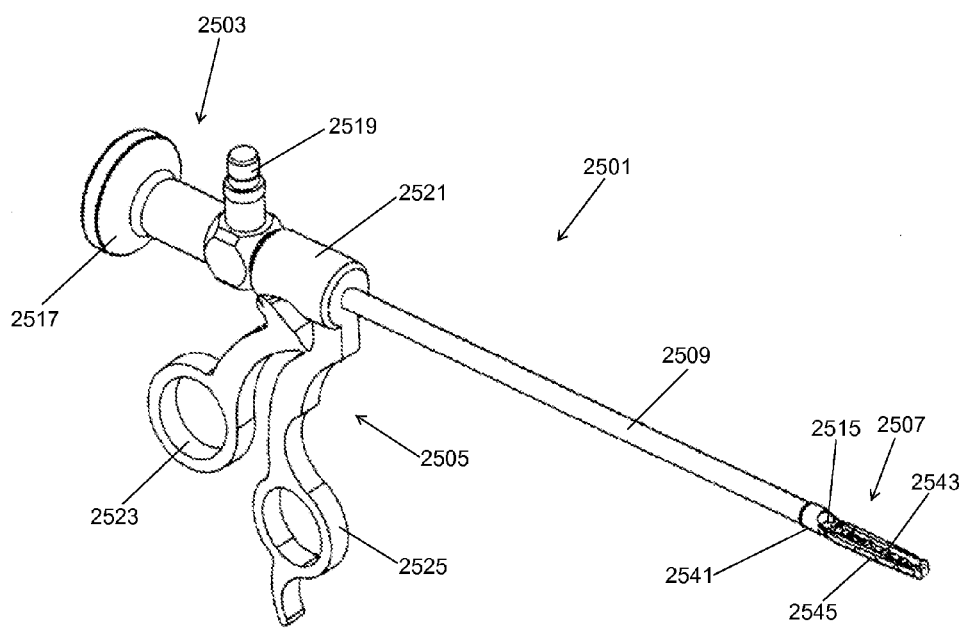
Figure 135:
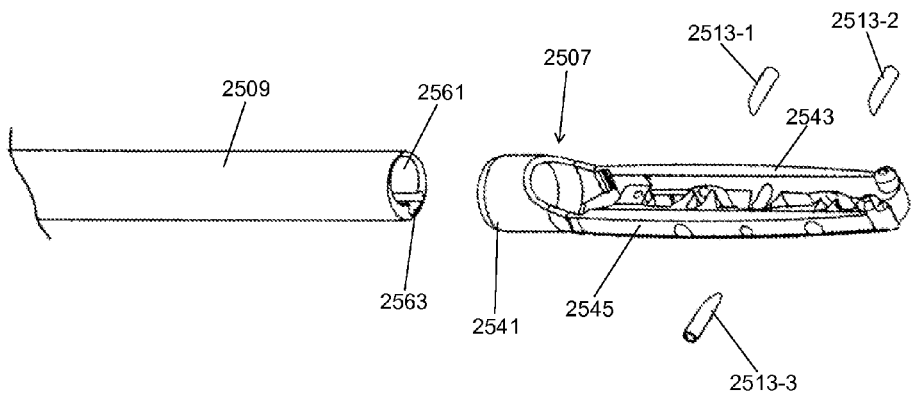
Figure 136A:
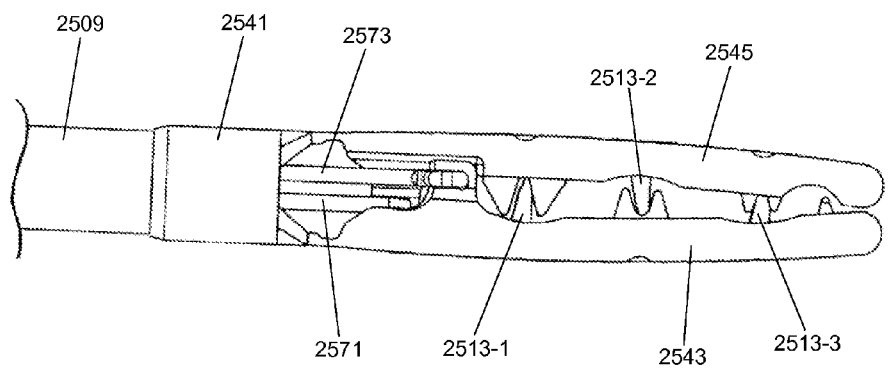
Figure 136B:
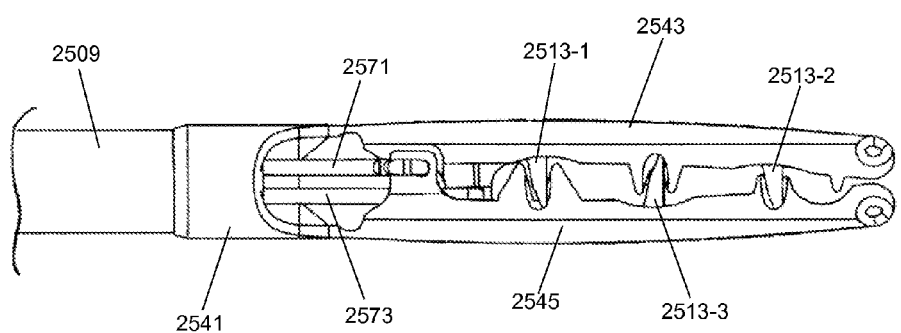
Figure 139A:
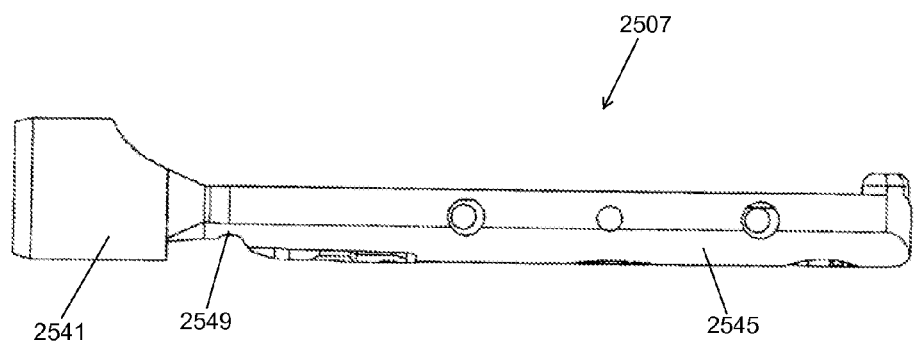
Figure 139B:
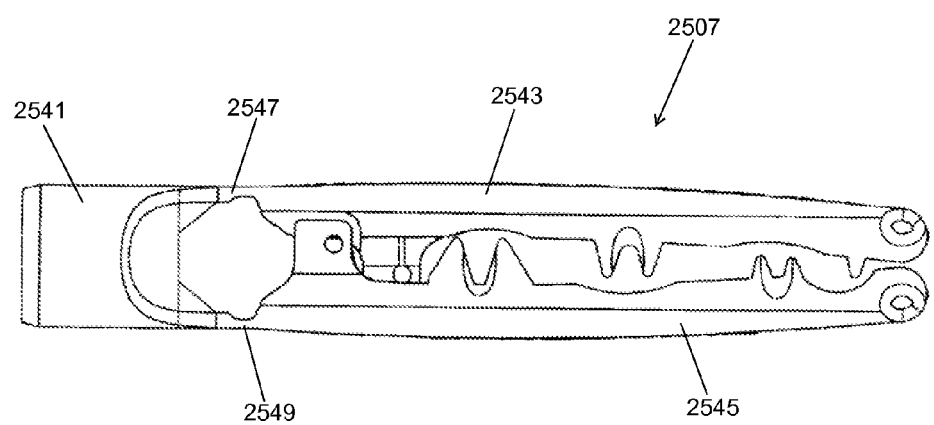
Figure 139C:
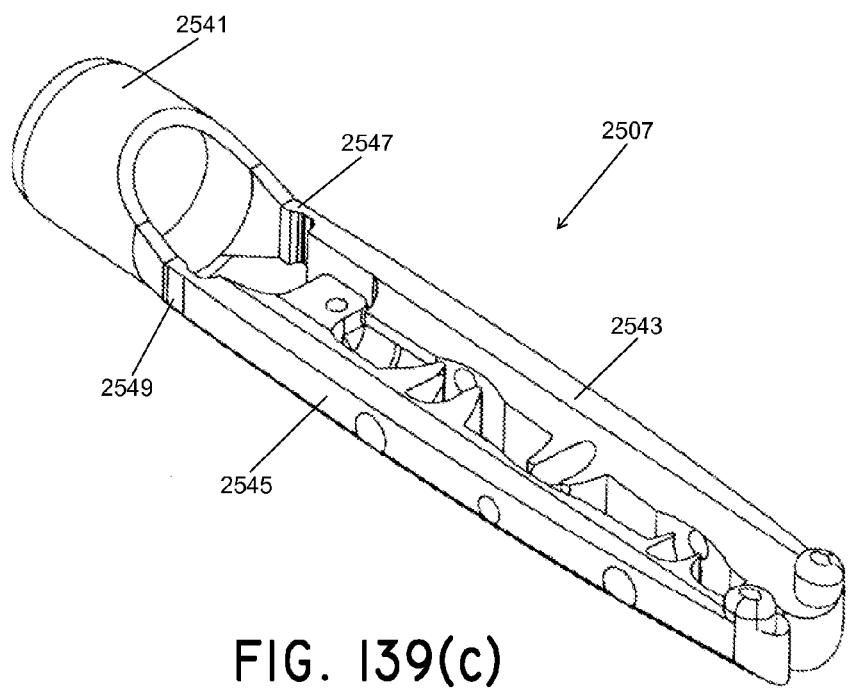
Figure 140A:
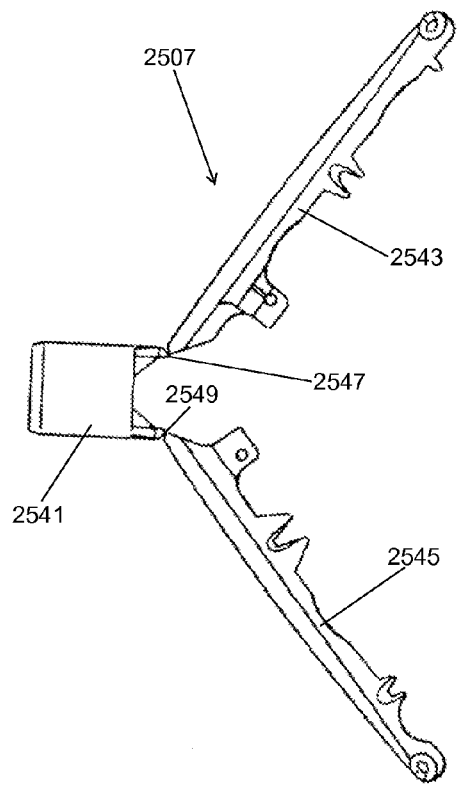
Figure 140B:
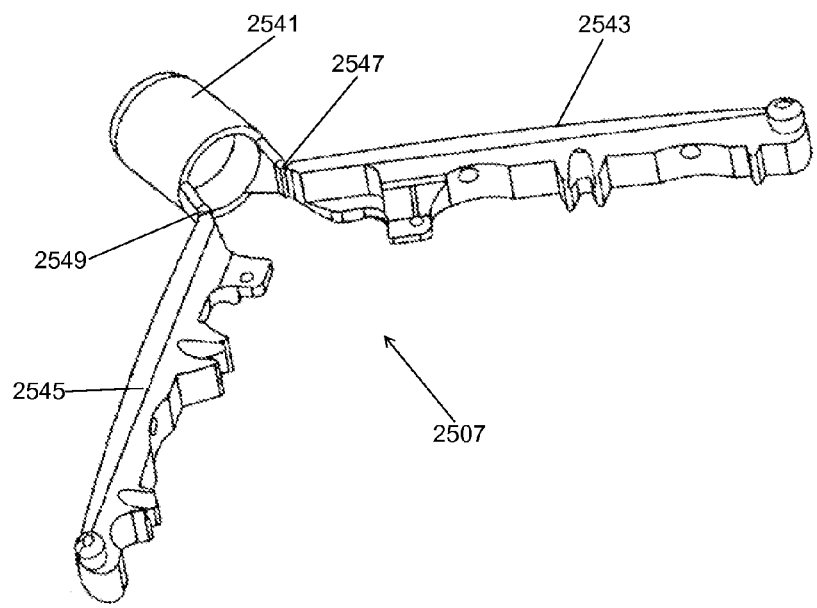
Figure 141A:
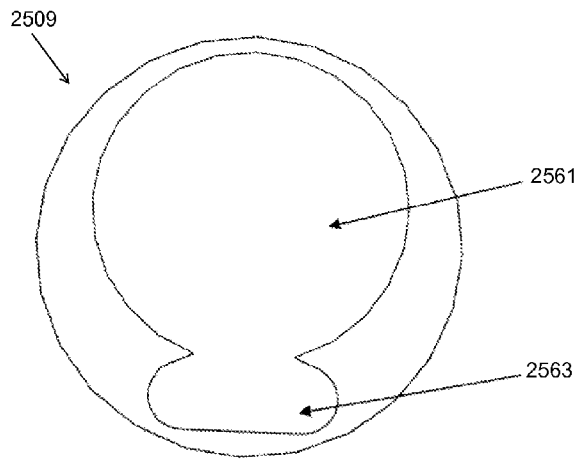
Figure 141B:
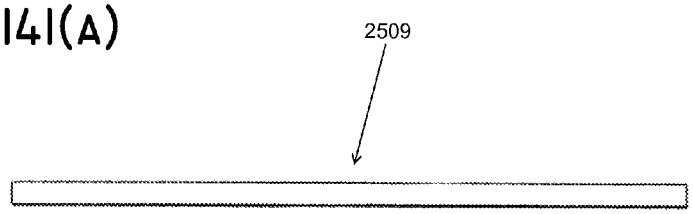
Figure 142A:
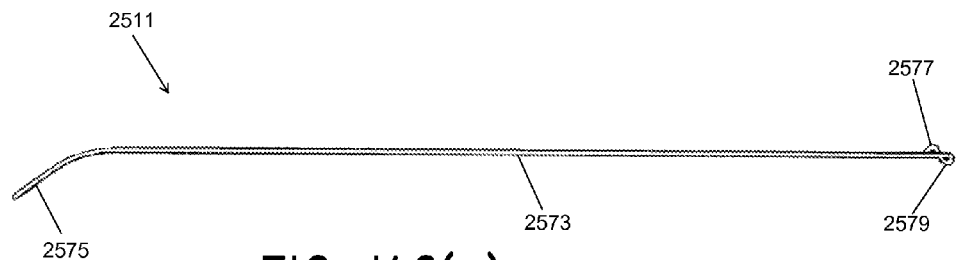
Figure 142B:
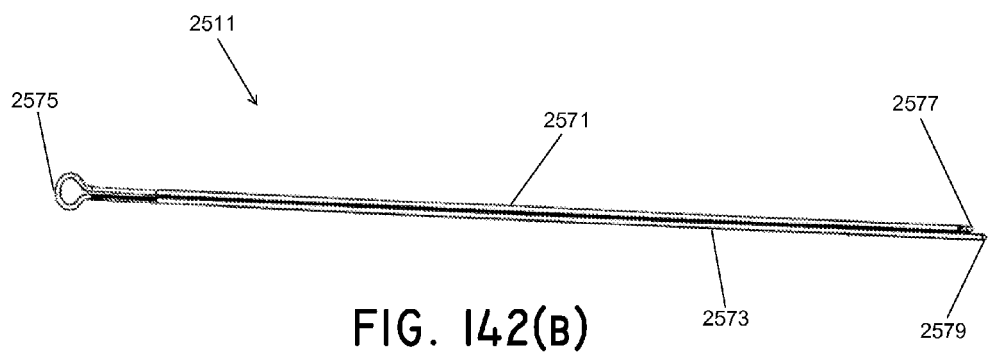
Figure 143:
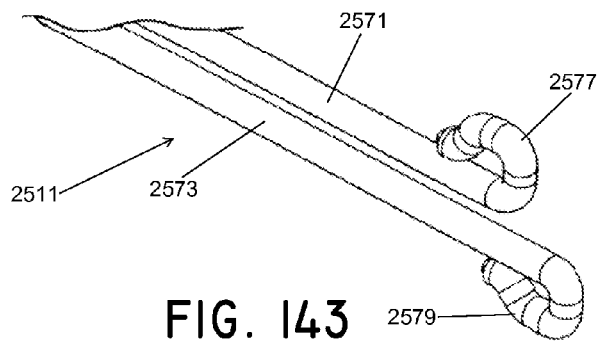
Figure 144:
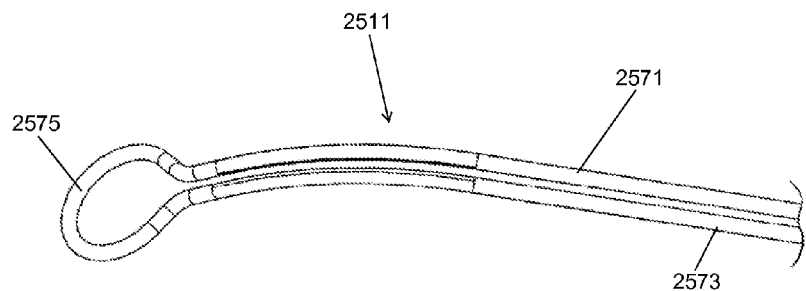
Figure 145A:
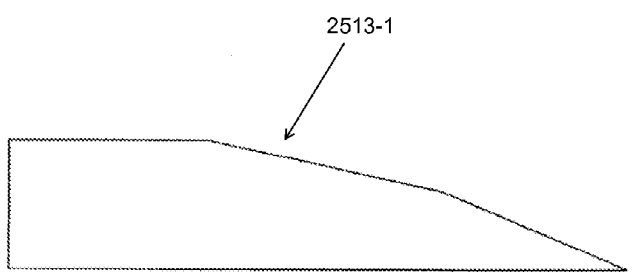
Figure 145B:
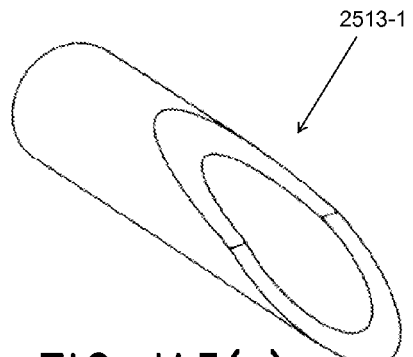

FIGS. 121(a) through 121(d) are left side, right side, top, and section views, respectively, of the other jaw shown in FIG. 109(b);

FIG. 122 is a flowchart, schematically illustrating one method of using the removal device of FIG. 109(a) to remove the pressure-attenuating device of FIG. 99(a) from a patient;

FIGS. 123(a) through 123(d) are fragmentary side views, partly in section, illustrating certain parts of steps of the method shown in FIG. 122;

FIGS. 124 and 125 are side views of first and second alternate embodiments to the sheath shown in FIGS. 4(a) and 4(b);

FIGS. 126(a) and 126(b) are fragmentary top views of a first alternate embodiment to the removal device shown in FIG. 1, the jaws of the removal device being shown in a closed state and in an open state, respectively;

FIG. 127 is a fragmentary section view of the removal device of FIGS. 126(a) and 126(b);

FIGS. 128(a) and 128(b) are fragmentary top views of a second alternate embodiment to the removal device shown in FIG. 1, the jaws of the removal device being shown in a closed state and in an open state, respectively;

FIG. 129 is a fragmentary section view of the removal device of FIGS. 128(a) and 128(b);

FIG. 130 is a side view of a third alternate embodiment to the removal device shown in FIG. 1, the removal device being shown in an open state;

FIG. 131 is an enlarged fragmentary side view of a proximal portion of the removal device shown in FIG. 130;

FIGS. 132(a) through 132(c) are enlarged fragmentary side, top, and perspective views, respectively, of a distal portion of the removal device shown in FIG. 130;

FIGS. 133(a) through 133(c) are side, perspective, and exploded views, respectively, of a fourth alternate embodiment to the removal device shown in FIG. 1, the removal device being shown with the two jaws in a closed state;

FIG. 134 is a side view of the removal device shown in FIGS. 133(a) through 133(c), the removal device being shown with the two jaws in an open state;

FIG. 135 is an enlarged fragmentary exploded view of a distal portion of the removal device shown in FIGS. 133(a) through 133(c), the two jaws being shown in a closed state, the cystoscope and the wires not being shown;

FIGS. 136(a) and 136(b) are enlarged fragmentary bottom and top views, respectively, of a distal portion of the removal device shown in FIGS. 133(a) through 133(c), the two jaws of the removal device being shown in a closed state, the cystoscope not being shown;

FIGS. 137(a) and 137(b) are enlarged fragmentary top and perspective views, respectively, of the distal portion of the removal device shown in FIGS. 133(a) through 133(c), the two jaws of the removal device being shown in an open state, the cystoscope not being shown;

FIG. 138 is an enlarged side view of the handle assembly shown in FIGS. 133(a) through 133(c);

FIGS. 139(a) through 139(c) are enlarged side, top, and perspective views, respectively, of the jaw assembly shown in FIGS. 133(a) through 133(c), the two jaws of the jaw assembly shown in a closed state;

FIGS. 140(a) and 140(b) are enlarged top and perspective views, respectively, of the jaw assembly shown in FIG. 134, the two jaws shown in an open state;

FIGS. 141(a) and 141(b) are enlarged end and side views, respectively, of the tube body shown in FIGS. 133(a) through 133(c);

FIGS. 142(a) and 142(b) are side and top views, respectively, of the wire shown in FIGS. 133(a) through 133(c);

FIG. 143 is an enlarged fragmentary perspective view of the distal end of the wire shown in FIGS. 141(a) and 141(b);

FIG. 144 is an enlarged fragmentary side view of the proximal end of the wire shown in FIGS. 141(a) and 141(b); and FIGS. 145(a) and 145(b) are enlarged side and perspective views, respectively, of one of the needles shown in FIG. 133(c).

Figure 146:
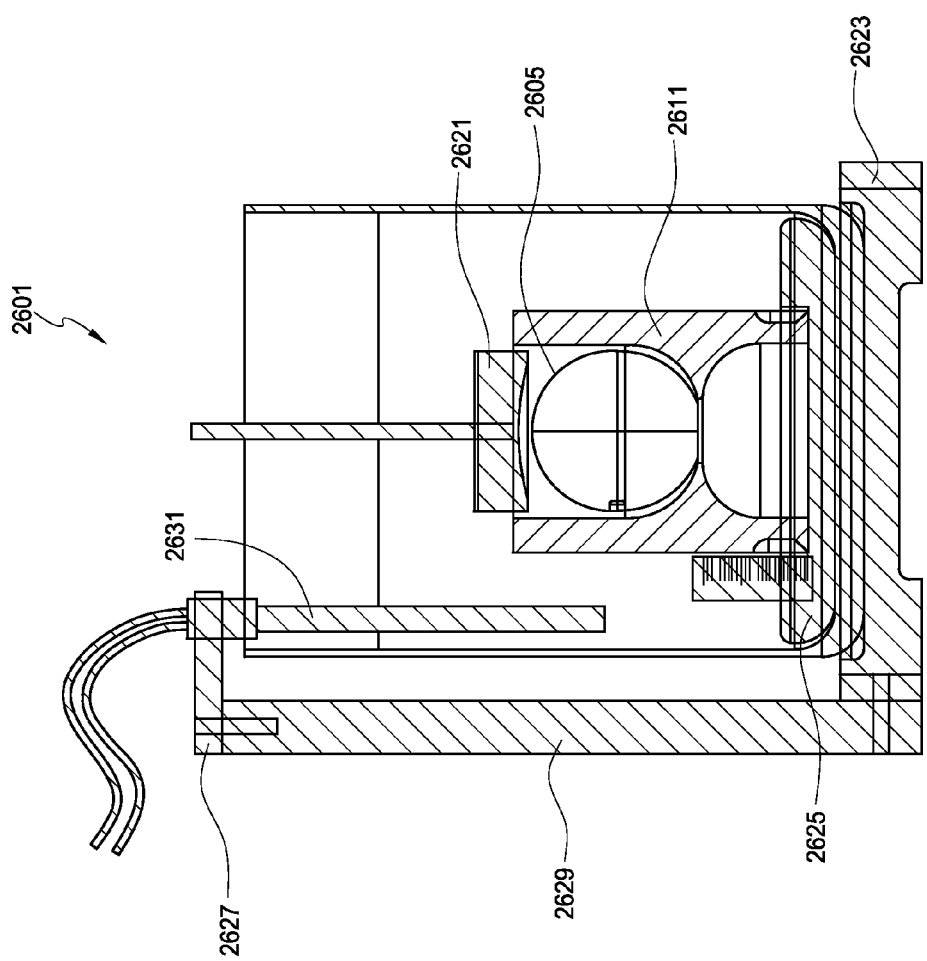
Figure 148D:
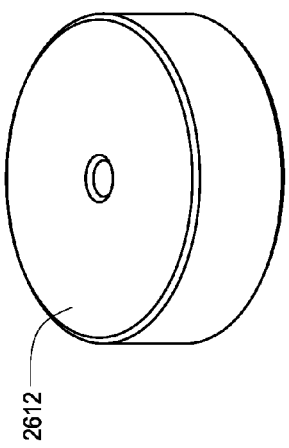
Figure 148C:
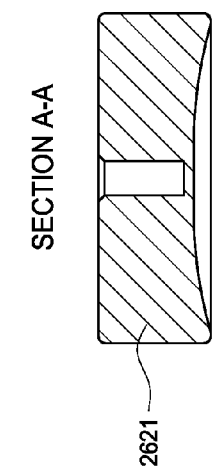
Figure 148B:
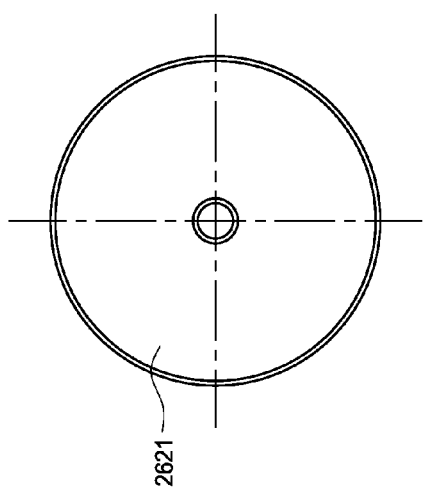
Figure 148A:
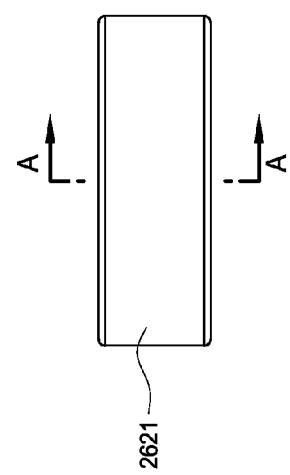
Figures 150A, 150B, 150C, 150D, 150E:
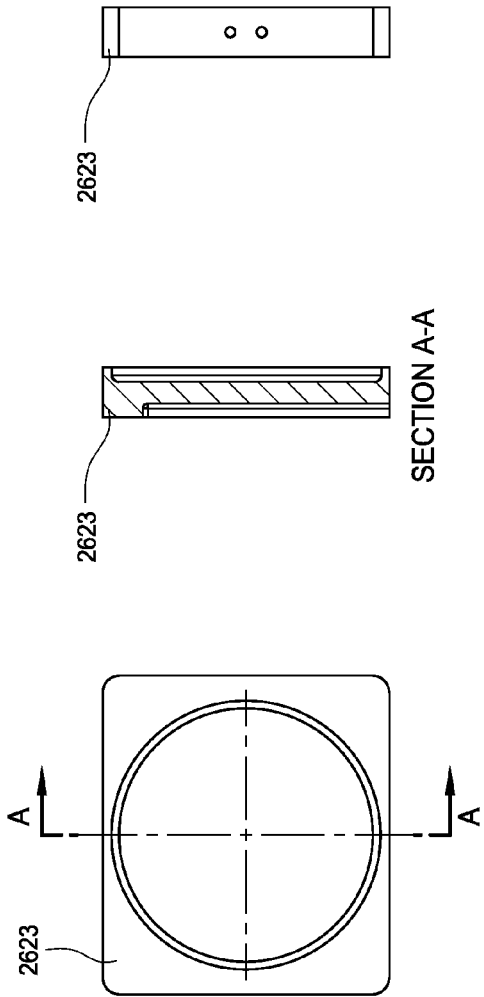
Figure 151D:
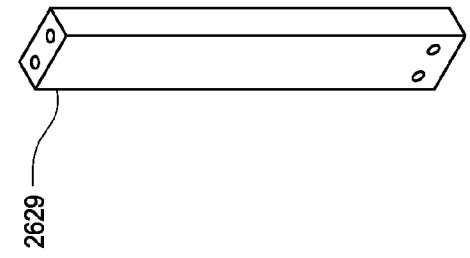
Figure 151C:
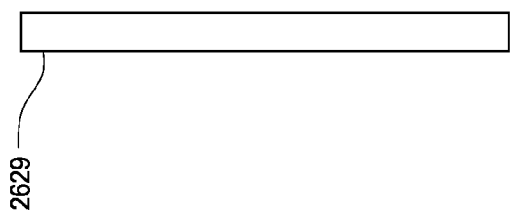
Figure 151B:
Figure 151A:
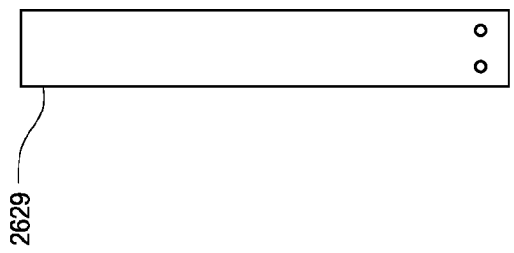

FIG. 146 illustrates an embodiment of an inflatable cell compression test fixture.

FIGS. 147(a) through (d) illustrate various views of an embodiment of a test vessel for the inflatable cell compression test fixture of FIG. 146.

FIGS. 148(a) through (d) illustrate various views of an embodiment of a piston for the inflatable cell compression test fixture of FIG. 146.

FIGS. 149(a) through (e) illustrate various views of an embodiment of a centering disk for the inflatable cell compression test fixture of FIG. 146.

FIGS. 150(a) through (e) illustrate various views of an embodiment of a base for the inflatable cell compression test fixture of FIG. 146.

FIGS. 151(a) through (d) illustrate various views of an embodiment of a bracket post for the inflatable cell compression test fixture of FIG. 146.

FIGS. 152(a) through (d) illustrate various views of an embodiment of a heater bracket for the inflatable cell compression test fixture of FIG. 146.

Figure 153:
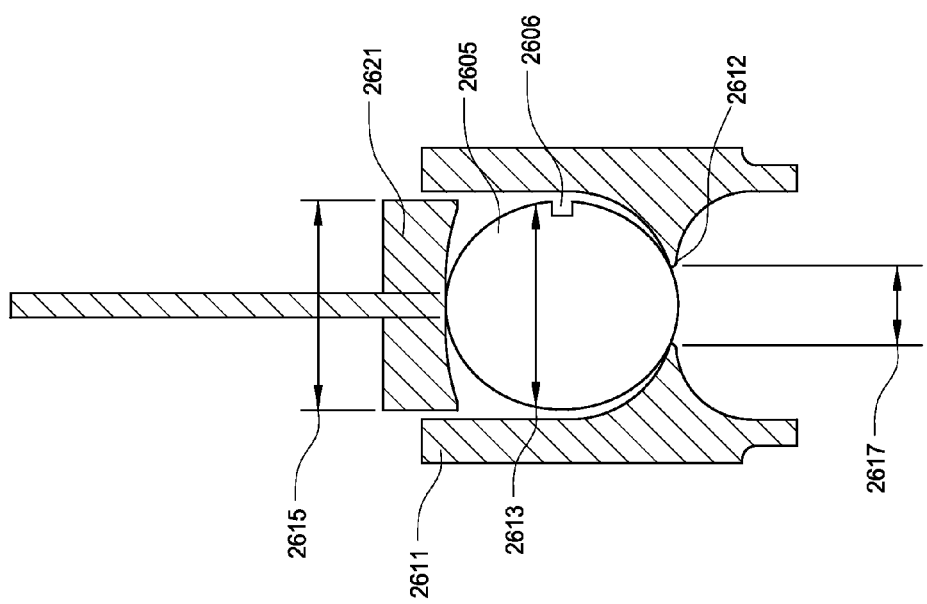
Figure 155:
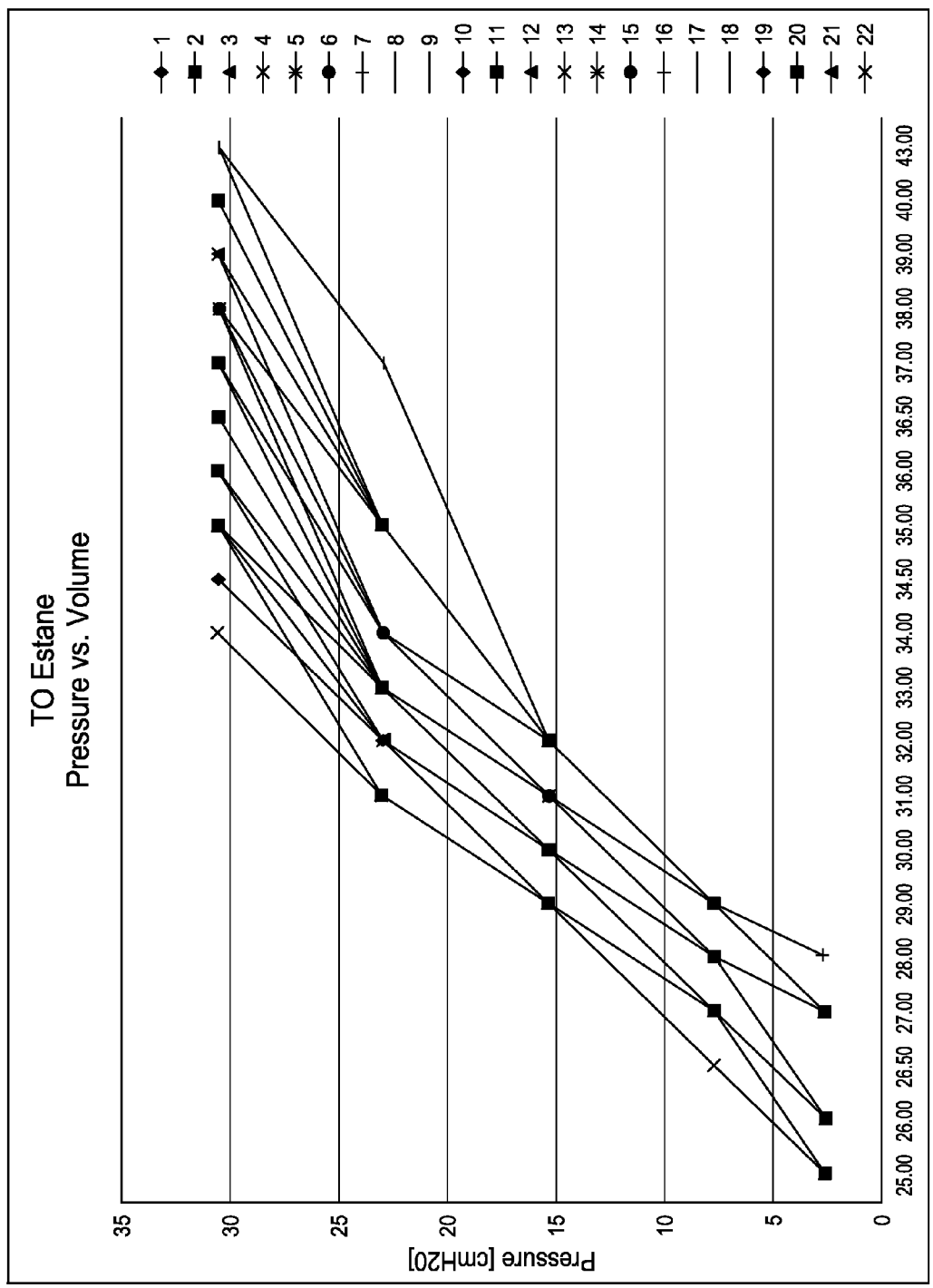
Figure 156:
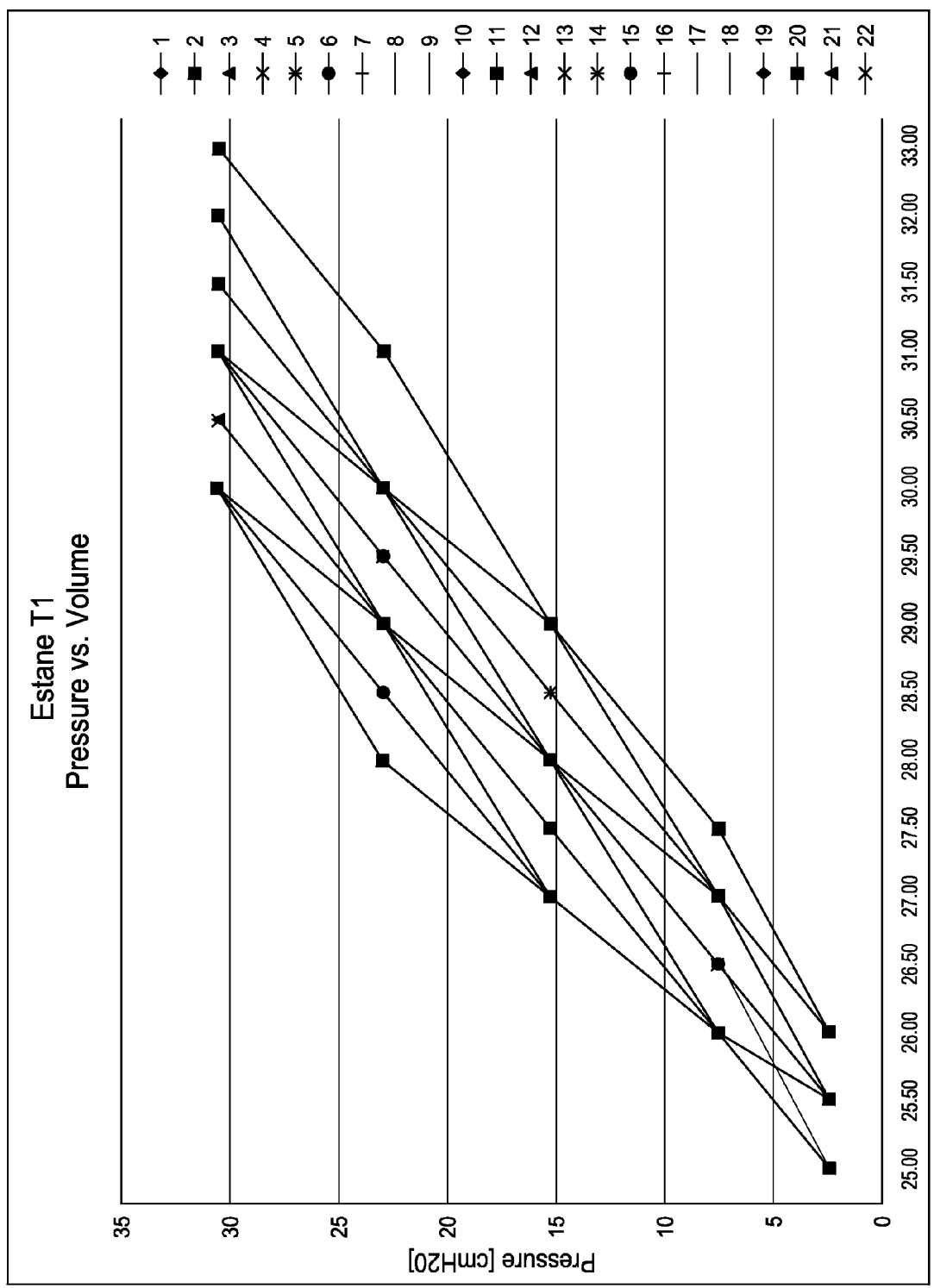
Figure 157:
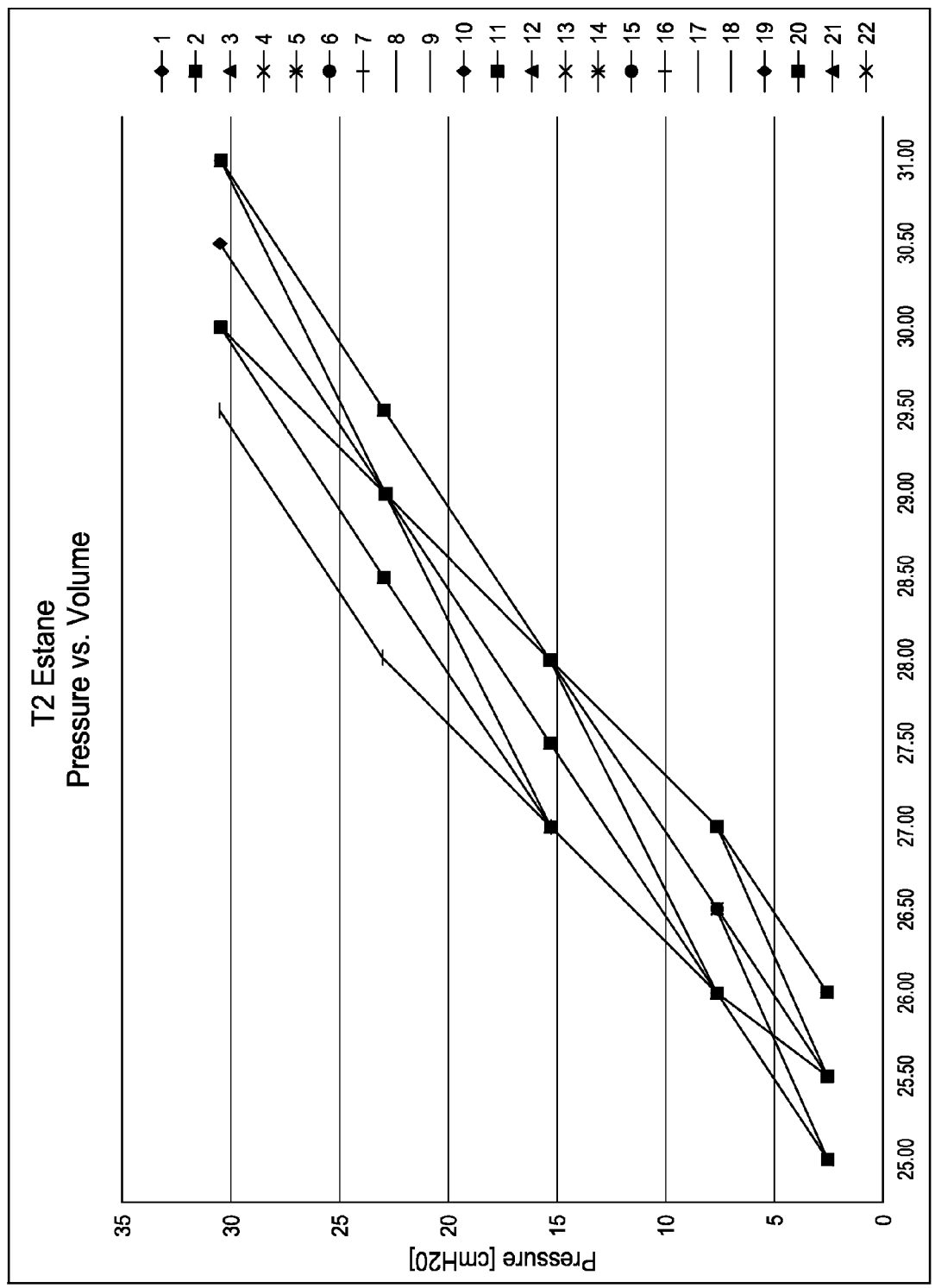
Figure 158:
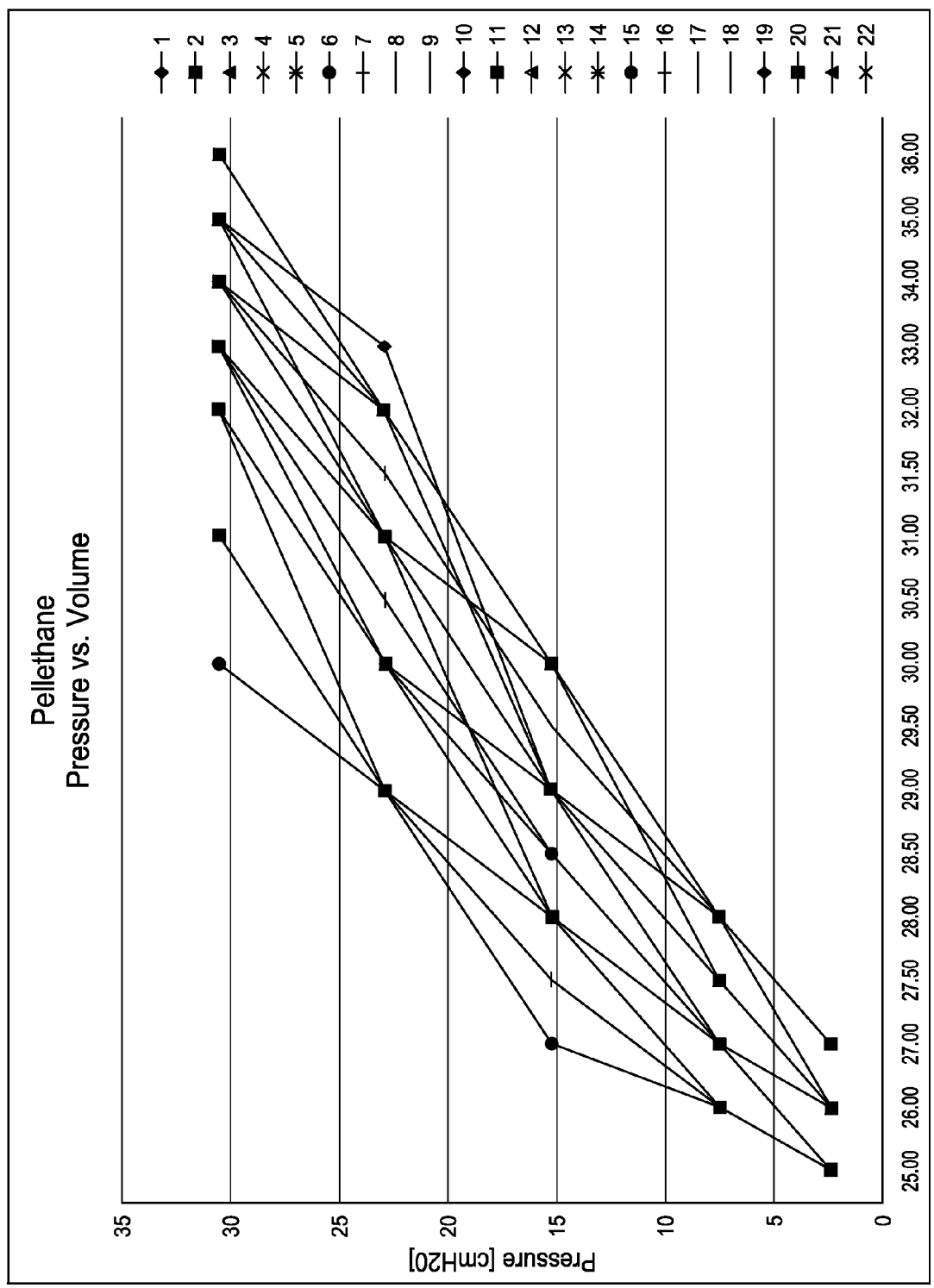

FIG. 153 illustrates a fragmentary section view of the inflatable cell compression test fixture of FIG. 146.

FIG. 154 illustrates an exemplary test data table.

FIG. 155-158 illustrate an exemplary pressure volume charts.

DETAILED DESCRIPTION OF THE PREFERRED EMBODIMENTS

Medical devices, methods, and systems related thereto for use within the body are disclosed. The medical devices and medical systems can include pressurized therapeutic devices, implants, implant delivery devices, implant retrieval devices, expandable or compressible membrane enclosures or balloons, sponges, foams, attenuators, space occupying members, and space creating devices, and therapeutic devices. Though urology and use in the bladder will be primarily discussed, it will be understood that the systems and methods can be used elsewhere. The medical devices and medical systems can be used for many purposes and in many places within the body including, but not limited to, the following systems of the human body: cardiovascular, pulmonary, renal/urological, gastrointestinal, hepatic/biliary, gynecological, neurological, musculoskeletal, otorhinolaryngical and ophthalmic, as well as in and around organs of the body, and in intra- and inter-organ spaces.

In one particular aspect, the disclosure relates generally to the field of urology, and in particular to the treatment of disorders of the urinary tract caused by sudden fluctuations of intravesical pressure. More specifically, in this aspect, methods, systems, and devices are provided for the treatment of urinary disorders, such as incontinence, urgency, frequency, interstitial cystitis, irritable bladder syndrome, and neurogenic bladders.

Some embodiments provide methods, systems, and devices for treating and/or compensating for reduced dynamic compliance of the bladder. In one embodiment, a device having a compressible element is placed within the human urinary bladder in a manner that allows the compressible element to act as a pressure attenuator to attenuate transient pressure events. The term "attenuator" refers generally to devices that attenuate pressure, force, or energy by dissipating or dampening the pressure, force, or energy. Gases, such as atmospheric air, carbon dioxide, nitrogen, and certain perfluorocarbons (PFC), are very compressible in the pressure ranges typically encountered in the human bladder and may be used in attenuation devices inserted in the bladder. Furthermore, when compared to the tissues encompassing liquid, gases are significantly more compliant than the immediate environment. The addition of a volume of gas can act as a low or variable rate spring in series with the native fluidic circuit of the urinary tract.

In accordance with one embodiment, an attenuation device is placed within the human urinary bladder. The attenuation device can be a pressurized container with a positive or negative pressure. The container can take many forms including a sphere. The attenuation device may be untethered in the bladder and may remain in the bladder for between several hours and one year. The attenuation device can be a small elastomeric gas cell with a relaxed (unstretched) volume of between about 0.1 and 500 cc, more preferably between about 1 and 180 cc, and more preferably still, between about 10 and 60 cc. The attenuation device can be a unitary component or can comprise two or more subcomponents. The attenuation device can be made with a seam or without a seam but preferably is made without a seam. The attenuation device can have a substantially uniform wall thickness of between about 0.25 inch to 0.0001 inch, more preferably between 0.0001 inch and 0.005 inch, but could vary greatly in wall thickness and still perform the intended function.

In the embodiment described above, attenuation devices having gas cells that are free-floating in the bladder have been described. In other embodiments, gas cells or similar attenuation devices could be surgically affixed to the bladder wall through the use of suture, staples or other accepted methods or could be placed submucosally or intramuscularly within the bladder wall. Some embodiments could induce endothelial encapsulation. Other embodiments could also include attenuation devices with programmable, variable and adjustable buoyancy by using ballasting, specific inflation/deflation solutions, alternative materials of construction or by other means.

Referring now to FIG. 1, there is shown a side view of components of a first embodiment of a system for treating a patient, the treatment system being represented generally by reference numeral 11. (For ease of illustration and understanding, certain aspects of system 11 may not be shown in FIG. 1.)

System 11 may comprise an access device 13, a delivery device 15, a pressure-attenuating device 17, and a removal device 19. The access device may be used to create a transurethral passageway to a patient's bladder. The delivery device may be inserted through the passageway created by the access device and may be used to deliver the pressure-attenuating device to the bladder in a compacted state, then may be used to inflate the pressure-attenuating device, and then may be used to release the inflated, pressure-attenuating device. The removal device may be inserted through the passageway created by the access device and may be used to view the bladder and/or to capture, to deflate and to remove the pressure-attenuating device.

Each of access device 13, delivery device 15, and pressure-attenuating device 17 may be a single-use (i.e., disposable) device or a multiple-use (i.e., reusable) device, but each is preferably a single-use device. Removal device 19 may be a single-use device or a multiple-use device, but preferably is a multiple-use device.

Access Device

As has been mentioned, an access device may be used to create a passageway into the body. For example, the passageway can be a trans-urethral passageway to a patient's bladder. The access device may be used to drain fluid from the body, such as from the bladder. The access device can be used to protect tissue between the access entry location and the exit location within the body. The access device may further be used as a positioning device to properly position other tools, such as the delivery device within the body. For example, the access device can include a meatal stop, to properly position portions of the delivery device within the bladder.

An access device may include one or more of a housing assembly, a sheath assembly, and a fluid control system. A housing assembly can comprise one or more housing structures that define a body of the access device.

A sheath assembly can comprise an elongated sheath or cannula, and a longitudinal channel extending therethrough. In some embodiments, as will be discussed more fully below, the sheath assembly may include a slide ring assembly that is slidably mounted around the sheath, and it may include a protective sleeve. The slide ring assembly can be moved between a distal position and a proximal position. In some embodiments the slide ring assembly can have one or more mechanisms to secure the slide ring assembly in the distal position and/or the proximal position, and positions therebetween. The protective sleeve can be coupled to the slide ring assembly. In some embodiments the access device can include an obturator that can be removably mounted within the longitudinal channel of the sheath.

A fluid control system can control fluid communication between the anatomical structure within the patient and the access device. For example, the fluid control system can be used to drain the bladder of a patient. The fluid control system can have one or more fluid conduits in fluid communication with the sheath. The fluid conduits can be used to remove and/or deliver fluid to/from the patient. The fluid control system can have one or more mechanisms to control the rate of fluid transfer through the access device. In some embodiments the fluid control system can provide a fully open fluid conduit or a fully closed fluid conduit. In some embodiments, the fluid control system can have a mechanism to provide a variable flow rate for each fluid conduit. In some embodiments the flow rate of each fluid conduit can be controlled individually.

Additional embodiments of access devices are described in U.S. Patent Application Publication No. 2010/0222802, incorporated herein by reference, and referring to cannulas, sheaths, tubular bodies, and/or tubular hubs, meatal stop surface, etc., often as part of a delivery system. See for example, paragraphs [0153]-[0206] and FIGS. 6-7B and 9-18H. Embodiments of an access device, often as part of a delivery system, are also provided in U.S. Pat. No. 6,976,950, incorporated by reference herein. See for example: FIGS. 6-11A, 34A-35B and 48A-48D, and the accompanying discussion, including at columns 13-16, and 35.

Figure 2B:
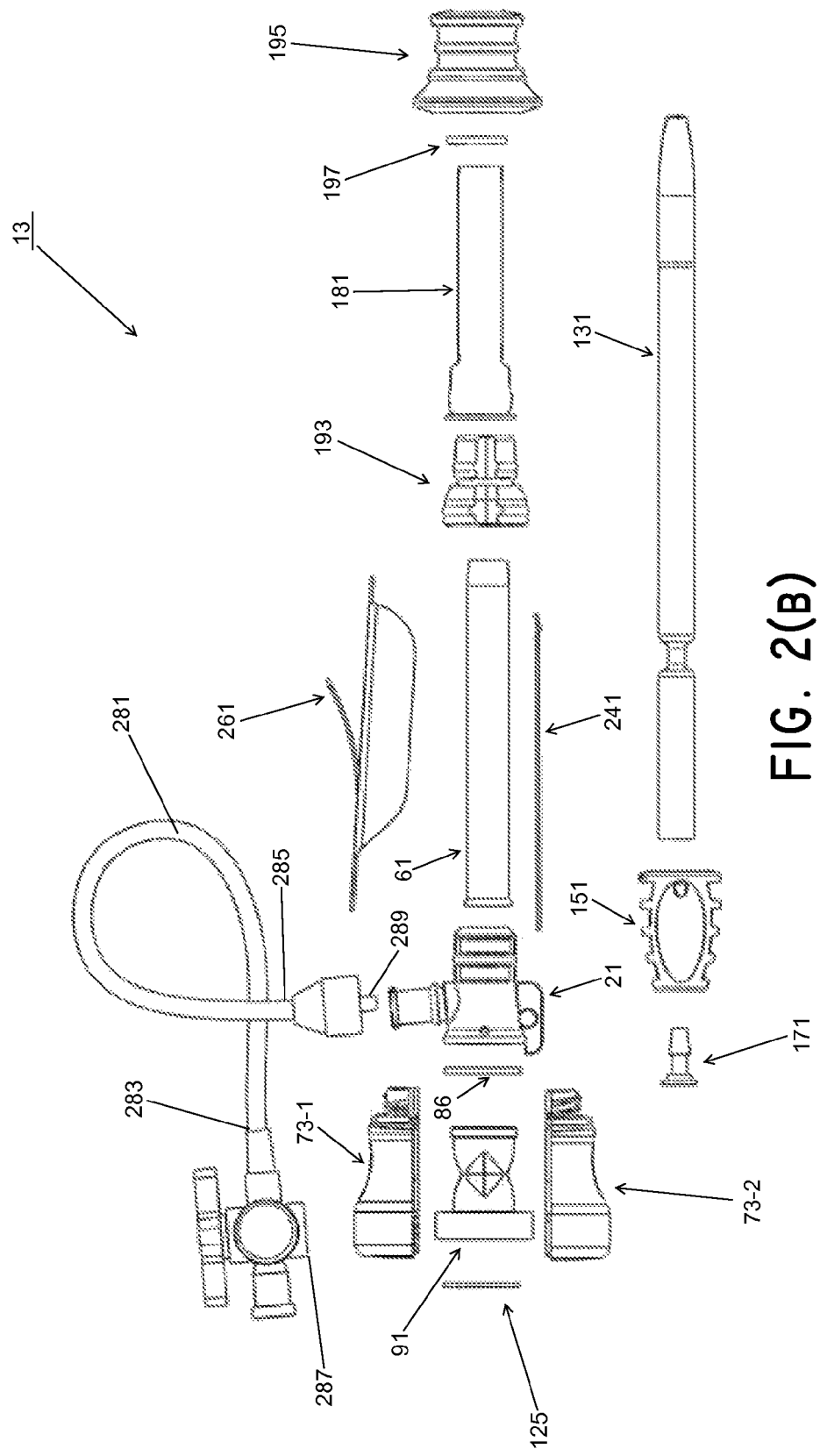
FIGS. 2(a) through 2(c) are side, partially exploded side, and side-partly in section, views, respectively, of the access device shown in FIG. 1.
Figure 2C:
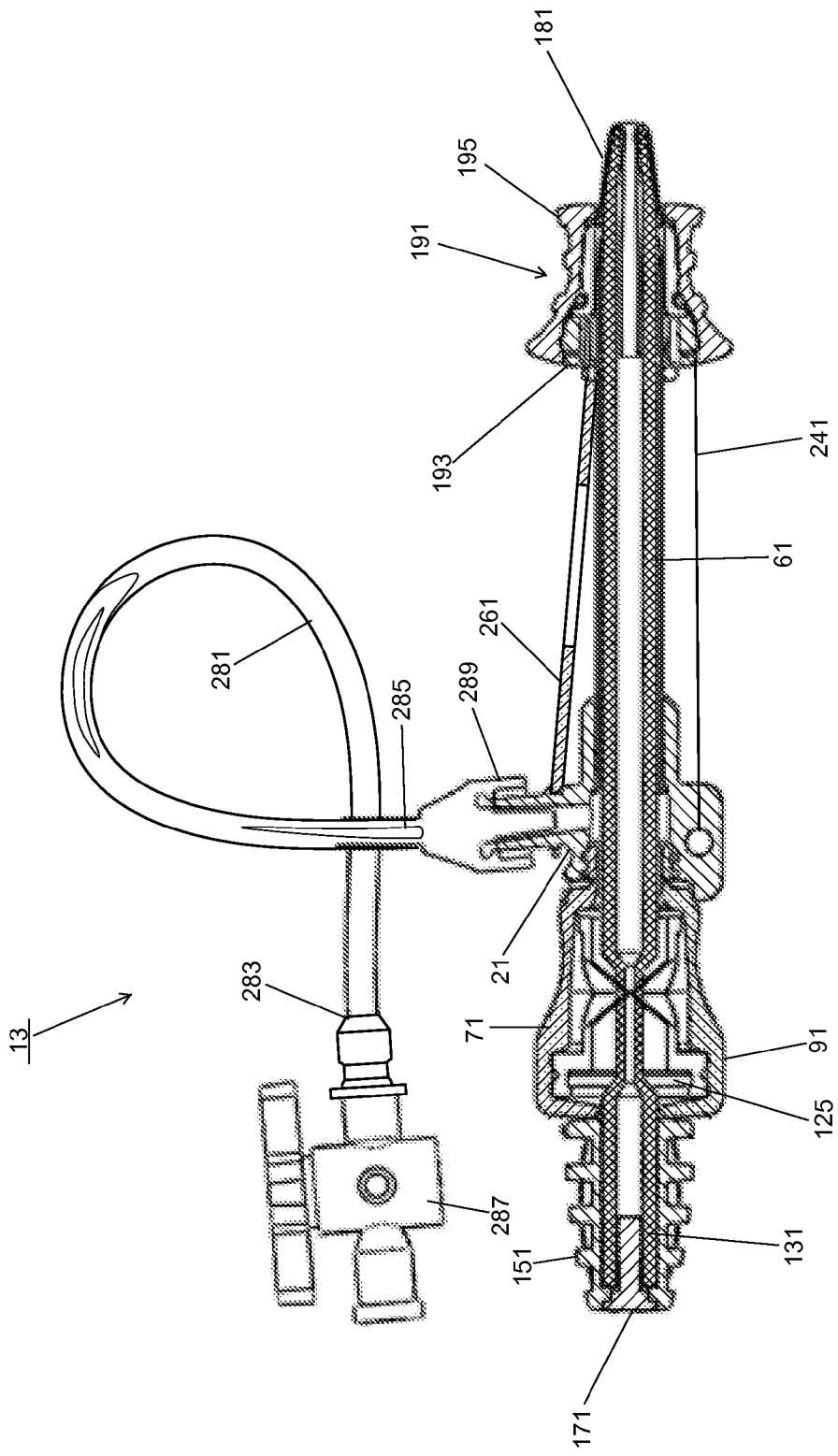

As shown in FIGS. 2(a) through 2(c), access device 13 may include a housing assembly, a sheath assembly, and a fluid control system. The housing assembly may comprise a handle 71. The sheath assembly may comprise a cannula or sheath 61, a dilator or obturator 131, an obturator handle 151, a handle plug 171, a protective sleeve 181, a slide ring assembly 191, and one or more restraining mechanisms 241 and 261. The fluid control system may comprise one or more of a hub 21, a valve assembly 91, a seal 125, and a fluid extension line 281. In some embodiments, the access device 13 may simply comprise a cannula, but may also include a valve assembly and an obturator. It will be understood that other combinations of components could also be used. Each of the components will now be discussed in detail.

Referring now to FIGS. 3(a) and 3(b), the hub 21 may comprise a unitary structure, preferably made of a hard, medical-grade polymer or a similarly suitable material. Hub 21 may be shaped to include a first tubular member 23 and a second tubular member 25.

First tubular member 23 may comprise an open proximal end 27, an open distal end 29, and a longitudinal channel 31 extending from proximal end 27 to distal end 29. Member 23 may include a generally frusto-conical proximal portion 32-1 of comparatively greater inside diameter, a generally cylindrical distal portion 32-2 of comparatively lesser inside diameter, and a generally cylindrical intermediate portion 32-3 of intermediate inside diameter. Proximal portion 32-1 may be shaped to include an internal helical thread 33 extending distally a short distance from proximal end 27. Distal portion 32-2 and intermediate portion 32-3 may be interconnected by a frusto-conical wall 35. The exterior of distal portion 32-2 may be shaped to include first and second circumferential ribs 37 and 39, respectively, and first and second axial ribs 41 and 43, respectively.

Second tubular member 25, which may be oriented generally perpendicularly to first tubular member 23, may comprise an open proximal end 45, an open distal end 47, and a longitudinal channel 49 that extends from proximal end 45 to distal end 47 and that tapers gradually in diameter from proximal end 45 to distal end 47. Proximal end 45 may be in the shape of a female luer lock connector. Distal end 47 may be positioned relative to first tubular member 23 so that the distal end of channel 49 opens into channel 31 at a location within intermediate portion 32-3. A barb 51 may be formed on the exterior of member 25 proximate to distal end 47 in such a way that barb 51 and distal end 47 jointly define a waist 53 therebetween.

Hub 21 may further comprise a tab 55 disposed on the exterior of member 23. Tab 55 may be positioned on the circumference of member 23 at a position generally opposite to member 25 and may be oriented on member 23 to extend generally axially. Tab 55 may be shaped to include a transverse opening 57.

Access device 13 may also comprise a cannula or sheath 61 (see FIGS. 2(a)-2(c)). Sheath 61, shown in FIGS. 4(a) and 4(b), may comprise a unitary structure, preferably made of a medical-grade polymer or a similarly suitable material having columnar strength as well as angular flexibility. Sheath 61, which may be a tubular member having a longitudinal channel 62, may be shaped to include a proximal portion 61-1, a distal portion 61-2, and an intermediate portion 61-3. Proximal portion 61-1, which may have a frusto-conical shape tapering inwardly from an open proximal end 63, may be fixedly secured by adhesive or other suitable means to the hub 21. This can be at the interior of member 23 along wall 35 of the hub 21, with the remainder of sheath 61 extending distally therefrom. Distal portion 61-2 may have a wall thickness that tapers distally to a distal end 64. Sheath 61 may be appropriately dimensioned so that the exposed portion of sheath 61, i.e., the portion of sheath 61 that extends distally from hub 21, has a length that is slightly greater than the length of a typical female human urethra and additionally has an external diameter that permits the exposed portion of sheath 61 to easily traverse a typical female human urethra. For illustrative purposes, sheath 61 may have a length of approximately 4.1 in and an external diameter of about 24 Fr.

Figure 5A:
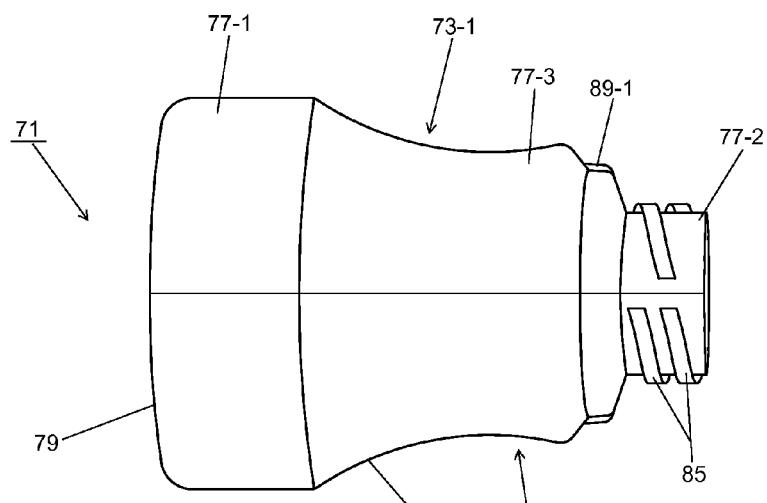
FIGS. 5(a) through 5(c) are side, proximal, and distal views, respectively, of the handle shown in FIG. 2(b)
Figure 5B:
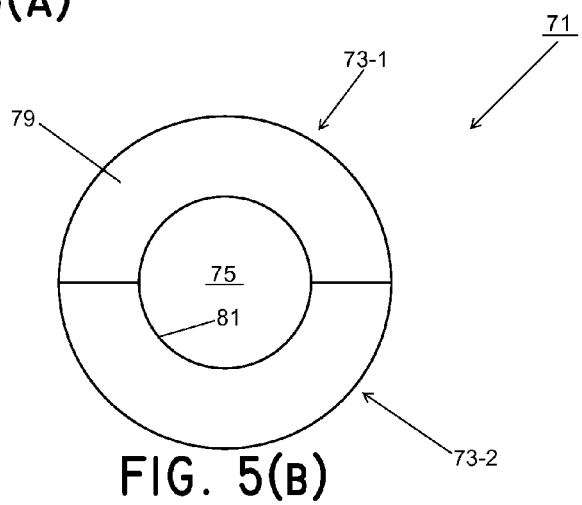
Figure 5C:
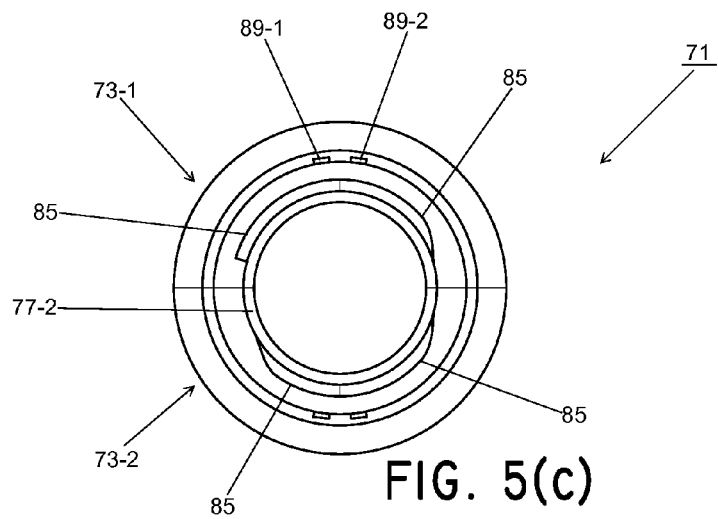
Figure 6:
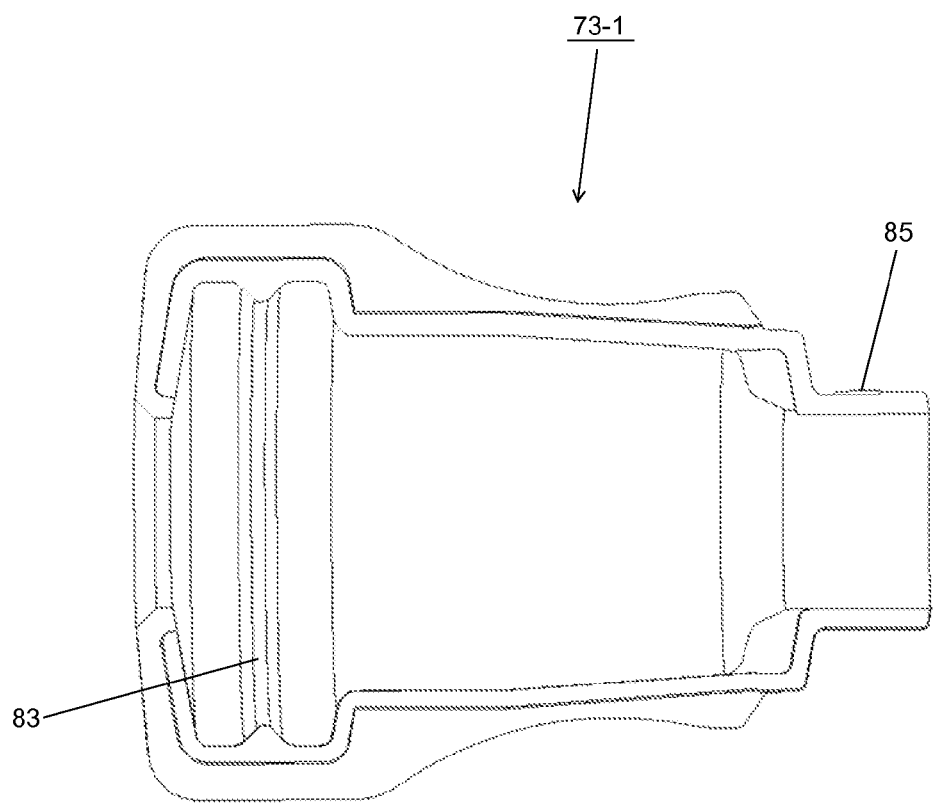
FIG. 6 is a bottom view of one half of the handle shown in FIGS. 5(a) through 5(c)
Figure 7A:
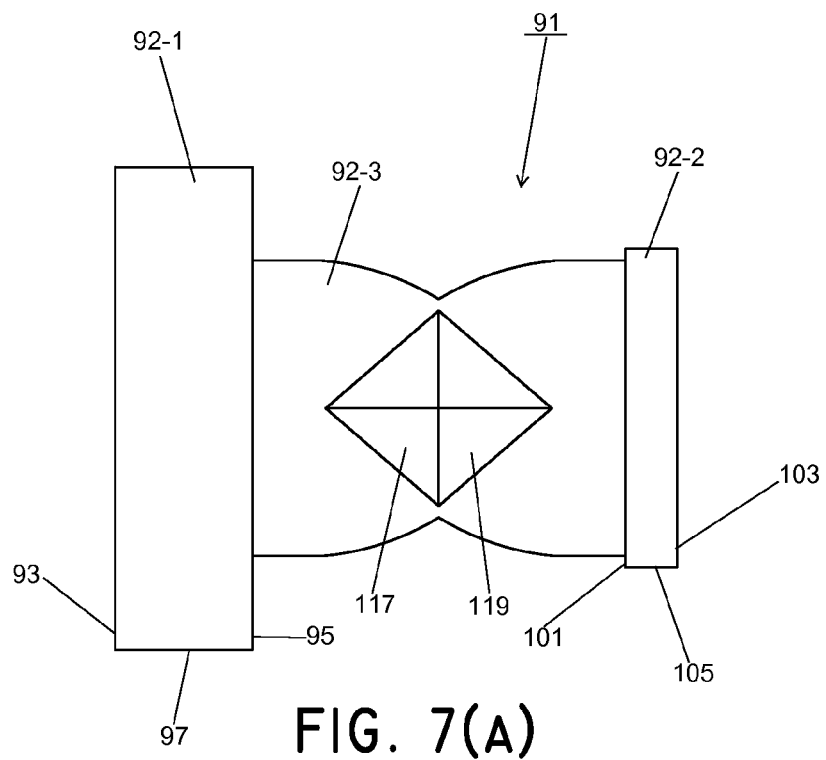
FIGS. 7(a) and 7(b) are side and section views, respectively, of the valve assembly shown in FIG. 2(b)
Figure 7B:
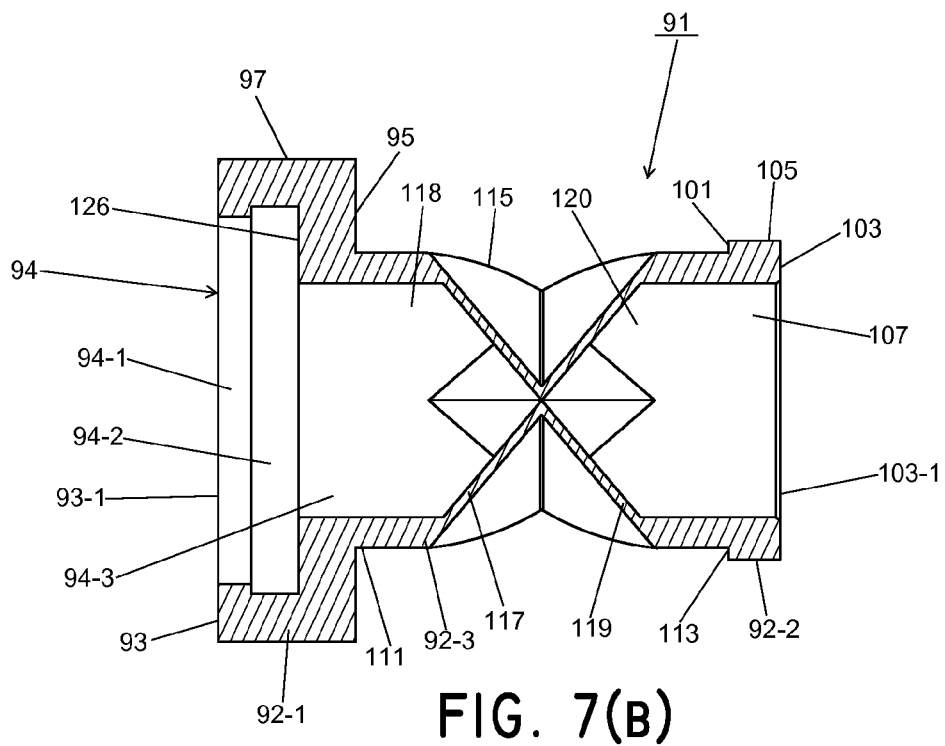

Access device 13 may further comprise a handle 71 (see FIGS. 2(a)-2(c)). Handle 71, shown in FIGS. 5(a) through 5(c), may comprise a pair of identical, nearly identical, or simply corresponding handle halves 73-1 and 73-2, each of which may be a unitary structure preferably made of a hard, medical-grade polymer or a similarly suitable material. Half 73-1 (which is also shown separately in FIG. 6) and half 73-2 may be secured to one another by suitable means (e.g., adhesive, welding, etc.) to form a tubular structure having a longitudinal channel 75 and comprising a proximal portion 77-1 of comparatively greater diameter, a distal portion 77-2 of comparatively lesser diameter, and an intermediate portion 77-3 of intermediate diameter. Proximal portion 77-1, which may be generally cylindrical in shape, may include a proximal end 79 having an opening 81 and an internal circumferential ridge 83 (seen best in FIG. 6) spaced distally a short distance from proximal end 79. Distal portion 77-2, which may be generally cylindrical in shape, may be appropriately dimensioned for insertion into proximal portion 32-1 of hub 21 and may include external helical threads 85 adapted to engage thread 33. In this manner, distal portion 77-2 of handle 71 may be screwed into proximal portion 32-1 of hub 21. (A sealing ring 86, shown in FIG. 2(b), which may be made of silicone or a similarly suitable material, may be inserted around distal portion 77-2 of handle 71 for providing a seal between hub 21 and handle 71.) Intermediate portion 77-3 may have an exterior surface 87 that is appropriately contoured to permit being held by a person, for example, using two fingers of one hand. Intermediate portion 77-3 may additionally include a pair of axial ribs 89-1 and 89-2, which may be used to receive therebetween a proximal end 55-1 of tab 55 and, thereby, limit rotation of handle 71 relative to hub 21.

Access device 13 may further comprise a valve assembly 91 (see FIGS. 2(b)-2(c)), which may be disposed within handle 71. Any of a number of different valve assemblies can be used. Valve assembly 91, shown in FIGS. 7(a) and 7(b), may comprise a unitary structure, preferably made of a medical-grade silicone or a similarly suitable material. Valve assembly 91 may be shaped to include a proximal portion 92-1, a distal portion 92-2, and an intermediate portion 92-3. Proximal portion 92-1 may be a generally tubular structure shaped to include a proximal end 93, a distal end 95, and a circular side wall 97. Proximal end 93 may be shaped to include a central opening 93-1 leading to a longitudinal channel 94 extending from proximal end 93 to distal end 95. Channel 94 may include a proximal section 94-1, an intermediate section 94-2, and a distal section 94-3, with intermediate section 94-2 having a comparatively greater diameter, with distal section 94-3 having a comparatively lesser diameter, and with proximal section 94-1 having an intermediate diameter. Distal portion 92-2 of valve assembly 91 may be a generally tubular structure shaped to include a proximal end 101, a distal end 103, and a circular side wall 105. Distal end 103 may have a central opening 103-1 leading to a longitudinal channel 107 extending from proximal end 101 to distal end 103. Intermediate portion 92-3 of valve assembly 91 may be a generally tubular structure shaped to include a proximal end 111, a distal end 113, and a side wall 115. Side wall 115 may be appropriately shaped to define a proximal valve 117 and a distal valve 119. Valves 117 and 119 may divide the interior of intermediate portion 92-3 into a proximal channel 118 that is in fluid communication with distal section 94-3 of proximal portion 92-1 and a distal channel 120 that is in fluid communication with channel 107 of distal portion 92-2. Valves 117 and 119, each of which may be a four-sided duckbill valve, may be oriented in opposite directions relative to one another, with valve 117 tapering in a distal direction and with valve 119 tapering in a proximal direction. Moreover, the distal end of valve 117 and the proximal end of valve 119 may be conjoined so that valves 117 and 119 open and close in unison. As will be discussed further below, valves 117 and 119 may be constructed so as to be biased towards a closed state. While in such a closed state, valves 117 and 119 may serve to prevent fluids or other matter from passing through valve assembly 91. In particular, because of its distally-tapered orientation, valve 117 may serve to prevent fluid from flowing proximally through valve assembly 91. In addition, as will also be discussed further below, valves 117 and 119 may be opened, when desired, by inserting an appropriate medical device through valve assembly 91. A benefit of the opposed orientation of valve 119 relative to valve 117 is that valve 119 may reduce the likelihood that, as a medical device that has previously been inserted through valve assembly 91 is thereafter withdrawn from valve assembly 91, valve 117 will scrape against the exterior of the medical device being withdrawn. Such scraping may be undesirable, for example, where the medical device is a removal device used to remove a pressure-attenuating device from a patient and the scraping causes the pressure-attenuating device to become detached from the removal device.

Referring now to FIG. 8(a), there is shown a side view, partly in cross-section, of the combined handle 71 and valve assembly 91. As can be seen, distal portion 92-2 of valve assembly 91 may be dimensioned relative to the interior surface of intermediate portion 77-3 of handle 71 such that a gap 121 may be provided therebetween. Without wishing to be limited to any particular theory of operation, the present inventors believe that gap 121 may be advantageous in permitting a portion of the fluid entering handle 71 through distal portion 77-2 to flow proximally around distal portion 92-2 and to accumulate around the exterior of intermediate portion 92-3 of valve 91. Such accumulated fluid may serve to equalize the fluid pressures within intermediate portion 92-3 of valve assembly 91 and around the exterior of intermediate portion 92-3 of valve assembly 91, thereby promoting the biasing of valves 117 and 119 to a normally closed state. According to one embodiment, gap 121 may be sized to be approximately 0.0001-2 inches, preferably about 0.001-0.500 inch, more preferably about 0.010-0.050 inch.

Figure 8B:
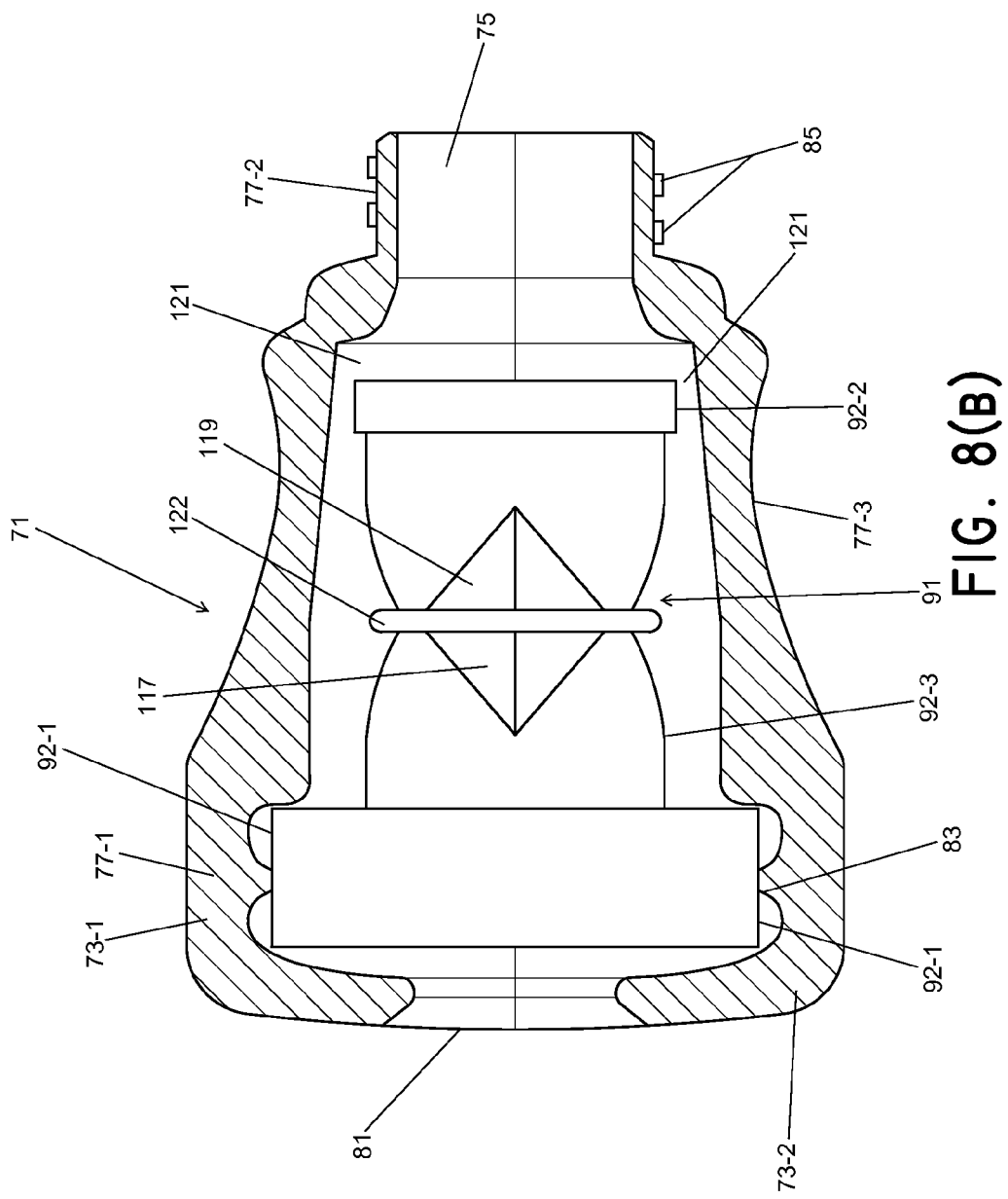
FIG. 8(b) shows the combination of the handle and valve assembly of FIG. 8(a), together with an O-ring.
Figure 12A:
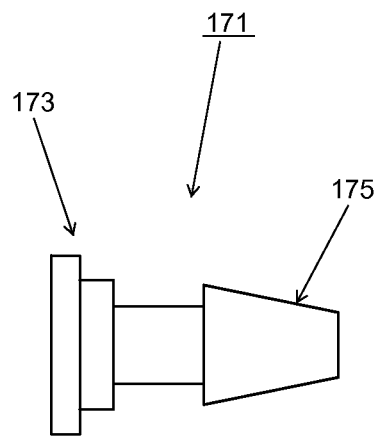
FIGS. 12(a) and 12(b) are side and section views, respectively, of the handle plug shown in FIG. 2(b)
Figure 12B:
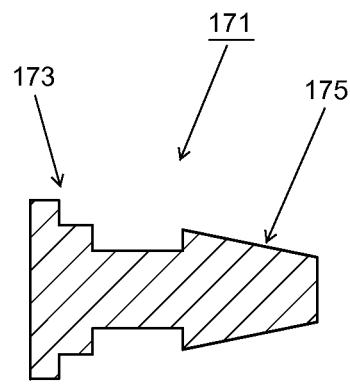
Figure 14B:
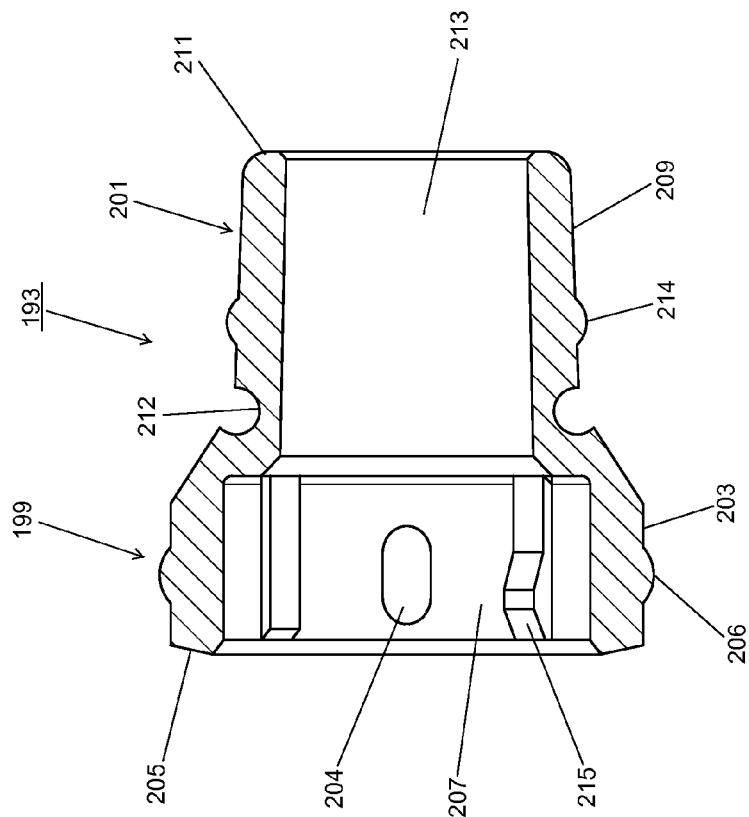
FIGS. 14(a) and 14(b) are side and section views, respectively, of the slide ring assembly inner member shown in FIG. 2(b)
Figure 14A:
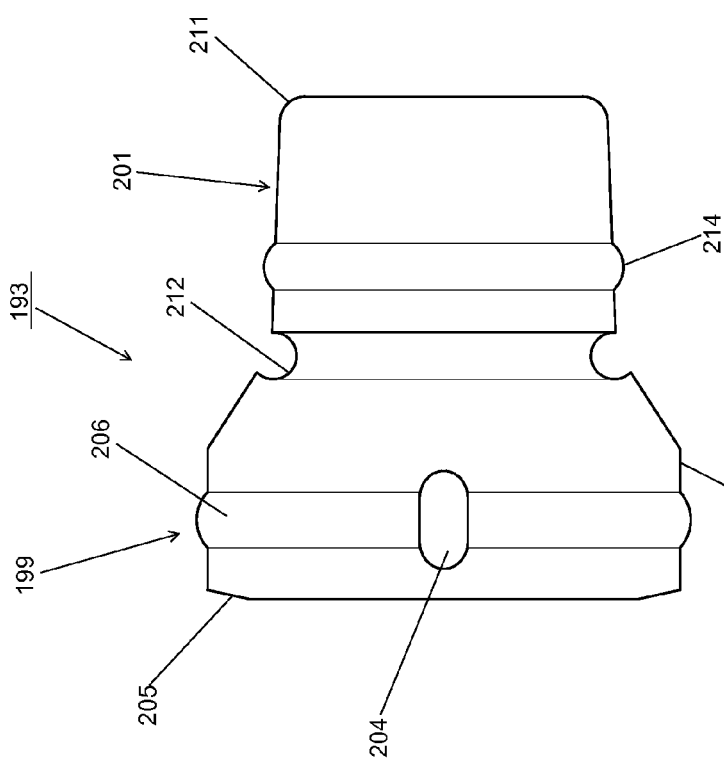

As can also be seen in FIG. 8(a), proximal portion 92-1 of valve assembly 91 may be dimensioned relative to proximal portion 77-1 of handle 71 such that proximal portion 92-1 may form a fluid-tight seal with ridge 83. In this manner, fluid flowing proximally through gap 121 may be kept from flowing proximally past ridge 83. As can be seen in FIG. 8(b), a structure, such as an O-ring 122 may be added around valve assembly 91 to help valves 117 and 119 coapt without relying on cavity pressure. In some embodiments, the valve assembly 91 can be made together with or as part of the handle 71.

Referring now to FIGS. 2(b)-2(c) and 9(a)-9(b), access device 13 may further comprise a seal 125. Seal 125 may comprise a unitary structure, which may be made of a medical-grade silicone or a similarly suitable material. Seal 125 may be of annular shape having a central opening 126. Seal 125 may be appropriately dimensioned to be mounted within valve assembly 91 as shown in FIG. 2(c). Seal 125 may be positioned in valve assembly 91 in intermediate section 94-2 of channel 94, with a rear surface 125-1 of seal 125 fixed by suitable means (e.g., ultrasonic welding, adhesive, etc.) to a shelf 126 (see FIG. 7(b)) within valve assembly 91. Central opening 126 may be appropriately dimensioned to form a fluid-tight seal coaxially around a medical device (e.g., delivery device 15, removal device 19, etc.) that has been inserted through valve assembly 91. In this manner, if valves 117 and 119 are opened by such a medical device inserted through valve assembly 91, seal 125 may serve to minimize the proximal leakage of fluid around said medical device.

Access device 13 may further comprise a dilator or obturator 131 (see FIGS. 2(b)-2(c)). Obturator 131, shown in FIGS. 10(a) and 10(b), may comprise a unitary structure, preferably made of a medical-grade polymer or a similarly suitable material having columnar strength as well as angular flexibility. Obturator 131, which may be a tubular member having a cavity or channel 132, may be shaped to include a proximal portion 133-1, a distal portion 133-2, and an intermediate portion 133-3. It should be understood that, although obturator 131 is shown in the present embodiment as having a longitudinal channel, such a channel need not be a longitudinal channel and, alternatively, could be a channel, at least portion of which does not extend along the longitudinal axis of obturator 131. For example, channel 132 could have a proximal opening and/or a distal opening that is positioned on the side of obturator 131, or obturator 131 could simply have one opening, such as in the case of a pocket or cavity located at or near the distal end of the obturator.

Referring to FIG. 10(a)-10(b), each of proximal portion 133-1, distal portion 133-2, and intermediate portion 133-3 may be generally cylindrical in shape, with proximal portion 133-1 and distal portion 133-2 having similar outer diameters over much of their respective lengths and with intermediate portion 133-3 having a narrowed outer diameter as compared to that of proximal portion 133-1 and distal portion 133-2. Distal portion 133-2 may include a frusto-conical distal end 135 that may be formed, in part, by a wall thickness that tapers distally. Channel 132, which may extend from a proximal end 137 of obturator 131 to distal end 135, may be narrowed within intermediate portion 133-3, as well as in the adjacent portions of proximal portion 133-1 and distal portion 133-2, and also may be narrowed as it approaches distal end 135.

Obturator 131 may be appropriately dimensioned so as to permit its distal end 135 to be inserted coaxially through the combination of seal 125, valve assembly 91, tubular member 23, and sheath 61, with distal end 135 of obturator 131 extending a short distance distally beyond distal end 64 of sheath 61, with proximal end 137 of obturator 131 extending a short distance proximally of proximal end 63 of sheath 61, with proximal portion 133-1 possibly but not necessarily forming a fluid-tight seal with seal 125, and with intermediate portion 133-3 residing within valves 117 and 119 of valve assembly 91 (FIG. 2(c)). Intermediate portion 133-3 preferably has a narrowed diameter so as not to open valves 117 and 119 any more than is minimally needed. Intermediate portion 133-3 may have a length $l_1$ of approximately 0.001-3 inches, preferably approximately 0.050-2 inches, and even more preferably about 0.050-1 inch.

Access device 13 may further comprise an obturator handle 151 (see FIGS. 2(a)-2(c)). Handle 151, shown in FIGS. 11(a) and 11(b), may comprise a unitary structure, preferably made of a hard, medical-grade polymer or a similarly suitable material. Handle 151 may be a tubular member shaped to include a side wall 153, a proximal end 155, and a distal end 157. A longitudinal channel 159 may extend from proximal end 155 to distal end 157. Channel 159 may include a proximal portion 159-1, a distal portion 159-2, and an intermediate portion 159-3. Proximal portion 159-1 and distal portion 159-2 may have generally similar diameters to one another whereas intermediate portion 159-3 may have a reduced diameter relative to proximal portion 159-1 and distal portion 159-2. Distal portion 159-2 may be appropriately dimensioned to receive proximal portion 133-1 of obturator 131, with proximal end 137 of obturator 131 being positioned flush against a proximal end 160 of distal portion 159-2. Obturator 131 may be secured to handle 151 by suitable means, such as ultrasonic welding. To facilitate digital manipulation of handle 151 by a user, the exterior surface of handle 151 may be appropriately shaped with a pair of opposing contoured faces 163 (of which only one is shown) and with a pair of opposing ribbed faces 165-1 and 165-2.

Access device 13 may further comprise a handle plug 171 (see FIGS. 2(a)-2(c)). Plug 171, shown in FIGS. 12(a) and 12(b), may comprise a unitary structure, preferably made of a hard, medical-grade polymer or a similarly suitable material. Plug 171 may be shaped to include a base portion 173 and a barbed stem portion 175. Base portion 173 may be appropriately dimensioned to matingly fit within proximal portion 159-1 of handle 151. Barbed stem portion 175 may be appropriately dimensioned to frictionally fit within proximal portion 133-1 of obturator 131 and to form a fluid-tight seal therewith to prevent fluid flow proximally through proximal end 137 of obturator 131. (Alternatively, plug 171 could be provided with a narrow longitudinal bore to allow some fluid to flow proximally through proximal end 137 of obturator 131, for example, in order to alert a user that obturator 131 has been inserted to a particular location or depth.) In addition to preventing such proximal fluid flow through obturator 131, plug 171 may also serve to provide some mechanical strength to the joint between handle 151 and obturator 131.

Access device 13 may further comprise a protective sleeve 181 (see FIGS. 2(a)-2(c)). Sleeve 181, shown in FIGS. 13(a) and 13(b), may comprise a tubular structure preferably comprising a flexible material, such as polytetrafluoroethylene (PTFE) or a similarly suitable material. As will be discussed further below, at least a portion of sleeve 181 may be positioned within channel 132 of obturator 131, and the material used to make sleeve 181 may additionally be lubricious (and/or channel 132 may have a lubricious surface in contact with the sleeve 181) in order to assist in the deployment of sleeve 181 from channel 132 in the manner to be described further below. Sleeve 181 may comprise a first end 183, a second end 185, and a longitudinal channel 187 extending from first end 183 to second end 185. Sleeve 181 may be shaped to include a first portion 182-1 of comparatively greater diameter and a second portion 182-2 of comparatively lesser diameter. As will be described further below, sleeve 181 may be used to coaxially cover what would otherwise be the exposed lengths of obturator 131 and sheath 61 passing through an anatomical structure, such as the urethra of a patient, with sleeve 181 lining the inside walls of the anatomical structure, such as the urethra. In so doing, sleeve 181 may facilitate the insertion of obturator 131 and sheath 61 through the anatomical structure by reducing the shear force with the walls of the anatomical structure. Moreover, where access device 13 is used, for example, to provide access to the bladder through the urethra, sleeve 181 additionally may serve to minimize the transport of microorganisms into the urethra or bladder of the patient.

Information relating to materials and methods that may be used to form sleeve 181 may be found in the following patents and patent applications, all of which are incorporated herein by reference: U.S. Pat. No. 7,255,687, Huang et al., issued Aug. 14, 2007; U.S. Pat. No. 6,240,968, Bigonzi-Jaker et al., issued Jun. 5, 2001; U.S. Pat. No. 6,007,488, Jaker et al., issued Dec. 28, 1999; U.S. Pat. No. 5,897,535, Feliziani et al., issued Apr. 27, 1999; U.S. Pat. No. 5,711,841, Jaker, issued Jan. 27, 1998; U.S. Pat. No. 5,676,688, Jaker et al., issued Oct. 14, 1997; U.S. Pat. No. 5,531,717, Roberto et al., issued Jul. 2, 1996; U.S. Patent Application Publication No. US 2008/0015518, Huang et al., published Jan. 17, 2008; U.S. Patent Application Publication No. US 2005/0197627, Huang et al., published Sep. 8, 2005; German Patent No. DE 692 25 599 T2, published Jan. 28, 1999; and European Patent No. 0 605 427 B1, published May 20, 1998.

It is to be understood that although sleeve 181 has been described herein as being a tubular structure, sleeve 181 could alternatively be provided in the form of one or more flat sheets.

Referring back to FIGS. 2(*a*) and 2(*c*), access device 13 may further comprise a slide ring assembly 191 coaxially mounted around sheath 61. Slide ring assembly 191 may comprise an inner member 193, an outer member 195, and an O-ring 197 illustrated in FIG. 2(*b*). Inner member 193, shown in detail in FIGS. 14(*a*) and 14(*b*), may comprise a unitary structure, preferably made of a hard, medical-grade polymer or a similarly suitable material. Inner member 193 may be a tubular structure shaped to include a proximal portion 199 and a distal portion 201. Proximal portion 199 may include a continuous side wall 203 defining a proximal end 205 and a longitudinal channel 207. One or more transverse slots 204 may be provided in side wall 203, and one or more ribs 206 may be arranged along an exterior circumference of side wall 203. Distal portion 201 may include a generally circular side wall 209 defining a distal end 211 and a longitudinal channel 213. A generally circular groove 212 may be formed on the exterior surface of side wall 209 at its proximal end, and one or more ribs 214 may be arranged along an exterior circumference of side wall 209 at a location intermediate to groove 212 and distal end 211. Channels 207 and 213 may be collinearly aligned with one another, with channel 213 having a comparatively lesser diameter and with channel 207 having a comparatively greater diameter. Channel 213 may be appropriately dimensioned to permit member 193 to be freely slid over sheath 61 in the manner to be discussed further below. Channel 207 may be appropriately dimensioned to permit proximal portion 199 to reversibly snap-lock onto the exterior of distal portion 32-2 of hub 21 by engaging circumferential rib 37. One or more internal axial ribs 215 may be provided on the interior surface of wall 203 to delimit rotation of proximal portion 199 on distal portion 32-2 of hub 21 by abutting one or more of ribs 41 and 43 on distal portion 32-2.

Outer member 195, shown in FIGS. 15(*a*) and 15(*b*), may comprise a unitary structure, preferably made of a hard, medical-grade polymer or a similarly suitable material. Outer member 195 may be a tubular structure shaped to include a continuous side wall 221 defining a proximal end 223, a distal end 225 and a longitudinal channel 227 extending from proximal end 223 to distal end 225. Proximal end 223 and longitudinal channel 227 may be appropriately dimensioned to receive inner member 193, which may be fixedly secured to outer member 195 by suitable means. O-ring 197 (FIG. 16) may be appropriately constructed to mate tightly with groove 212 of inner member 193.

Side wall 221 of the outer member 195 may have a generally tapered shape to facilitate digital manipulation by a user, with proximal end 223 having a comparatively greater diameter than distal end 225. (Alternatively, distal end 225 could have a comparatively greater diameter than proximal end 223.) One or more circumferential ribs 229, which may facilitate gripping, may be provided on the exterior of side wall 221.

Figure 17A:
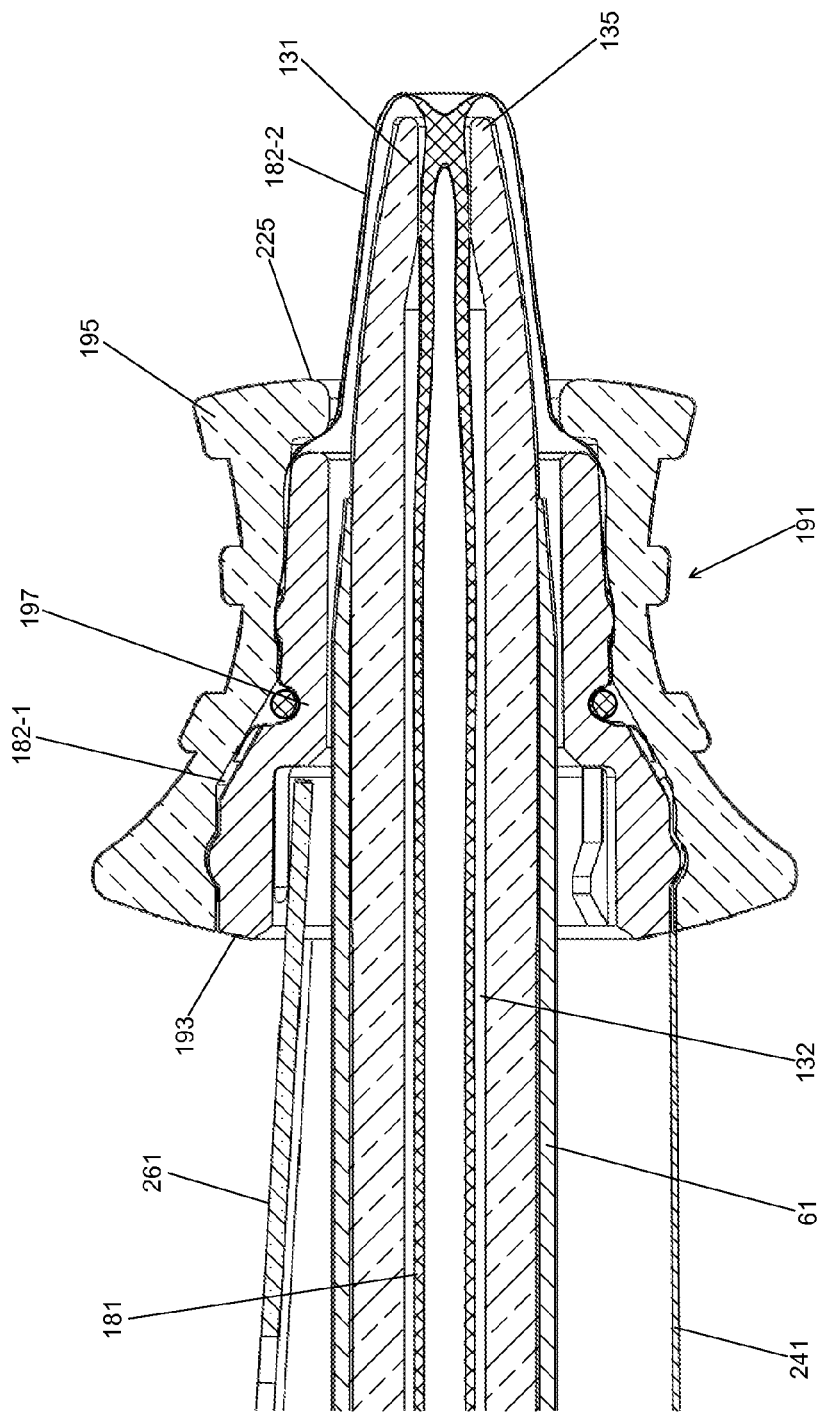

Moving now to FIGS. 17(*a*)-17(*b*), the assembled slide ring assembly 191 can be seen together with other components of the system. The slide ring assembly 191 can engage and secure one end of the sleeve. As can be seen best in FIGS. 17(*a*) and 17(*b*), first portion 182-1 of sleeve 181 may be tightly secured between O-ring 197 and inner member 193, with second portion 182-2 of sleeve 181 extending distally through distal end 225 of outer member 195. By securing sleeve 181 to inner member 193 in this manner, sleeve 181 may be mechanically coupled to sliding ring assembly 191 for sliding movement therewith relative to sheath 61. Consequently, as seen in FIG. 17(*a*), when ring assembly 191 is in its initial distal position, a length of second portion 182-2 of sleeve 181 may serve to cover the portion of obturator 131 that is located distal to ring assembly 191, with the remainder of second portion 182-2 of sleeve 181 wrapping around distal end 135 of obturator 131 and being tucked into channel 132 of obturator 131.

Thereafter, as ring assembly 191 may be slid proximally relative to sheath 61, the length of second portion 182-2 of sleeve 181 residing within channel 132 of obturator 131 may be withdrawn from within obturator 131 through distal end 135 and may be everted, or pulled outward and inside out, over obturator 131 and sheath 61 until the entirety of sleeve 181 has been withdrawn from channel 132. As can be seen in FIG. 17(*b*), when ring assembly 191 is in its most proximal position, distal end 185 of sleeve 181 may be positioned proximal to distal end 65 of sheath 61, thereby exposing the distal ends of sheath 61 and obturator 131. Nonetheless, sleeve 181 preferably has an appropriate length so that, for example, where access device 13 is used to provide access to the bladder through the urethra, the distal ends of sheath 61 and obturator 131 may be covered by sleeve 181 as the distal ends of sheath 61 and obturator 131 pass through the urethra of a patient. In some embodiments, the ring assembly 191 is maintained in position, while the rest of the access device is advanced distally.

To position distal end 185 of sleeve 181 within channel 132 of obturator 131, one may, prior to the insertion of plug 171 into obturator handle 151, insert a device having a distal loop (not shown) distally through obturator handle 151, through obturator 131, and through distal end 185 of sleeve 181, then thread distal end 185 of sleeve 181 through the distal loop of the inserted device, and then retract the inserted device, with sleeve 181 attached thereto, until distal end 185 of sleeve 181 is located within channel 132, the device thereafter detaching from sleeve 181 after its continued withdrawal. In positioning distal end 185 of sleeve 181 within obturator 131 in the aforementioned manner, the length of second portion 182-2 of sleeve 181 positioned within channel 132 of obturator 131 may not necessarily lie flat against the interior surface of obturator 131, but such an occurrence should be of no consequence.

Referring back now to FIGS. 2(*a*) through 2(*c*), access device 13 may further comprise one or more restraining mechanisms for limiting distal and/or proximal sliding movement of slide ring assembly 191 relative to sheath 61. As can be appreciated, absent such a restraint, slide ring assembly 191 may be free to slide relative to sheath 61. Consequently, if access device 13 is held in such a way that sheath 61 is pointed downwardly, assembly 191 may slide distally relative to sheath 61, even possibly sliding entirely off of sheath 61. Such a decoupling of assembly 191 from sheath 61 would be highly undesirable since, amongst other things, it may preclude keeping the distal ends of sheath 61 and obturator 131 covered by sleeve 181 until after the distal ends of sheath 61 and obturator 131 have passed through the urethra or other desired anatomical structure of a patient. Further, the slide ring assembly 191 may be inadvertently slid proximally on sheath 61, either all the way to hub 21 or substantially all the way to hub 21. Such proximal movement of assembly 191 would be highly undesirable since, amongst other things, it could cause end 185 of sleeve 181 to be prematurely withdrawn from obturator 131, which, in turn, may preclude keeping the distal ends of sheath 61 and obturator 131 covered by sleeve 181 until after the distal ends of sheath 61 and obturator 131 have passed through the urethra or other desired anatomical structure of a patient. Though two separate restraining mechanisms are disclosed herein, it will be understood that a single restraining mechanism could also perform the functions of both.

One of the two restraining mechanisms may comprise a tether 241. Tether 241 may be a string, suture, band, or a similarly suitable structure. The tether 241 may comprise an elongated member having a proximal end 243 and a distal end 245 (FIG. 18). Proximal end 243 may be secured to hub 21, for example, by being looped through opening 57 and tied to tab 55. Distal end 245 may be secured to slide ring assembly 191, for example, through an interference-fit by being inserted between inner member 193 and outer member 195. Therefore, because tether 241 is secured at one end to hub 21 and at the opposite end to ring assembly 191 and because tether 241 is sized appropriately in length, distal movement of assembly 191 relative to sheath 61 may be restricted and, in particular, assembly 191 may be restrained from moving beyond a desired axial position on sheath 61.

Figure 19A:
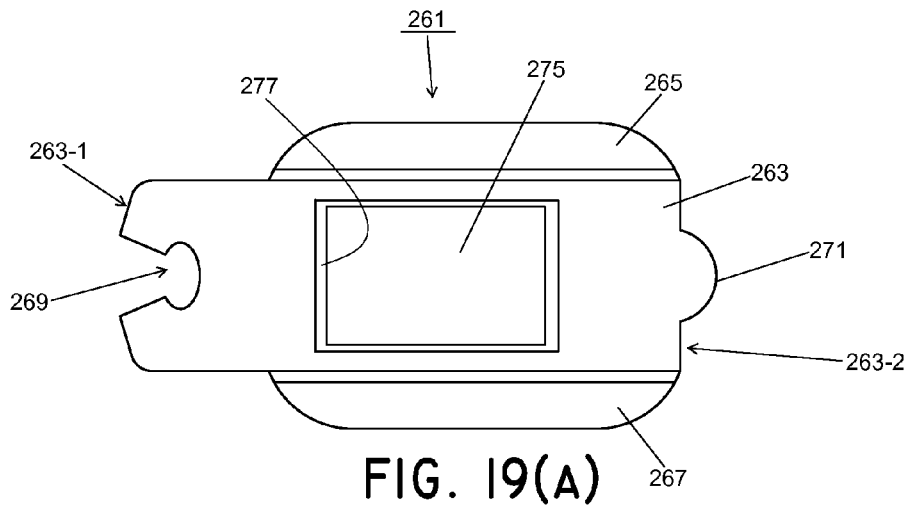
FIGS. 19(a) through 19(c) are top, bottom, and left side views, respectively, of the retaining card shown in FIG. 2(b)
Figure 19B:
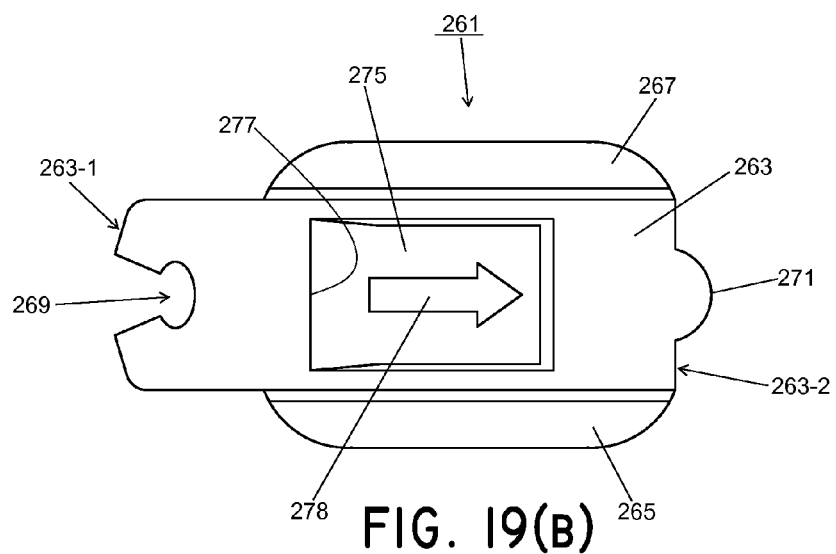
Figure 19C:
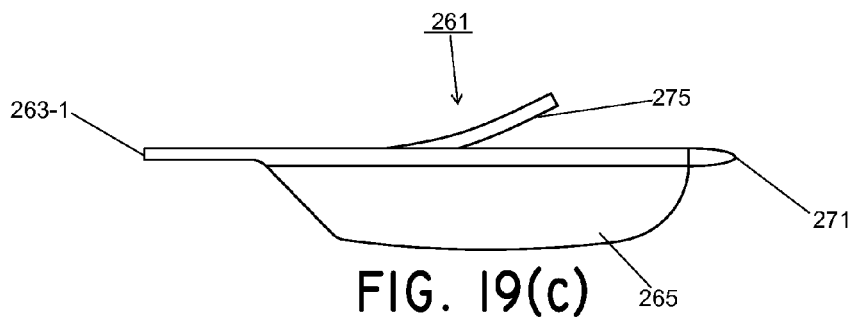

The other of the two restraining mechanisms may comprise a retaining card 261. Card 261, shown in FIGS. 19(a) through 19(c), may comprise a unitary structure, preferably made of a rigid cardstock, polymer, or a similarly suitable material. Card 261 may be cut and scored from a sheet of suitable material to define a top portion 263, a left flap 265 extending downwardly a short distance from a left side of top portion 263, and a right flap 267 extending downwardly a short distance from a right side of top portion 263. Top portion 263 may have a width that may exceed the diameter of sheath 61. In this manner, with top portion 263 positioned over sheath 61, left flap 265 may be positioned on one side of sheath 61 and right flap 267 may be positioned on the opposite side of sheath 261. A proximal end 263-1 of top portion 263 may be shaped to include a recess 269 that may be appropriately dimensioned to matingly engage waist 53 of tubular member 25. A distal end 263-2 of top portion 263 may be appropriately dimensioned to engage slide ring assembly 191 and may be shaped to include a tab 271 that may be inserted into inner member 193 of assembly 191. In this manner, with recess 269 engaging waist 53 and with tab 271 inserted into inner member 193 of assembly 191, retaining card 261 may be used to prevent proximal movement of assembly 191 relative to sheath 61. Card 261 may also serve to prevent rotation of slide ring assembly 191 relative to sheath 61 and, in so doing, may limit the extent to which sleeve 181 may become twisted within obturator 131. Such a twisting of sleeve 181 within obturator 131 may be undesirable as it may increase the resistance of sleeve 181 to evert properly when such eversion is eventually desired. Card 261 is preferably removed from device 13 when proximal movement of assembly 191 relative to sheath 61 is desired. Preferably, card 261 is removed immediately before insertion of the distal end of device 13 into a patient (although card 261 could alternatively be removed after insertion of the distal end of device 13 into a patient). To facilitate the removal of card 261, top portion 263 may be shaped to include a tab 275 connected via a living hinge 277 at a proximal end of tab 275. Tab 275 may be marked, either through direct printing or via an adhesive label, with an arrow 278 or similar indicia to indicate that tab 275 may be pulled distally to disengage waist 53 from recess 269. Thereafter, tab 271 may be removed from inner member 193.

Access device 13 may further comprise a fluid extension line 281 (see FIGS. 2(a)-2(c)). Line 281, which may be a unitary tubular structure preferably made from a medical-grade polymer or a similarly suitable material, may comprise a proximal end 283 and a distal end 285. A stopcock valve 287, which may be a three-way stopcock valve, may be coupled to proximal end 283 of line 281 and may also be coupled to a fluid source (not shown) and to a drain (not shown). A male luer connector 289, which may be connectable to second tubular member 25 of hub 21, may be coupled to distal end 285 of line 281. Where access device 13 is used to provide access to a urinary bladder, the combination of line 281, stopcock valve 287, and connector 289 may be used, after obturator 131 has been removed, to deliver fluids to the patient's bladder or to drain fluids from the patient's bladder. As can be appreciated, one advantage to the aforementioned combination of line 281, stopcock valve 287, and connector 289 is that, where stopcock valve 287 is being operated to drain fluid from the patient's bladder, such urine may be collected from a patient at a location remote from the patient's meatus.

Prior to use, access device 13 may be sterilized by a suitable sterilization technique, for example, ethylene oxide treatment.

Figure 20A:
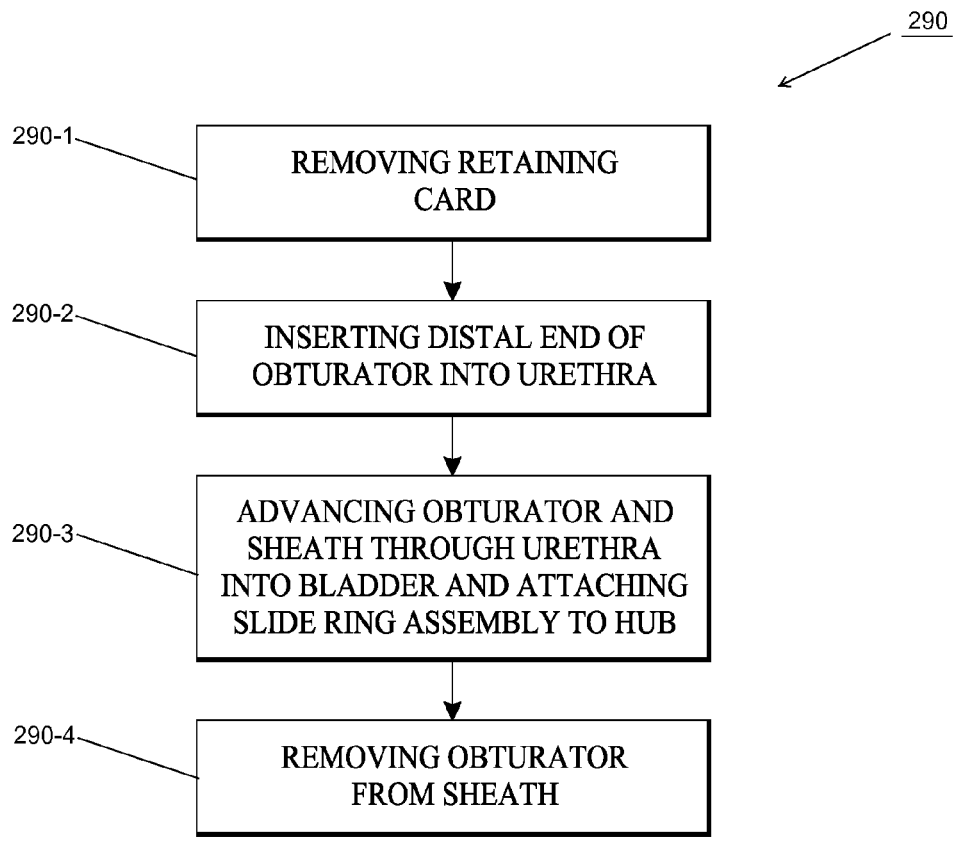
FIGS. 20A-B are flowcharts, schematically illustrating methods of implanting the access device of FIGS. 2(a) through 2(c) in a patient.
Figure 20B:
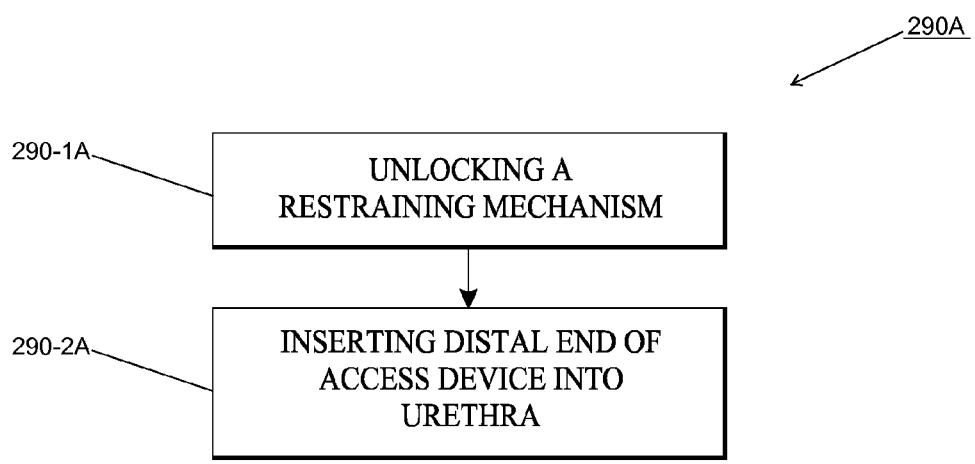
Figure 2I:
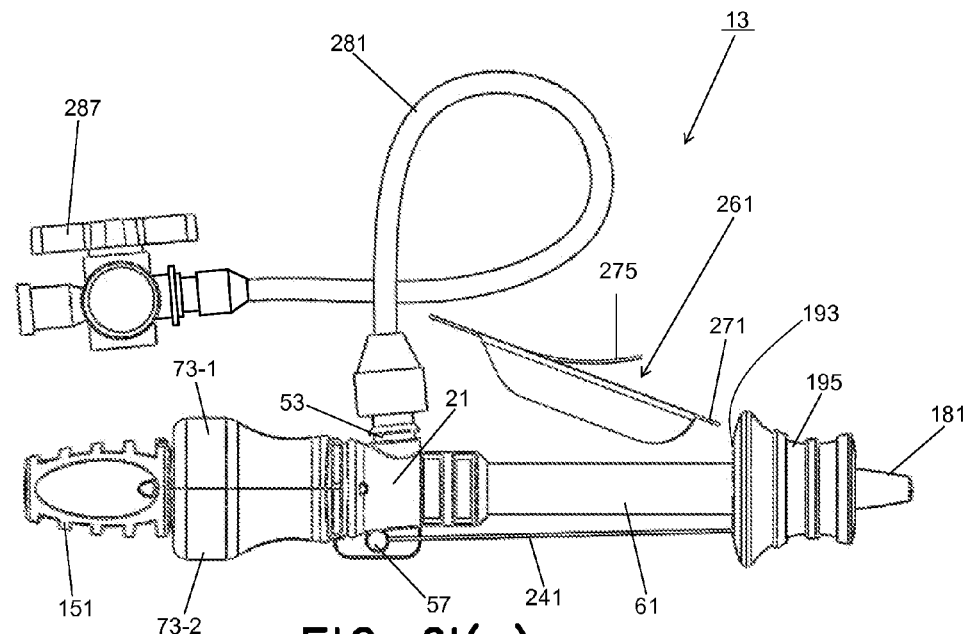
Figure 2I:
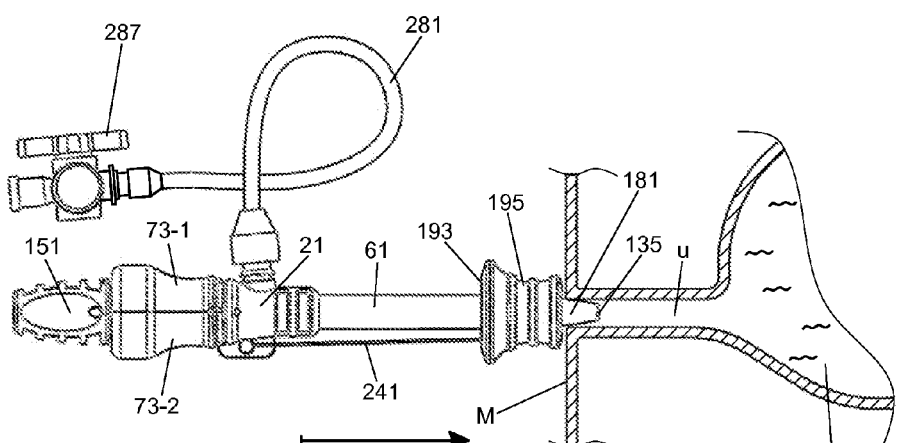
Figure 21C:
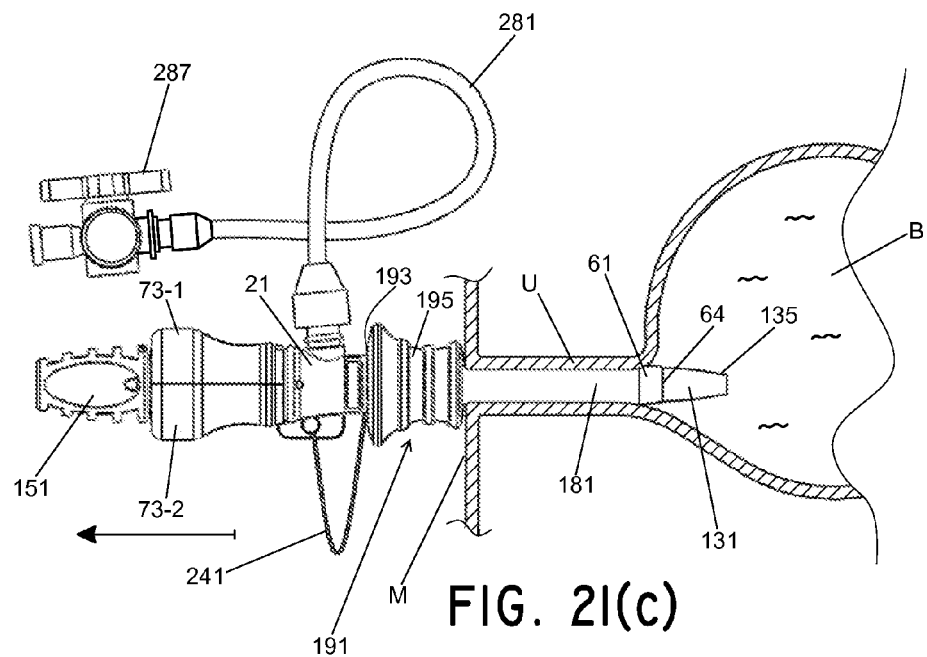

Referring now to FIGS. 20A-B, there are shown two flowcharts, schematically depicting possible methods 290A and 290, respectively, of using access device 13 to provide access to a desired anatomical structure. Such access can be, for example, trans-urethral access to a female human urinary bladder. Method 290A may begin with a step 290-1A of unlocking a restraining mechanism. This can be done, for example, by removing card 261 from device 13, preferably by pulling tab 275 distally until waist 53 of hub 21 disengages from recess 269 of tab 275 and then by removing tab 271 from inner member 193 of slide ring assembly 191 (see FIG. 21(a)). Method 290A may then continue with a step 290-2A of aligning and inserting the distal end of the access device into a body. This can include positioning a meatal stop next to the meatus. This may also include aligning and inserting distal end 135 of obturator 131 into the outer opening of the urethra, with the distal end of slide ring assembly 191 contacting the meatus of the patient and with distal end 135 of obturator 131 being covered by sleeve 181 (see FIG. 21(b) with the urethra being represented by the reference letter U, the meatus being represented by the reference letter M, and the bladder being represented by the reference letter B). Though illustrated schematically, in some embodiments, the slide ring assembly 191 can engage the body tissue at the meatus. Method 290 may then continue with a step 290-3 of advancing obturator 131 and sheath 61 distally through the urethra U in a straight and steady motion until sleeve 181 events completely (is pulled outward and turned inside out) and slide ring assembly 191 snaps onto the distal end of hub 21 (see FIG. 21(c)). (With obturator 131 and sheath 61 advanced in the manner discussed above, distal end 135 of obturator 131 and distal end 64 of sheath 61 may be positioned within the bladder B of a patient.) Preferably, as obturator 131 and sheath 61 are advanced distally in the manner discussed above, rotation of obturator 131 and sheath 61 relative to slide ring assembly 191 is avoided so as to minimize twisting of sleeve 181, which twisting may impede eversion of sleeve 181.

Figure 21D:
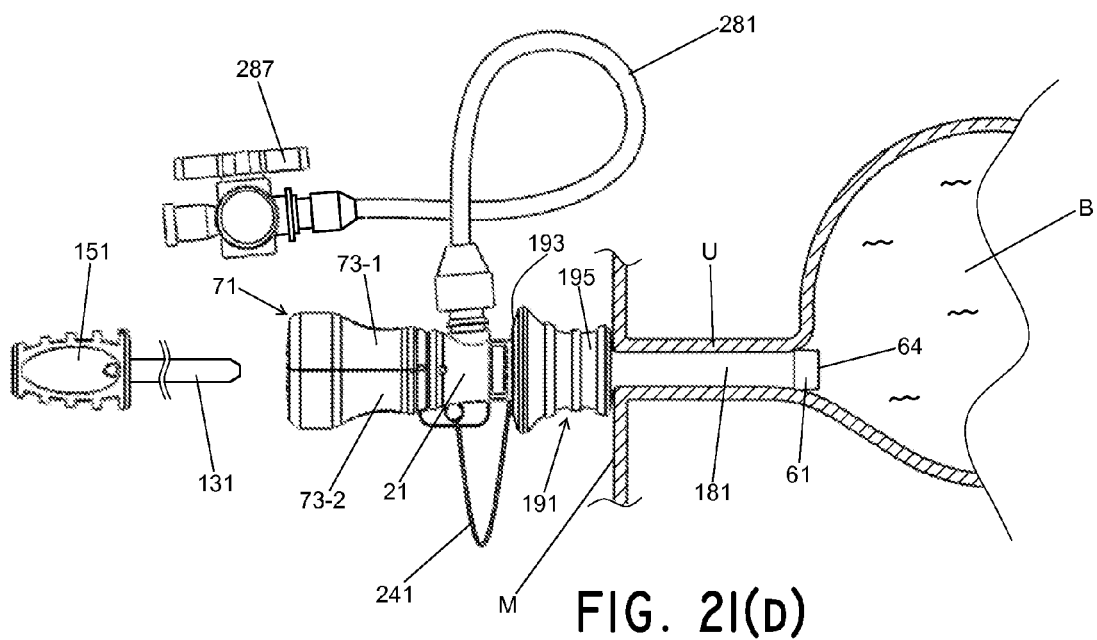

Method 290 may then proceed to step 290-4 of withdrawing obturator 131 proximally from sheath 61, hub 21, and handle 71 by holding hub 21 stationary with one hand while grasping and pulling on obturator handle 151 with the other hand (see FIG. 21(d)). With obturator 131 thus removed, the remaining implanted portion of access device 13 may provide a conduit through which medical devices, such as delivery device 15, pressure-attenuating device 17, and removal device 19, may be delivered to a desired anatomical structure.

During the above-recited steps, stopcock valve 287 may be either opened or closed, depending upon the design of the access device and whether or not one wishes to allow fluid from the patient's bladder to empty. In some embodiments, the obturator 131 can block access to the fluid extension line 281 and the stopcock valve 287. Thus, fluid may be drained after the access sheath is positioned and the obturator 131 removed.

As has been mentioned, other access devices or systems can be used. The access sheath can vary from a basic cannula to any number of different combinations involving at least some of the access sheath components described herein.

As noted above, it may be desirable to minimize the rotation of slide ring assembly 191 relative to obturator 131 and sheath 61 so as to minimize the twisting of sleeve 181 within obturator 131. Although card 261 may satisfactorily prevent such rotation prior to its removal from access device 13, once card 261 has been removed from access device 13, there may be no remaining mechanism in access device 13 for restraining such rotation. Therefore, according to one aspect, certain alternate embodiments are disclosed below that may include a rotation-restraining mechanism.

Figure 22A:
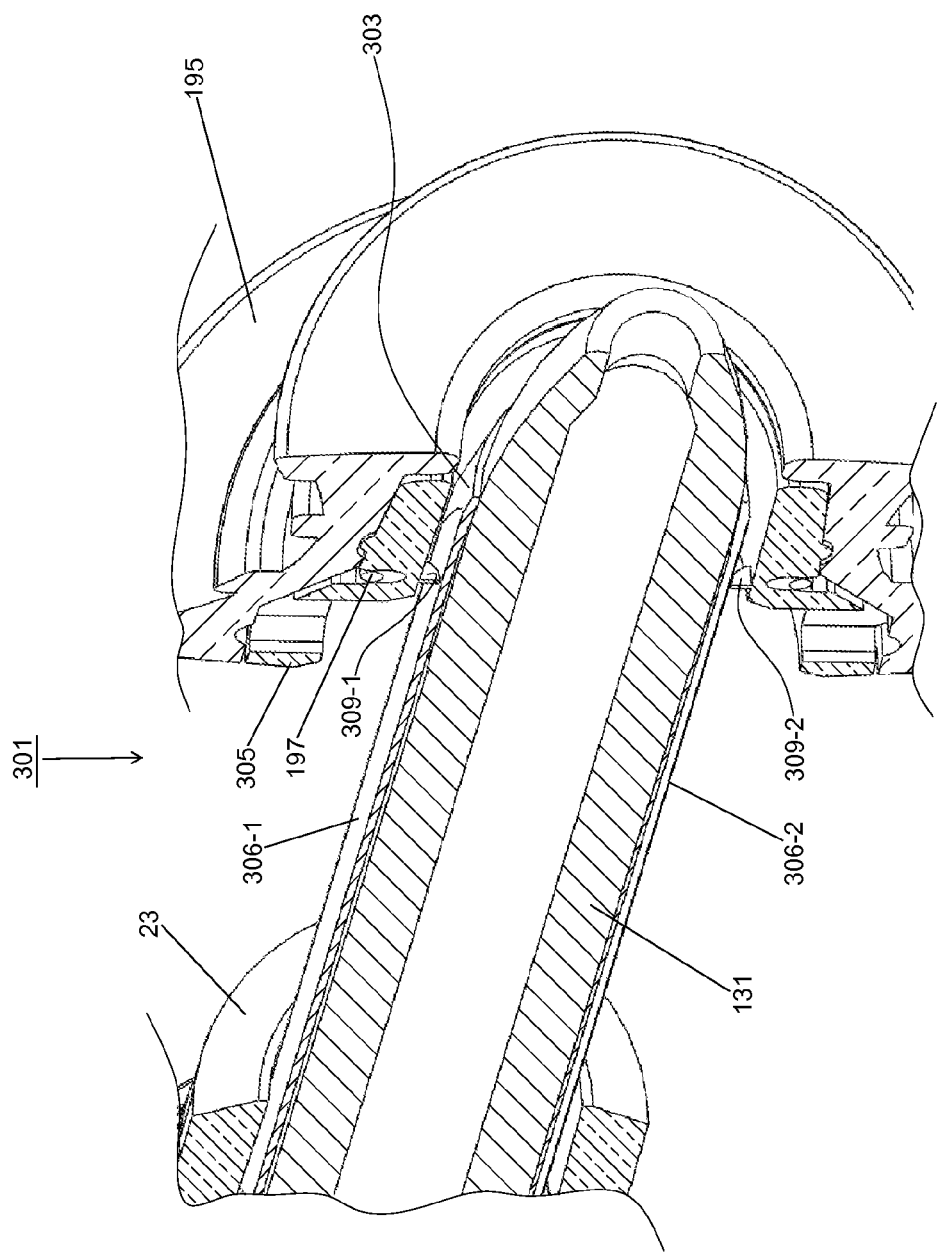
FIGS. 22(a) through 22(c) are fragmentary perspective, partly in section, fragmentary distal, and fragmentary section views, respectively, of a first alternate embodiment to the access device of FIG. 1.
Figure 22B:
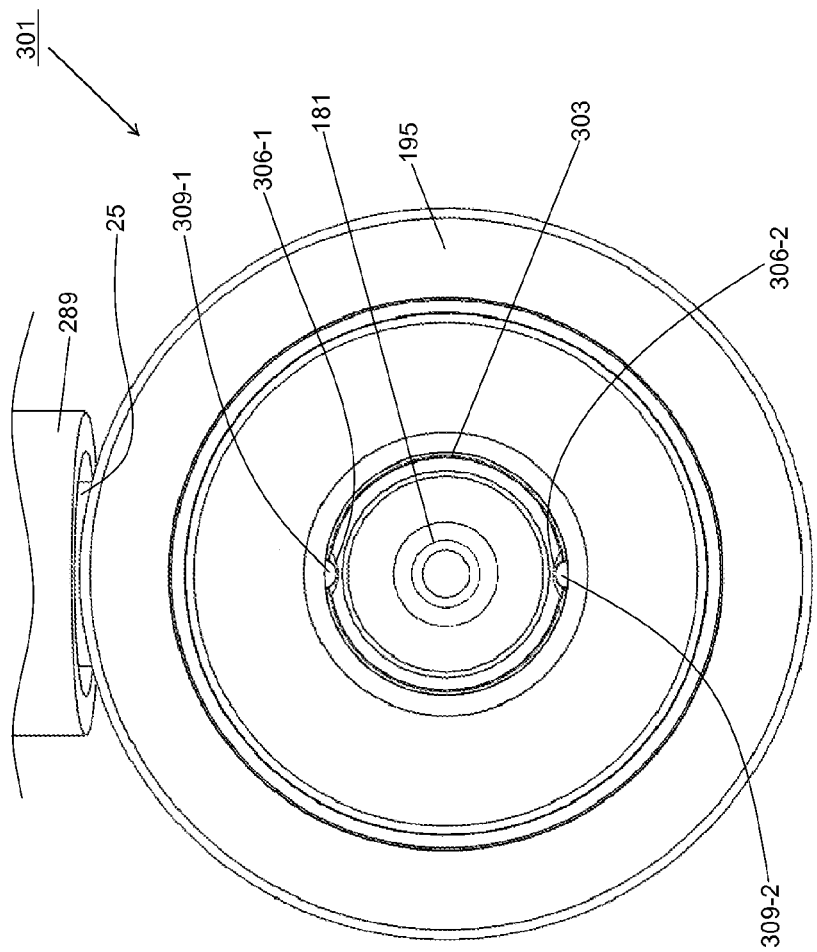
Figure 22C:
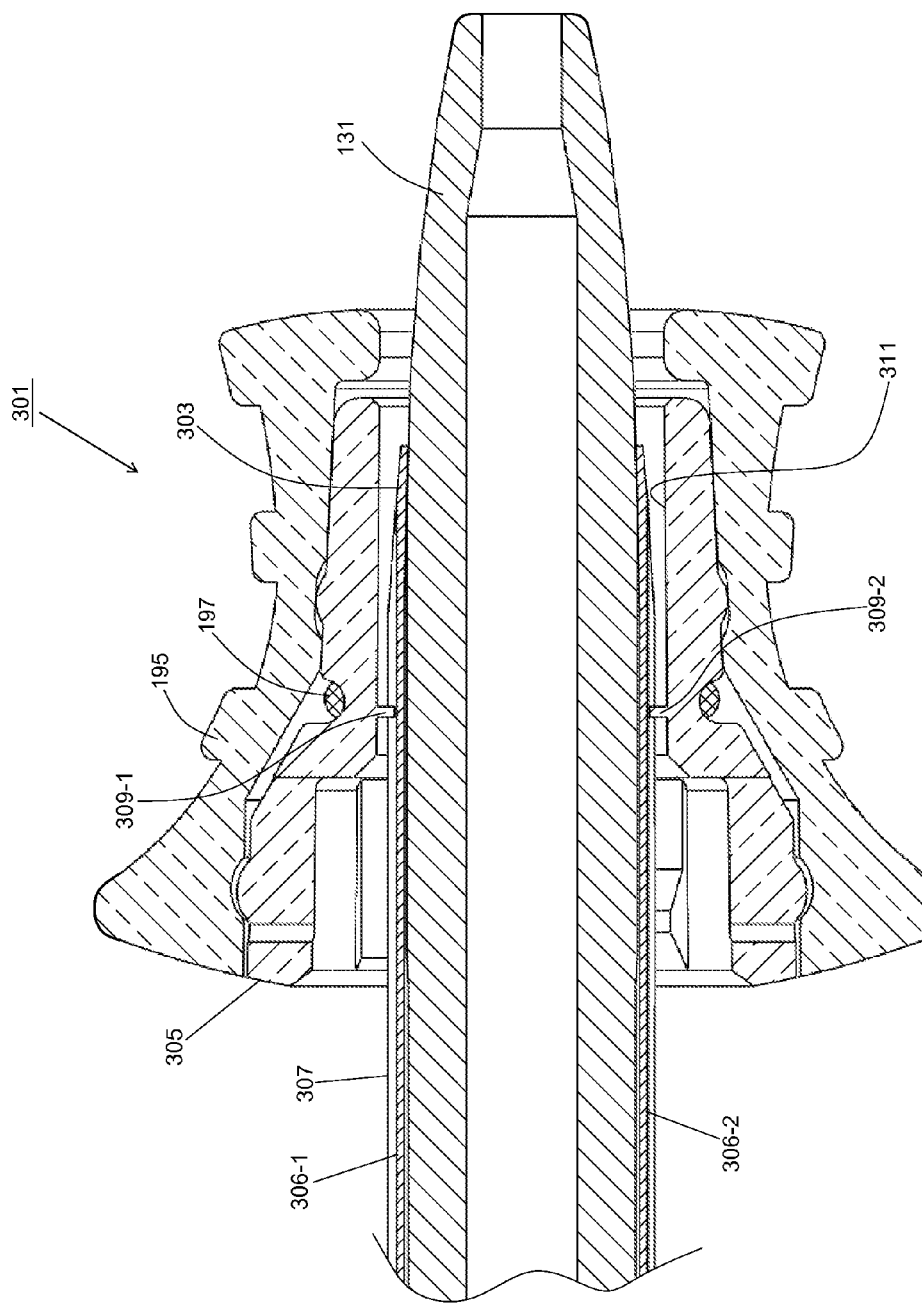

Referring now to FIGS. 22(a) through 22(c), there are shown various views of a first alternate embodiment of an access device 301. Access device 301 may be similar in most respects to access device 13, the principal difference between the two devices being that access device 301 may further include a mechanism for restraining rotational movement of the slide ring assembly relative to the sheath and the obturator in the absence of a retaining card. In the present embodiment, said mechanism may include a sheath 303 and an inner ring member 305. Sheath 303 and inner ring member 305 may be similar in most respects to sheath 61 and inner ring member 193, respectively, of device 13. A principal difference between sheath 61 and sheath 303 may be that sheath 303 may additionally include a pair of axially-extending grooves 306-1 and 306-2 provided in a side wall 307 at approximately opposing points along the circumference of side wall 307. A principal difference between inner ring member 193 and inner ring member 305 may be that inner ring member 305 may additionally include a pair of tongues 309-1 and 309-2 extending radially inwardly from a side wall 311, tongues 309-1 and 309-2 being appropriately positioned and appropriately dimensioned to mate with and to travel within grooves 306-1 and 306-2, respectively, in such a way as to restrain rotational movement of inner ring member 305 relative to sheath 61. It will be understood that the tongue and groove can be switched to be on opposite components from that described above. In addition, there may be one or more tongues and grooves.

Figure 23:
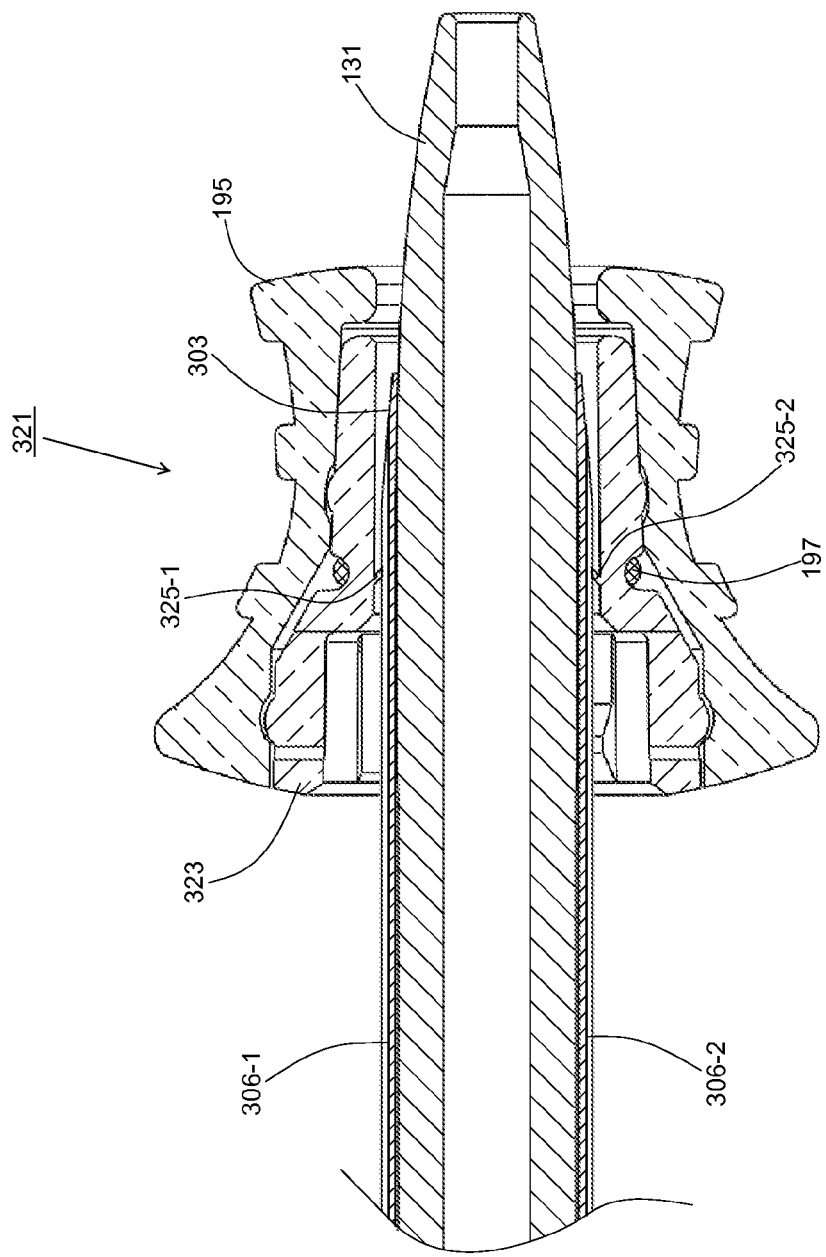
FIG. 23 is a fragmentary section view of a second alternate embodiment to the access device of FIG. 1.

Referring now to FIG. 23, there is shown an enlarged fragmentary longitudinal section view of a second alternate embodiment of an access device 321. Access device 321 may be similar in most respects to access device 301. A principal difference between the two devices may be that access device 321 may comprise barbs 325-1 and 325-2, instead of tongues 309-1 and 309-2 that mate with and are angled distally within grooves 306-1 and 306-2, respectively. The aforementioned arrangement of barbs 325-1 and 325-2 and grooves 306-1 and 306-2, respectively, can restrain facile distal movement of inner ring member 323 relative to sheath 303 and can restrain rotational movement of inner ring member 323 relative to sheath 303 but permits facile proximal movement of inner ring member 323 relative to sheath 303. It may be noted that, because the aforementioned arrangement restrains facile distal movement of inner ring member 323 relative to sheath 303, access device 321 need not additionally include tether 241.

Figure 24:
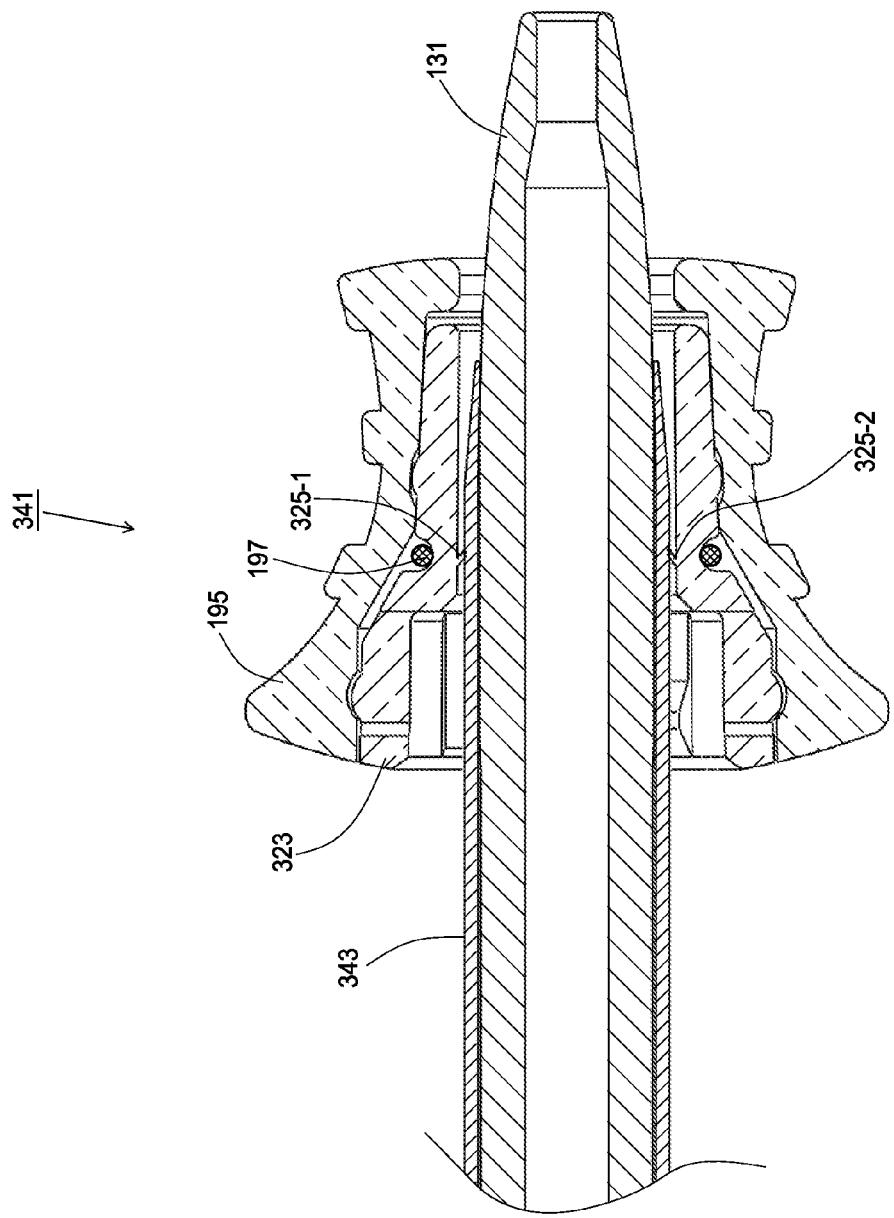
FIG. 24 is a fragmentary section view of a third alternate embodiment to the access device of FIG. 1.

Referring now to FIG. 24, there is shown an enlarged fragmentary longitudinal section view of a third alternate embodiment of an access device 341. Access device 341 may be similar in most respects to access device 321, but may be devoid of grooves. As can be appreciated, although the aforementioned arrangement of access device 341 may restrain facile distal movement of inner ring member 323 relative to sheath 343 while permitting facile proximal movement of inner ring member 323 relative to sheath 343, this arrangement does not provide any restraint of rotational movement of inner ring member 323 relative to sheath 343.

Figure 25:
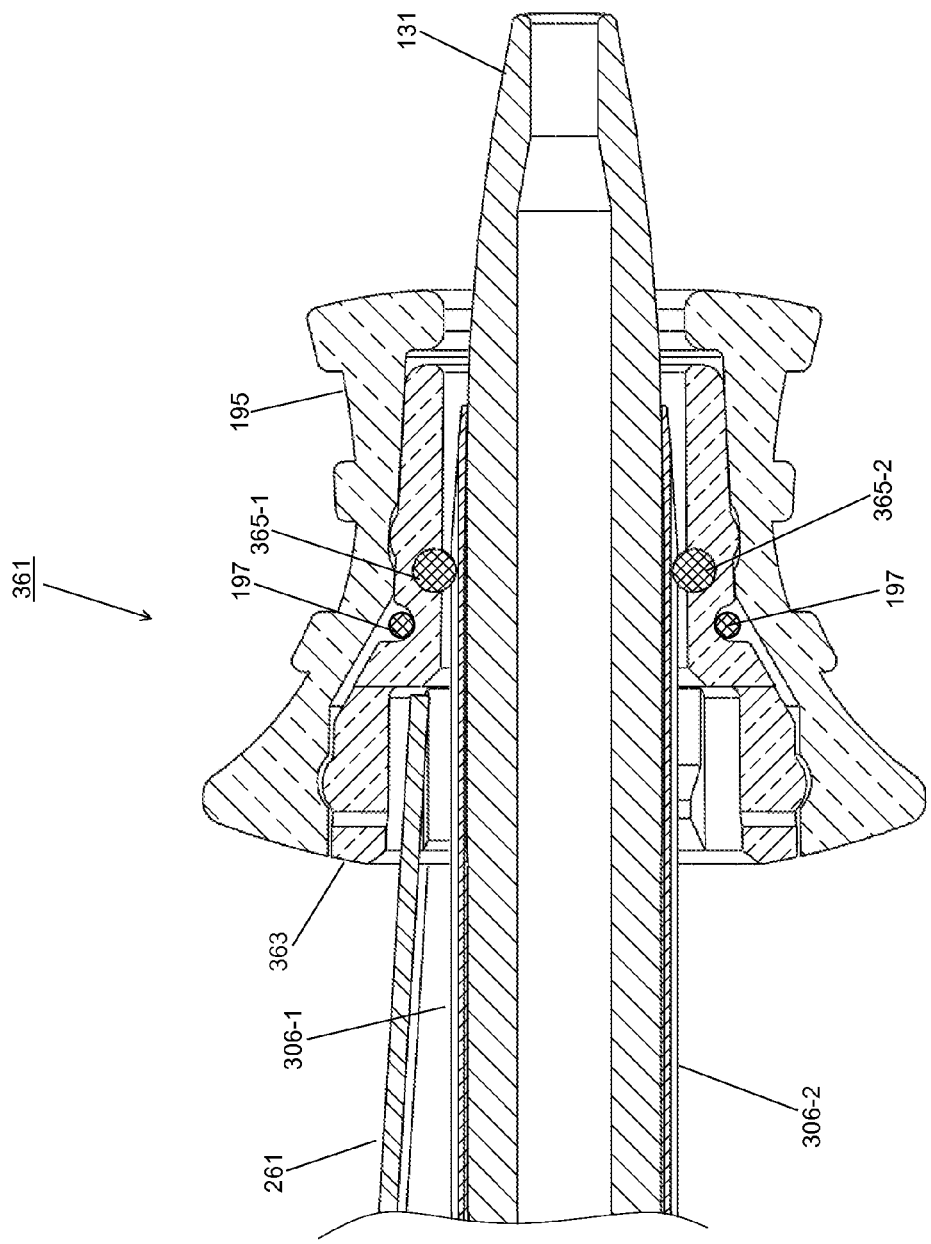
FIG. 25 is a fragmentary section view of a fourth alternate embodiment to the access device shown in FIG. 1.

Referring now to FIG. 25, there is shown an enlarged fragmentary longitudinal section view of a fourth alternate embodiment of an access device 361. Access device 361 may be similar in most respects to access device 301, but, instead of having a pair of tongues 309-1 and 309-2, access device 361 may comprise one or more one-way rollers. Two one-way rollers 365-1 and 365-2 can be coupled to inner ring member 363 and disposed within grooves 306-1 and 306-2, respectively, in such a manner as to permit facile proximal movement of inner ring member 363 relative to sheath 303 while restraining facile distal movement and facile rotational movement of inner ring member 363 relative to sheath 303.

Figure 26:
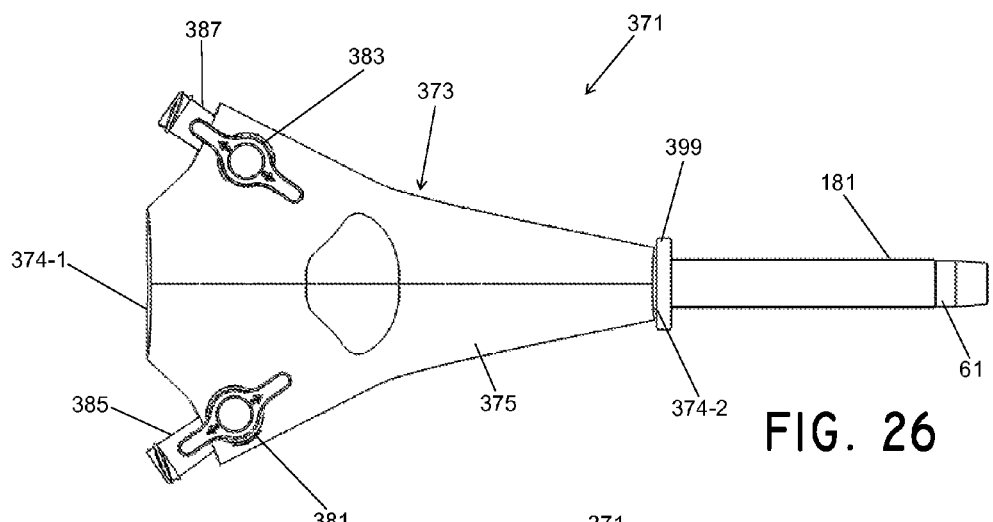
FIG. 26 is a top view of a fifth alternate embodiment to the access device shown in FIG. 1, the access device being shown with its slide ring assembly in a proximal position and with its protective sleeve everted over its sheath.
Figure 27:
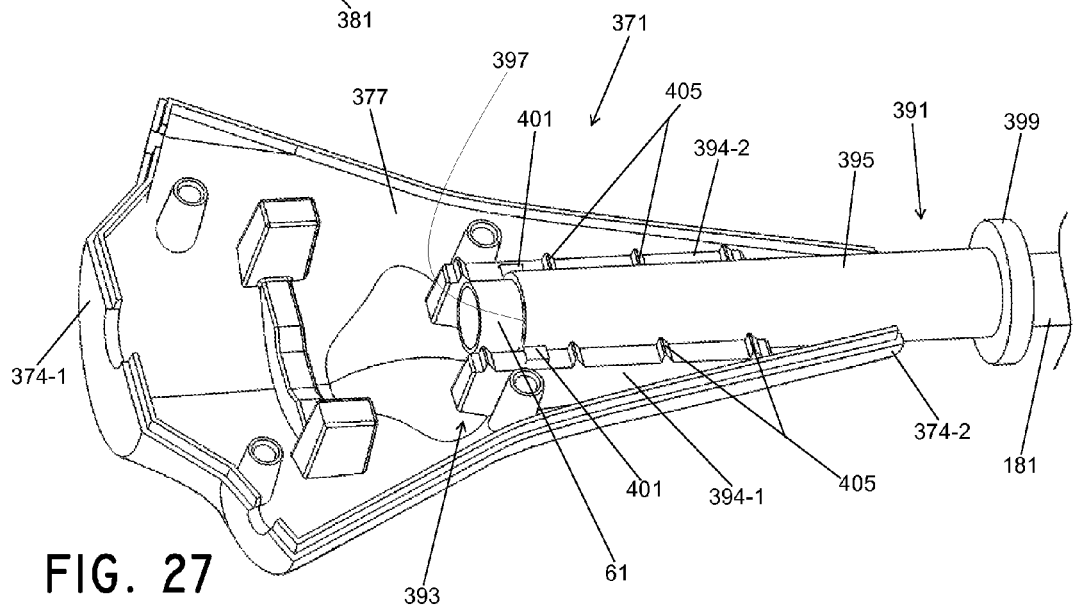
FIG. 27 is an enlarged fragmentary perspective view of the access device of FIG. 26, with one of the two housing portions, the two stopcocks, and certain of the internal components not being shown.

Referring now to FIGS. 26 and 27, there are shown top and enlarged fragmentary perspective views, respectively, of a fifth alternate embodiment of an access device 371. Access device 371 can comprise a housing assembly, a sheath assembly, and a fluid control system. Access device 371 may be similar in certain respects to access device 13. One difference between the two access devices may be that, whereas access device 13 may include hub 21 and handle 71, access device 371 may instead include a housing 373. Housing 373 may be a generally wing-shaped structure including a proximal end 374-1, which may be comparatively wider, and a distal end 374-2, which may be comparatively narrower. Housing 373 may comprise a first housing portion 375 and a second housing portion 377. Each of first housing portion 375 and second housing portion 377 may be made of a hard, medical-grade polymer or a similarly suitable material. First housing portion 375 and second housing portion 377 may be joined together by screws (not shown) or other suitable means.

Preferably, housing 373 of access device 371 is dimensioned to have a greater length, as measured from proximal end 374-1 to distal end 374-2, than the corresponding length of the combination of hub 21 and handle 71 of access device 13. Due in part to such an increased length, access device 371 may enable an operator to keep his hands farther away from a patient than may be the case with access device 13. This may be desirable insofar as it may improve patient comfort and may reduce the likelihood of urinary tract infections resulting from the operator contacting the patient's anatomy and then cross-contaminating access device 371 and/or tools inserted through access device 371.

Another difference between access device 371 and access device 13 may be that, whereas access device 13 may comprise a single stopcock valve 287, which may be a three-way stopcock valve, access device 371 may instead comprise a pair of stopcock valves 381 and 383, each of which may be a two-way stopcock valve. Valve 381, which may be mounted in first housing portion 375, may be used to control the flow of fluid through a first port 385 disposed on one side of proximal end 374-1 of housing 373. Valve 383, which may be mounted in first housing portion 375, may be used to control the flow of fluid through a second port 387 disposed on another side of proximal end 374-1 of housing 373. One of ports 385 and 387 may be connected, for example, to a fluid source so that fluid may be delivered to the patient, and the other of ports 385 and 387 may be connected, for example, to a drain or similar fluid collection device so that fluid may be drained from the patient.

Due in part to the design of housing 373 and the placement of stopcock valves 381 and 383 relative to housing 373, an operator may hold access device 371 and may operate stopcocks 381 and 383 using only one hand. This is in contrast with access device 13, where for most operators at least one hand may be needed to hold handle 71 and another hand may be needed to operate stopcock 287. The fact that access device 371 may be held and operated with a single hand may be desirable as it may reduce the likelihood of cross-contamination, as well as simplifying fluid control.

Still another difference between access device 371 and access device 13 may be that, whereas device 13 may comprise a slide ring assembly 191 and one or more restraining mechanisms 241 and 261, device 371 may instead comprise a slide assembly 391 and a ratchet track 393. Slide assembly 391 may comprise a slide 395, which may be a tubular member made of a hard, medical-grade polymer or similarly suitable material. Slide 395, which may be coaxially mounted over sheath 61, may be shaped to include a proximal end 397 and a distal end 399. Proximal end 397 may be shaped to include a pair of spring clips 401 substantially evenly spaced on the outer circumference of slide 395. Distal end 399 may be in the shape of an outwardly-extending circumferential flange. Distal end 399 may be used to engage slide 395 so that slide 395 may be slid relative to sheath 61. (Such sliding may be effected either by gripping distal end 399 in one hand and manually sliding slide 395 proximally over sheath 61 or, more preferably, by pressing distal end 399 against the patient and using the patient's body, such as the patient's meatus, to cause slide 395 to slide proximally over sheath 61.) Slide assembly 391 may further comprise a mechanism (not shown) disposed within slide 395 proximate to distal end 399 for retaining the proximal end of protective sleeve 181.

Ratchet track 393 may comprise a pair of rails 394-1 and 394-2. Rails 394-1 and 394-2, which may be integrally formed with second housing portion 377 and disposed within the interior of housing 373, may be arranged parallel to one another and may be positioned so as to be on opposite sides of sheath 61 and slide 395. Rails 394-1 and 394-2 may be dimensioned and positioned so that spring clips 401 may slide thereover as slide 395 is moved proximally. A plurality of detents 405 may be formed on rails 394-1 and 394-2. Detents 405 may be shaped to permit facile proximal movement of clips 401 over detents 405 but to prevent facile distal movement of clips 401 over detents 405. In this manner, slide assembly 391 may be effectively permitted to move only proximally, with distal and rotational movement being constrained by ratchet track 393. As can be appreciated, the number and spacing of detents 405 on rails 394-1 and 394-2 may be modified as desired. For example, detents 405 may be positioned at regular or irregular intervals along the entire length of travel of slide assembly 391 or may be positioned at regular or irregular intervals only at a latter part of the length of travel of slide assembly 391.

As can be appreciated, access device 371 may be shaped so that those portions thereof that may come into contact with the patient, such portions including, for example, distal end 399 of slide 395 and/or distal end 374-2 of housing 373, may be relatively smooth, with a minimal number of sharp edges. In this manner, irritation of the patient caused by contact with access device 371 may be minimized.

Although access device 371 is shown without an obturator, access device 371 may include an obturator, such as an obturator similar to obturator 131.

Figure 28:
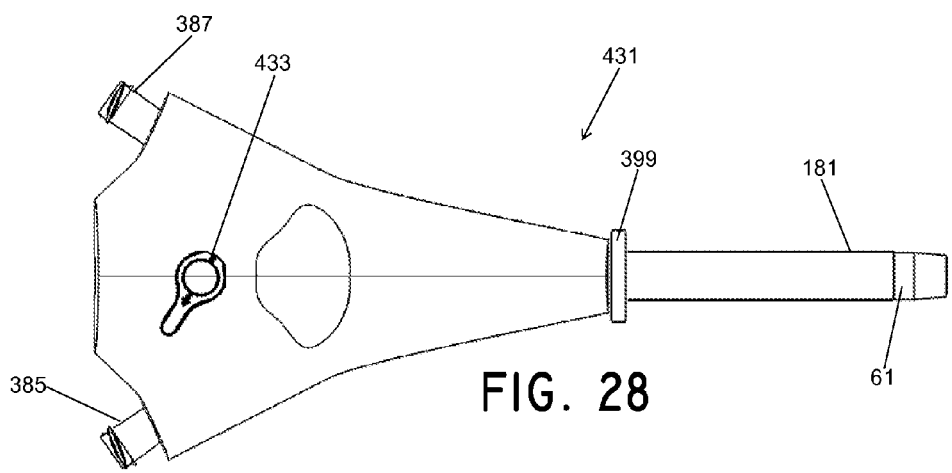
FIG. 28 is top view of a sixth alternate embodiment to the access device shown in FIG. 1, the access device being shown with its slide ring assembly in a proximal position and with its protective sleeve everted over its sheath.

Referring now to FIG. 28, there is shown a top view of a sixth alternate embodiment of an access device 431. Access device 431 can comprise a housing assembly, a sheath assembly, and a fluid control system. Access device 431 may be similar in certain respects to access device 371. One difference between the two access devices may be that, whereas access device 371 may comprise stopcock valve 381 for controlling the flow of fluid through first port 385 and stopcock valve 383 for controlling the flow of fluid through second port 387, device 431 may instead comprise a single stopcock valve 433. Stopcock valve 433 may be a three-way stopcock valve that may be used to control the flow of fluid both through port 385 and through port 387, for example, by having a first position in which port 385 is open and port 387 is closed, a second position in which port 387 is open and port 385 is closed, and a third position in which both ports 385 and 387 are closed.

Although access device 431 is shown without an obturator, access device 431 may include an obturator, such as an obturator similar to obturator 131.

Figure 29A:
FIGS. 29(a) through 29(c) are top, side, and perspective views, respectively, of a seventh alternate embodiment to the access device shown in FIG. 1, the access device being shown with its slide ring assembly in a proximal position and with its protective sleeve everted over its sheath.
Figure 29B:
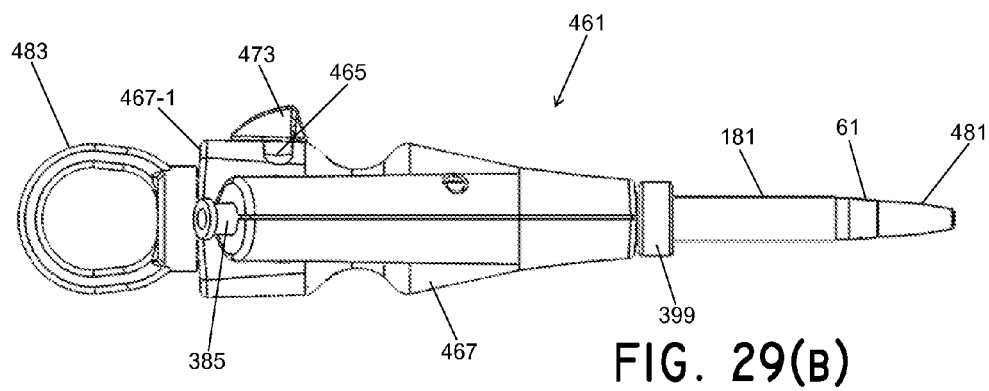
Figure 29C:
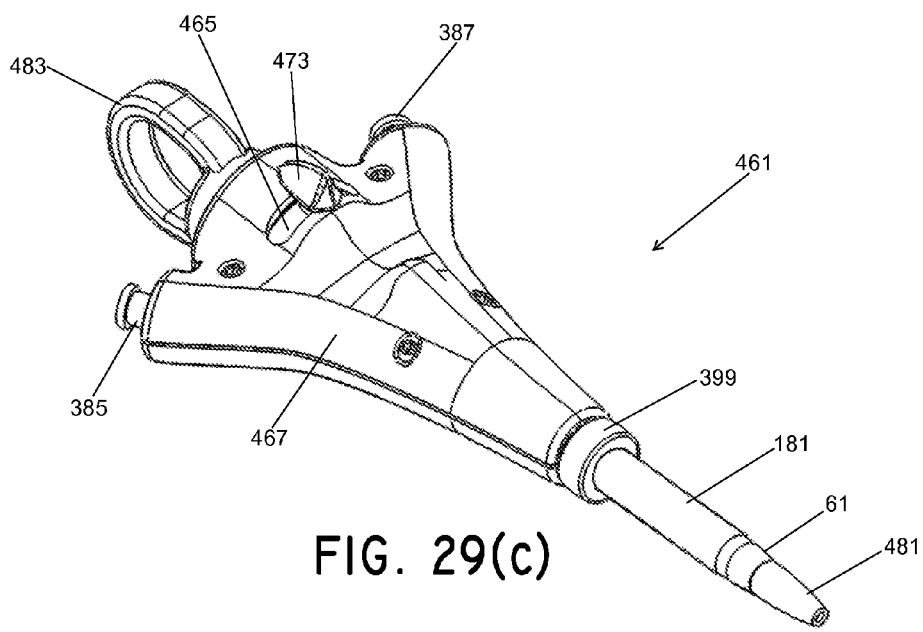

Referring now to FIGS. 29(a) through 29(c), there are shown top, side, and perspective views, respectively, of a seventh alternate embodiment of an access device 461. Access device 461 can comprise a housing assembly, a sheath assembly, and a fluid control system. Access device 461 may be similar in certain respects to access device 431. One difference between the two access devices may be that, whereas access device 431 may comprise stopcock 433 for controlling the flow of fluid through ports 385 and 387, access device 461 may instead comprise a cam-actuated valve mechanism 463, extending through a slot 465 in a housing 467, for controlling the flow of fluid through ports 385 and 387.

Figure 30:
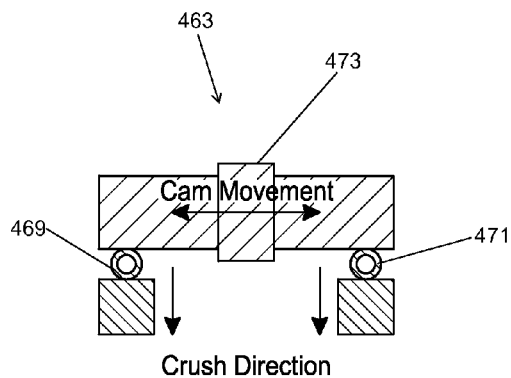
FIG. 30 is a simplified schematic representation of the cam-actuated valve mechanism of the access device shown in FIGS. 29(a) through 29(c)

Referring also now to FIG. 30, there is shown a simplified schematic representation of a fluid control system 463 such as a cam-actuated valve mechanism 463. The cam-actuated valve mechanism 463 may comprise a first compliant tube 469, a second compliant tube 471, and a cam 473. First compliant tube 469 may be connected at one end to port 385 and at an opposite end to sheath 61, and second compliant tube 471 may be connected at one end to port 387 and at an opposite end to sheath 61. Cam 473, which may be accessible to an operator through a slot 465 provided in a housing 467 of access device 461, may be used selectively to pinch shut or to keep open first compliant tube 469 and second compliant tube 471. Tubes 469 and 471 and cam 473 may be arranged relative to one another so that cam 473 may axially compress tubes 469 and 471 positioned on the same side of cam 473. Tubes 469 and 471 may be compressed distally (away from a proximal end 467-1 of housing 467). Cam 473 may be mounted coaxial to sheath 61 (see FIGS. 29(a) through 29(c) for sheath 61). Cam 473 may be designed to dependently control each valve, providing 3 functions: fill, drain, and closed (i.e., no flow). A fourth "flush" position may be included—where both the inlet and the outlet are open at the same time.

Another difference between access device 461 and access device 431 may be that access device 461 may further comprise an obturator 481 and an obturator handle 483. Obturator 481 may be similar to obturator 131. Obturator handle 483 may differ from obturator handle 151 in that obturator handle 483 may comprise a D-ring. The non-circular shape of a D-ring may enable a user alternately to rest his thumb inside the D-ring during insertion of access device 461 into a patient and to accommodate his forefinger being inserted through the D-ring to facilitate removal of obturator 481 from the patient.

It should be understood that access device 461 could include, instead of obturator handle 483, an obturator handle like obturator handle 151. Alternatively, access device 461 could simply not include an obturator or obturator handle.

Figure 31:
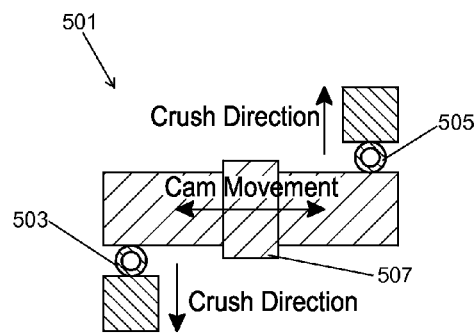
FIG. 31 is a simplified schematic representation of a first alternate embodiment to the cam-actuated valve mechanism shown in FIG. 30.
Figure 32A:
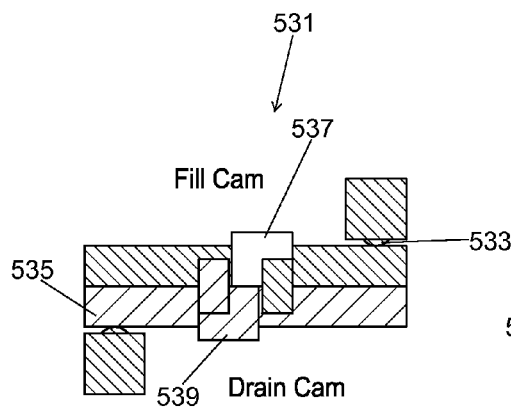
FIGS. 32(a) through 32(d) are simplified schematic representations of a second alternate embodiment to the cam-actuated valve mechanism shown in FIG. 30, the cam-actuated valve mechanism being shown in closed, fill, drain, and flush positions, respectively.
Figure 32B:
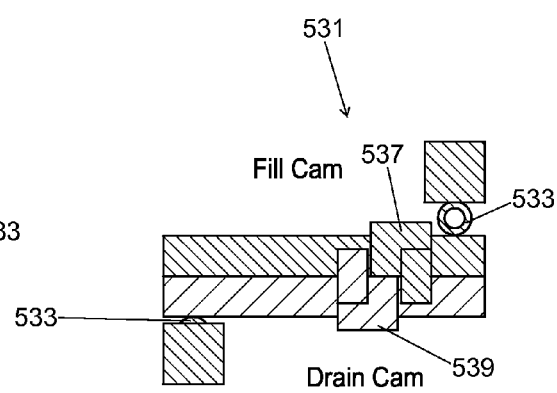
Figure 32C:
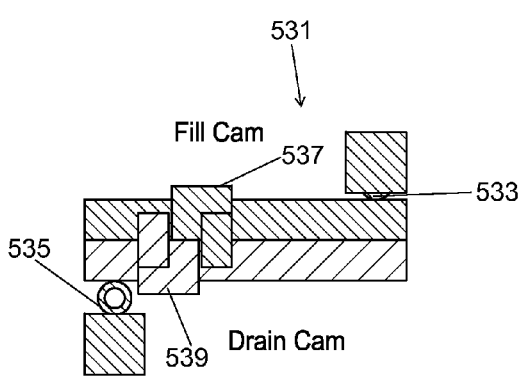
Figure 32D:
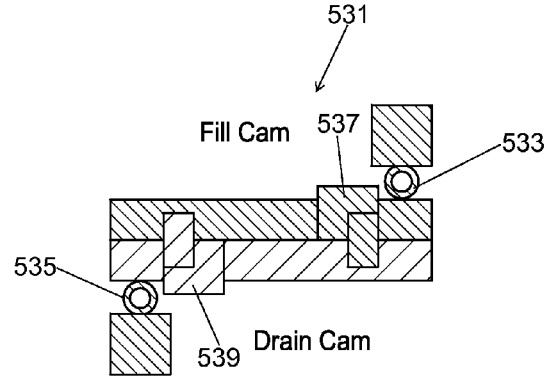

Referring now to FIG. 31, there is shown a simplified schematic representation of a fluid control system 501 such as a first alternate embodiment of a cam-actuated valve mechanism 501. Cam-actuated valve mechanism 501, which may be a dependent-control, double-sided, axially-compressing mechanism, may comprise a first compliant tube 503, a second compliant tube 505, and a cam 507. As can be seen, first compliant tube 503 and second compliant tube 505 may be positioned on opposite sides of cam 507 in cam-actuated valve mechanism 501.

Referring now to FIGS. 32(*a*) through 32(*d*), there are shown simplified schematic representations of a fluid control system 531 such as a second alternate embodiment of a cam-actuated valve mechanism 531. Cam-actuated valve mechanism 531 may include a first compliant tube 533, a second compliant tube 535, a first cam 537, and a second cam 539. First cam 537 may be used to pinch shut first compliant tube 533, and second cam 539 may be used to pinch shut second compliant tube 535. First cam 537 and second cam 539 may be independently operable. In this manner, cam-actuated valve mechanism 531 may be operated to assume any one of a "closed" position as shown in FIG. 32(*a*), a "fill" position as shown in FIG. 32(*b*), a "drain" position as shown in FIG. 32(*c*), and a "flush" position as shown in FIG. 32(*d*).

Referring now to FIGS. 33(*a*) through 33(*c*), there are shown simplified schematic representations of a fluid control system 571 such as a third alternate embodiment of a cam-actuated valve mechanism 571. Cam-actuated valve mechanism 571 may include a first compliant tube 573, a second compliant tube 575, and a linear cam 577. Linear cam 577 may be used to pinch shut one or both of first compliant tube 573 and second compliant tube 575. In this manner, cam-actuated valve mechanism 571 may be operated to assume any one of a "closed" position as shown in FIG. 33(*a*), a "fill" position as shown in FIG. 33(*b*), and a "drain" position as shown in FIG. 33(*c*).

It should be appreciated that fluid control systems with a cam-actuated valve mechanism may operate in a radial direction, instead of in an axial direction as disclosed above. Such a cam may be used to pinch shut the compliant tubes towards the central axis or away from such an axis. An example of a fluid control system with a radially-compressing, cam-actuated valve mechanism is shown in FIG. 34 and is represented generally by reference numeral 591. Cam-actuated valve mechanism 591, which may be designed to be inwardly-compressing, may include a first compliant tube 593, a second compliant tube 595, and a cam 597. Another example of a fluid control system with a radially-compressing, cam-actuated valve mechanism is shown in FIG. 35 and is represented generally by reference numeral 611. Cam-actuated valve mechanism 611, which may be designed to be outwardly-compressing, may include a first compliant tube 613, a second compliant tube 615, and a cam 617.

In any cam configuration, including the various cam configurations described above, the cam may be detented at a flow position to provide tactile feedback that the cam is in a desired position. Also, instead of positioning the selector switch of the cam at the top of the housing, the switch may be located on the bottom of the housing or at any point along the travel of the cam. In addition, in any cam configuration disclosed herein, the cam may be constructed to provide more than merely a "flow" position and a "no-flow" position, but rather, to additionally include one or more "intermediate-flow" positions having flow rates intermediate to that of the "no-flow" and "flow" positions.

Moreover, in the embodiments described herein, the cam face may slide directly across the compliant tubes. Such sliding may create an undesirable amount of friction, thereby requiring too much force to move the cam selector switch. To reduce the friction at this interface, pushrods may be used to follow the cam face and to translate its displacement into pure linear motion. Such pushrods would then pinch the compliant tubes without shearing across them, thereby reducing the amount of friction generated.

Figure 36A:
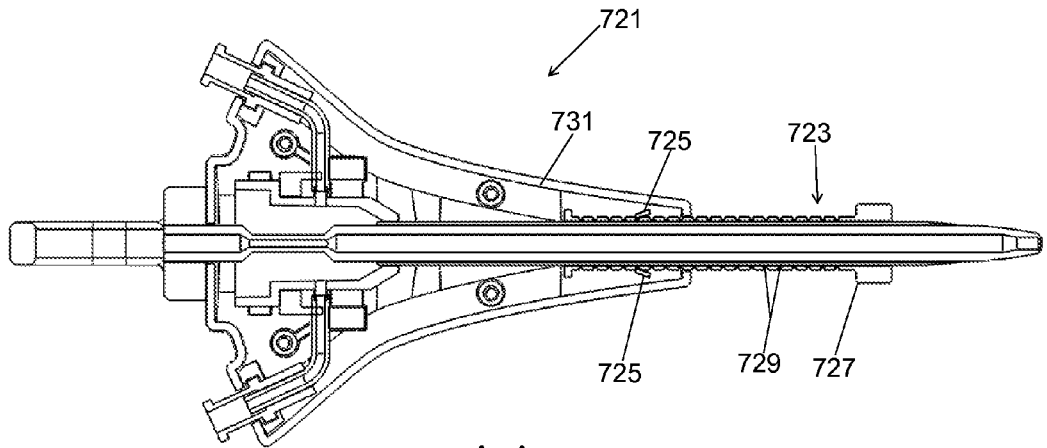
FIGS. 36(a) through 36(c) are partly in section top, partly in section enlarged fragmentary top, and partly in section perspective views, respectively, of an eighth alternate embodiment to the access device shown in FIG. 1, the access device being shown without one of its two housing portions and without its protective sleeve.
Figure 36B:
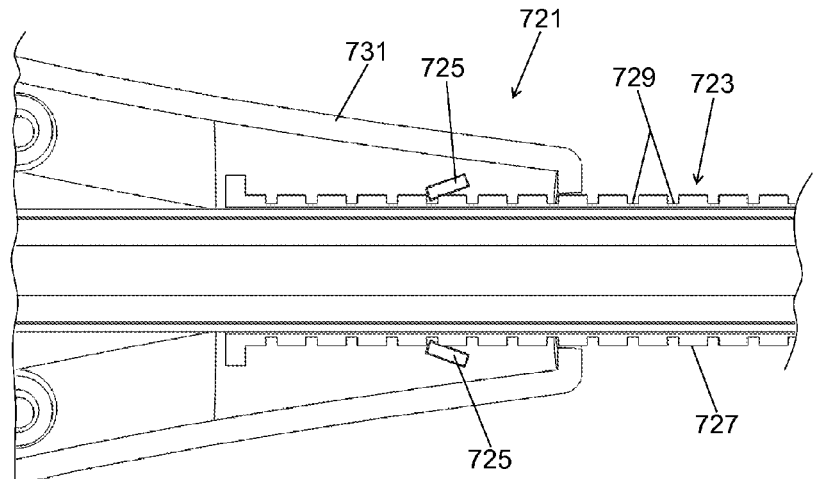
Figure 36C:
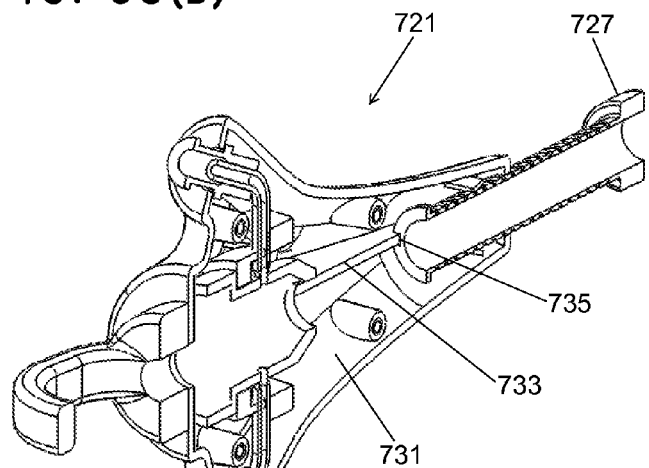

Referring now to FIGS. 36(*a*) through 36(*c*), there are shown various views of an eighth alternate embodiment of an access device 721. The access device 721 can comprise a housing assembly, a sheath assembly, and a fluid control system. Access device 721 may be similar in certain respects to access device 431. One difference between the two access devices may be that, whereas access device 431 may include slide assembly 391 and ratchet track 393, access device 721 may include a slide assembly 723 and a pair of bosses 725. Slide assembly 723 may comprise a slide 727, which may be a tubular member made of a hard, medical-grade polymer or a similarly suitable material. Slide 727 may be provided with a plurality of notches 729, which may be positioned at regular intervals along substantially the entire length of travel of slide 727. Bosses 725, which may be integrally formed on a housing portion 731 of access device 721, may be oriented to engage notches 729 in such a way as to permit facile proximal movement of slide 727 while preventing facile distal movement of slide 727. Rotational movement of slide 727 relative to the housing of access device 721 may be constrained by an axially-extending rib 733 provided on the interior surface of housing portion 731 that may travel within a corresponding axially-extending notch 735 on slide 727. (An additional rib may be provided on the housing portion that is not shown, and a corresponding notch may be provided in the portion of slide 727 that is not shown.) Slide assembly 723 may further comprise a mechanism (not shown) disposed within slide 727 for retaining the proximal end of the protective sleeve (not shown).

It is to be understood that, although notches 729 are disclosed above as being positioned at regular intervals along substantially the entire length of slide 727, notches 729 may be positioned at irregular intervals and/or may be positioned only along a portion of the length of travel of slide 727.

Figure 37A:
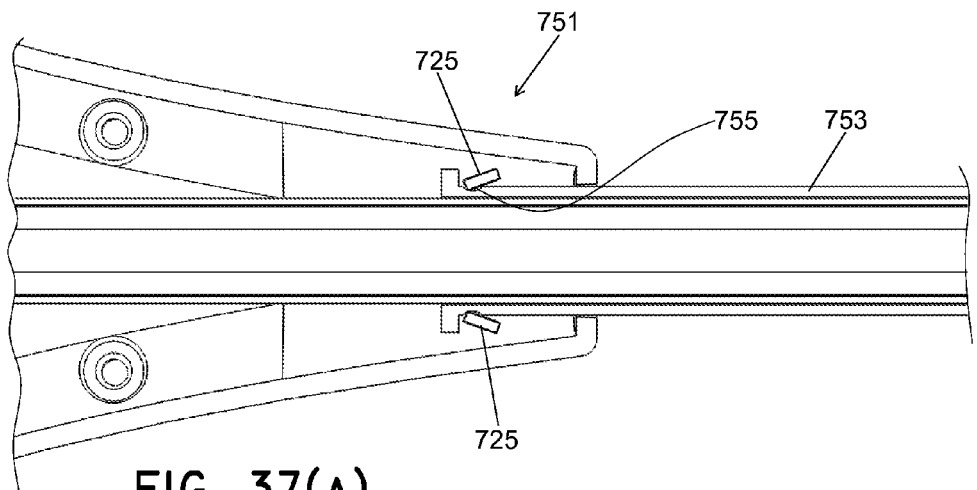
FIGS. 37(a) and 37(b) are top views, partly in section, of a ninth alternate embodiment to the access device shown in FIG. 1, the access device being shown with its slide in its distal and proximal positions, respectively, the access device also being shown without one of its two housing portions and without its protective sleeve.
Figure 37B:
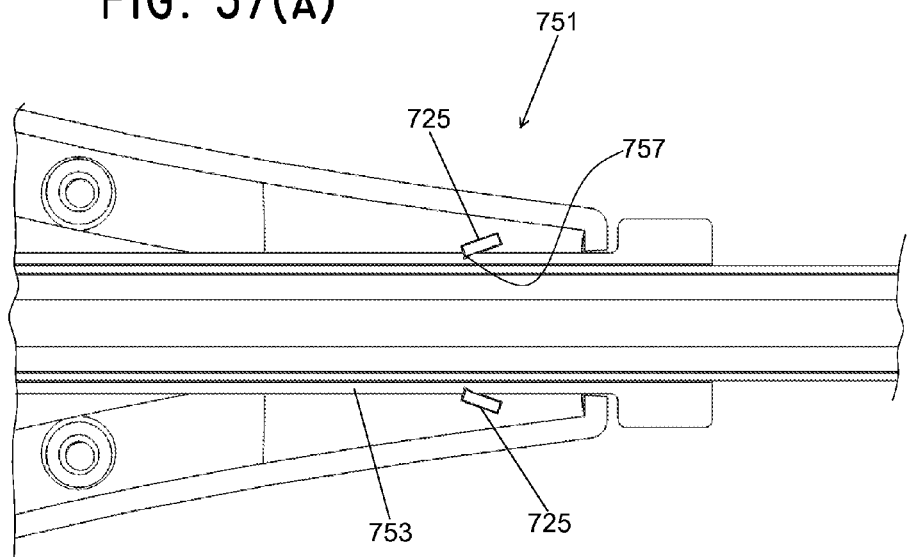
Figure 38:
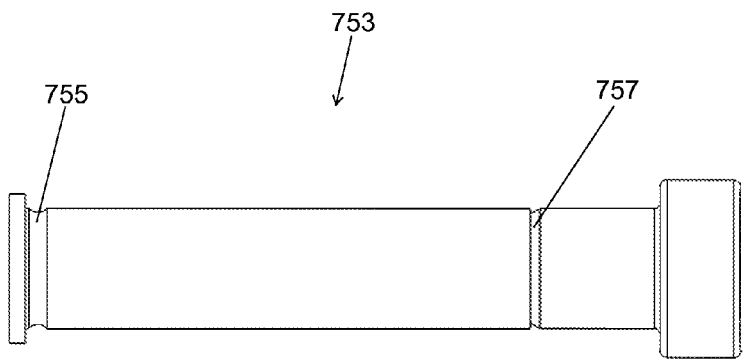
FIG. 38 is a top view of the slide shown in FIGS. 37(a) and 37(b)

For example, referring now to FIGS. 37(*a*) and 37(*b*), there are shown various views of a ninth alternate embodiment of an access device 751. Access device 751 can comprise a housing assembly, a sheath assembly, and a fluid control system. Access device 751 may differ from access device 721 in that, whereas access device 721 may include slide 727 having notches 729 positioned at regular intervals substantially along its entire length, access device 751 may instead include a slide 753 (shown separately in FIG. 38) including only a proximal notch 755 and a distal notch 757. As seen best in FIG. 37(*a*), with slide 753 in its distal position (i.e., before insertion of access device 751 into a patient), bosses 725 may engage proximal notch 755 of slide 753. Proximal notch 755 may be shaped to provide only slight resistance to movement of slide 753 in either axial direction. A purpose of the proximal notch 755 is to position slide 753 during assembly and to keep slide 753 in its distal position before deployment of access device 751. During insertion of access device 751 into a patient, the slide 753 can be moved past proximal notch 755 with only slight resistance from bosses 725. There may be clearance between bosses 725 and notch 755 to prevent bosses 725 and slide 753 from permanently deforming at elevated temperatures or after extended periods of time. As slide 753 moves between proximal notch 755 and distal notch 757, bosses 725 may deflect and may apply light pressure to the outer diameter of slide 753 due to an interference fit. When slide 753 is in its proximal position (i.e., upon full insertion of access device 751 into a patient), bosses 725 may snap into distal notch 757, which may be beveled or otherwise positioned to lock bosses 725 in place.

Figure 39A:
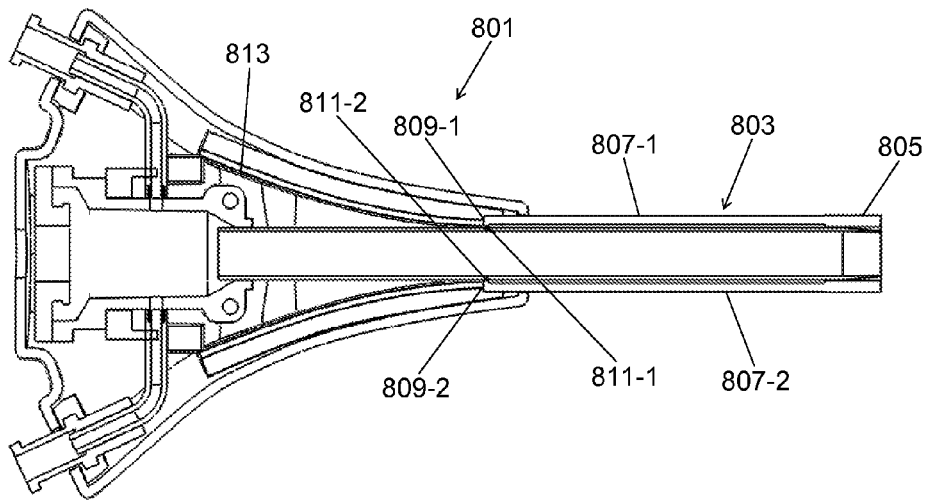
FIGS. 39(a) and 39(b) are top views, partly in section, of a tenth alternate embodiment to the access device shown in FIG. 1, the access device being shown with its slide in its distal and proximal positions, respectively, the access device also being shown without one of its two housing portions and without its protective sleeve.
Figure 39B:
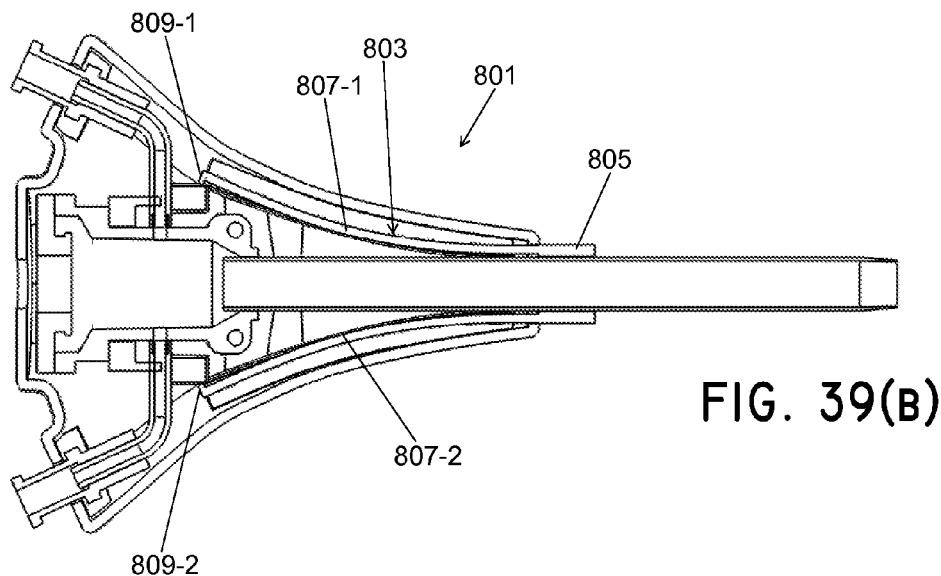
Figure 40:
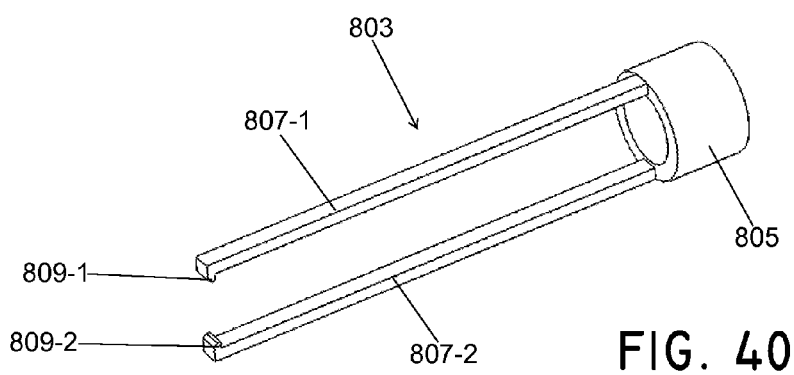
FIG. 40 is a perspective view of the slide shown in FIGS. 39(a) and 39(b)
Figure 41A:
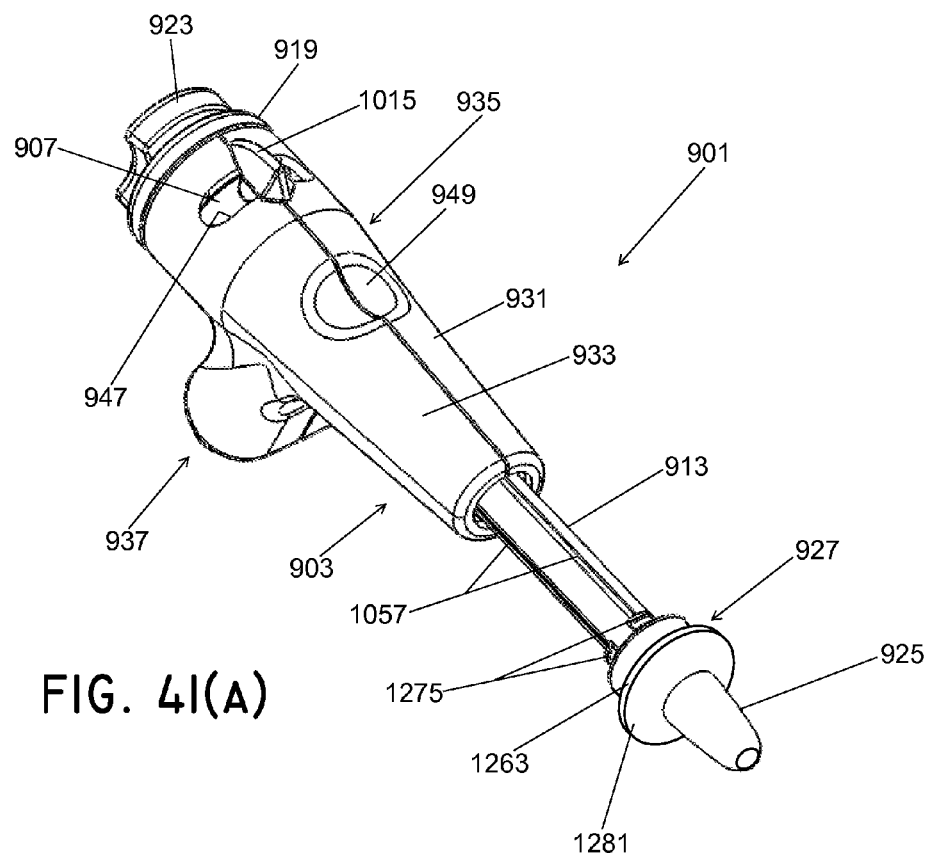
Figure 41B:
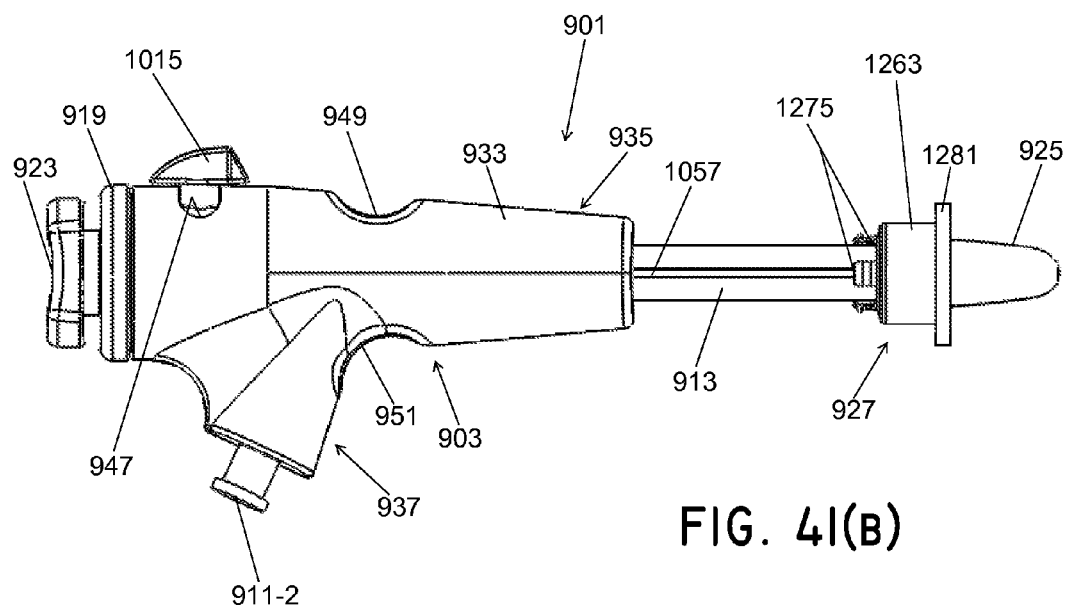
Figure 41C:
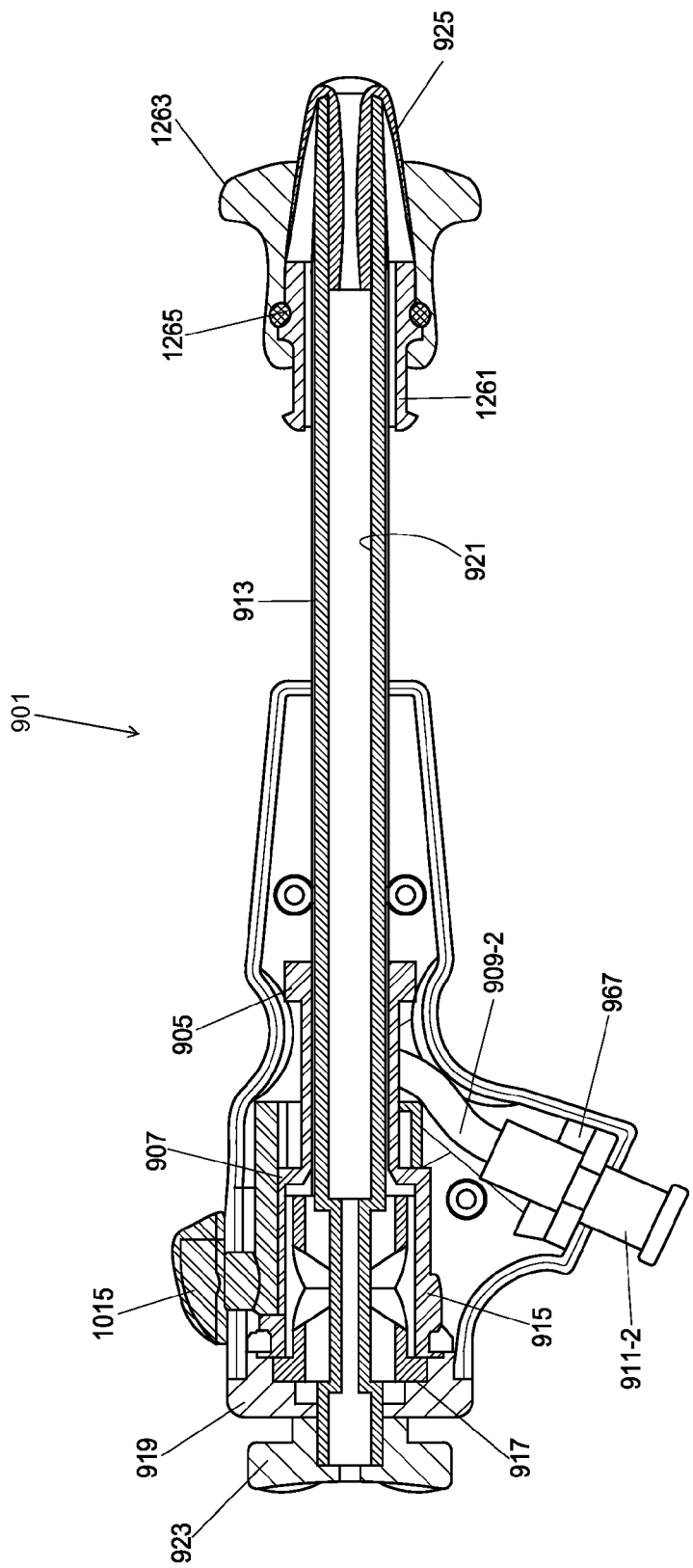

Referring now to FIGS. 39(a) and 39(b), there are shown various views of a tenth alternate embodiment of an access device 801. Access device 801 can comprise a housing assembly, a sheath assembly, and a fluid control system. Access device 801 may differ from access device 751 in that, whereas access device 721 may include slide 753, access device 801 may instead include a slide 803 (also shown separately in FIG. 40). Slide 803 may be shaped to include a ring portion 805 and a pair of angularly deflectable or splaying legs 807-1 and 807-2 extending from ring portion 805. As seen best in FIG. 39(a), with slide 803 in its distal position (i.e., before insertion of access device 801 into a patient), feet 809-1 and 809-2 at the ends of legs 807-1 and 807-2, respectively, may engage notches 811-1 and 811-2, respectively, provided on the exterior surface of a sheath 813. During insertion of access device 801 into a patient, feet 809-1 and 809-2 may be easily moved proximally past notches 811-1 and 811-2 with only slight resistance and may move proximally along an outwardly-tapering track 813 formed along the inside of the housing of access device 801. When slide 803 is in its proximal position (i.e., upon full insertion of access device 803 into a patient), feet 809-1 and 809-2 may engage the proximal end of track 813 in such a way as to lock slide 803 in place.

One advantage of access device 801, as compared to access devices like access device 751, is that splaying legs 807-1 and 807-2 may permit access device 801 to have a reduced axial length.

Referring now to FIGS. 41(a) through 41(d), there are shown various views of an eleventh alternate embodiment of an access device 901. Access device 901 can include a housing assembly 903, a sheath assembly, and a fluid control system. The sheath assembly may include a cannula or sheath 913, a protective sleeve 925, a slide ring assembly 927, a dilator or obturator 921, and an obturator handle 923. The fluid control system can include a hub 905, a cam 907, a pair of compliant tubes 909-1 and 909-2, a pair of fluid connectors 911-1 and 911-2, a valve assembly 915, a seal 917, and a cap 919. Each of the foregoing components will now be discussed in detail.

Figure 43A:
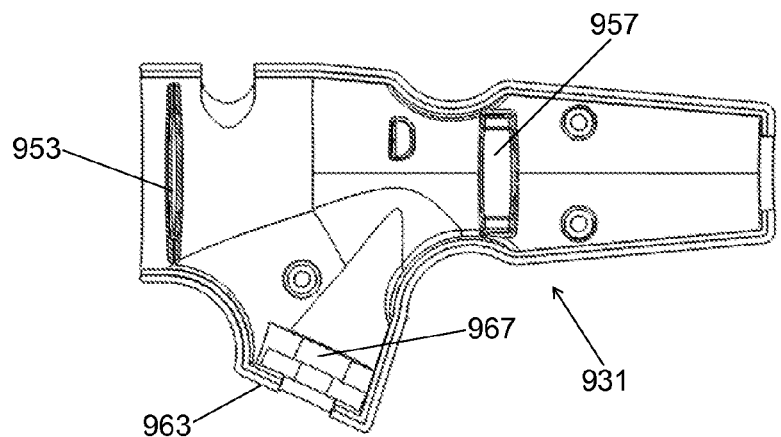
FIGS. 43(a) and 43(b) are side and perspective views, respectively, of the left housing half shown in FIGS. 42(a) and 42(b)
Figure 43B:
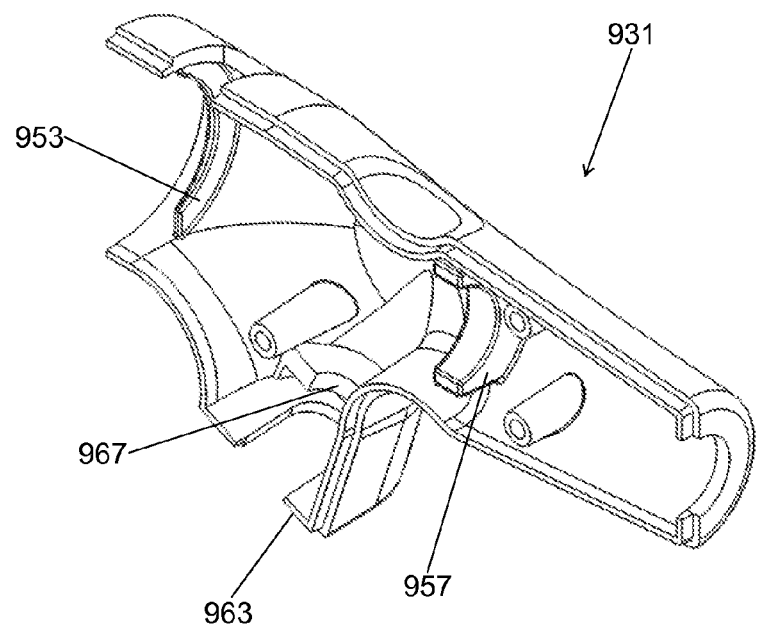
Figure 44A:
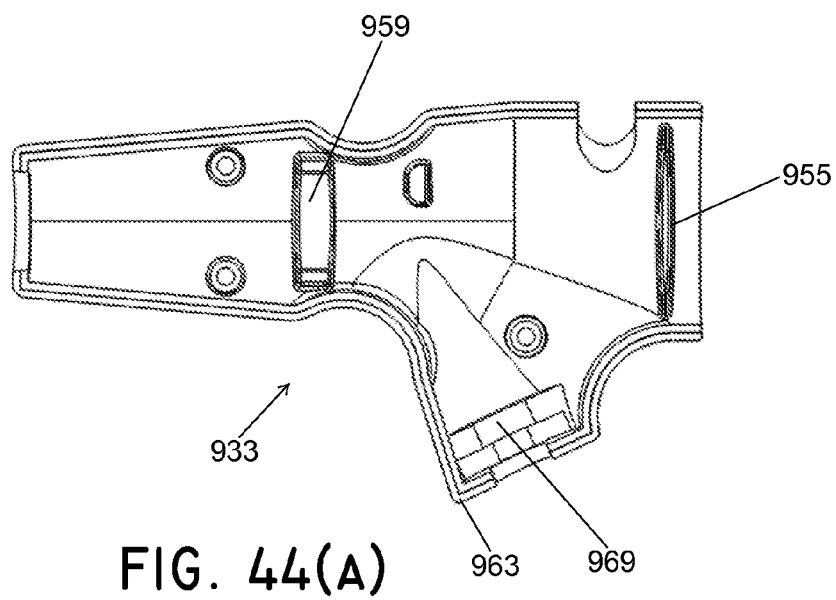
FIGS. 44(a) and 44(b) are side and perspective views, respectively, of the right housing half shown in FIGS. 42(a) and 42(b)
Figure 44B:
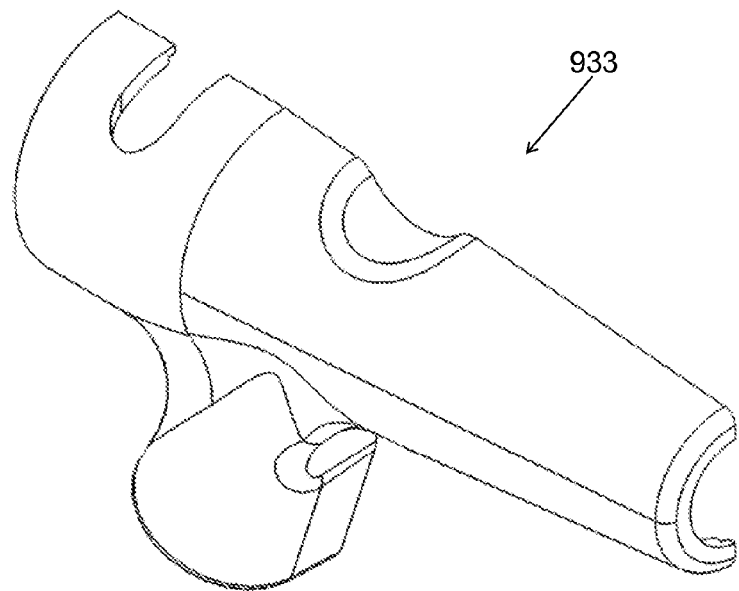
Figure 45A:
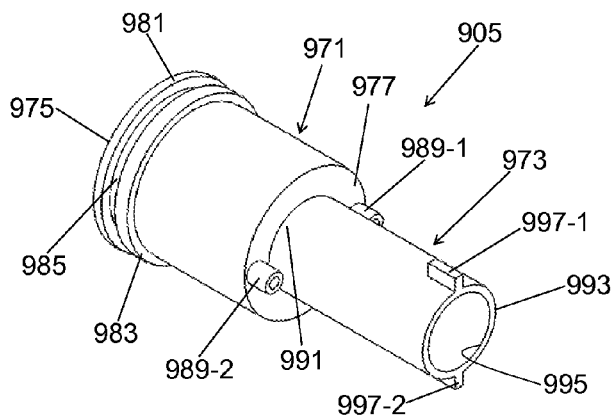
FIGS. 45(a) through 45(d) are perspective, side, front and rear views, respectively, of the hub shown in FIG. 41(d)
Figure 45B:
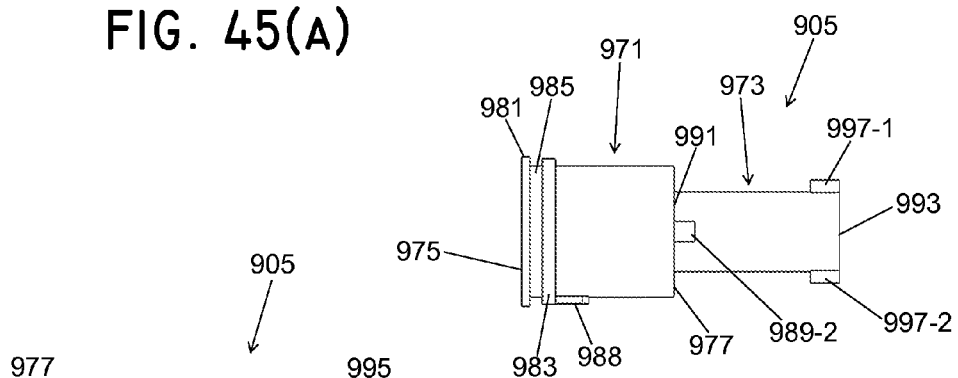
Figure 45C:
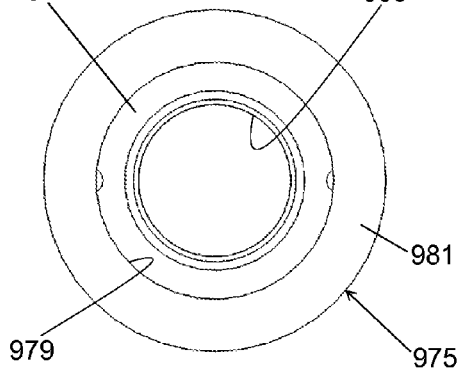
Figure 45D:
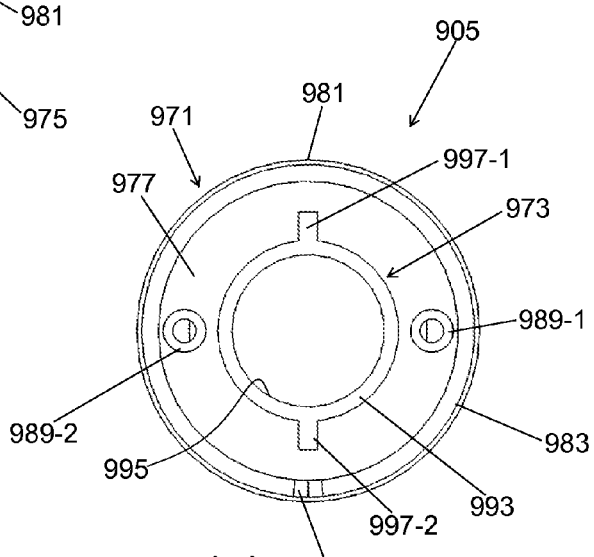

Referring now to FIGS. 42(a) and 42(b), housing 903 may comprise a pair of complementary housing halves 931 and 933, each of which may be a unitary structure made of a hard, medical-grade polymer or a similarly suitable material. Housing half 931 is also shown separately in FIGS. 43(a) and 43(b), and housing half 933 is also shown separately in FIGS. 44(a) and 44(b). Housing halves 931 and 933 may be joined together by suitable means, such as by screws, adhesive, or ultrasonic welding, to jointly define a generally gun-shaped structure including a barrel portion 935 and a handle portion 937.

Barrel portion 935, which may be generally circular in transverse cross-section, may be a tubular structure shaped to include a proximal end 939 and a distal end 941. Barrel portion 935 may taper in cross-sectional diameter from proximal end 939 to distal end 941. Proximal end 939 may be shaped to include an opening 943, and distal end 941 may be shaped to include an opening 945. A circumferentially-extending slot 947, the purpose of which will become apparent below, may be provided along the top surface of barrel portion 935 and may be spaced distally a short distance from proximal end 939. Slot 947 may have a first end 948-1 and a second end 948-2. Indentations 949 and 951, which may be used as finger rests to receive the forefinger and middle finger, respectively, of an operator, may be provided along the top and bottom surfaces, respectively, of barrel portion 935 at the interface of barrel portion 935 and handle portion 937 and may be used to facilitate the holding of housing 903 in one hand. (The thumb of the same hand of the user may also rest on housing 903 below barrel portion 935 and proximal to handle portion 937; alternatively, as will become apparent below, the thumb of the same hand of the user may also be used to operate cam 907.) Rib 953 (see, for example, FIGS. 43(a) and 43(b)) and rib 955 (see, for example, FIG. 44(a)), which may be formed on the interior surfaces of housing halves 931 and 933, respectively, between proximal end 939 and slot 947, may be used to axially secure hub 905 within housing 903. Rib 957 (see, for example, FIGS. 43(a) and 43(b)) and rib 959 (see, for example, FIG. 44(a)), which may be formed on the interior surfaces of housing halves 931 and 933, respectively, just distal to indentations 949 and 951, may be used to rotationally secure hub 905 within housing 903.

Handle portion 937, which may be generally elliptical in transverse cross-section, may be a tubular structure shaped to include a joined end 961 and a free end 963. Handle portion 937 may extend downwardly at an angle from barrel portion 935, with joined end 961 being joined to barrel portion 935 at a location between slot 947 and indentations 949 and 951. Free end 963 may be shaped to include an opening 965 (see, for example, FIG. 42(b)), the purpose of which will become apparent below. Rib 967 (see, for example, FIGS. 43(a) and 43(b)) and rib 969 (see, for example, FIG. 44(a)) may be formed on the interior surfaces of housing halves 931 and 933, respectively, just above free end 963 and may be used, in combination with free end 963, to securely receive fluid connectors 911-1 and 911-2, respectively.

Referring now to FIGS. 45(a) through 45(d), hub 905 may be a unitary structure made of a hard, medical-grade polymer or a similarly suitable material. Hub 905 may comprise a proximal portion 971 and a distal portion 973, each of which may be generally tubular in shape. Proximal portion 971 and distal portion 973 may be coaxial with one another, with proximal portion 971 having a comparatively larger diameter and with distal portion 973 having a comparatively smaller diameter.

Proximal portion 971 of hub 905 may comprise a proximal end 975 and a distal end 977. Proximal end 975 may be shaped to include a proximal opening 979 and a circumferential flange 981 extending radially outwardly a short distance therefrom. A circumferential rib 983 may be provided on the exterior of proximal portion 971 and may be spaced distally a short distance from flange 981. Rib 983 and flange 981 may jointly define a waist 985 therebetween. Waist 985 may be appropriately dimensioned to receive rib 953 (see, for example, FIGS. 43(a) and 43(b)) and rib 955 (see, for example, FIG. 44(a)) of housing 903 to axially secure hub 905 within housing 903. A rib 988, which may extend distally a short distance from rib 983, may be formed on the exterior of proximal portion 971. As will be discussed further below, rib 988 may be used to delimit the rotation of cam 907 relative to hub 905. A pair of tubular posts 989-1 and 989-2 may extend distally a short distance from distal end 977 of proximal portion 971. Posts 989-1 and 989-2, which may be in fluid communication with the interior of proximal portion 971, may be appropriately dimensioned for compliant tubes 909-1 and 909-2 (see, for example, FIG. 41(*d*)), respectively, to be inserted coaxially thereover and to be retained thereon by an interference fit.

Distal portion 973 of hub 905 may comprise a proximal end 991 and a distal end 993. Distal end 993 may be shaped to include a distal opening 995 and a pair of tabs 997-1 and 997-2 extending radially outwardly a short distance from the top and bottom surfaces, respectively, of distal portion 973. Tabs 997-1 and 997-2 may be appropriately dimensioned to engage rib 957 (see, for example, FIGS. 43(*a*) and 43(*b*)) and rib 959 (see, for example, FIG. 44(*a*)) of housing 903 in such a way as to rotationally secure hub 905 within housing 903.

Figure 46E:
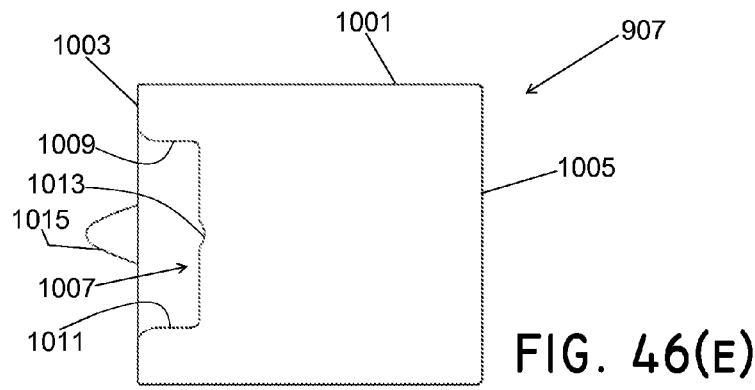

Referring now to FIGS. 46(*a*) through 46(*e*), cam 907 may be a generally tubular unitary structure made of a hard, medical-grade polymer or a similarly suitable material. Cam 907, which may be rotatably mounted over hub 905, may comprise a circular side wall 1001 having a proximal end 1003 and a distal end 1005. Side wall 1001 may be appropriately dimensioned to coaxially receive hub 905, as well as to receive compliant tubes 909-1 and 909-2 inserted axially therethrough. A circumferentially-extending recess 1007 may be provided in side wall 1001 proximate to proximal end 1003. Recess 1007, which may include a first end 1009, a second end 1011, and a midpoint notch 1013, may be appropriately dimensioned to receive rib 988 of hub 905 in such a way that rib 988 may delimit the rotation of cam 907 relative to hub 905.

Figure 47:
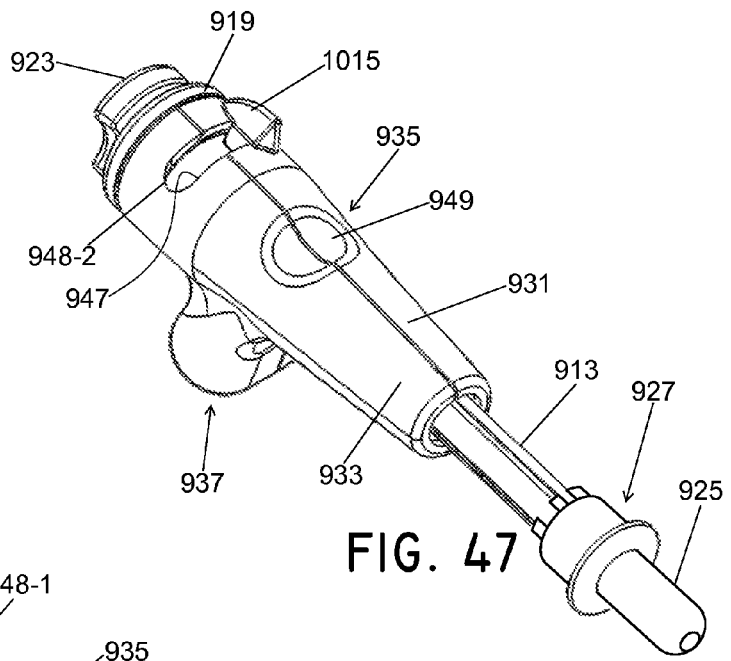
FIG. 47 is a perspective view of the access device shown in FIGS. 41(a) through 41(d), with the cam being positioned in one of its two open positions.
Figure 48:
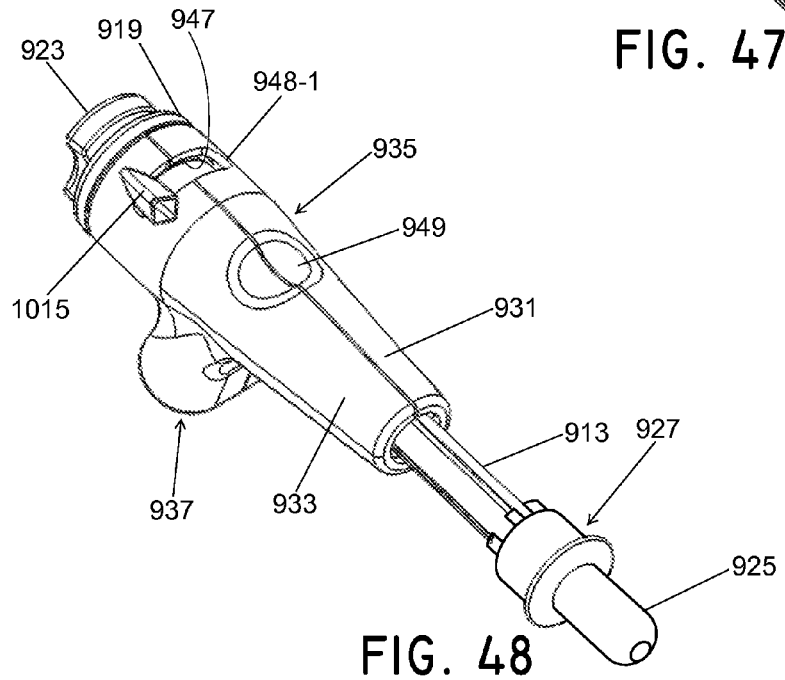
FIG. 48 is a perspective view of the access device shown in FIGS. 41(a) through 41(d), with the cam being positioned in the other of its two open positions.

Cam 907 may further comprise a handle 1015, which may extend radially outwardly from side wall 1001. Handle 1015 may be appropriately dimensioned to extend through slot 947 (see, for example, FIG. 41(*a*)) in housing 903. In this manner, an operator may, for example, using his thumb, manipulate the handle 1015 to different positions within slot 947, e.g., a first position in which handle 1015 is centered within slot 947 (as shown, for example, in FIG. 41(*a*)), a second position in which handle 1015 is positioned at end 948-1 (as shown, for example, in FIG. 47), and a third position in which handle 1015 is positioned at end 948-2 (as shown, for example, in FIG. 48). Slot 947 may be appropriately dimensioned so that (i) when handle 1015 is positioned against end 948-1 of slot 947, rib 988 may be positioned against first end 1009 of recess 1007, (ii) when handle 1015 is positioned against end 948-2 of slot 947, rib 988 may be positioned against second end 1011 of recess 1007, and (iii) when handle 1015 is centered within slot 947, the distal tip of rib 988 may be positioned within notch 1013 of recess 1007.

Cam 907 may further comprise a distal wall 1017 disposed within distal end 1005 of side wall 1001. Distal wall 1017, which may be generally U-shaped, may be appropriately dimensioned so that, depending on the angular position of cam 907, one or both of compliant tubes 909-1 and 909-2 may be pinched shut between distal wall 1017 and distal portion 973 of hub 905. For example, when cam 907 is angularly positioned so that handle 1015 is centered within slot 947, distal wall 1017 may pinch shut both compliant tube 909-1 and compliant tube 909-2 against distal portion 973 of hub 905. Alternatively, when cam 907 is angularly positioned so that handle 1015 is positioned at end 948-1 of slot 947, distal wall 1017 may pinch shut compliant tube 909-2 against distal portion 973 of hub 905 while permitting compliant tube 909-1 to remain open, and when cam 907 is angularly positioned so that handle 1015 is positioned at end 948-2 of slot 947, distal wall 1017 may pinch shut compliant tube 909-1 against distal portion 973 of hub 905 while permitting compliant tube 909-2 to remain open.

FIGS. 49(*a*) through 49(*c*) are rear fragmentary views of access device 901, with certain components, such as compliant tubes 909-1 and 909-2, not being shown for clarity. More specifically, FIG. 49(*a*) shows access device 901 with handle 1015 of cam 907 centered within slot 947 (as in FIG. 41(*a*)), FIG. 49(*b*) shows access device 901 with handle 1015 of cam 907 positioned at end 948-1 of slot 947 (as in FIG. 47), and FIG. 49(*c*) shows access device 901 with handle 1015 of cam 907 positioned at end 948-2 of slot 947 (as in FIG. 48). As can be seen in FIG. 49(*a*), when handle 1015 of cam 907 is centered within slot 947, distal wall 1017 is positioned so as to be substantially aligned with both post 989-1 and post 989-2. As a result, with distal wall 1017 thus positioned, compliant tubes 909-1 and 909-2, which are not shown but are mounted on posts 989-1 and 989-2, respectively, are pinched shut between distal wall 1017 of cam 907 and distal portion 973 of hub 905. By comparison, as seen in FIG. 49(*b*), when handle 1015 of cam 907 is positioned at end 948-1 of slot 947, distal wall 1017 is positioned so as to be substantially aligned with post 989-2 but not with post 989-1. Consequently, with distal wall 1017 thus positioned, compliant tube 909-2 is pinched shut between distal wall 1017 of cam 907 and distal portion 973 of hub 905 whereas compliant tube 909-1 is not pinched shut between distal wall 1017 of cam 907 and distal portion 973 of hub 905. Finally, as seen in FIG. 49(*c*), when handle 1015 of cam 907 is positioned at end 948-2 of slot 947, distal wall 1017 is positioned so as to be substantially aligned with post 989-1 but not with post 989-2. As a result, with distal wall 1017 thus positioned, compliant tube 909-1 is pinched shut between distal wall 1017 of cam 907 and distal portion 973 of hub 905 whereas compliant tube 909-2 is not pinched shut between distal wall 1017 of cam 907 and distal portion 973 of hub 905.

It is to be understood that, although distal wall 1017 of cam 905 is constructed in the present embodiment to have three positions, namely, (i) a position in which both compliant tube 909-1 and compliant tube 909-2 are simultaneously pinched shut, (ii) a position in which compliant tube 909-1 is allowed to be open and compliant tube 909-2 is pinched shut, and (iii) a position in which compliant tube 909-1 is pinched shut and compliant tube 909-2 is allowed to be open, distal wall 1017 of cam 905 may be constructed to have additional positions, such as a flush position in which both compliant tube 909-1 and compliant tube 909-2 are allowed to be open. In addition, device 901 may be constructed so that each of compliant tubes 909-1 and 909-2 may not be limited to being placed only in either a fully opened state or a fully closed state, but rather, may additionally be placed in a finite number or in an infinite number (i.e. continuously adjustable) of partially opened states having flow rates varying by equal or unequal increments between a fully opened state and a fully closed state.

Referring back now to FIG. 41(*d*), compliant tubes 909-1 and 909-2 each may be a generally tubular unitary member made of a flexible medical-grade silicone or a similarly suitable material. Compliant tube 909-1 may include a first end 1031 and a second end 1033, and compliant tube 909-2 may include a first end 1035 and a second end 1037. First end 1031 of compliant tube 909-1 may be coaxially mounted over post 989-1 and may be secured thereto, for example, by an interference fit or other suitable means, and first end 1035 of compliant tube 909-2 may be coaxially mounted over post 989-2 and may be secured thereto, for example, by an interference fit or other suitable means. In the above manner, compliant tubes 909-1 and 909-2 may be placed in fluid communication with the interior of proximal portion 971 of hub 905 and, thus, may be placed in fluid communication with the interior of sheath 913 when obturator 921 is removed from sheath 913.

Second end 1033 of compliant tube 909-1 may be coaxially inserted into a first end 1041-1 of fluid connector 911-1 and may be secured thereto, for example, by adhesive or other suitable means, and second end 1037 of compliant tube 909-2 may be coaxially inserted into a first end 1041-2 of fluid connector 911-2 and may be secured thereto, for example, by adhesive or other suitable means. A second end 1043-1 of fluid connector 911-1 may be in the shape of a female luer lock connector, and a second end 1043-2 of fluid connector 911-2 may be in the shape of a female luer lock connector. One of fluid connectors 911-1 and 911-2 may be connected to a male luer lock connector (not shown) that, in turn, may be connected to a fluid source, and the other of fluid connectors 911-1 and 911-2 may be connected to a male luer lock connector (not shown) that, in turn, may be connected to a drain. Consequently, one of compliant tubes 909-1 and 909-2 may be used to deliver fluid to a patient, and the other of compliant tubes 909-1 and 909-2 may be used to drain fluid from the patient. Fluid connector 911-1 may be further shaped to include a flange 1045-1, and fluid connector 911-2 may be further shaped to include a flange 1045-2. Flange 1045-1 may be appropriately dimensioned to mate with housing half 931 between rib 967 (see FIGS. 43(*a*) and 43(*b*)) and free end 963, thereby securing fluid connector 911-1 to housing half 931. Similarly, flange 1045-2 may be appropriately dimensioned to mate with housing half 933 between rib 969 (see FIG. 44(*a*)) and free end 963, thereby securing fluid connector 911-2 to housing half 933.

The fluid flow rates for access device 901 may be in the range of about 1 cc/min to about 1000 cc/min, preferably about 10 cc/min to about 500 cc/min, and more preferably about 100 cc/min to about 250 cc/min. Moreover, the following dimensions, which may affect how cam 907 pinches shut tubes 909-1 and 909-2, may be used:

| Dimension | Range | Preferred | More Preferred |
| --- | --- | --- | --- |
| Tubing OD | 0.001"-5.00" | 0.01"-0.50" | 0.1"-0.49" |
| Tubing ID | 0.001"-5.00" | 0.01"-0.50" | 0.05"-0.49" |
| Cam "Closed" Diameter | 0.001"-5.00" | 0.01"-1.00" | 0.1"-0.50" |
| Cam "Open" Diameter | 0.001"-5.00" | 0.01"-1.00" | 0.1"-0.70" |
| Compression Applied by Cam (stroke length) | 0.001"-5.00" | 0.01"-1.00" | 0.05"-0.10" |
| Cam Ramp Angle (each side) | 0-360 degrees | 0-90 degrees | 0-60 degrees |

Although not shown in the present embodiment, housing 903 may be provided with appropriate markings proximate to slot 947 to indicate the various positions that handle 1015 of cam 907 may be located so that fluid may be delivered to a patient, so that fluid may be drained from a patient, or neither. For example, to indicate a "filling" function, i.e., where fluid is to be delivered to the patient, one may use, for example, the following indicia: "IN," "FILL," "+," or an arrow indicating inflow. To indicate a "draining" function, i.e., where fluid is to be drained from the patient, one may use, for example, the following indicia: "OUT," "DRAIN," "−," or an arrow indicating outflow. To indicate that the device is closed for fluid transfer in either direction, one may use, for example, the following indicia: "CLOSED," a circle with a single line through it, or an "X" circumscribed with a circle. If a flush function were added, one may use, for example, the following indicia: "FLUSH" or "↔"

Figure 50A:
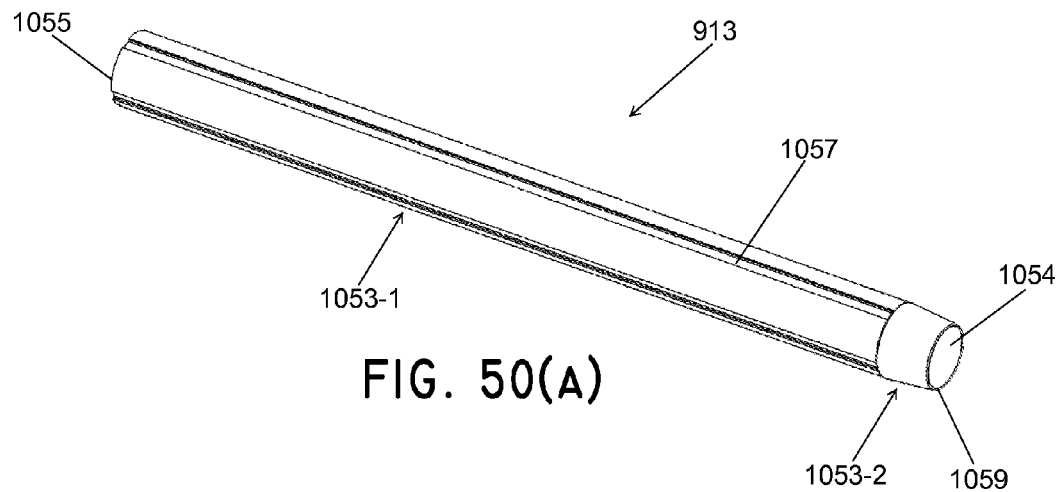
FIGS. 50(a) through 50(c) are enlarged perspective, front, and side views, respectively, of the sheath shown in FIG. 41(d)
Figure 50B:
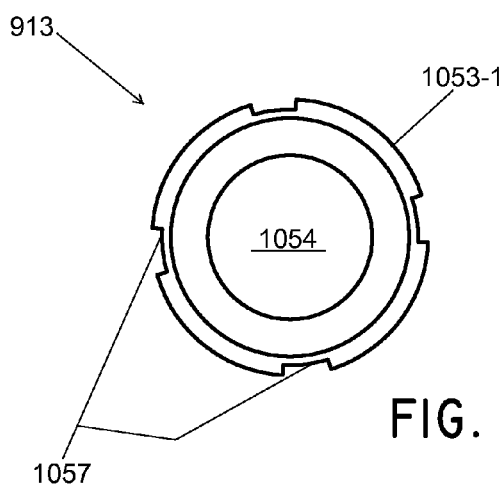
Figure 50C:
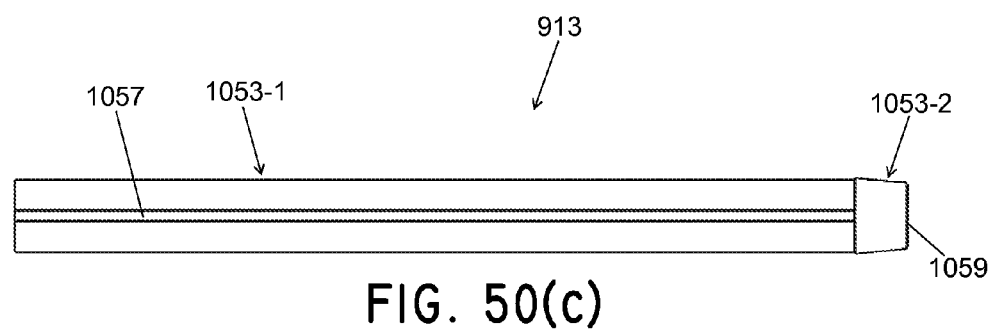
Figure 52A:
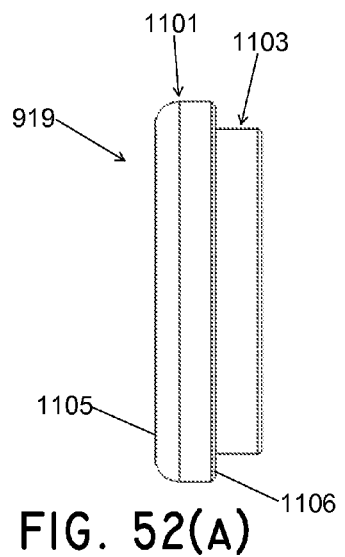
FIGS. 52(a) through 52(d) are side, front, rear, and perspective views, respectively, of the cap shown in FIGS. 41(a) through 41(d)
Figure 52B:
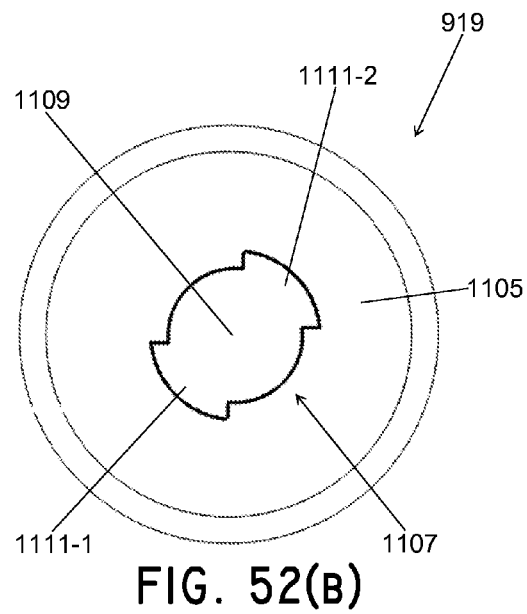
Figure 52C:
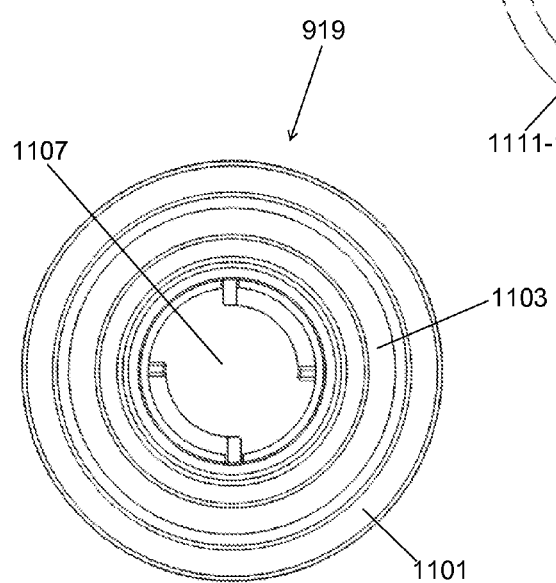
Figure 52D:
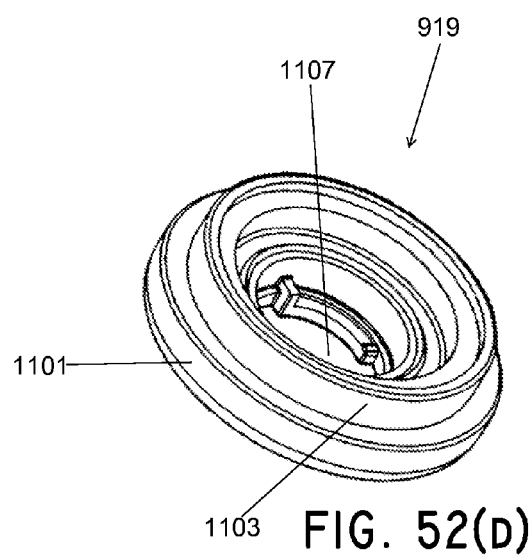
Figure 53:
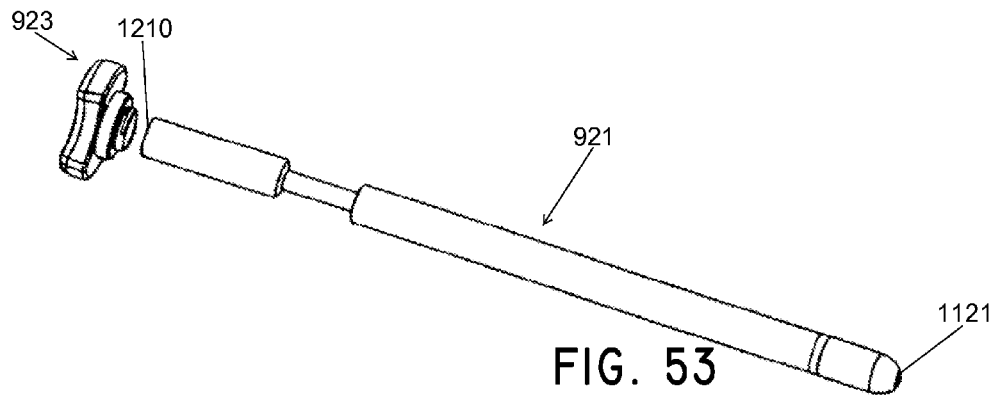
FIG. 53 is an exploded perspective view of the combination of the obturator and the obturator handle shown in FIGS. 41(a) through 41(d)
Figure 54:
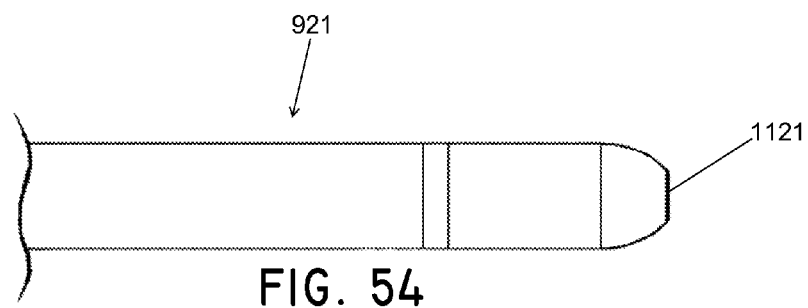
FIG. 54 is an enlarged fragmentary side view of the obturator shown in FIG. 53.
Figure 55A:
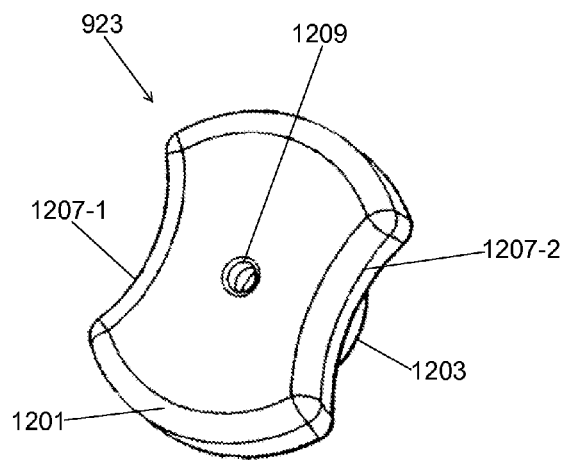
FIGS. 55(a) and 55(b) are enlarged perspective views of the obturator handle shown in FIG. 53.
Figure 55B:
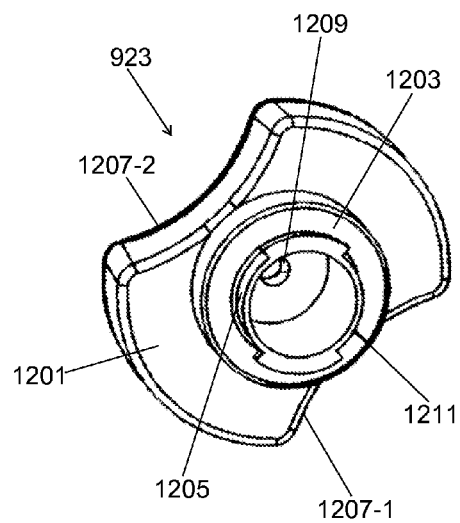
Figure 56A:
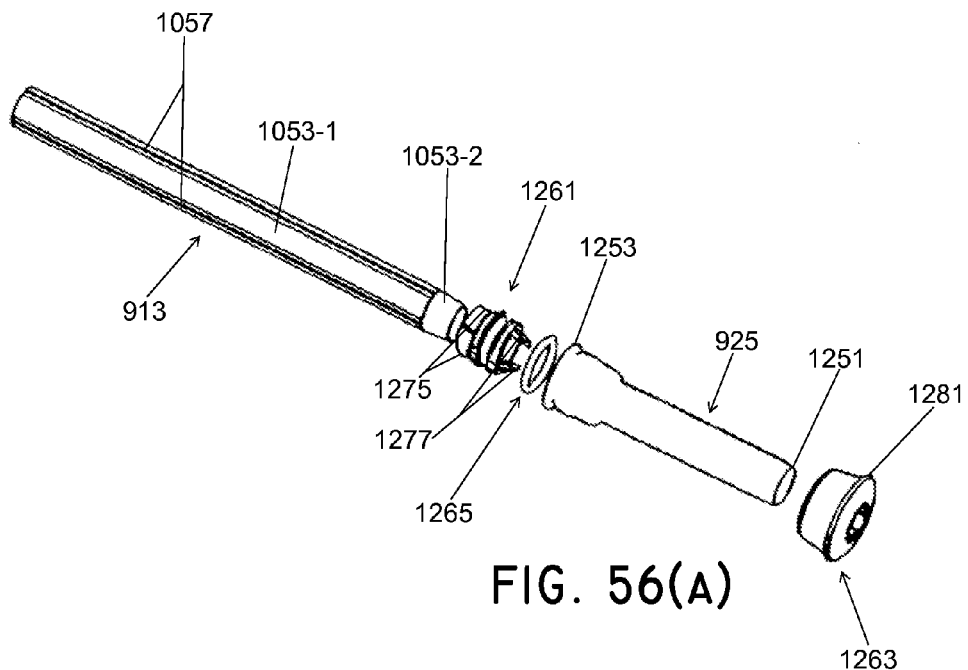
FIGS. 56(a) and 56(b) are exploded perspective and exploded side views, respectively, of the combination of the sheath, the protective sleeve and the slide ring assembly shown in FIG. 41(d)
Figure 56B:
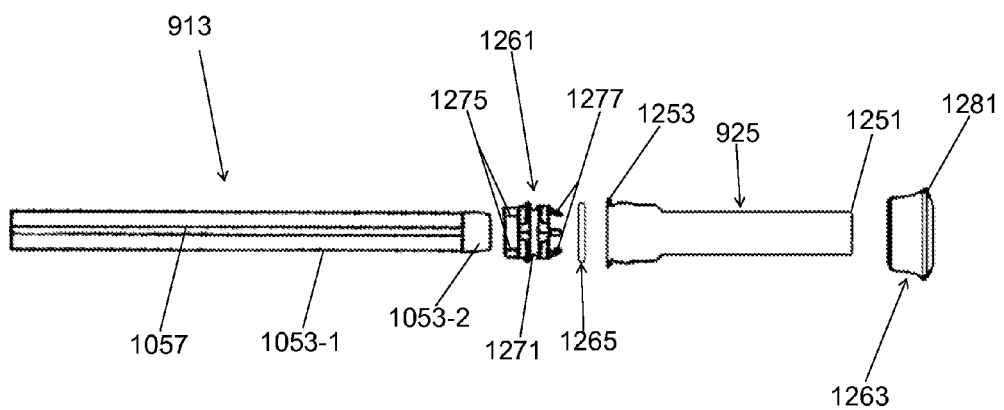

Referring now to FIGS. 50(*a*) through 50(*c*), sheath 913, which may comprise a generally tubular unitary structure made of a medical-grade polymer or a similarly suitable material having columnar strength as well as angular flexibility, may be shaped to include a proximal portion 1053-1, a distal portion 1053-2, and a longitudinal channel 1054, longitudinal channel 1054 extending through the entire respective lengths of proximal portion 1053-1 and distal portion 1053-2. Proximal portion 1053-1, which may have a generally cylindrical shape, may include a proximal end 1055, which may be fixedly secured, for example, by adhesive or other suitable means within hub 905 proximate to the interface of proximal portion 971 and distal portion 973, with the remainder of proximal portion 1053-1 of sheath 913 extending distally therefrom. A plurality of longitudinally-extending grooves 1057 may be provided on the exterior of proximal portion 1053-1 of sheath 913. As will be discussed further below, grooves 1057, which may terminate at the interface of proximal portion 1053-1 and distal portion 1053-2, may serve as a track along which slide ring assembly 927 (see, for example, FIGS. 41(*a*) and 41(*b*)) may slide.

Distal portion 1053-2 of sheath 913, which may have a generally frusto-conical shape, may include a distal end 1059. Distal portion 1053-2 may have a wall thickness that tapers distally to distal end 1059.

Sheath 913 may be appropriately dimensioned so that the exposed portion of sheath 913, i.e., the portion of sheath 913 that extends distally from housing 903, has a length that is slightly greater than the length of a typical female human urethra and additionally has an external diameter that permits the exposed portion of sheath 913 to easily traverse a typical female human urethra. For illustrative purposes, sheath 913 may have an external diameter of about 24 Fr and may be dimensioned so that the length of sheath 913 inserted into the patient's urethra has a length in the range of about 0.001 inch to about 100 inches, preferably about 1 inch to about 10 inches, more preferably about 1.5 inch to about 2 inches.

Referring now to FIGS. 41(*c*), 41(*d*), and FIG. 51, valve assembly 915, which may be similar in size, shape, construction, and function to valve assembly 91 of access device 13, may comprise a proximal portion 1071-1 that may be similar to proximal portion 92-1 of valve assembly 91, a distal portion 1071-2 that may be similar to distal portion 92-2 of valve assembly 91, and an intermediate portion 1071-3 that may be similar to intermediate portion 92-3 of valve assembly 91. One difference between valve assembly 915 and valve assembly 91 may be that, whereas proximal portion 92-1 of valve assembly 91 may be shaped for seal 125 to be mounted therewithin, valve assembly 915 may not be so shaped. Instead, seal 917, which may be similar to seal 125 but having a greater outer diameter, may have its distal surface 917-1 positioned flush against a proximal end 1072 of proximal portion 1071-1 of valve assembly 915. Valve assembly 915 may be partially coaxially inserted into proximal portion 971 of hub 905, with a distal end 1073 of proximal portion 1071-1 of valve assembly 915 abutting proximal end 975 of hub 905 and with a distal end 1075 of distal portion 1071-2 of valve assembly 915 being spaced a short distance from distal end 977 of proximal portion 971 of hub 905 to define a gap 1080. In this manner, for example, fluid from the patient may flow proximally to gap 1080 through sheath 913 (proximal end 1055 of sheath 913 being disposed just distal to gap 1080), and such fluid may then flow from gap 1080 into posts 989-1 and 989-2. Then, depending on the positioning of cam 907 and the respective patencies of compliant tubes 909-1 and 909-2, such fluid may flow through compliant tube 909-1, compliant tube 909-2 or neither. In a corresponding fashion, fluid may be delivered from compliant tube 909-1 or compliant tube 909-2 to sheath 913 via gap 1080.

Referring also now to FIGS. 52(a) through 52(d), cap 919, which may be a unitary structure made of a hard, medical-grade polymer or similarly suitable material, may comprise a proximal portion 1101 and a distal portion 1103, each of which may be generally tubular in shape. Proximal portion 1101 and distal portion 1103 may be coaxial with one another, with proximal portion 1101 being comparatively larger in diameter and with distal portion 1103 being comparatively smaller in diameter. Proximal portion 1101 may include a proximal face 1105 and a distal face 1106. An opening 1107 may be provided in proximal face 1105. Opening 1107, the purpose of which will become apparent below, may be shaped to include a generally circular central portion 1109 and a pair of side lobes 1111-1 and 1111-2. Cap 919 may be appropriately dimensioned so that distal end 1106 of proximal portion 1101 may lie flush against proximal end 939 of housing 903, with distal portion 1103 residing within housing 903 (see FIG. 41(c)). Cap 919 may also be appropriately dimensioned to coaxially receive the combination of seal 917, proximal portion 1071-1 of valve assembly 915, and flange 981 of hub 905 (see FIG. 51). Distal portion 1103 of hub 905 may be secured to flange 981 of hub 905 by any suitable means, such as, for example, ultrasonic welding. The securing of cap 919 to hub 905 may serve not only to fasten cap 919 to hub 905 but also to compress seal 917 and valve assembly 915 to ensure that these components create a fluid-tight seal and to constrain these components against axial or other movement during use of access device 901.

Referring now to FIGS. 41(c), 41(d), 53, and 54, obturator 921 may be similar in most respects to obturator 131 of access device 13. One difference between the two obturators may be that obturator 921 may include a distal end 1121 that is more blunted than distal end 135 of obturator 131. Such a blunted end may reduce the likelihood that the distal end of the obturator may cause injury or discomfort to the patient during its insertion.

Referring now to FIGS. 41(a) through 41(d), 53, 55(a) and 55(b), obturator handle 923, which may be a unitary structure made of a hard, medical-grade polymer or similarly suitable material, may comprise a proximal portion 1201, an intermediate portion 1203, and a distal portion 1205. Proximal portion 1201, which may be a generally planar member having an hourglass profile, may be shaped to include a pair of recesses 1207-1 and 1207-2 at opposing locations on its periphery. Recesses 1207-1 and 1207-2 may be appropriately dimensioned to accommodate the thumb and forefinger, respectively, of a user or the forefinger and thumb, respectively, of a user. Proximal portion 1201 may be further shaped to include a transverse opening 1209, which may be centrally located. Intermediate portion 1203, which may be generally tubular in shape, may be concentrically positioned around opening 1209 and may extend distally a short distance from proximal portion 1201. Distal portion 1205, which may be generally tubular in shape, may extend distally a short distance from intermediate portion 1203, distal portion 1205 being coaxial with but comparatively smaller in diameter than intermediate portion 1203. Distal portion 1205 and intermediate portion 1203 may be appropriately dimensioned so that a proximal end 1210 of obturator 921 may be axially received therewithin and may be fixed to handle 923 by suitable means. With obturator 921 thus secured to handle 923, opening 1209 may be in fluid communication with the interior of obturator 921. Consequently, where, for example, access device 901 is used to provide access to a bladder, correct placement of obturator 921 in the bladder may be noted by the proximal flow of urine through opening 1209. However, if such confirmation is unnecessary or undesirable, opening 1209 may be eliminated.

Distal portion 1205 may comprise a distal end 1211 that is mateable with opening 1107 in proximal face 1105 of cap 919. Consequently, by inserting distal end 1211 of handle 923 through opening 1107 and, thereafter, rotating handle 923 clockwise relative to cap 919 by approximately 90 degrees, one may lock handle 923 to cap 919 and, in so doing, may prevent unwanted axial movement of obturator 921 relative to cap 919 and, thus, relative to sheath 913. For example, such locking may prevent undesired proximal movement of obturator 921 relative to sheath 913 as obturator 921 is being inserted into a patient. After access device 901 has been properly placed in a patient, obturator 921 may be removed from the remainder of access device 901 by rotating handle 923 counterclockwise relative to cap 919 until distal end 1211 of handle 923 may be withdrawn through opening 1107 of cap 919.

It should be understood that a flush adapter may be used in place of obturator 921 to provide flushing capabilities at the tip of sheath 913. It should also be understood that a multiple lumen sheath could be used in place of sheath 913 to provide flushing capabilities. Alternatively, the end of the obturator handle may include a luer or other attachment that may allow for the flow of fluid through the obturator to distend the urethra during insertion of the access device. Such an attachment may alternatively be used to introduce fluids or tools into the bladder through the obturator before the obturator is removed.

Referring now to FIGS. 41(a) through 41(d), 56(a) and 56(b), protective sleeve 925 may be identical in size, shape, construction, and function to protective sleeve 181 of access device 13. Protective sleeve 925 may comprise a first end 1251 and a second end 1253. Prior to deployment of access device 901, first end 1251 may be disposed within obturator 921.

Figure 57:
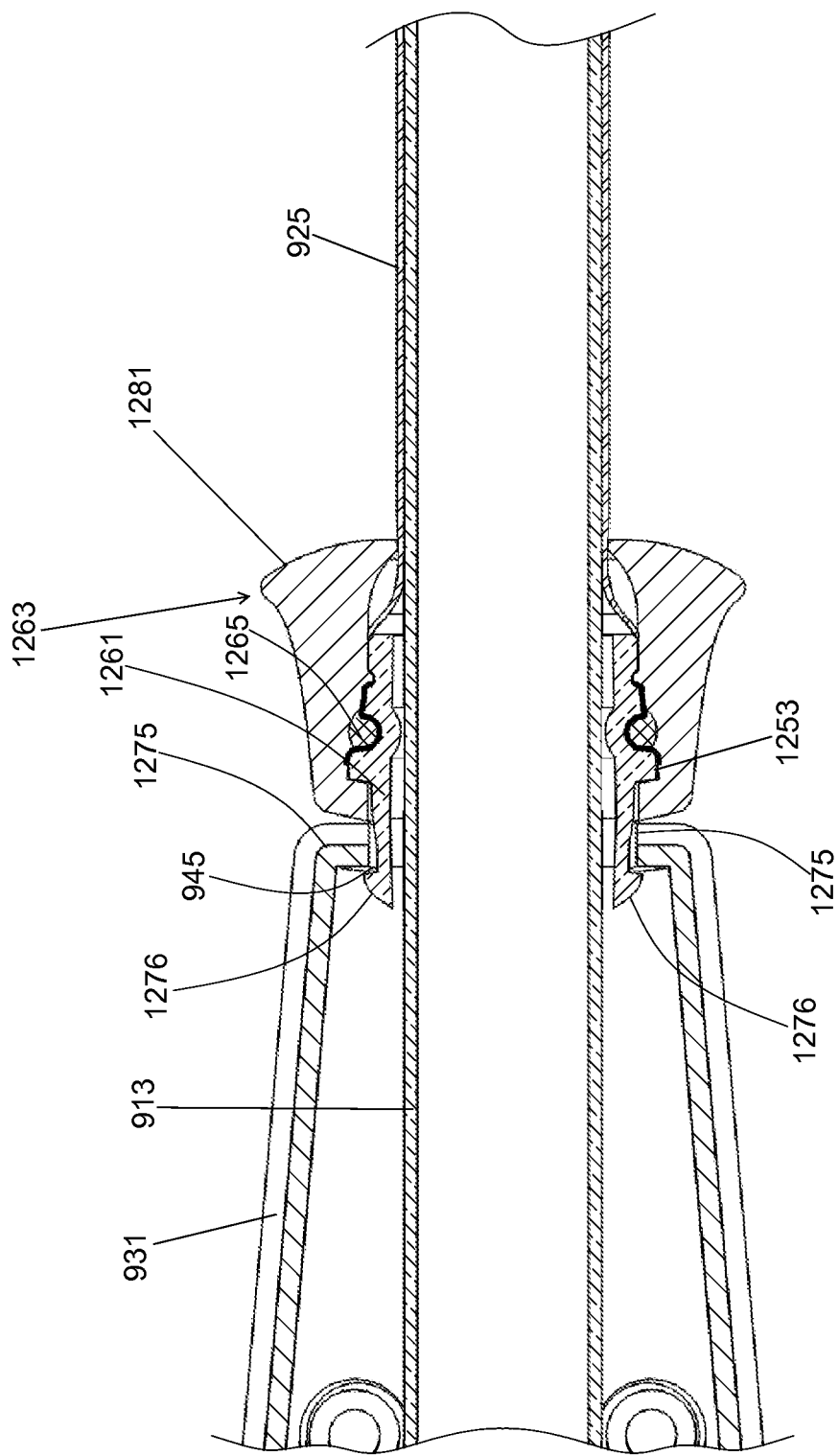
FIG. 57 is an enlarged section view of the combination of the housing, the sheath and the slide ring assembly shown in FIG. 41(d), the slide ring assembly being shown locked in its proximal position.
Figure 58A:
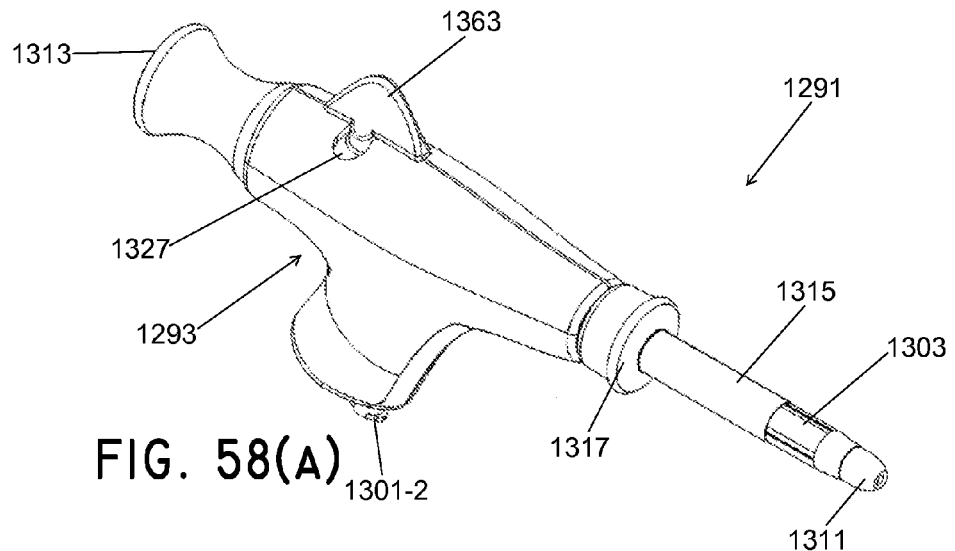
FIGS. 58(a) through 58(d) are perspective, side, section, and partially exploded perspective views, respectively, of a twelfth alternate embodiment to the access device shown in FIG. 1, the access device being shown in FIGS. 58(a) through 58(c) with the cam-actuated switch in the closed position and with the slide ring assembly in its proximal position.
Figure 58B:
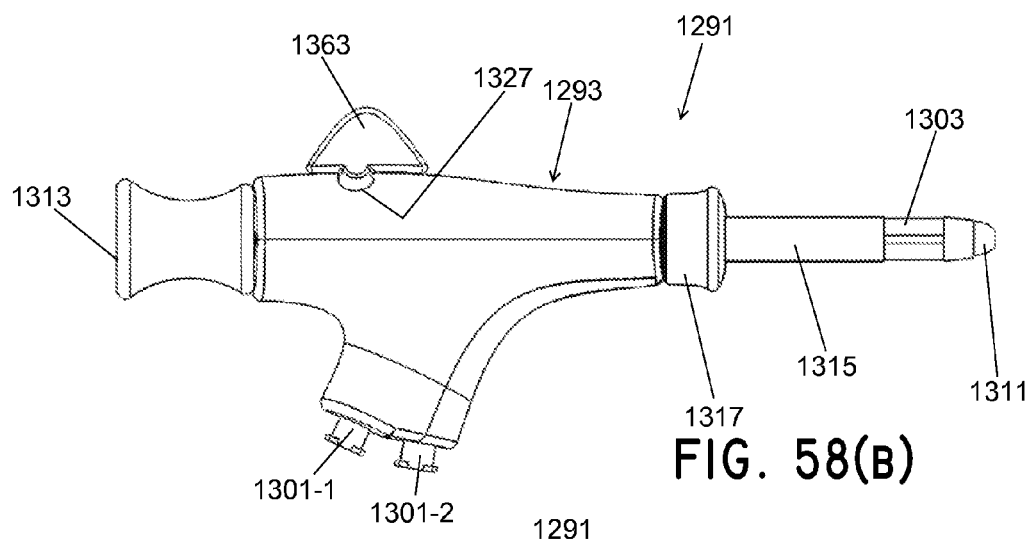
Figure 58C:
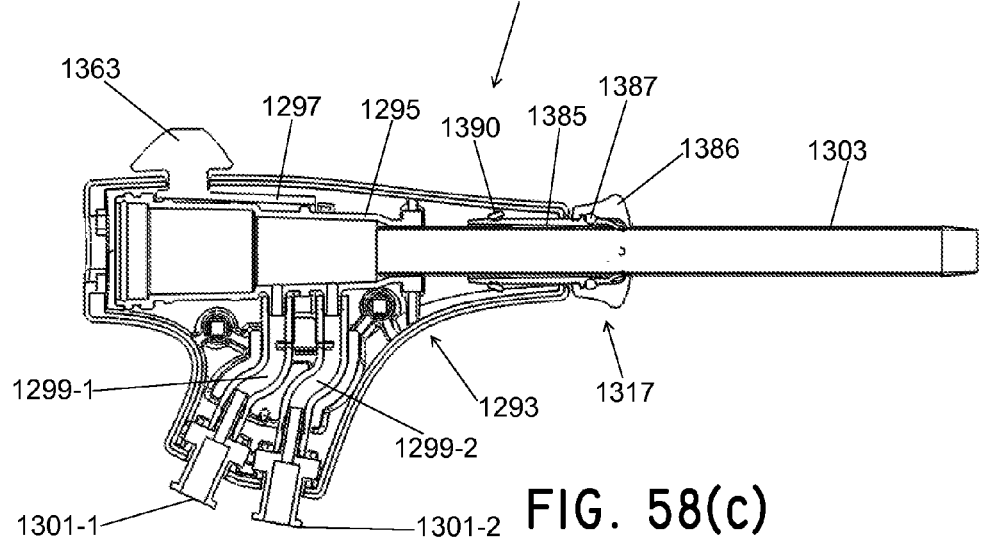
Figure 58D:
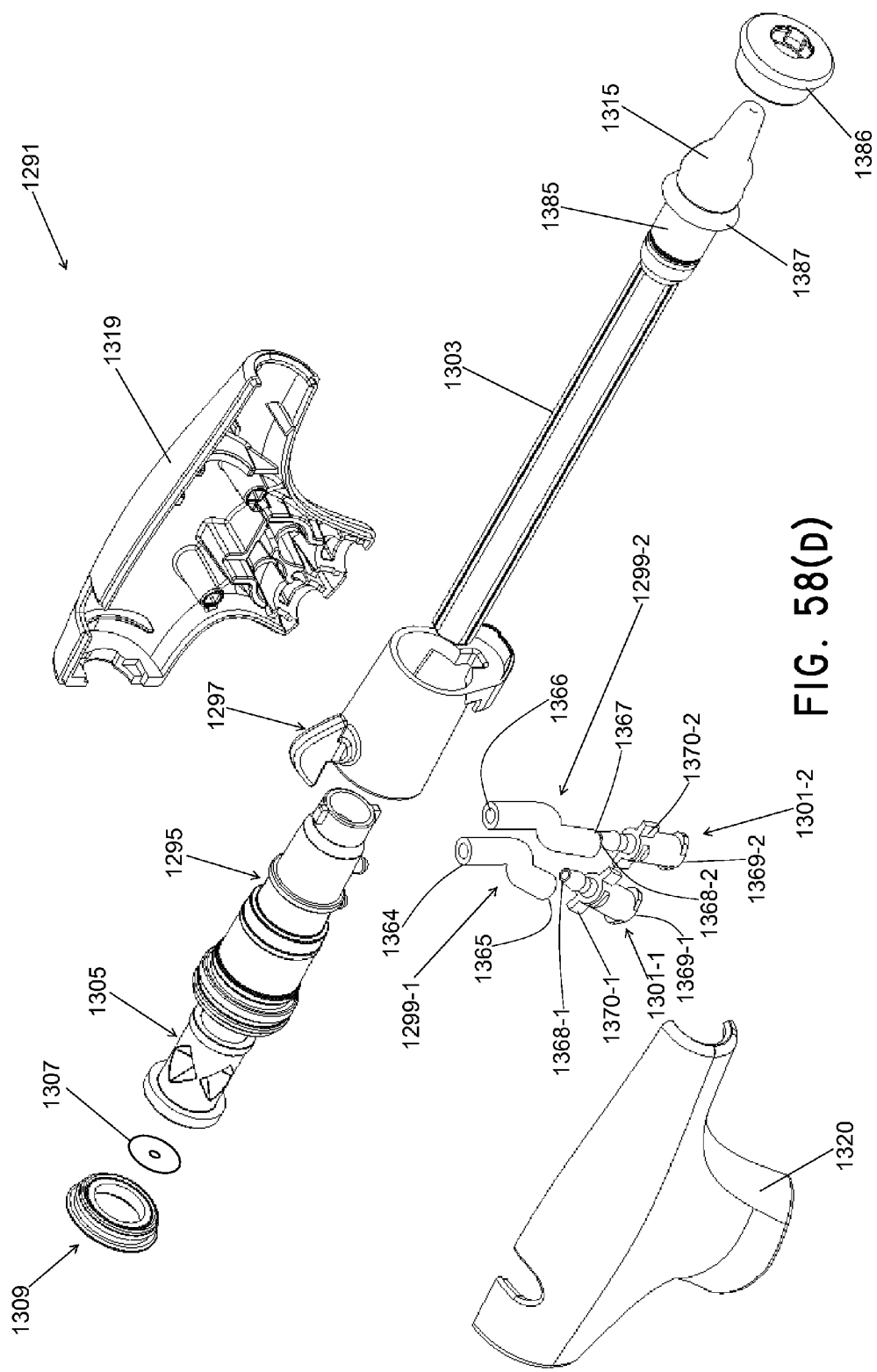

Referring also now to FIG. 57, slide ring assembly 927 may comprise an inner member 1261, an outer member 1263, and an O-ring 1265. Inner member 1261, which may be a unitary structure, preferably made of a hard, medical-grade polymer or a similarly suitable material, may comprise a tubular portion 1271. A plurality of angularly-deflectable legs 1275 may be spaced around the periphery of tubular portion 1271 and may extend proximally a short distance therefrom. Legs 1275 may be shaped to include feet 1276 that may lockably engage the interior of housing 903 once feet 1276 have been inserted into opening 945 of housing 903. Such locking may also provide tactile feedback that slide ring assembly 927 has been fully moved to its proximal position. A plurality of legs 1277 may be spaced around the periphery of tubular portion 1271 and may extend distally a short distance therefrom. Legs 1277, which may be biased radially inwardly, may be appropriately configured and dimensioned to ride within grooves 1057 of sheath 913 and, in so doing, may constrain rotational movement of inner member 1261 relative to sheath 913. In addition, distal movement of inner member 1261 may be constrained by the fact that grooves 1057 may terminate at the distal end of proximal portion 1053-1 of sheath 913 and may not continue in distal portion 1053-2 of sheath 913. Consequently, distal portion 1053-2 of sheath 913 may effectively act as a stop for distal movement of inner member 1261.

Second end 1253 of sleeve 925 may be inserted coaxially over tubular portion 1271 of inner member 1261 and may be secured thereto by O-ring 1265. Outer member 1263, which may be a generally tubular unitary member made of a soft or compressible medical-grade polymer or a similarly suitable material, may be coaxially and fixedly mounted over O-ring 1265 and inner member 1261. Outer member 1263, which may be shaped to minimize irritation of a patient, may include a distal flange 1281, which may be used to move slide ring assembly 927 proximally relative to sheath 913.

Access device 901 may have an overall length in the range of about 0.001 inch to about 20 inches, preferably about 0.1 inch to about 10 inches, more preferably about 1 inch to about 6 inches.

Access device 901 may be used in a manner similar to that discussed above for access device 13. For example, for transurethral access to a female human urinary bladder, cam 907 may be switched to its closed position (as in FIG. 41(a)), i.e., so that both compliant tubes 909-1 and 909-2 may be pinched shut, and distal end 1121 of obturator 921 may be aligned with and inserted into the patient. As access device 901 may continue to be inserted into the patient, the meatus of the patient may cause slide ring assembly 927 to be slid proximally, thereby causing the portion of sleeve 925 that is disposed within obturator 921 to be removed therefrom and to be everted over the exterior of sheath 913, thereby providing a barrier between the patient's urethra and sheath 913. Further insertion of access device 901 into the patient may cause inner member 1261 of slide ring assembly 927 to be slid proximally until it lockably engages housing 903 (as in FIG. 57). With slide ring assembly 927 thus engaged with housing 903, the distal end of access device 901 should be located in the bladder of the patient. Confirmation of such placement may be noted by the proximal flow of urine through opening 1107 of obturator handle 923. Obturator 921 may then be removed from the patient by rotating obturator handle 923 until distal portion 1205 of obturator handle 923 is aligned with opening 1107 of cap 919 and then by withdrawing proximally the combination of obturator handle 923 and obturator 921 from the remainder of access device 901. With obturator 921 thus removed, the remaining implanted portion of access device 901 may provide a conduit through which medical devices, such as delivery device 15, pressure-attenuating device 17, and removal device 19, may be delivered to the bladder. If desired, fluid may be delivered to or drained from the bladder by switching cam 907 from its closed position to one of its open positions (see FIGS. 47 and 48), whereby compliant tube 909-1 is pinched shut and compliant tube 909-2 is allowed to be open or vice versa.

Referring now to FIGS. 58(a) through 58(d), there are shown various views of a twelfth alternate embodiment of an access device 1291. (For simplicity and clarity, one or more of the components of access device 1291 may not be shown in all of FIGS. 58(a) through 58(d).) Access device 1291 can include a housing assembly 1293, a sheath assembly, and a fluid control system. The sheath assembly can include a cannula or sheath 1303, a dilator or obturator 1311, an obturator handle 1313, a protective sleeve 1315, and a slide ring assembly 1317. The fluid control system can include a hub 1295, a cam 1297, a pair of compliant tubes 1299-1 and 1299-2, a pair of fluid connectors 1301-1 and 1301-2, a valve assembly 1305, a seal 1307, and a cap 1309. Each of the foregoing components will now be discussed further below.

Figure 61A:
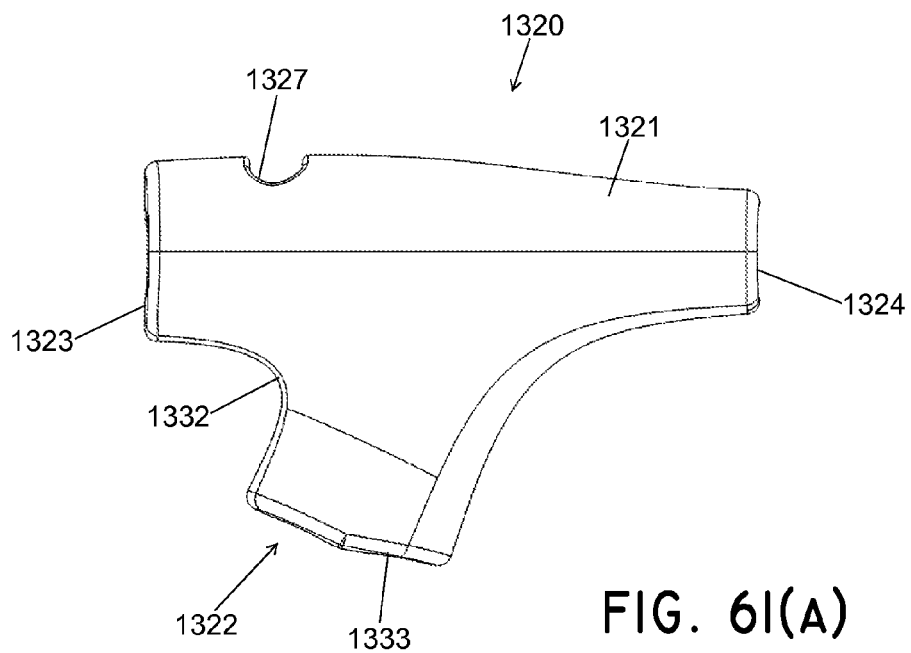
FIGS. 61(a) and 61(b) are side and perspective views, respectively, of the right housing half shown in FIG. 59.
Figure 61B:
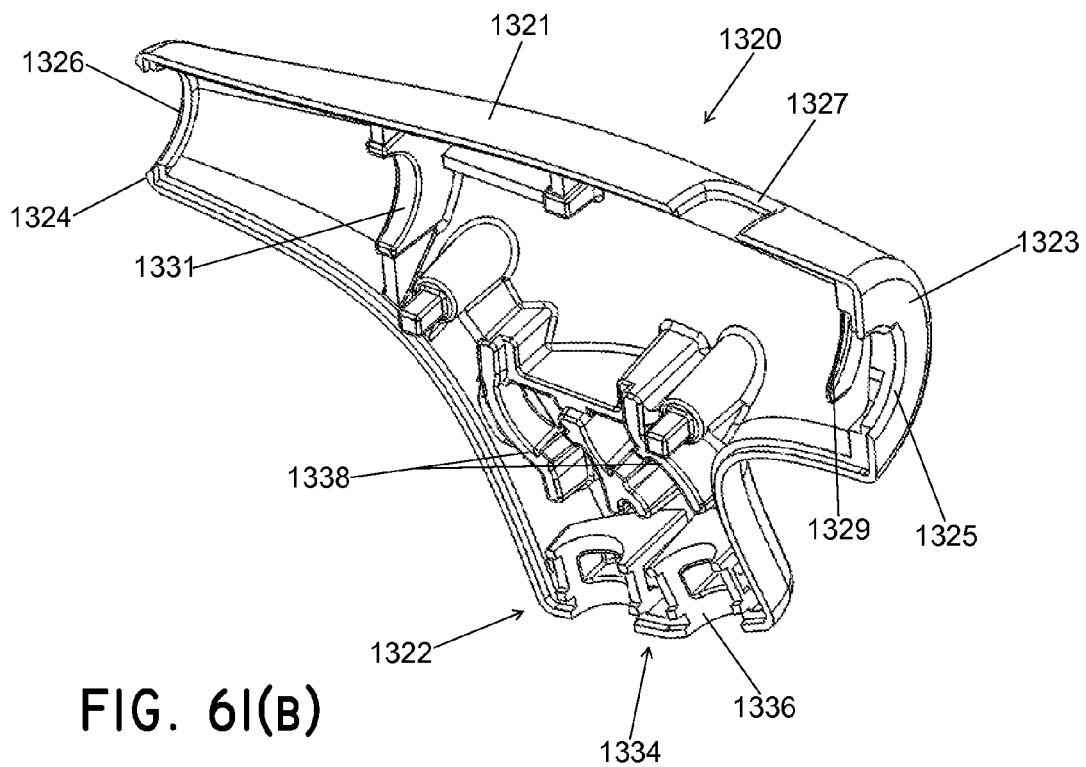

Referring now to FIG. 59, housing 1293 may comprise a pair of complementary housing halves 1319 and 1320, each of which may be a unitary structure made of a hard, medical-grade polymer or a similarly suitable material. Housing half 1319 is also shown separately in FIGS. 60(a) and 60(b), and housing half 1320 is also shown separately in FIGS. 61(a) and 61(b). Housing halves 1319 and 1320 may be joined together by suitable means, such as by screws, adhesive, or ultrasonic welding, to jointly define a generally gun-shaped structure including a barrel portion 1321 and a handle portion 1322.

Barrel portion 1321, which may be generally circular in transverse cross-section, may be a tubular structure shaped to include a proximal end 1323 and a distal end 1324. Barrel portion 1321 may taper in cross-sectional diameter from proximal end 1323 to distal end 1324. Proximal end 1323 may be shaped to include an opening 1325, and distal end 1324 may be shaped to include an opening 1326. A circumferentially-extending slot 1327, the purpose of which will become apparent below, may be provided along the top surface of barrel portion 1321 and may be spaced distally a short distance from proximal end 1323. Slot 1327 may have a first end 1327-1 and a second end 1327-2. A rib 1328 (see, for example, FIGS. 60(a) and 60(b)) may be formed on the interior surface of housing half 1319 between proximal end 1323 and slot 1327, and a rib 1329 (see, for example, FIG. 61(b)) may be formed on the interior surface of housing half 1320 between proximal end 1323 and slot 1327. Ribs 1328 and 1329 may serve to axially secure hub 1295 within housing 1293. A rib 1330 (see, for example, FIGS. 60(a) and 60(b)) may be formed on the interior surface of housing half 1319 between handle portion 1322 and distal end 1324, and a rib 1331 (see, for example, FIG. 61(b)) may be formed on the interior surface of housing half 1320 between handle portion 1322 and distal end 1324. Ribs 1330 and 1331 may be used to rotationally secure hub 1295 within housing 1293.

Handle portion 1322, which may be generally elliptical in transverse cross-section, may be a tubular structure shaped to include a joined end 1332 and a free end 1333. Handle portion 1322 may extend downwardly at an angle from barrel portion 1321, with joined end 1332 being joined to barrel portion 1321 at a location between slot 1327 and distal end 1324. Free end 1333 may be shaped to include an opening 1334 (see, for example, FIGS. 60(b) and 61(b)), the purpose of which will become apparent below. A rib 1335 (see, for example, FIGS. 60(a) and 60(b)) may be formed on the interior surface of housing half 1319, and a rib 1336 (see, for example, FIG. 61(b)) may be formed on the interior surface of housing half 1320. Ribs 1335 and 1336 may be used, in combination with free end 1333, to securely receive fluid connectors 1301-1 and 1301-2, respectively. A first plurality of ribs 1337 (see, for example, FIGS. 60(a) and 60(b)) may be formed on the interior surface of housing half 1319 between rib 1335 and barrel portion 1321, and a second plurality of ribs 1338 (see, for example, FIG. 61(b)) may be formed on the interior surface of housing half 1320 between rib 1336 and barrel portion 1321. Ribs 1337 and 1338 may be used to form channels for receiving compliant tubes 1299-1 and 1299-2.

Referring now to FIGS. 62(a) and 62(b), hub 1295 may be a unitary structure made of a hard, medical-grade polymer or a similarly suitable material. Hub 1295 may comprise a proximal portion 1339 and a distal portion 1340, each of which may be generally tubular in shape. Proximal portion 1339 and distal portion 1340 may be coaxial and in fluid communication with one another, with proximal portion 1339 having a comparatively larger inner diameter and with distal portion 1340 having a comparatively smaller inner diameter.

Proximal portion 1339 of hub 1295 may comprise a proximal end 1341 and a distal end 1342. Proximal end 1341 may be shaped to include a proximal opening 1343. A pair of circumferential ribs 1344 and 1345 may be provided on the exterior of proximal portion 1339 and may be spaced distally a short distance from proximal end 1341. Ribs 1344 and 1345 may jointly define a waist 1346 therebetween. Waist 1346 may be appropriately dimensioned to receive rib 1335 (see, for example, FIGS. 60(a) and 60(b)) and rib 1336 (see, for example, FIG. 61(b)) of housing 1293 to axially secure hub 1295 within housing 1293. The interior of proximal portion 1339 of hub 1295 may be appropriately dimensioned to coaxially receive valve assembly 1305.

Distal portion 1340 of hub 1295 may comprise a proximal end 1347 and a distal end 1348. Distal end 1348 may be shaped to include a distal opening 1349 and a pair of tabs 1350-1 and 1350-2 extending radially outwardly a short distance from the top and bottom surfaces, respectively, of distal portion 1340. Tabs 1350-1 and 1350-2 may be appropriately dimensioned to engage rib 1330 (see, for example, FIGS. 60(a) and 60(b)) and rib 1331 (see, for example, FIG. 61(a)) of housing 1293 in such a way as to rotationally secure hub 1295 within housing 1293. A pair of tubular posts 1351-1 and 1351-2 may extend downwardly from the bottom of distal portion 1340. Post 1351-1 may be positioned proximate to proximal end 1347 of distal portion 1340, and post 1351-2 may be spaced distally a short distance from post 1351-1. Posts 1351-1 and 1351-2, which may be in fluid communication with the interior of distal portion 1340, may be appropriately dimensioned for compliant tubes 1299-1 and 1299-2 (see, for example, FIG. 58(d)), respectively, to be inserted coaxially thereover and to be retained thereon by an interference fit.

Figure 63C:
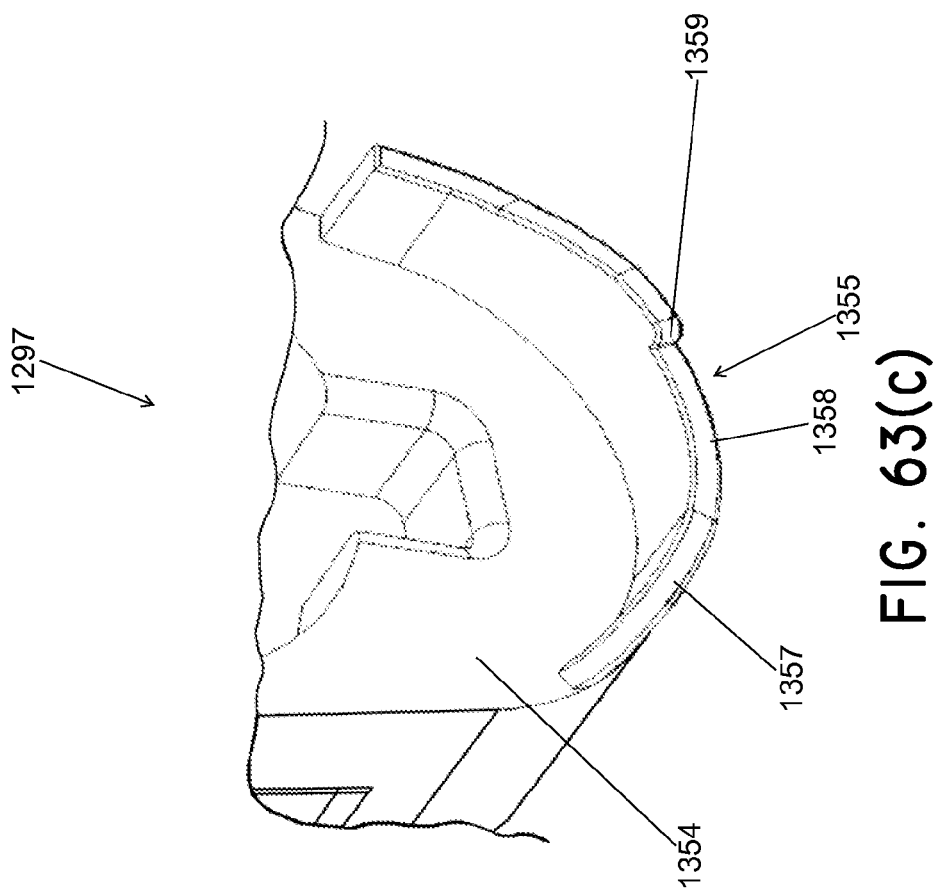

Referring now to FIGS. 63(a) through 63(c), cam 1297 may be a generally tubular, unitary structure made of a hard, medical-grade polymer or a similarly suitable material. Cam 1297, which may be rotatably mounted over hub 1295, may comprise a curved side wall 1352 having an open proximal end 1353 and an open distal end 1354. A wedge-shaped slot 1352-1 may be provided on the bottom surface of side wall 1352 and may extend from proximal end 1353 to a short distance proximal to distal end 1354. A first cam surface 1355 may extend distally a short distance from distal end 1354, and a second cam surface 1356 may extend proximally a short distance from distal end 1354.

Cam surface 1355 may be appropriately contoured and dimensioned to control fluid flow through compliant tube 1299-2, and cam surface 1356 may be appropriately contoured and dimensioned to control fluid flow through compliant tube 1299-1. More specifically, cam surface 1355 may include a ramp portion 1357, a plateau portion 1358, and a detent 1359, and cam surface 1356 may include a ramp portion 1360, a plateau portion 1361, and a detent 1362. As will become apparent below, as cam 1297 is rotated in one direction, thereby effectively causing compliant tube 1299-2 to ride along cam surface 1355 in the direction of detent 1359, the patency of compliant tube 1299-2 may be reduced by ramp portion 1357 and may be completely closed by plateau portion 1358. Similarly, as cam 1297 is rotated in an opposite direction, thereby effectively causing compliant tube 1299-1 to ride along cam surface 1356 in the direction of detent 1362, the patency of compliant tube 1299-1 may be reduced by ramp portion 1360 and may be completely closed by plateau portion 1361. Detent 1359 may be used to provide some resistance to the movement of compliant tube 1299-2 relative to cam surface 1355 as compliant tube 1299-1 rides along ramp portion 1360 of cam surface 1356, and detent 1362 may be used to provide some resistance to the movement of compliant tube 1299-1 relative to cam surface 1356 as compliant tube 1299-2 rides along ramp portion 1357 of cam surface 1355. As seen best in FIG. 63(b), ramp surfaces 1355 and 1356 may have symmetrically opposing contours. In this manner, cam surface 1355 may be arranged to provide patency for compliant tube 1299-2 at the same time that cam surface 1356 may prevent patency for compliant tube 1299-1, and cam surface 1356 may be arranged to provide patency for compliant tube 1299-1 at the same time that cam surface 1355 may prevent patency for compliant tube 1299-2.

Figure 64:
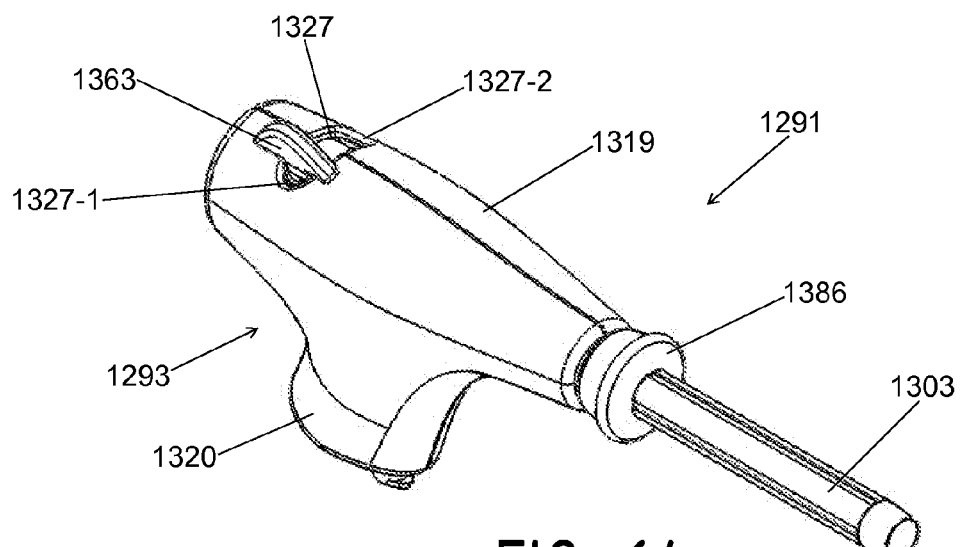
FIG. 64 is a perspective view of the access device shown in FIGS. 58(a) through 58(d), with the cam being positioned in one of its two open positions (the obturator and the protective sleeve not being shown)
Figure 65:
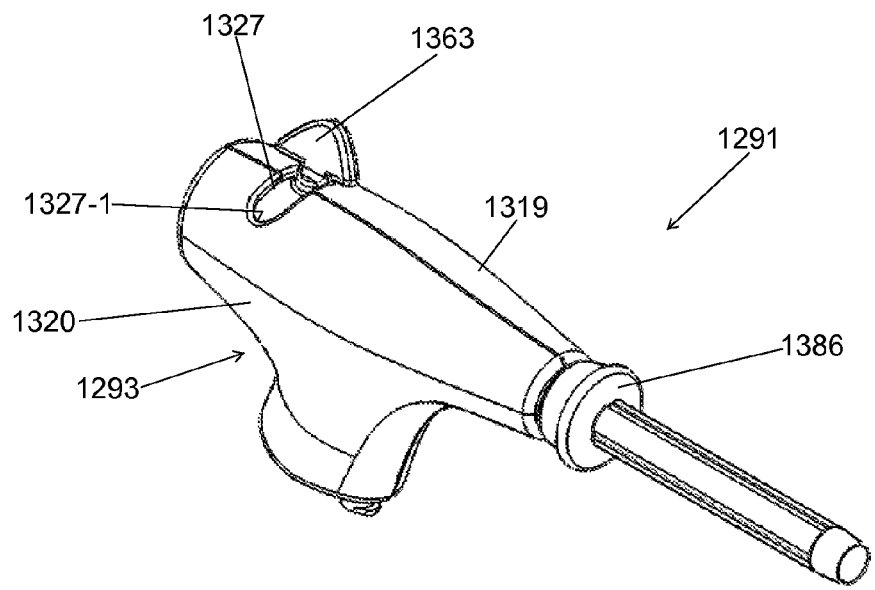
FIG. 65 is a perspective view of the access device shown in FIGS. 58(a) through 58(d), with the cam being positioned in the other of its two open positions (the obturator and the protective sleeve not being shown)

Cam 1297 may further comprise a handle 1363, which may extend upwardly from the top of side wall 1352. Handle 1363 may be appropriately dimensioned to extend through slot 1327 (see, for example, FIG. 58(a)) in housing 1293. In this manner, an operator may, for example, using his thumb, slide handle 1363 to any one of three different positions within slot 1327, i.e., a first position in which handle 1363 is centered within slot 1327 (as shown, for example, in FIG. 58(a)), a second position in which handle 1363 is positioned at end 1327-1 (as shown, for example, in FIG. 64), and a third position in which handle 1363 is positioned at end 1327-2 (as shown, for example, in FIG. 65).

Figure 66A:
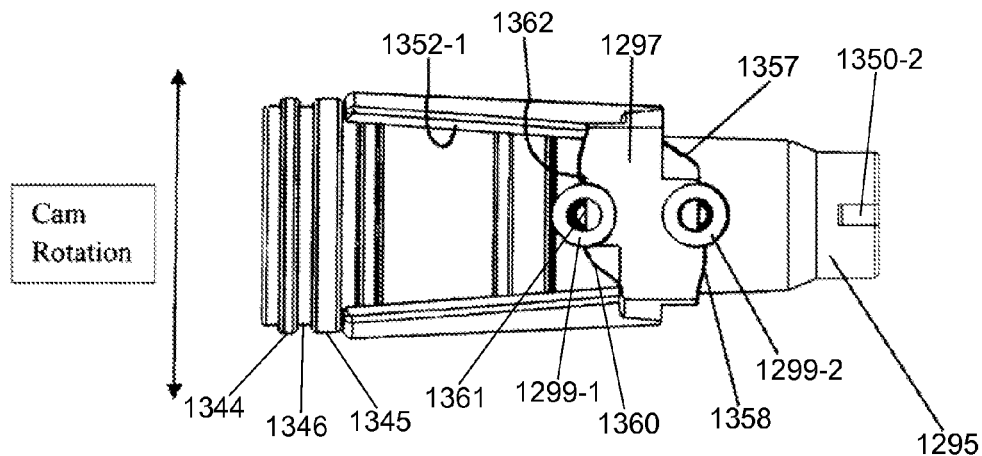
FIGS. 66(a) and 66(b) are bottom and perspective views, respectively, of the combination of the cam, the hub, and the compliant tubes of the access device shown in FIGS. 58(a) through 58(d), with the cam shown in its closed position.
Figure 66B:
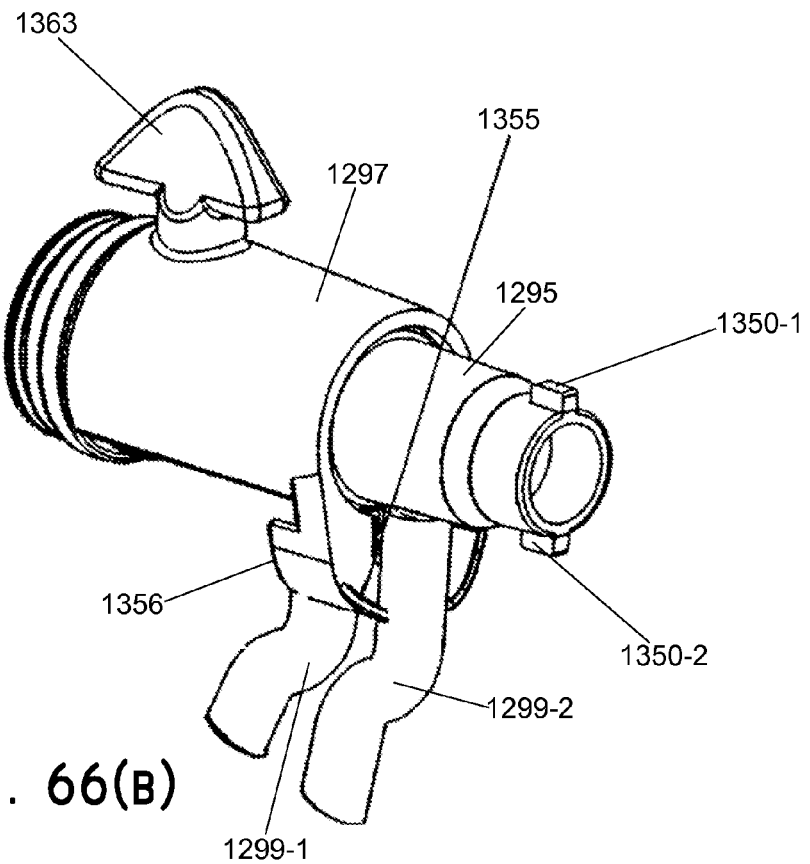

FIGS. 66(a) and 66(b) are bottom and perspective views, respectively, of the combination of hub 1295, cam 1297, and compliant tubes 1299-1 and 1299-2 of access device 1291, with cam 1297 being rotated relative to hub 1295 so that handle 1363 faces directly upwardly. As can be seen best in FIG. 66(a), in this angular orientation, compliant tube 1299-2 is closed off by plateau portion 1358 of cam surface 1355, and compliant tube 1299-1 is closed off by plateau portion 1361 of cam surface 1356.

Figure 67A:
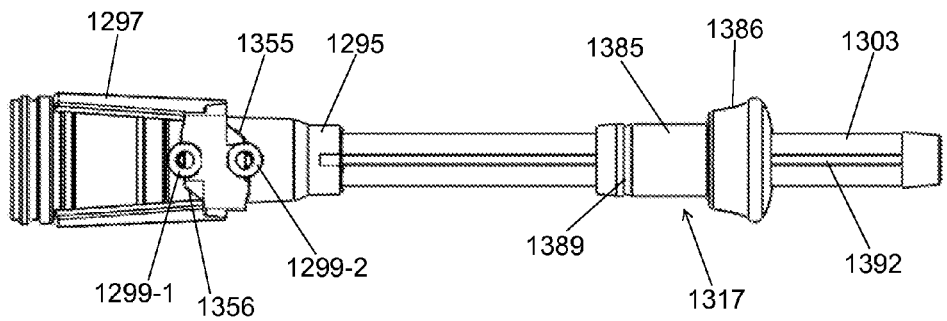
FIGS. 67(a) through 67(c) are bottom views of the combination of the cam, the hub, the compliant tubes, the sheath, and the slide ring assembly of the access device shown in FIGS. 58(a) through 58(d), with the cam shown in its closed position, with the cam shown in one of its two open positions, and with the cam shown in the other of its two open positions, respectively.
Figure 67B:
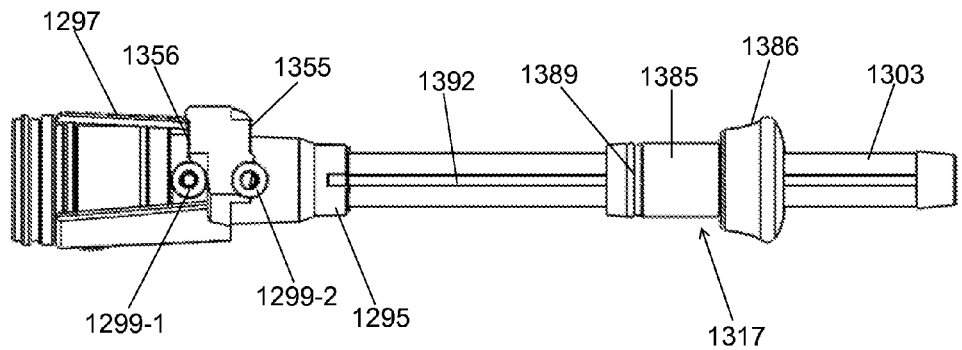
Figure 67C:
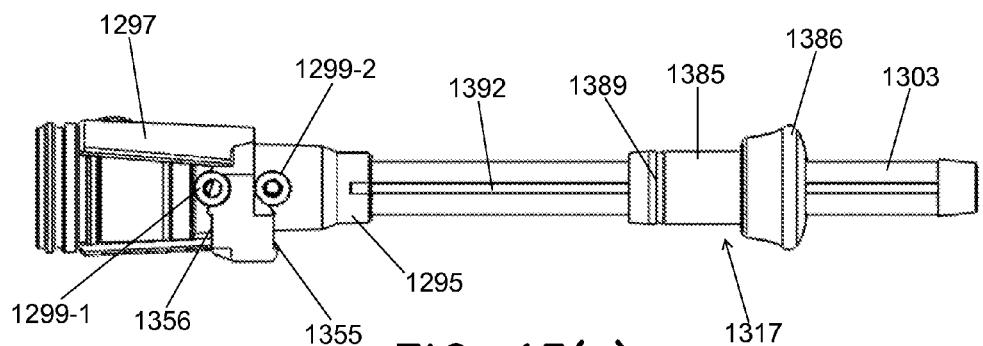

FIGS. 67(a) through 67(c) are bottom views of the combination of hub 1295, cam 1297, compliant tubes 1299-1 and 1299-2, sheath 1303, and slide ring assembly 1317 of access device 1291. FIG. 67(a) shows cam 1297 in its closed position, with compliant tube 1299-2 being closed off by cam surface 1355 and with compliant tube 1299-1 being closed off by cam surface 1356. FIG. 67(b) shows cam 1297 rotated relative to hub 1295 so that compliant tube 1299-1 is no longer closed off by cam surface 1356 whereas compliant tube 1299-2 is still closed off by cam surface 1355. FIG. 67(c) shows cam 1297 rotated relative to hub 1295 in the opposite direction to that shown in FIG. 67(b) so that compliant tube 1299-1 is now closed off by cam surface 1356 whereas compliant tube 1299-2 is no longer closed off by cam surface 1355.

It is to be understood that, although cam 1297 is constructed in the present embodiment to have three positions, namely, (i) a position in which both compliant tube 1299-1 and compliant tube 1299-2 are simultaneously pinched shut, (ii) a position in which compliant tube 1299-1 is allowed to be open and compliant tube 1299-2 is pinched shut, and (iii) a position in which compliant tube 1299-1 is pinched shut and compliant tube 1299-2 is allowed to be open, cam 1297 may be constructed to have additional positions, such as a flush position in which both compliant tube 1299-1 and compliant tube 1299-2 are allowed to be open. In addition, device 1291 may be constructed so that each of compliant tubes 1299-1 and 1299-2 may not be limited to being placed only in either a fully opened state or a fully closed state, but rather, may additionally be placed in a finite number or in an infinite number (i.e. continuously adjustable) of partially opened states having flow rates varying by equal or unequal increments between a fully opened state and a fully closed state.

Referring back now to FIG. 58(d), compliant tubes 1299-1 and 1299-2 each may be a generally tubular unitary member made of a flexible medical-grade silicone or a similarly suitable material. Compliant tube 1299-1 may include a first end 1364 and a second end 1365, and compliant tube 1299-2 may include a first end 1366 and a second end 1367. First end 1364 of compliant tube 1299-1 may be coaxially mounted over post 1351-1 and may be secured thereto, for example, by an interference fit or other suitable means, and first end 1366 of compliant tube 1299-2 may be coaxially mounted over post 1351-2 and may be secured thereto, for example, by an interference fit or other suitable means. In the above manner, compliant tubes 1299-1 and 1299-2 may be placed in fluid communication with the interior of distal portion 1340 of hub 1295 and, thus, may be placed in fluid communication with the interior of sheath 1303.

Second end 1365 of compliant tube 1299-1 may be coaxially inserted into a first end 1368-1 of fluid connector 1301-1 and may be secured thereto, for example, by adhesive or other suitable means, and second end 1367 of compliant tube 1299-2 may be coaxially inserted into a first end 1368-2 of fluid connector 1301-2 and may be secured thereto, for example, by adhesive or other suitable means. A second end 1369-1 of fluid connector 1301-1 may be in the shape of a female luer lock connector, and a second end 1369-2 of fluid connector 1301-2 may be in the shape of a female luer lock connector. One of fluid connectors 1301-1 and 1301-2 may be connected to a male luer lock connector (not shown) that, in turn, may be connected to a fluid source, and the other of fluid connectors 1301-1 and 1301-2 may be connected to a male luer lock connector (not shown) that, in turn, may be connected to a drain. Consequently, one of compliant tubes 1301-1 and 1301-2 may be used to deliver fluid to a patient, and the other of compliant tubes 1301-1 and 1301-2 may be used to drain fluid from the patient. Fluid connector 1301-1 may be further shaped to include a flange 1370-1, and fluid connector 1301-2 may be further shaped to include a flange 1370-2. Flanges 1370-1 and 1370-2 may be appropriately dimensioned to mate with rib 1335 of housing half 1319 (see, for example, FIGS. 60(a) and 60(b)) and with rib 1336 of housing half 1320 (see, for example, FIG. 61(b)) to secure fluid connectors 1301-1 and 1301-2 to housing 1293.

It is believed that, because compliant tubes 1299-1 and 1299-2 may be supported within the channels defined by ribs 1337 and 1338, compliant tubes 1299-1 and 1299-2 may be less likely to kink, particularly when subjected to the action of cam 1297.

The fluid flow rates for access device 1291 may be in the range of about 1 cc/min to about 1000 cc/min, preferably about 10 cc/min to about 500 cc/min, and more preferably about 100 cc/min to about 300 cc/min, and the inlet pressure for access device 1291 may be in the range of, for example, 0.01 in $H_2O$ to 1000 in $H_2O$ (0.0254 cm$H_2O$ to 2540 cm$H_2O$), preferably 1.0 in $H_2O$ to 100 in $H_2O$ (2.54 cm$H_2O$ to 254 cm$H_2O$), and more preferably 20 in $H_2O$ to 50 in $H_2O$ (50.8 cm$H_2O$ to 127 cm$H_2O$). The tubing inner diameter for compliant tubes 1299-1 and 1299-2 may be similar to that for tubes 909-1 and 909-2 of device 901.

Housing 1293 may be provided with markings similar to those discussed above in connection with housing 903 for indicating the various positions in which handle 1363 of cam 1297 may be placed so that device 1291 may be used for filling, draining, flushing, or the like.

Referring back now to FIGS. 58(d), sheath 1303, valve assembly 1305, seal 1307, and protective sleeve 1315 may be identical to sheath 913, valve assembly 915, seal 917, and protective sleeve 925, respectively, of device 901.

Cap 1309, which may be shown separately in FIGS. 68(a) through 68(c), may be a unitary member structure made of a hard, medical-grade polymer or similarly suitable material. Cap 1309 may comprise a proximal portion 1371 and a distal portion 1372, each of which may be generally tubular in shape. Proximal portion 1371 and distal portion 1372 may be coaxial with one another, with proximal portion 1371 being comparatively larger in diameter and with distal portion 1372 being comparatively smaller in diameter. Proximal portion 1371 may include a proximal face 1373 and a distal face 1374. An opening 1375 may be provided in proximal face 1373.

Distal portion 1372 may include a proximal end 1376 and a distal end 1377. An annular wall 1378 may be provided within distal end 1377 of distal portion 1372. A circumferential rib 1379 may be provided around the exterior of distal portion 137. Rib 1379 may be used to provide an interference fit with a groove 1380 provided on the interior of hub 1295 (see FIG. 62(b)) so that cap 1309 may be joined to hub 1295.

Figure 69:
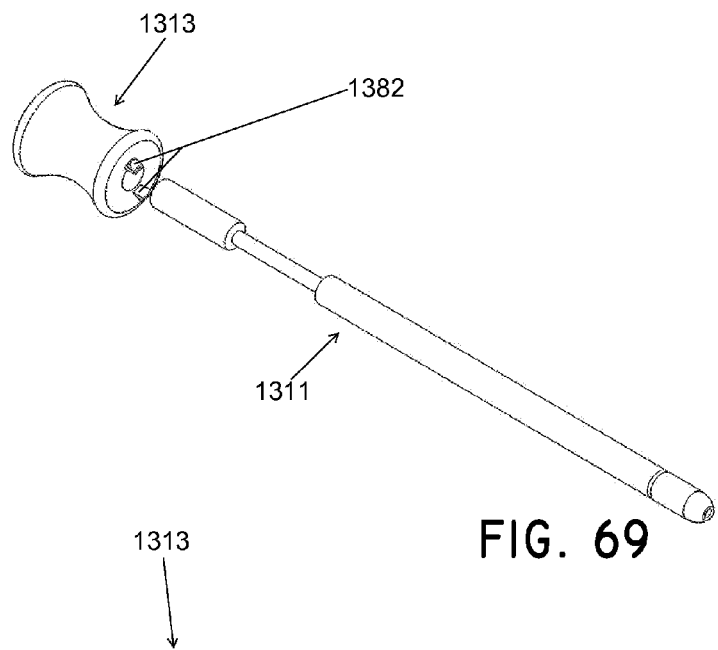
FIG. 69 is an exploded perspective view of the combination of the obturator and obturator handle shown in FIG. 58(b)
Figure 70A:
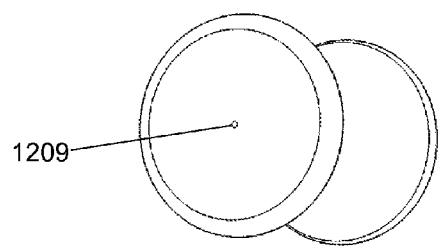
FIGS. 70(a) and 70(b) are enlarged front perspective and enlarged rear perspective views, respectively, of the obturator handle shown in FIG. 69.
Figure 70B:
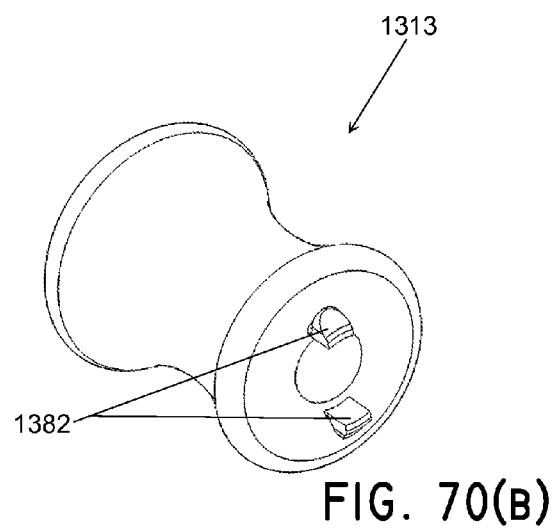
Figure 7I:
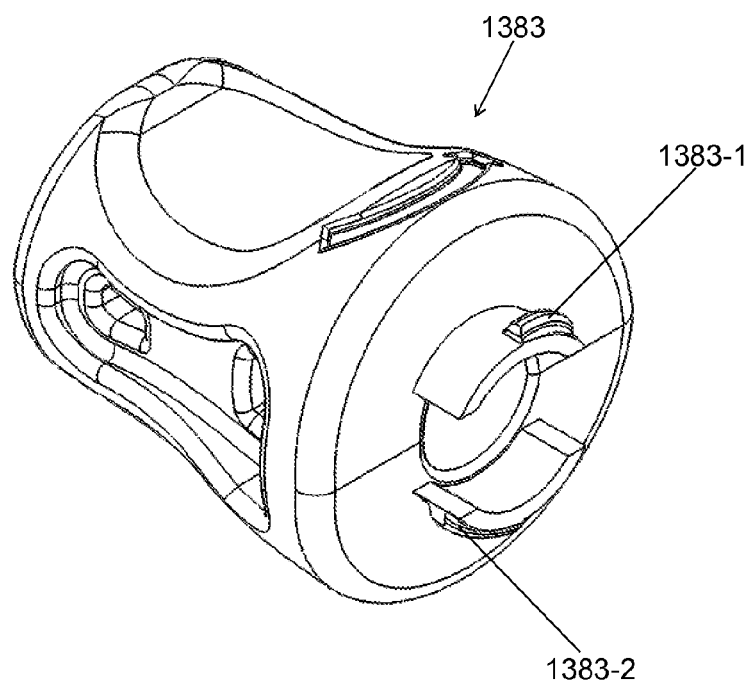
Figure 7I:
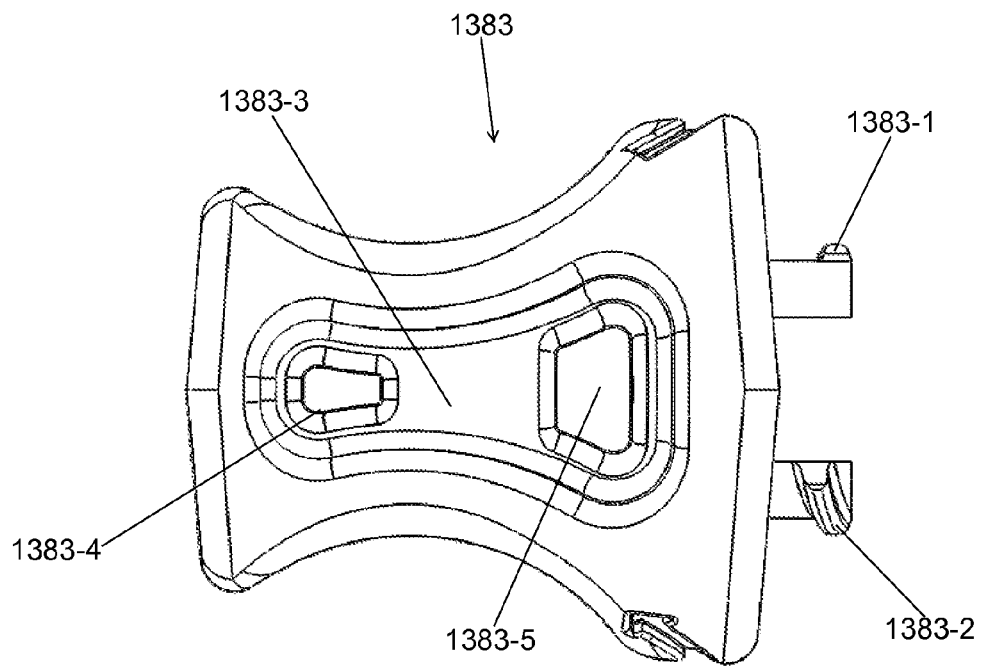

The combination of obturator 1311 and obturator handle 1313 is shown in FIG. 69. As can be seen, obturator 1311 may be identical to obturator 921 of device 901. Obturator handle 1313, which may be shown separately in FIGS. 70(a) and 70(b), may be fixed to obturator 1311 and may be shaped to include spring tabs 1382 that may be inserted through opening 1325 of housing 1293 (see, for example, FIGS. 60(b) and 61(b)) and then locked in place within housing 1293 by being rotated approximately 90 degrees against a cam 1381 (see, for example, FIGS. 60(b) and 61(b)). Such locking of obturator handle 1313 to housing 1293 may prevent undesired proximal movement of obturator 1311 relative to housing 1293 as obturator 1311 is being inserted into a patient. After access device 1291 has been properly placed in a patient, obturator 1311 may be removed from the remainder of access device 1291 by rotating obturator handle 1313 counterclockwise until spring tabs 1382 are no longer engaged by cam 1381, thereby enabling obturator handle 1313 to be withdrawn from housing 1293.

Figure 72:
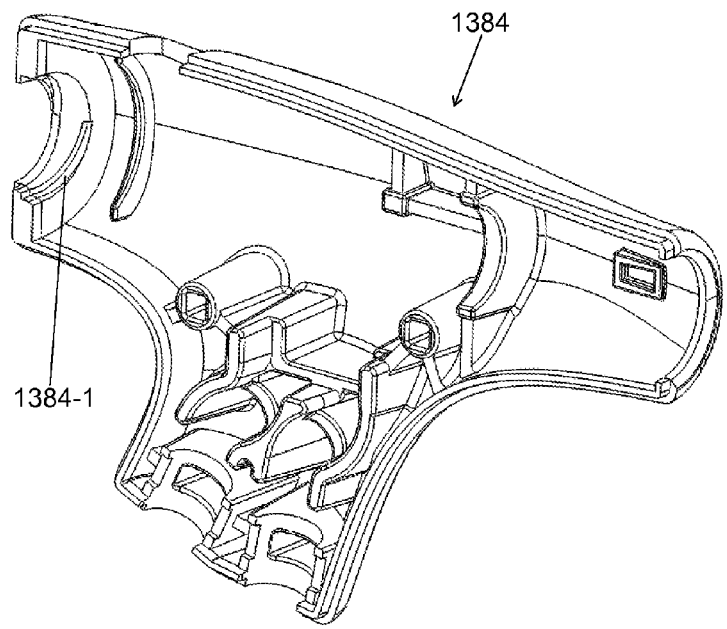
FIG. 72 is a perspective view of a first alternate left housing half to the left housing half shown in FIGS. 60(a) and 60(b)

Referring now to FIGS. 71(a) and 71(b), there are shown various views of a first alternate obturator handle 1383 to obturator handle 1313. Obturator handle 1383 may differ from obturator handle 1313 in that obturator handle 1383 may include threaded tabs 1383-1 and 1383-2, as opposed to spring tabs 1382. Handle 1383 may be particularly well-suited for use with a housing having a complementarily threaded proximal opening. (See, for example, FIG. 72, which shows left housing half 1384 with a threaded proximal opening 1384-1.) Handle 1383 may also differ from handle 1313 in that handle 1383 may be shaped to include a large pocket 1383-3 and inner pockets 1383-4 and 1383-5. Large pocket 1383-3 may have a uniform wall thickness, for example, to facilitate its manufacture by injection molding. Inner pockets 1383-4 and 1383-5 may have a reduced wall thickness, for example, to enable better securing of obturator 1311 to obturator handle 1383, for example, by welding.

Figure 73:
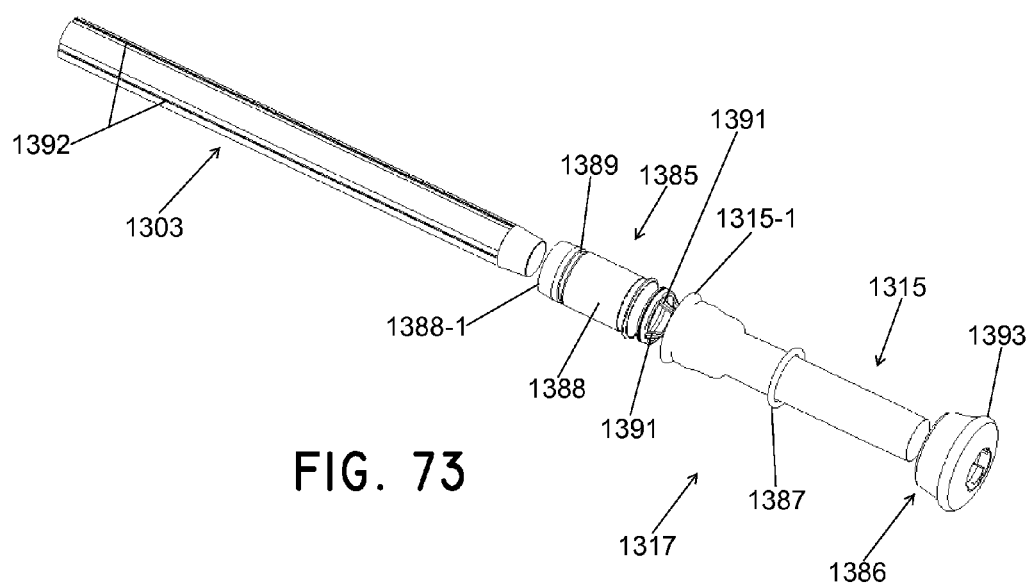
FIG. 73 is an exploded perspective view of the combination of the sheath, the protective sleeve and the slide ring assembly shown in FIG. 58(d)
Figure 74:
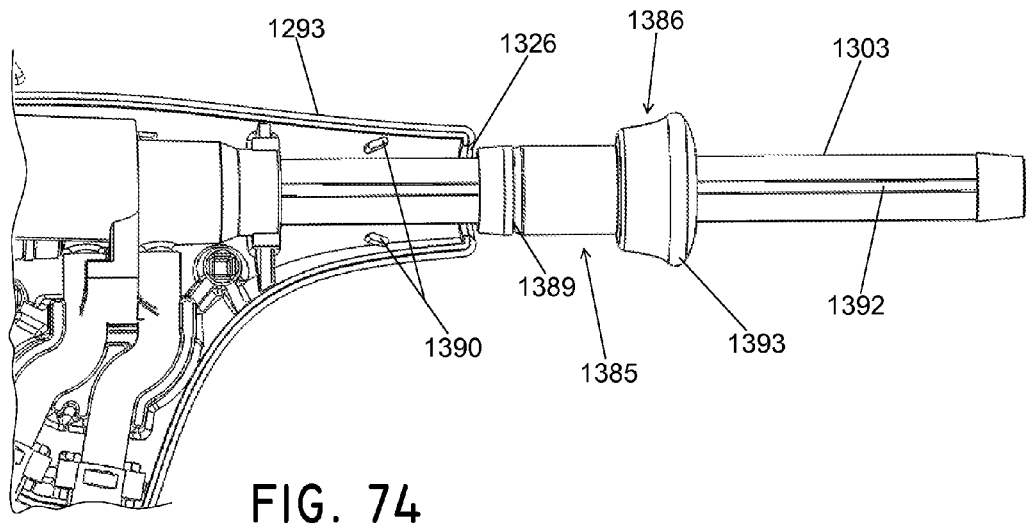
FIG. 74 is an enlarged side view of the access device shown in FIGS. 58(a) through 58(d), with the right housing half not being shown and with the slide ring assembly being shown in an intermediate position between in proximal and distal positions.
Figure 75:
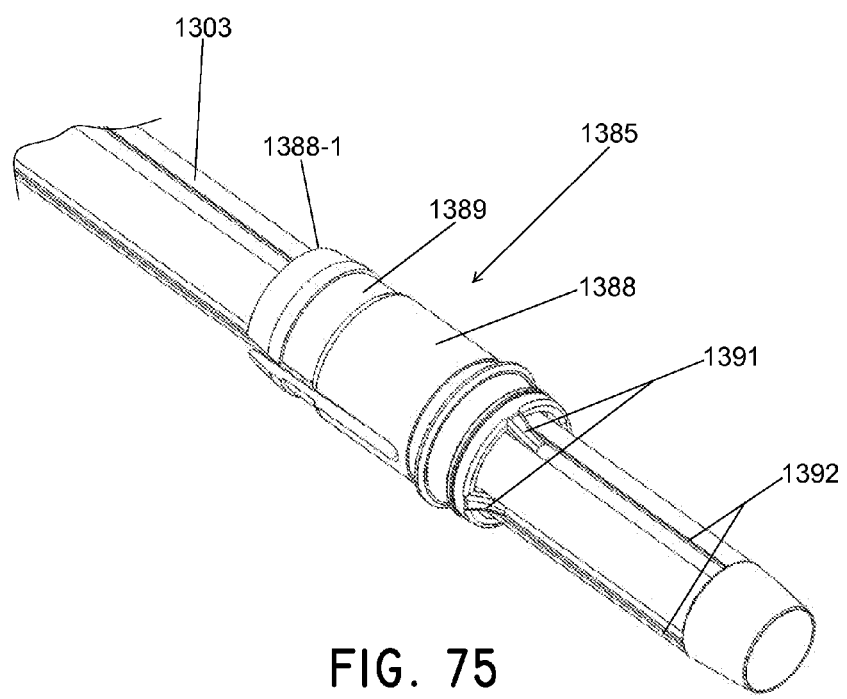
FIG. 75 is an enlarged fragmentary perspective view of the inner member of the slide ring assembly and the sheath shown in FIG. 73.

Referring now to FIG. 73, there is shown the combination of sheath 1303, protective sleeve 1315, and slide ring assembly 1317. Slide ring assembly 1317 may comprise an inner member 1385, an outer member 1386, and an O-ring 1387. Inner member 1385, which may be a unitary structure, preferably made of a hard, medical-grade polymer or a similarly suitable material, may comprise a tubular portion 1388. A circumferential notch 1389 may be provided in tubular portion 1388 near a proximal end 1388-1 of tubular portion 1388. Notch 1389 may be used to matingly receive a pair of deflectable fins 1390 provided on the interior of housing 1293 and spaced proximally a short distance from opening 1326 (see, for example, FIG. 74). The mating of fins 1390 to notch 1389 may be used to limit proximal movement of inner member 1385 and to provide a tactile indication to a user that inner member 1385 has been moved fully to its proximal position. A plurality of angularly-deflectable legs 1391 may be spaced around the periphery of tubular portion 1388 and may extend distally a short distance therefrom. Legs 1391, which may be biased radially inwardly, may be appropriately configured and dimensioned to ride within grooves 1392 of sheath 1303 and, in so doing, may constrain rotational movement of inner member 1385 relative to sheath 1303 (see, for example, FIG. 75).

An end 1315-1 of sleeve 1315 may be inserted coaxially over tubular portion 1388 of inner member 1385 and may be secured thereto by O-ring 1387. Outer member 1386, which may be a generally tubular unitary member made of a soft or compressible medical-grade polymer or a similarly suitable material, may be coaxially and fixedly mounted over O-ring 1387 and inner member 1385. Outer member 1386, which may be shaped to minimize irritation of a patient, may include a distal flange 1393, which may be used to move slide ring assembly 1317 proximally relative to sheath 1313.

Access device 1291 may have an overall length in the range of about 0.001 inch to about 20 inches, preferably about 0.1 inch to about 10 inches, more preferably about 1 inch to about 6 inches.

Access device 1291 may be used in a manner similar to that discussed above for access device 13. For example, for transurethral access to a female human urinary bladder, cam 1297 may be switched to its closed position (as in FIG. 58(a)), i.e., so that both compliant tubes 1299-1 and 1299-2 may be pinched shut, and the distal end of obturator 1311 may be aligned with and inserted into the patient. As access device 1291 may continue to be inserted into the patient, the meatus of the patient may cause slide ring assembly 1317 to be slid proximally, thereby causing the portion of sleeve 1315 that is disposed within obturator 1311 to be removed therefrom and to be everted over the exterior of sheath 1303, thereby providing a barrier between the patient's urethra and sheath 1303. Further insertion of access device 1291 into the patient may cause inner member 1385 of slide ring assembly 1317 to be slid proximally until it lockably engages fins 1390. With slide ring assembly 1317 thus engaged with fins 1390, the distal end of access device 1291 should be located in the bladder of the patient. Confirmation of such placement may be noted by the proximal flow of urine through an opening in obturator handle 1313. Obturator 1311 may then be removed from the patient by rotating obturator handle 1313 until it disengages from cam 1381 and then by withdrawing proximally the combination of obturator handle 1313 and obturator 1311 from the remainder of access device 1291. With obturator 1311 thus removed, the remaining implanted portion of access device 1291 may provide a conduit through which medical devices, such as delivery device 15, pressure-attenuating device 17, and removal device 19, may be delivered to the bladder. If desired, fluid may be delivered to or drained from the bladder by switching cam 1297 from its closed position to one of its open positions (see FIGS. 64 and 65), whereby compliant tube 1299-1 is pinched shut and compliant tube 1299-2 is allowed to be open or vice versa.

Referring now to FIG. 76, there is shown a perspective view of a first alternate cam 1395 for use in device 1291. Cam 1395 may differ from cam 1297 in that cam 1395 may have a longer ramp portion 1396 than that of cam 1297. In this manner, cam 1395 may be used to provide one or more states of partial patency. Additionally, the shape of the cam allows the body of the shell (or housing containing the cam/tubes/hub/sheath) to be narrower than if a constant radius arc (or circle) were used. The variable radius that is imparted onto the two cam surfaces (relative to the axis of rotation) can provide beneficial changes in force throughout the rotational travel of the lever or user interface (i.e., higher ramp force, when the cam surface is transitioning from smaller radius to larger radius).

Referring now to FIGS. 77(a) and 77(b), there are shown perspective and partly exploded perspective views, respectively, of a second alternate cam 1397. Cam 1397 may include a first cam surface 1398-1 and a second cam surface 1398-2, each of which may be capable of being operated independently of the other. Such independent operation may be enabled by removing a block 1399 that may be used to couple handles 1400-1 and 1400-2 for rotating surfaces 1398-1 and 1398-2, respectively. By independently operating cam surfaces 1398-1 and 1398-2, it may be possible for device 1291 to be used for "fill," "drain," "flush," and "off" functions.

Delivery Device

A delivery device may be inserted through the passageway created by the access device. The delivery device may be used to deliver a pressure-attenuating device to the body, such as to the bladder. The delivery device may deliver the pressure-attenuating device in a compacted state which may then be inflated and released. The steps of inflation and/or release may be performed by the delivery device. The delivery device can include a delivery tube, an inflation tube, a connection to inflation media and a release mechanism, among other features.

Certain embodiments of a delivery device are described in U.S. Patent Application Publication No. 2010/0222802, incorporated by reference herein. See for example: FIGS. 6-18H, and the accompanying discussion, including at paragraphs [0153]-[0206]. Embodiments of a delivery device are also provided in U.S. Pat. No. 6,976,950, incorporated by reference herein. See for example: FIGS. 6-11A, 34A-35B and 48A-48D, and the accompanying discussion, including at columns 13-16, and 35.

Referring now to FIGS. 78(a), 78(b), 79, and 80, delivery device 15 may comprise a housing 1401. Housing 1401, in turn, may comprise a pair of complementary housing halves 1403-1 and 1403-2, housing half 1403-1 also being shown separately in FIGS. 81(a) and 81(b) and housing half 1403-2 also being shown separately in FIGS. 82(a) and 82(b). Each of housing halves 1403-1 and 1403-2 may comprise a unitary structure preferably made of a hard, medical-grade polymer or a similarly suitable material. Housing halves 1403-1 and 1403-2, which may be aligned with one another by pins 1405 extending from half 1403-1 and complementary sockets 1407 provided in half 1403-2, may be secured to one another by suitable means, such as by adhesive or by ultrasonic welding. Halves 1403-1 and 1403-2 may be appropriately shaped to jointly define a generally hollow, gun-shaped structure comprising a barrel portion 1409 and a handle portion 1411.

The housing 1401 may include one or more openings at the proximal end. The housing 1401 may be shaped to include a first opening 1413 at a proximal end 1415 of barrel portion 1409, a second opening 1417 spaced inwardly a short distance from first opening 1413, and a third opening 1419 at a distal end 1421 of barrel portion 1409. For reasons to become apparent below, first opening 1413 may be of greater diameter than second opening 1417, and each of openings 1413 and 1417 may be angled downwardly slightly relative to the longitudinal axis of barrel portion 1409, with opening 1417 being angled downwardly to a greater extent than is opening 1415.

Figure 79:
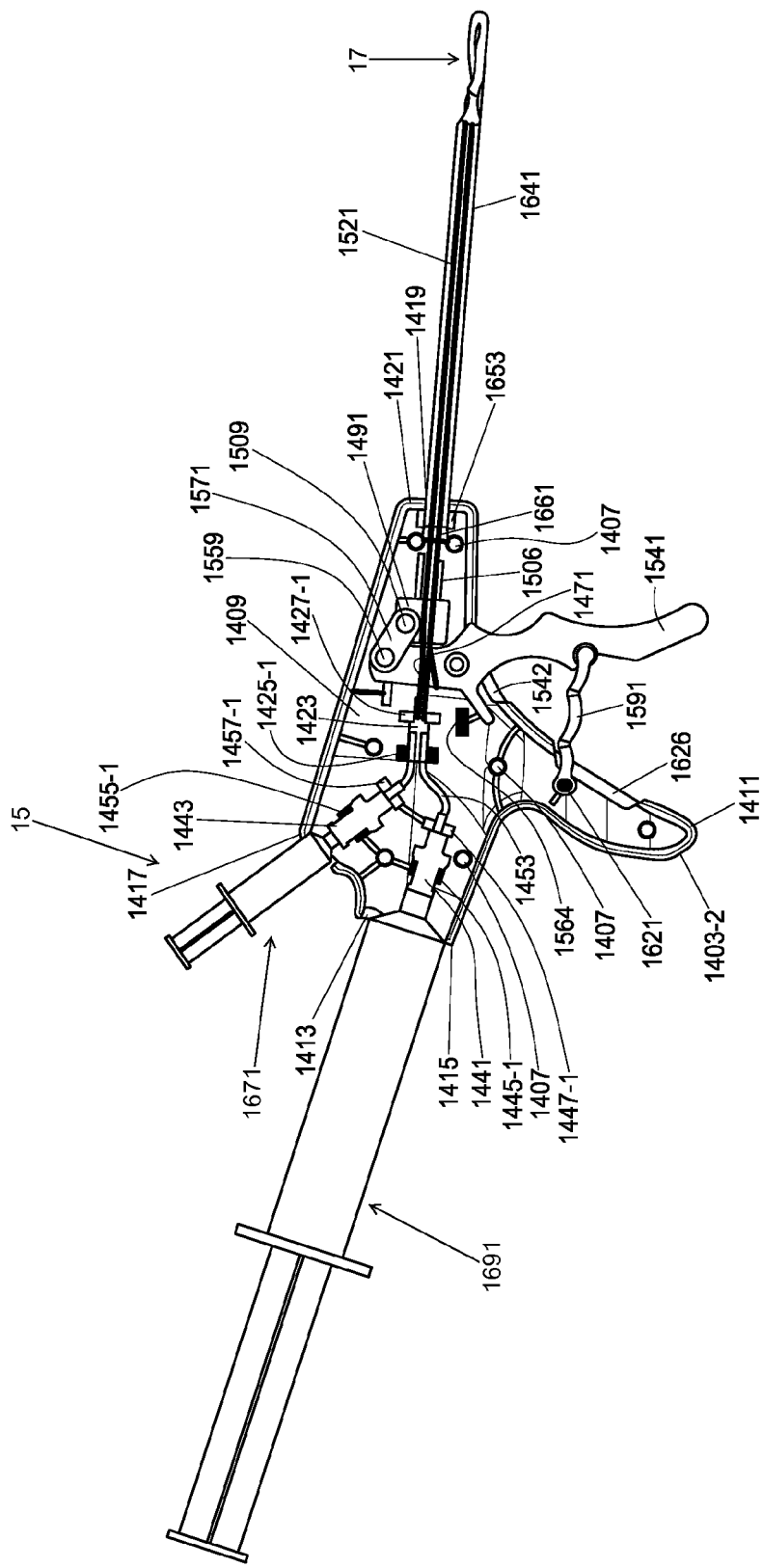
FIG. 79 is a side view, partly in section, of the delivery device shown in FIG. 1, with one of the housing halves removed to reveal certain components located within the housing, the delivery device being shown with the pressure-attenuating device of FIG. 1 in a deflated state loaded thereinto.
Figure 80:
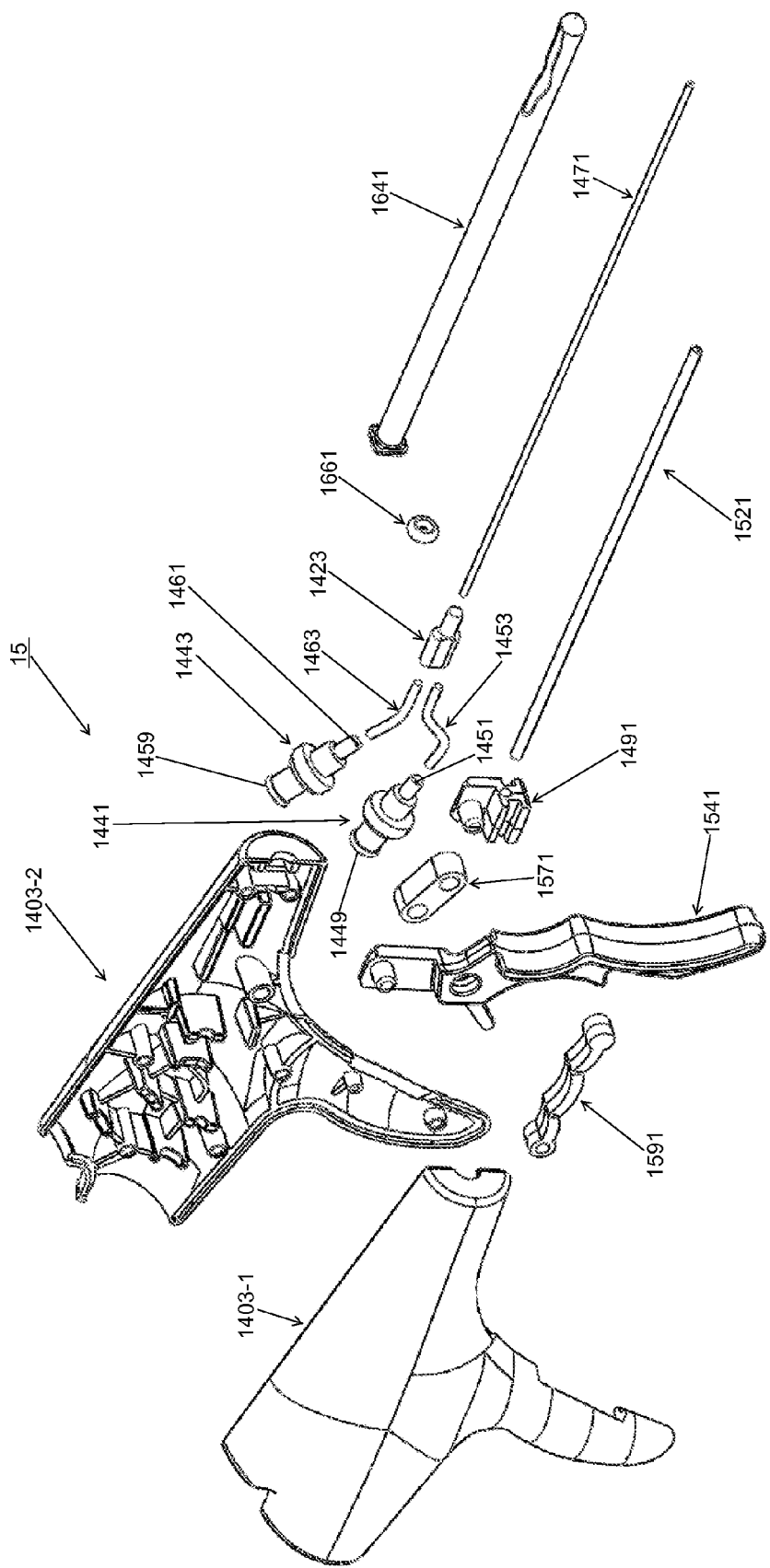
FIG. 80 is a partially exploded perspective view of the delivery device shown in FIGS. 78(a) and 78(b)
Figure 83:
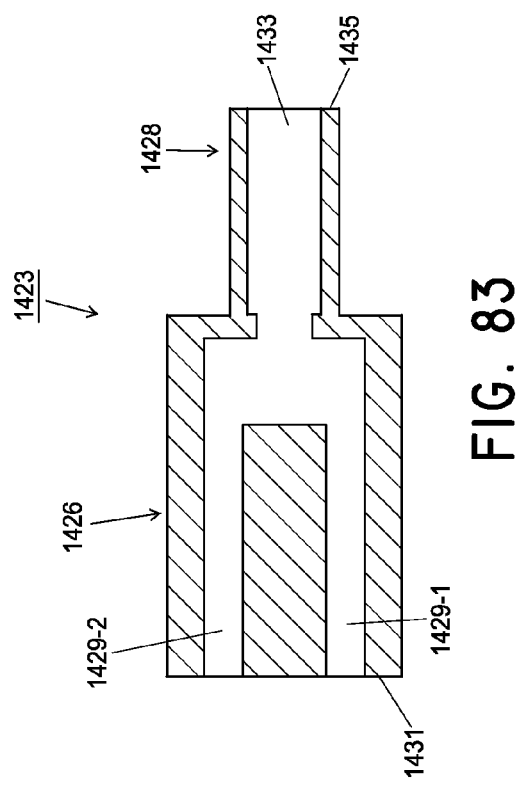
FIG. 83 is a section view of the fluid connector shown in FIG. 79.

Delivery device 15 may further comprise a fluid connector 1423 (see FIGS. 79-80). Connector 1423, shown separately in FIG. 83, may be disposed within housing 1401 and may be fixedly mounted on a pair of supports 1425-1 and 1427-1 formed on half 1403-2. (Complementary supports 1425-2 and 1427-2 on half 1403-1 may be provided to furnish additional support to connector 1423.) The connector can receive one, two, or more lines in and can have one line out. Connector 1423, which may be a unitary structure preferably made from a hard, medical-grade polymer or a similarly suitable material, may be shaped to include a proximal portion 1426 of comparatively greater width and a distal portion 1428 of comparatively lesser width. A pair of fluid channels 1429-1 and 1429-2 may be provided in proximal portion 1426 and may extend in a generally parallel fashion distally from a proximal end 1431 of proximal portion 1426. A fluid channel 1433 may be provided in distal portion 1428 and may extend proximally from a distal end 1435 of distal portion 1428. The distal ends of channels 1429-1 and 1429-2 may be joined to the proximal end of channel 1433 such that each of channels 1429-1 and 1429-2 may be in fluid communication with channel 1433.

Figure 84:
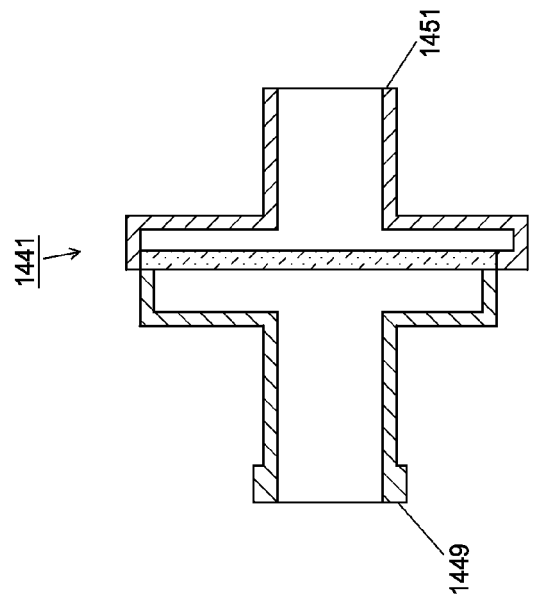
FIG. 84 is a section view of one of the check valve shown in FIG. 79.

Delivery device 15 may further comprise a pair of connectors and/or check valves 1441 and 1443 (FIGS. 79-80). The connectors and/or check valves can be identical or different. Though the connectors and/or check valves will be described generally as check valves, it will be understood that a check valve is not required. Check valve 1441, shown in FIG. 84, may be disposed within barrel portion 1409 and may be fixedly mounted on a pair of supports 1445-1 and 1447-1 formed on half 1403-2. (Complementary supports 1445-2 and 1447-2 on half 1403-1 may be provided to furnish additional support to valve 1441.) Valve 1441, which may be made, for example, of a hard, medical-grade polymer or a similarly suitable material, may comprise a proximal end 1449 and a distal end 1451. Proximal end 1449, which may be in the shape of a female luer connector, may be oriented coaxially with opening 1413 but spaced distally a short distance therefrom. Distal end 1451 may be fluidly connected to fluid channel 1429-1 of connector 1423 by a fluid line 1453. Check valve 1443 may be disposed within barrel portion 1409 and may be fixedly mounted on a pair of supports 1455-1 and 1457-1 formed on half 1403-2. (Complementary supports 1455-2 and 1457-2 on half 1403-1 may be provided to furnish additional support to valve 1443.) Valve 1443 may comprise a proximal end 1459 and a distal end 1461. Proximal end 1459 may be oriented coaxially with opening 1417 but spaced distally a short distance therefrom. Distal end 1461 may be fluidly connected to fluid channel 1429-2 of connector 1423 by a fluid line 1463.

Figure 85:
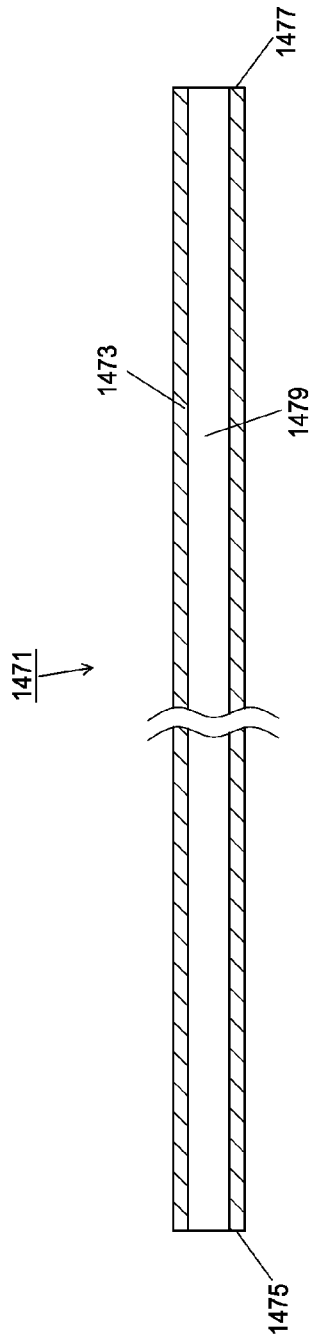
FIG. 85 is a section view of the inflation tube shown in FIG. 79.
Figure 9I:
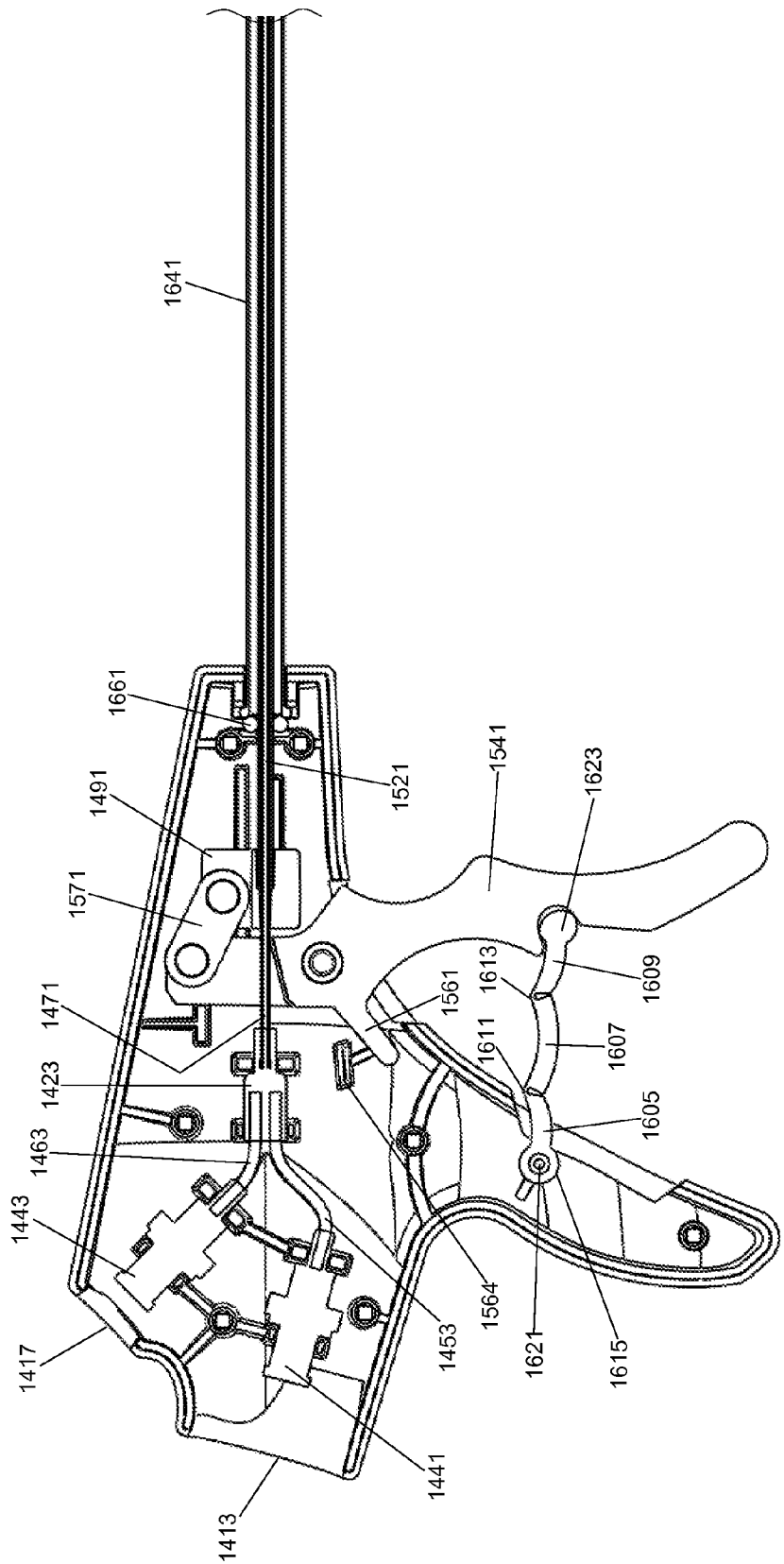
FIGS. 9(a) and 9(b) are section and distal views, respectively, of the seal shown in FIG. 2(b)
Figure 9I:
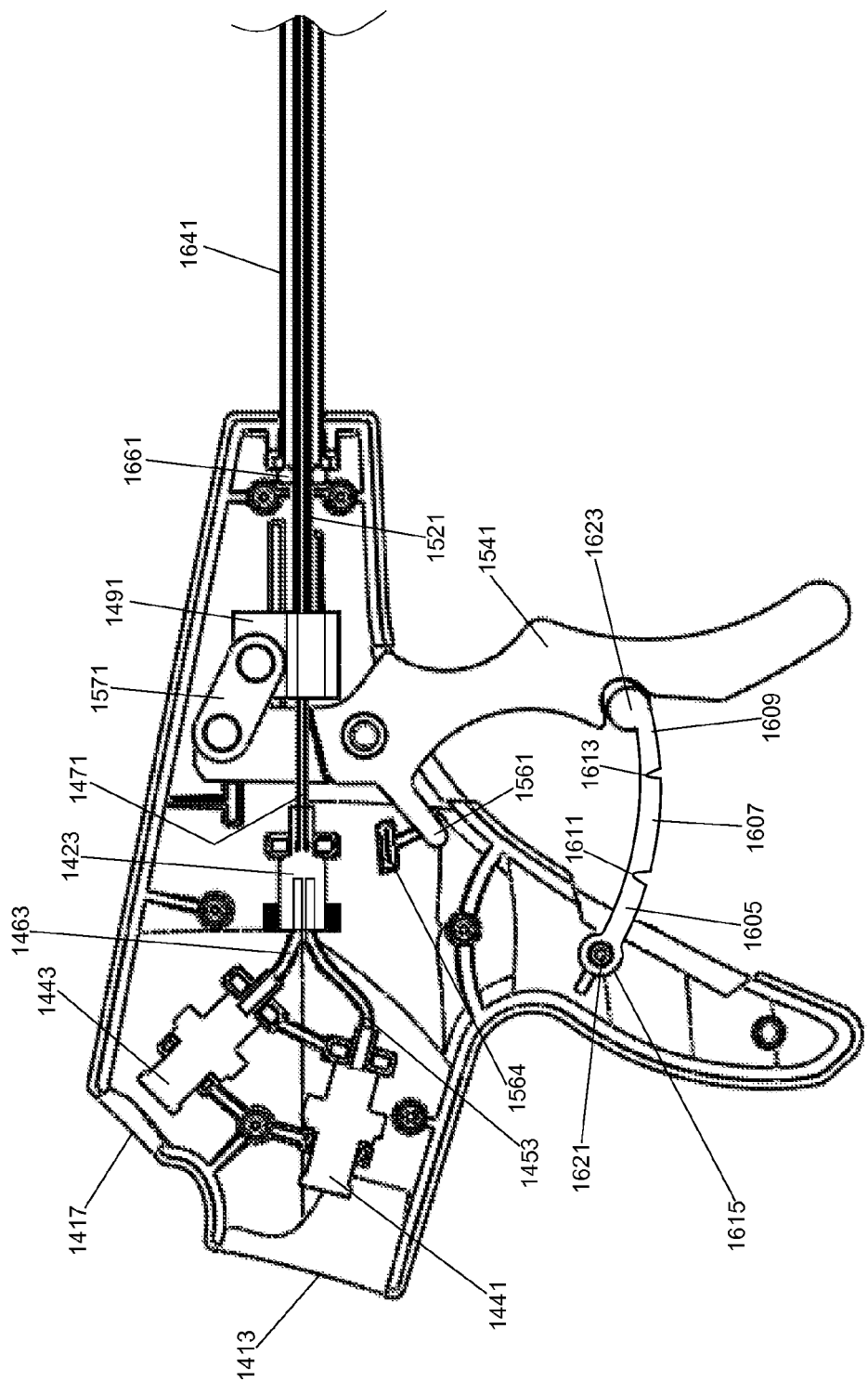

Delivery device 15 may further comprise an inflation tube 1471 (FIGS. 79-80). Tube 1471, which is also shown separately in FIG. 85, may be a unitary structure preferably made of a medical-grade stainless steel or a similarly suitable material. Tube 1471 may comprise a circular side wall 1473 defining a proximal end 1475, a distal end 1477, and a longitudinal channel 1479 extending from proximal end 1475 to distal end 1477. Proximal end 1475 of tube 1471 may be fixedly mounted within channel 1433 of connector 1423 in such a way that channels 1433 and 1479 are aligned and in fluid communication with one another. The remainder of tube 1471 may extend distally from connector 1423 through opening 1419 of housing 1401, with distal end 1477 of tube 1471 being positioned a distance, e.g., several inches, from distal end 1421 of housing 1401. As will be discussed further below, distal end 1477 of inflation tube 1471 may be inserted into pressure-attenuating device 17 for use in inflating device 17; therefore, inflation tube 1471, or at least the distal end, may have an outer diameter that is appropriately dimensioned for this purpose.

It should be understood that, although inflation tube 1471 of the present embodiment has a single channel 1479, inflation tube 1471 could have two or more such channels, with said two or more channels being fluidly coupled to channel 1433. Alternatively, one or more of such channels could be fluidly coupled to connector and/or check valve 1441, and one or more of such channels could be fluidly coupled to connector and/or check valve 1443. In this manner, for example, the materials passing through connector and/or check valve 1441 could be conducted to one of said two or more channels, and the materials passing through connector and/or check valve 1443 could be conducted to another of said two or more channels.

Delivery device 15 may further comprise a carriage 1491 and a decoupling or push-off member 1521 (FIGS. 79-80). These components can be part of a release mechanism used to decouple the inflated implant from the inflation tube 1471 as will be described below. Carriage 1491, shown in FIGS. 86(*a*) through 86(*e*), may be a unitary structure preferably made of a hard, medical-grade polymer or a similarly suitable material. Carriage 1491 may be shaped to comprise a top 1493, a bottom 1495, a left side 1497, a right side 1499, a proximal end 1501, and a distal end 1503. There may be one or more slots and complimentary protrusions or ribs on either the carriage or the housing. For example, left side 1497 may be shaped to include a longitudinal slot 1505, and right side 1499 may be shaped to include a similar longitudinal slot 1507. Slot 1505 may be appropriately dimensioned to permit carriage 1491 to slide on a complementarily shaped rib 1506 formed on half 1403-2 and extending in the direction of the longitudinal axis of barrel portion 1409. Slot 1507 may be appropriately dimensioned to permit carriage 1491 to slide on a corresponding rib 1508 formed on half 1403-1. Left side 1497 may additionally be shaped to include a post 1509 extending towards half 1403-1, the purpose of post 1509 to become apparent below. Carriage 1491 may be additionally shaped to include a longitudinal channel 1511 extending from proximal end 1501 to distal end 1503. Longitudinal channel 1511 may be aligned with and may be appropriately dimensioned relative to inflation tube 1471 such that carriage 1491 may be permitted to ride freely along a portion of inflation tube 1471. For reasons to become apparent below, channel 1511 may include a proximal portion 1511-1 of comparatively lesser diameter and a distal portion 1511-2 of comparatively greater diameter.

Push-off member 1521, shown in FIG. 87, may comprise a unitary structure preferably made of a medical-grade polymer or a similarly suitable material. Push-off member 1521 may comprise a tube with a circular side wall 1523 defining a proximal end 1525, a distal end 1527, and a longitudinal channel 1529 extending from proximal end 1525 to distal end 1527. Proximal end 1525 of push-off member 1521 may be fixedly mounted by glue or other suitable means within distal portion 1511-2 of channel 1511, with the remainder of push-off member 1521 extending distally from carriage 1491 and through opening 1419 of housing 1401. Member 1521 may be mounted coaxially around tube 1471, and the inner diameter of push-off member 1521 may be sufficiently larger than the outer diameter of tube 1471 to permit member 1521 to slide freely over tube 1471. Push-off member 1521 may have a length such that, when push-off member 1521 is positioned in its most proximal position, distal end 1527 of push-off member 1521 may be positioned sufficiently proximal to distal end 1477 of tube 1471 so as not to interfere with the coupling of tube 1471 to a pressure-attenuating device 17 mounted thereon, and such that, when push-off member 1521 is positioned in its most distal position, distal end 1527 of tube may be positioned sufficiently distal to distal end 1477 of tube 1471 so as to cause tube 1471 to be physically decoupled from a pressure-attenuating device 17 mounted thereon. Although distal end 1527 has been shown herein as having a straight end, it should be understood that distal end 1527 could alternatively be shaped so as to be biased towards the outer diameter of push-off member 1521 to minimize the possibility of skiving against device 17 as it approaches the pushing-off surface of device 17.

Also, it is to be understood that, although inflation tube 1471 has been described herein as being fixed to housing 1401 and push-off member 1521 has been described herein as sliding relative both to tube 1471 and to housing 1401, both tube 1471 and push-off member 1521 could be slidably mounted relative to housing 1401, or tube 1521 could be fixed relative to housing 1401 and tube 1471 could be slidably mounted relative to housing 1401. It is also to be understood that, although push-off member 1521 has been described herein as being tubular in shape, push-off member 1521 could be a non-tubular member.

Delivery device 15 may further comprise a trigger 1541 (FIGS. 79-80). Trigger 1541, shown in FIGS. 88(*a*) and 88(*b*), may comprise a unitary structure preferably made of a hard, medical-grade polymer or a similarly suitable material. Trigger 1541 may be an elongated member that may be shaped to include a left side 1543, a right side 1545, a proximal end 1547, a distal end 1549, a top 1551, and a bottom 1553. Trigger 1541 may be partially inserted into barrel portion 1409 of housing 1401 through an opening 1542 provided in housing 1401 and may be mounted for pivotal movement using a pair of posts 1555-1 and 1555-2 formed on housing halves 1403-1 and 1403-2, respectively, and extending through a transverse opening 1557 in trigger 1541. For reasons to become apparent below, left side 1543 may be shaped to include a post 1559 extending in the direction of housing half 1403-1. Proximal end 1547 of trigger 1541 may be shaped to include a tab 1561 that may extend proximally at an angle for a short distance. Tab 1561 may have a beveled surface 1563 that may permit tab 1561 to slide across a rib 1564 extending from housing 1403-2 as trigger 1541 completes its trigger stroke (i.e., as trigger 1541 pivots clockwise) but that, thereafter, prevents tab 1561 from returning to its original position by sliding back across rib 1564 (i.e., as trigger 1541 pivots counterclockwise). In this manner, tab 1561 and rib 1564 may effectively prevent the return of trigger 1541 to its original position after being actuated, thereby ensuring that trigger 1541 is squeezed only once. As tab 1561 slides across rib 1564, an audible click may be produced, which may be desirable in notifying an operator of device 15 that trigger 1541 has completed its clockwise trigger stroke. (As will be discussed further below, the squeezing of trigger 1541 is used to release an inflated pressure-attenuating device 17 from delivery device 15. Therefore, the audible click produced by tab 1561 sliding across rib 1564 may signal to a user that pressure-attenuating device 17 has been released from delivery device 15.)

Delivery device 15 may further comprise a linkage 1571 (FIGS. 79-80). Linkage 1571, shown in FIGS. 89(*a*) and 89(*b*), may comprise a unitary structure preferably made of a hard, medical-grade polymer or a similarly suitable material. Linkage 1571 may be an elongated member of generally oval-shape in transverse cross-section comprising a pair of transverse openings 1573 and 1575. Opening 1573 may be appropriately dimensioned to receive post 1509 of carriage 1491, and opening 1575 may be appropriately dimensioned to receive post 1559 of trigger 1541. In this manner, by inserting posts 1509 and 1559 into openings 1573 and 1575, respectively, linkage 1571 may be used to mechanically couple trigger 1541 and carriage 1491 such that the squeezing of trigger 1541 causes carriage 1491 to be slid from its most proximal position to its most distal position. Consequently, because push-off member 1521 may be mechanically coupled to carriage 1491 in the manner described above, the squeezing of trigger 1541 may cause push-off member 1521 to be moved from its most proximal position to its most distal position. The trigger 1541 and the linkage 1571 can be part of the release mechanism. In some embodiments, the trigger 1541 can engage one or more of the cartridge and the push-off member directly with or without some of the intermediate components.

Delivery device 15 may further comprise a safety 1591 (FIGS. 79-80). Safety 1591, shown in FIG. 90, can effectively prevent actuation of the trigger. Safety 1591 may comprise a unitary structure preferably made of a medical-grade polymer or a similarly suitable material. Safety 1591 may be an elongated member shaped to include a top surface 1593 and a bottom surface 1595. A pair of spaced-apart, wedge-shaped cuts 1601 and 1603 may be provided in safety 1591, cuts 1601 and 1603 extending from bottom surface 1595 towards, but not completely to, top surface 1593. Cuts 1601 and 1603 may define a proximal segment 1605, an intermediate segment 1607, and a distal segment 1609, with proximal segment 1605 and intermediate segment 1607 being interconnected by a bridge 1611 and with intermediate segment 1607 and distal segment 1609 being interconnected by a bridge 1613. Proximal segment 1605 may include a proximal end 1615 that may be circular in longitudinal cross-section. End 1615 may be shaped to include a transverse opening 1617 that may be appropriately dimensioned to receive a pair of posts 1619 and 1621 formed on housing halves 1403-1 and 1403-2, respectively. Distal segment 1609 may include a distal end 1623 that may be circular in longitudinal cross-section. End 1623 may be appropriately dimensioned to be received within a recess 1625 provided in trigger 1541. In this manner, safety 1591 may be coupled at one end to housing 1401 by virtue of the engagement of posts 1619 and 1621 with opening 1617, and safety 1591 may be coupled at the opposite end to trigger 1541 by virtue of the engagement of end 1623 with recess 1625, with an intermediate length of safety 1591 extending through an opening 1626 in handle portion 1411 of housing 1401.

As can be seen best in FIGS. 91(*a*) and 91(*b*), because of the construction of safety 1591 and because of the manner in which safety 1591 may be coupled to housing 1401 and to trigger 1541, safety 1591 may assume either a locked state or an unlocked state. When in such a locked state, which is shown, for example, in FIG. 91(*a*), proximal segment 1605 is bent downwardly at bridge 1611 relative to intermediate segment 1607, and distal segment 1609 is bent downwardly at bridge 1613 relative to intermediate segment 1607. In this state, compressive pressure applied to safety 1591 at ends 1615 and 1623, such as by applying a squeezing force to trigger 1541, cannot readily cause ends 1615 and 1623 to be drawn appreciably closer to one another; thus, trigger 1541 is effectively prevented from being actuated. By contrast, as seen in FIG. 91(*b*), when proximal segment 1605 is bent upwardly at bridge 1611 and when distal segment 1609 is bent upwardly at bridge 1613, compressive pressure applied to safety 1591 at ends 1615 and 1623, such as by applying a squeezing force to trigger 1541, causes ends 1615 and 1623 to be drawn considerably closer to one another as safety 1591 bends at bridge 1611, thereby enabling trigger 1541 to be actuated. Moreover, safety 1591 may be transformed from its locked state to its unlocked state simply by applying sufficient force to the top surface of intermediate segment 1607 to cause proximal segment 1605 and distal segment 1609 to pivot about bridges 1611 and 1613, respectively. Such force may be provided, for example, using the index finger or thumb of the hand used to grip trigger 1541. The safety can be an ambidextrous safety.

Delivery device 15 may further comprise a window catheter 1641 (FIGS. 79-80). Catheter 1641, which is also shown separately in FIGS. 92(*a*) through 92(*c*), may comprise a unitary structure preferably made of a medical-grade polymer or a similarly suitable material having columnar strength with some angular flexibility. Though illustrated as a separate piece from the housing 1401, it will be understood that the window catheter 1641 can be part of housing and may be made integral with one or more of the other housing components or parts. Catheter 1641 may comprise a side wall 1643 defining an open proximal end 1645, a closed distal end 1647, a channel 1649 extending longitudinally from open proximal end 1645 up to closed distal end 1647, and a window 1651 spaced a short distance from distal end 1647 and providing top access to channel 1649 through side wall 1643. The closed distal end 1647 can be an atraumatic end or shape, such as a rounded or hemispherical end. Proximal end 1645 of catheter 1641 may have an enlarged profile relative to the remainder of catheter 1641, which can be generally circular in transverse cross-section for most of its length. The enlarged cross section can be may be generally rectangular in transverse cross-section. This enlarged proximal end 1645 of catheter 1641 may be fixedly mounted within barrel portion 1409 of housing 1401 and may be disposed on a support 1653 formed on half 1403-2, with the remainder of catheter 1641 extending distally through opening 1419 in housing 1401 and continuing distally for several inches. (A complementary support 1655 on half 1403-1 may be provided to furnish additional support to end 1645.) Inflation tube 1471 and push-off member 1521 may be coaxially received within channel 1649 (with inflation tube 1471 also being coaxially received within push-off member 1521), with channel 1649 having a sufficiently large diameter to permit push-off member 1521 to slide freely therewithin.

As will be discussed further below, pressure-attenuating device 17 may be disposed at least partially within channel 1649 during the insertion of device 15 into a desired anatomical structure of a patient and during inflation of pressure-attenuating device 17. Pressure-attenuating device 17 may be released from channel 1649 through window 1651 when deployment of device 17 is desired. Accordingly, window 1651 may be appropriately shaped to promote retention of pressure-attenuating device 17 within channel 1649 during the aforementioned insertion and inflation steps and to promote release of pressure-attenuating device 17 from channel 1649 through window 1651 when deployment is desired. To this end, in the present embodiment, window 1651 may be shaped to include a proximal portion 1652-1, a distal portion 1652-2, and an intermediate portion 1652-3. Proximal portion 1652-1 and distal portion 1652-2 may be substantially similar to one another and may be comparatively narrower and comparatively shallower than intermediate portion 1652-3, with intermediate portion 1652-3 transitioning from the width and depth of proximal portion 1652-1 and distal portion 1652-2 to a maximum width and depth between proximal portion 1652-1 and distal portion 1652-2. Each of window 1651 and catheter 1641 may be appropriately dimensioned in length so that the distal end 1477 of inflation tube 1471 may be approximately aligned with the transition in window 1651 from proximal portion 1652-1 to intermediate portion 1652-3. Moreover, each of window 1651 and catheter 1641 may be appropriately dimensioned in length so that, when push-off member 1521 is in its most distal position, the distal end 1527 of push-off member 1521 may be approximately aligned with the midpoint of intermediate portion 1652-3 of window 1651.

The cross section of catheter 1641 at the proximal portion of the window 1652-1 has an opening between 1 and 270 degrees, more preferably between 20 and 180 degrees, more preferably between 50 and 120 degrees, and more preferably approximately 95 degrees. The cross section of catheter 1641 at the middle portion of the window 1652-2 has an opening between 1 and 270 degrees, more preferably between 20 and 180 degrees, more preferably between 50 and 180 degrees, and more preferably approximately 151 degrees. The cross section of catheter 1641 at the distal portion of the window 1652-3 has an opening between 1 and 270 degrees, more preferably between 20 and 180 degrees, more preferably between 50 and 120 degrees, and more preferably approximately 102 degrees.

Figure 92C:
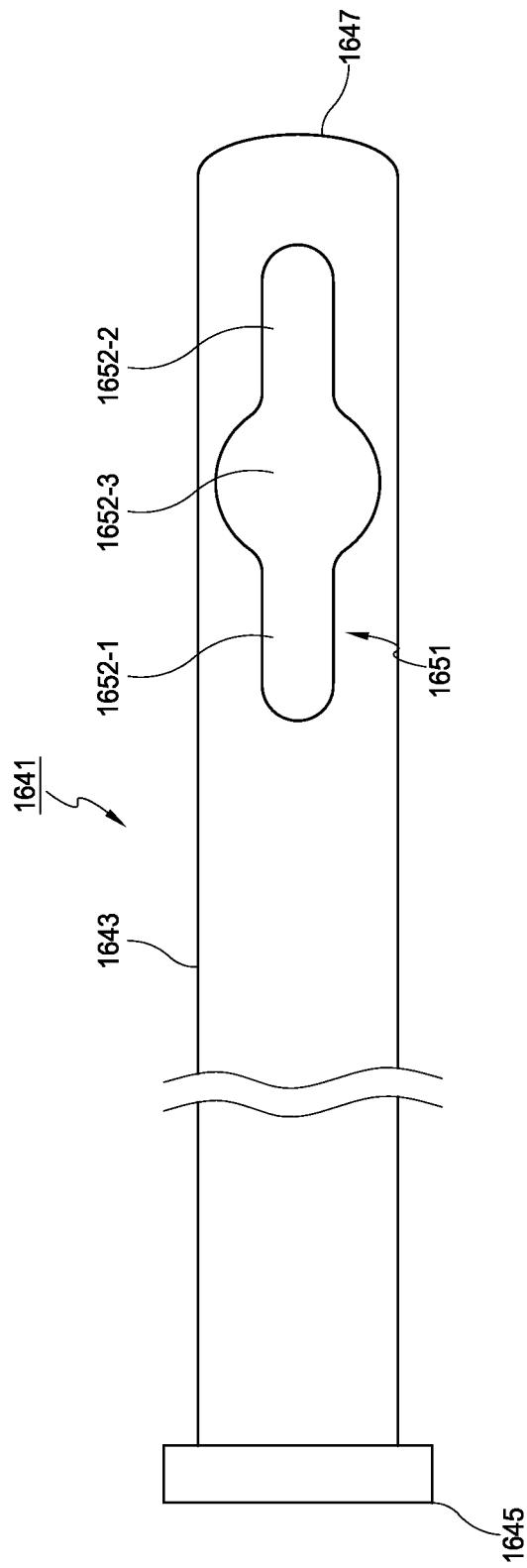
Figure 92F:
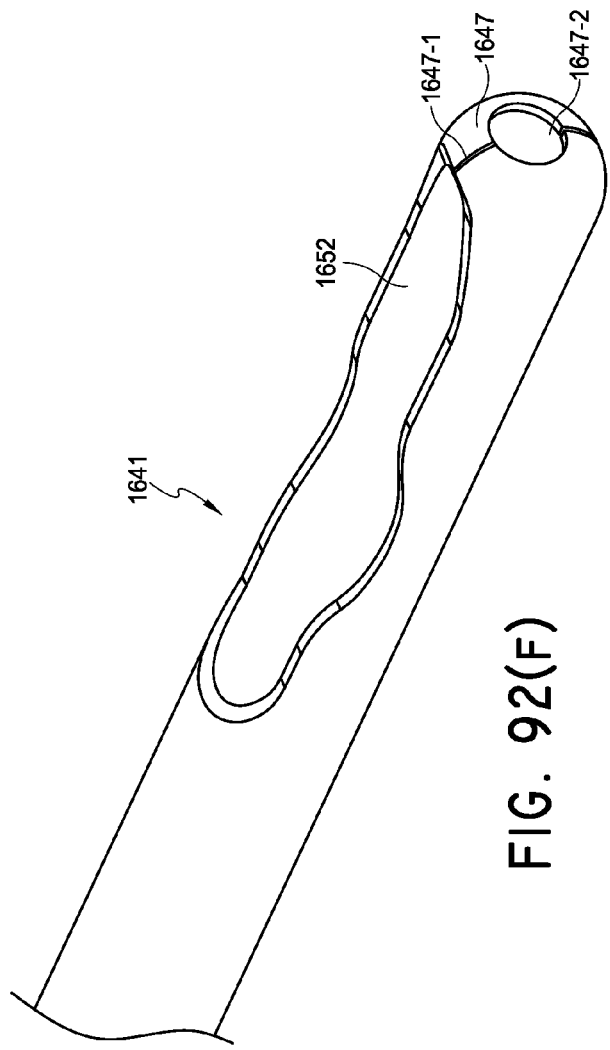
Figure 92G:
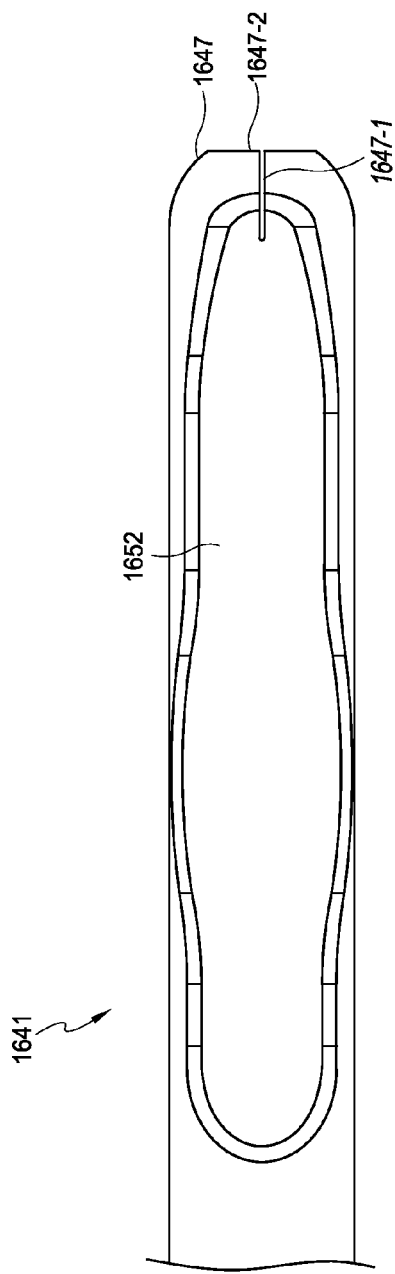

FIG. 92(*d*) illustrates an embodiment in which catheter 1641 includes a feature 1647-1 intended to manipulate the holding force and radial expansion force of the delivery system on an attenuator via spring-like compliance. A feature, such as 1647-1, may provide an advantageous force balance between retention force during the aforementioned insertion, and resistance to radial expansion during inflation steps to promote release of pressure-attenuating device 17 from channel 1649 through window 1652 when deployment is desired. In some embodiments, the distal end 1647 of catheter 1641 comprises a slit or cut 1647-1. The slit or cut 1647-1 may improve compliance of catheter 1641 without altering the material geometry of the catheter 1641, or geometry of window 1652. For example, small cuts or slits 1647-1 may improve the inflation and/or deployment of pressure-attenuating device 17 by reducing a restraining and radial expansion force of the catheter 1641 on the attenuator. FIG. 92(*e*) shows a top view of a catheter 1641 having a window 1652 and a cut or slit 1647-1 at the distal end 1647 of catheter 1641.

In some embodiments, slit 1647-1 has a length within a range of from about 0.010 inches (in.) to about 1.000 in., while in other embodiments this length is from about 0.015 in. to about 0.500 in. In some embodiments, the slit 1647-1 may have a length of about 0.25 in., about 0.20 in., or about 0.15 in. Slit 1647-1 may also comprise other lengths. In some embodiments, slit 1647-1 comprises a width less than about 0.200 in., such as less than about 0.125 in., and in some cases less than about 0.025 in. Slit 1647-1 may also comprise other widths.

The distal end 1647 of catheter 1641 may comprise an opening or hole 1647-2. For example, FIG. 92(*f*) shows a catheter 1641 having both a cut or slit 1647-1 and an opening 1647-2 at the distal end 1647 of the catheter 1641. In some embodiments, the opening 1647-2 may enable a reduced restraining force, reduced radial expansion force, and or increased flexibility during inflation of pressure-attenuating device 17 stored within catheter 1641. In some embodiments, the distal end 1647 comprises a chamfer, for example suitable for facilitating catheter 1641 placement. The chamfer provides a gradual widening in the width of the distal end 1647 to facilitate atraumatic advancement. FIG. 92(*g*) shows a top view of a catheter 1641 having both a slit 1647-1 and an opening 1647-2 at the distal end 1647 of catheter 1641. By providing the opening 1647-2, in the event of an improperly inflated or incomplete release of a device, the device can be manipulated into opening 1647-2 during the delivery devices retraction into or during the advancement of an over lying sheath, cover, or member to promote the tensile release of the device in the coaxial direction of catheter 1641.

In some embodiments, the opening 1647-2 comprises a circular or substantially circular shape. For example, a circular opening 1647-2 can comprise a diameter within the range of from about 0.010 in. to about 0.250 in., such as from about 0.025 in. to about 0.200 in., and including from about 0.050 in. to about 0.150 in. Opening 1647-2 may comprise other shapes and/or sizes.

Referring to FIG. 92(*h*), in some embodiments, catheter 1641 has a slit 1647-1 and a circular or substantially circular opening 1647-2 that comprises a substantially continuous slot 1647-3. FIG. 92(i) shows a top view of a catheter 1641 having both a slit 1647-1 and a circular or substantially circular opening 1647-2 at the distal end 1647 of catheter 1641, where the slit 1647-1 and the opening 1647-2 comprise a substantially continuous slot 1647-3. This arrangement may enable a reduced restraining force, reduced radial expansion force, and or increased flexibility during inflation of pressure-attenuating device 17 stored within catheter 1641. In addition, this arrangement provides a continuously open area connecting the opening 1652 and the opening 1647-2 so that in the event of an improperly inflated or incomplete release of a device, the device can be easily manipulated into opening 1647-2 during the delivery devices retraction into or during the advancement of an over lying sheath, cover, or member to promote the tensile release of the device in the coaxial direction of catheter 1641.

Referring to FIG. 92(j), a distance D between the distal end 1647 and a distal portion 1652-2 of window 1652 may be varied. A position of the window 1652 of the catheter 1641, for example a position relative to the distal end 1647 of the catheter 1641, may facilitate proper deployment of pressure-attenuating device 17. In some embodiments, the catheter 1641 having a window 1652 positioned a distance D from the distal end 1647 of catheter 1641 facilitates storage of pressure-attenuating device 17, for example during shipping and handling, and enables proper deployment of pressure-attenuating device 17 from the catheter 1641 into a patient. FIG. 92(j) shows a cross-sectional view of catheter 1641 having no opening 1647-2, the catheter 1641 having a distance D between a distal portion 1652-2 of window 1652 and the distal end 1647. In some embodiments, the distance D comprises a value less than about 0.500 in., such as less than about 0.250 in., and in some cases less than about 0.150 in.

FIG. 92(k) shows a cross-sectional view of catheter 1641 comprising an opening 1647-2, the catheter 1641 having a distance D1 between a distal portion 1652-2 of window 1652 and the distal end 1647. This variation may have the same dimensions as D set forth above, but provides the advantage that if an attenuator is fully advanced within the catheter 1641 there will be no contact between the device 17 disposed within the catheter 1641 and the area of the opening 1647-2. This may reduce restraining force in that region. Additionally, compared to the embodiment of FIG. 92(j), a smaller arcuate zone of contact is provided between the central longitudinal axis of the catheter 1641 and the opening 1652. The angle between the uppermost edge of the circumference of the opening 1647-2 and the distal-most edge of the opening 1652 may be less than 45 degrees, e.g., less than about 30 degrees, and in some cases 15 degrees or less. This reduces the amount of overhang between the inner surface of the distal end and the opening 1652 to reduce the restraining force at the distal end.

FIG. 92(1) shows a cross-sectional view of catheter 1641 having no opening 1647-2, the catheter 1641 having a reduced distance D2 between a distal portion 1652-2 of window 1652 and the distal end 1647. In this embodiment, there is very little and in some modified embodiments there is no overhang between the distal inner surface of the catheter 1641 and the opening 1652 because the opening extends to the end of the catheter 1641.

Delivery device 15 may further comprise a sealing ring 1661. Ring 1661, which is also shown separately in FIG. 93, may comprise a unitary structure preferably made of a medical-grade silicone or a similarly suitable material. Ring 1661 may be coaxially mounted over push-off member 1521 and may be fixedly mounted within barrel portion 1409 of housing 1401, with ring 1661 being sandwiched between proximal end 1645 of catheter 1641 and complementary supports 1663 and 1665 formed on housing halves 1403-1 and 1403-2, respectively. Ring 1661 may be appropriately dimensioned to provide a fluid-tight seal with proximal end 1645 of catheter 1641 so that any fluids entering catheter 1641 through window 1651 do not leak from proximal end 1645.

One or more syringes can be connected to or be part of the delivery device 15 (FIGS. 79-80). First syringe 1671, shown in FIG. 94, may comprise a tubular body 1675 containing a desired quantity of a first inflation medium 1677 for use in inflating pressure-attenuating device 17, a piston 1679 slidably mounted in body 1675, and a male luer connector 1681. Body 1675 may be appropriately sized for insertion into opening 1417, and connector 1681 may be appropriately sized for mating with proximal end 1459 of valve 1443. In the present embodiment, inflation medium 1677 may be a fluid and more specifically may be one or more high vapor pressure media that may serve as a pressure regulator to help keep device 17 inflated. The one or more high vapor pressure media may be, for example, one or more liquid perfluorocarbons (PFCs), preferably one or more liquid PFCs having a vapor pressure greater than 50 Pa. (The one or more liquid perfluorocarbons may sometimes alternatively be referred to herein as "AIRLOC®.") The one or more liquid PFCs may comprise a perfluorinated heptane, a perfluorinated octane, or one or more combinations thereof. Preferably, the one or more liquid PFCs are a mixture of perfluoroheptane and perfluorooctane. Such a mixture can range from about 0.05 mole fraction of perfluoroheptane and about 0.95 mole fraction of perfluorooctane to about 0.95 mole fraction of perfluoroheptane and about 0.05 mole fraction of perfluorooctane, more preferably can range from about 0.2730 mole fraction of perfluoroheptane and about 0.7270 mole fraction of perfluorooctane to about 0.7270 mole fraction of perfluoroheptane and about 0.2730 mole fraction of perfluorooctane, even more preferably can range from about 0.3640 mole fraction of perfluoroheptane and about 0.6360 mole fraction of perfluorooctane to about 0.5450 mole fraction of perfluoroheptane and about 0.4550 mole fraction of perfluorooctane. In one particular embodiment, the mixture includes about 0.4548 mole fraction of perfluoroheptane and about 0.5452 mole fraction of perfluorooctane. For example, about 25 ml of this perfluorocarbon mixture can be manufactured by mixing about 18.336 grams of perfluoroheptane with about 24.8099 grams of perfluorooctane.

Delivery device 15 may further comprise a second syringe 1691. Second syringe 1691, which is also shown separately in FIG. 95, may comprise a tubular body 1693 containing a desired quantity of a second inflation medium 1695 for use in inflating pressure-attenuating device 17, a piston 1697 slidably mounted in body 1693, and a male luer connector 1699. Body 1693 may be appropriately sized for insertion into opening 1413, and connector 1699 may be appropriately sized for mating with proximal end 1449 of valve 1441. In the present embodiment, medium 1695 may be a fluid and more specifically may be a gas, such as air. Where, for example, one or more PFCs are used as inflation medium 1677, and air is used as inflation medium 1695, the relative volumes of the one or more PFCs to air may range, for example, from about 1 (PFC(s)):1000(air) to about 1(PFC(s)):1(air). In addition, where, for example, pressure-attenuating device 17 is appropriately dimensioned for use in the human bladder, syringe 1691 may contain approximately 25-30 cc of air.

Preferably, the respective quantities of first medium 1677 disposed within body 1675 of syringe 1671 and second medium 1695 disposed within body 1693 of syringe 1691 are sufficient to inflate pressure-attenuating device 17 to a desired extent, taking into account the fact that the total volume of one or both fluid media may not be transferred entirely from syringes 1671 and 1691 to device 17, but rather, that a portion of the volume of one or both inflation media may be left behind in the fluid passageways extending from check valves 1443 and 1441 to distal end 1477 of inflation tube 1471. For example, the amount of first medium 1677 present within device 17 can range from about 0.01-1 liter, preferably from about 0.1 to 30 ml, more preferably from about 0.2 to 10 ml. Therefore, to determine the amount of first medium 1677 that should be loaded into syringe 1671, the amount of first medium 1677 that remains in the delivery system may be added to the minimum target amount of first medium 1677 to be delivered to device 17. For example, if the target amount of first medium 1677 is about 0.45 ml, and the potential retention of first medium 1677 remaining within the delivery system is 0.25 ml, the amount of first medium 1677 initially loaded into syringe 1671 may be about 0.7 ml. It should be apparent to one of ordinary skill in the art that more accurate and reproducible placement of first medium 1677 into device 17 may occur by reducing the amount of fluid volume retained in the delivery system. This can be achieved by first dispensing medium 1677 into device 17 and then by dispensing second medium 1695 and/or by reduction of the dimensions of the various components of the delivery device 15.

It is to be understood that, although media 1677 and 1695 have been described herein as being essentially inert or non-reactive with one another, media 1677 and 1695 may be reactive with one another to form, for example, a third medium which, itself, may be used to inflate device 17. It is also to be understood that, although media 1677 and 1695 have been described herein as being used to inflate device 17, medium 1677 could be used to inflate device 17 and medium 1695 could be used as a sealant to seal the valve or port through which medium 1677 is introduced into device 17 to prevent medium 1677 from leaking from device 17. In addition, it may be desirable to inject other substances into the balloon, such as a medication.

Figure 96A:
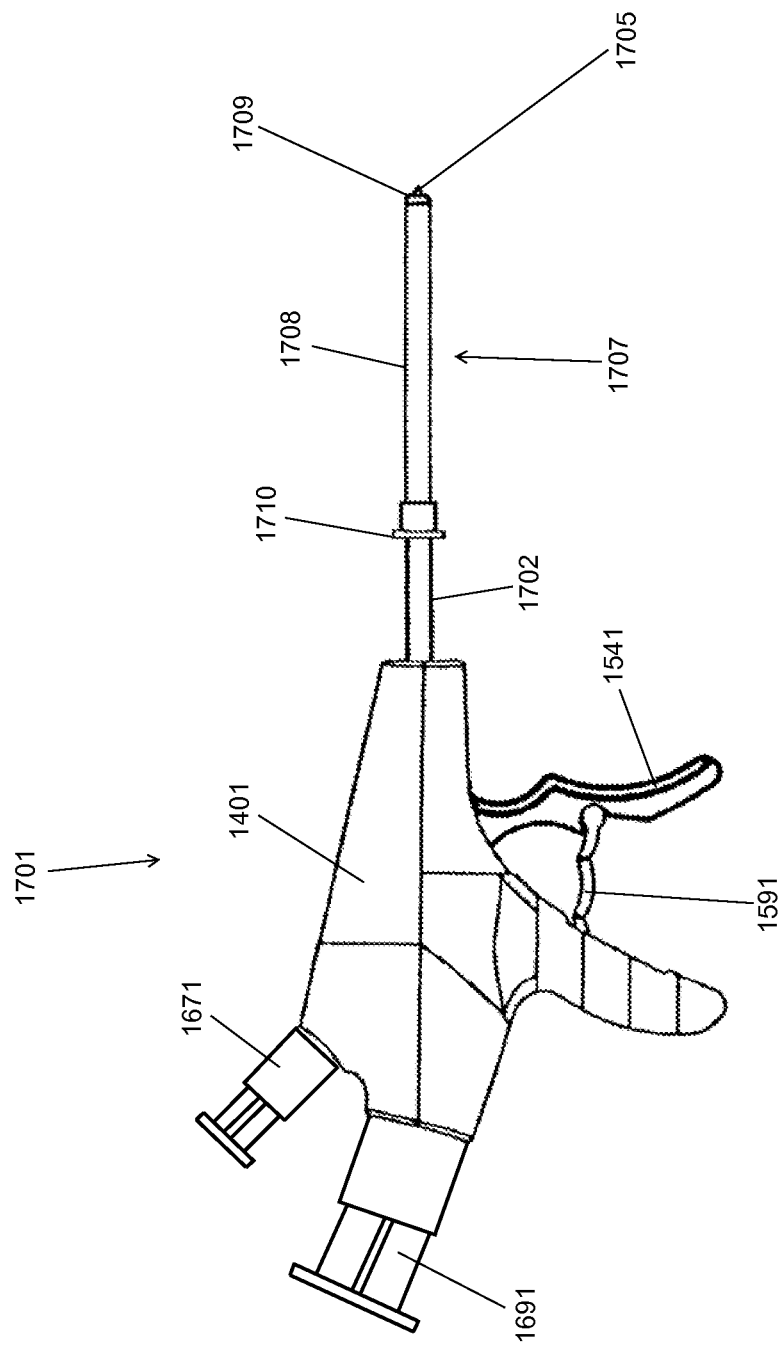
FIGS. 96(a) and 96(b) are side views of an alternate embodiment to the delivery device shown in FIG. 1, the alternate embodiment including a retractable cover shown in distal and proximal positions, respectively.
Figure 96B:
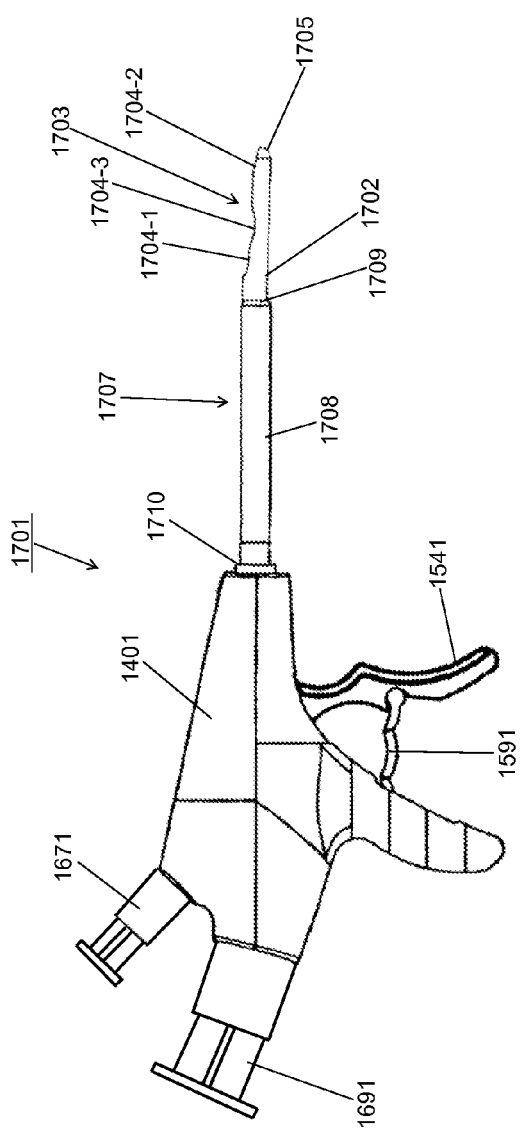

Referring now to FIGS. 96(*a*) and 96(*b*), there are shown side views of an alternate embodiment of a delivery device to delivery device 15, the alternate embodiment being represented generally by reference numeral 1701.

Delivery device 1701 may be similar in most respects to delivery device 15. One difference between the two delivery devices may be that, whereas device 15 may include window catheter 1641, delivery device 1701 may include a window catheter 1702. Window catheter 1702 may be similar in most respects to window catheter 1641, the principal difference between the two window catheters being that, whereas window catheter 1641 may include window 1651, window catheter 1702 may include a window 1703. Window 1703 may include a proximal portion 1704-1, a distal portion 1704-2, and an intermediate portion 1704-3. Proximal portion 1704-1 and intermediate portion 1704-3 may be similar to proximal portion 1652-1 and intermediate portion 1652-3, respectively, of window 1651. However, distal portion 1704-2 of window 1703 may differ from distal portion 1652-1 of window 1651 in that distal portion 1704-2 may extend all the way to distal end 1705 of window catheter 1702 and may be deeper than proximal portion 1704-1 and/or intermediate portion 1704-3 for at least some of its length. It is believed that the increased size of window 1703, as compared to the size of window 1651, may facilitate the passage and release of pressure-attenuating device 17 from the delivery device.

Figure 97:
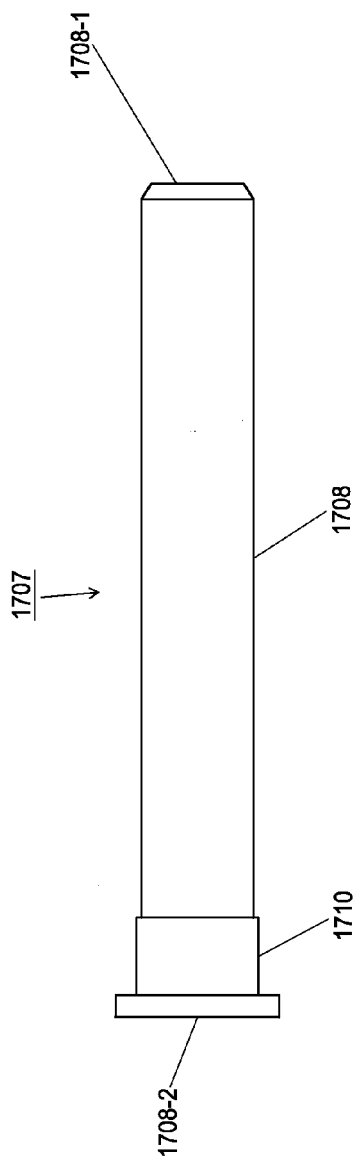
FIG. 97 is a side view of the retractable cover shown in FIGS. 96(a) and 96(b)

Another difference between the two delivery devices is that delivery device 1701 may further include a cover 1707 slidably mounted over catheter 1641. Cover 1707, which is also shown separately in FIG. 97, may comprise a generally tubular member 1708 having a proximal end 1708-1 and a distal end 1708-2. Cover 1707 may also comprise a hub 1710 secured to the proximal end 1708-1 of member 1708. As can be seen in FIG. 96(*a*), when cover 1707 is in its distal position, distal end 1708-2 may be positioned so that cover 1707 covers window 1703 of catheter 1702. This may be useful in retaining pressure-attenuating device 17 within catheter 1641. On the other hand, as can be seen in FIG. 96(*b*), when cover 1707 is in its proximal position, distal end 1708-2 may be positioned so that cover 1707 does not cover window 1703 of catheter 1702. In use, cover 1707 may initially be positioned as in FIG. 96(*a*), and that, as device 1701 is inserted through access device 13, handle 71 may engage hub 1710 and may cause cover 1707 to be slid proximally relative to catheter 1702 until it assumes the position shown in FIG. 96(*b*), thereby "opening" window 1703 to allow device 17 to pass therethrough in the manner described above. Distal end 1708-2 may have a tapered geometry to aid in its introduction through an orifice, such as that of access device 13 or some anatomical orifice. This tapered end can also decrease the likelihood that the cover will be prematurely retracted through contact with such an orifice. Also, it is to be understood that, although not shown, cover 1707 and/or catheter 1702 may be provided with some mechanism, such as a catch or one or more engagement surfaces, that may serve to impede, to a certain extent, axial movement of cover 1707 relative to catheter 1702 so that inadvertent proximal and/or distal movement of cover 1707 relative to catheter 1702 may be avoided.

Referring to FIG. 98(*a*), in some embodiments, a cover 1707, which may for example be suitable for retaining pressure-attenuating device 17 within any of the catheters described herein, e.g., the catheter 1702. The cover 1707 can be removed, e.g., retracted distally. The cover 1707 may comprise a proximal end 1708-1 and a distal end 1708-2. The cover 1707 may comprise a handle 1708-3 on the distal end 1708-2. In some embodiments, the proximal end 1708-1 is sized to slide over and cover, at least in part, the window 1703 of catheter 1702. For example, the cover 1707 may reduce displacement of the pressure-attenuating device 17 prior to removal of the cover 1707. In some embodiments, the cover 1707 comprises a plastic material (e.g., polytetrafluoroethylene (PTFE), polyethylene (PE), synthetic polymers such as nylon). In some embodiments, the cover 1707 comprises polyethylene terephthalate (PET) heat shrink. In some embodiments, cover 1707 comprises a metallic material (e.g., stainless steel, titanium, a nickel-titanium alloy (Nitinol), aluminum).

The cover 1707 may facilitate the un-inflated pressure-attenuating device 17 to "take a set" over time while stored in catheter 1702 having window 1703. For example, at time zero when the pressure-attenuating device 17 is folded and packed into the catheter 1702, the pressure-attenuating device 17 may be unstable and the cover 1707 and/or catheter 1702 may provide physical restraint upon the pressure-attenuating device 17. In some embodiments, the physical restraint enables the pressure-attenuating device 17 to take a set by facilitating retention of the device 17 within catheter 1702 having window 1703. For example, a pressure-attenuating device 17 may take a set by becoming more rigidly stored within catheter 1702, such that device 17 may be more stably retained in catheter 1703, including a catheter 1703 having features to increase catheter 1703 compliance (features as described herein). In some embodiments, a time to facilitate the pressure-attenuating device 17 to take a set can have a value within a range of from about 1 minute to about 1 month, including from about 1 hour to about 2 weeks, including from about 1 hour to about 1 week. In some embodiments, the catheter 1702 having a window 1703 and containing a pressure-attenuating device 17, and a cover 1707 covering at least a portion of window 1703 of catheter 1702, may be subjected elevated temperature during the manufacturing process to facilitate the pressure-attenuating device 17 to take set.

FIG. 98(b) shows a profile view of a cover 1707 having a handle 1708-3 at the distal end 1708-2 and a proximal end 1708-1 suitable for covering, at least in part, the window 1703 of catheter 1702. FIG. 98(c) shows a cross-sectional view of a cover 1707 having a handle at the distal end 1708-2 and a proximal end 1708-1 suitable for covering, at least in part, the window 1703 of catheter 1702.

Figure 106:
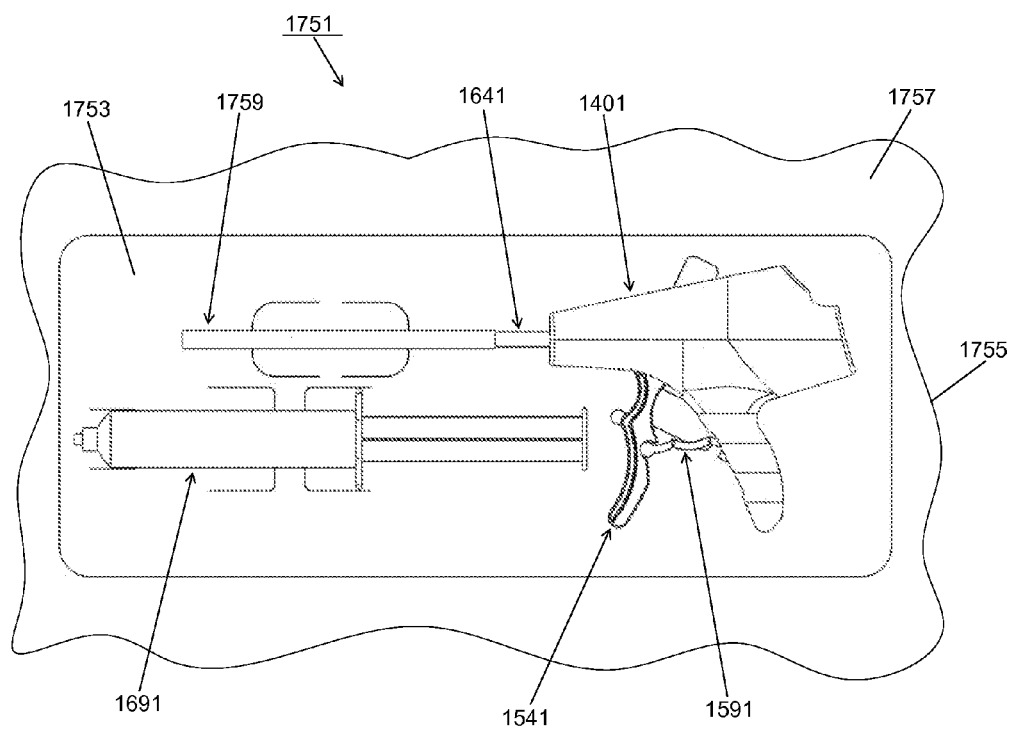
FIG. 106 is a top view of one embodiment of a sterilizable kit containing certain components of the system of FIG. 1.

The cover 1707 may be removed, for example, during manufacturing, immediately prior to packaging and sterilization, or immediately prior to the use of the delivery system. The cover 1707 can be removed manually, or can be attached to the packaging so that removal of the system from the packaging also removes the cover. Referring to FIG. 98(d), a tab 1709 may be attached to the cover 1707 distal end 1708-2, including for example the handle portion. In some embodiments, the tab 1709 facilitates removal of the cover 1707. For example, the cover 1707 having the tab 1709 may be placed over at least a portion of window 1703 of catheter 1702, catheter 1702 containing a pressure-attenuating device 17. In some embodiments, as the delivery system is removed from the packaging tube, the tab 1709 contacts the packaging tube and is restrained, and the catheter 1702 slides out of the cover 1707 and packaging tube. For example, the packaging tube may comprise the protective sleeve 1759 as shown in FIG. 106.

Implant

An implantable device having a compressible element can be placed within a body, such as the bladder. The compressible element can act as a pressure attenuator to attenuate transient pressure events. Gases, such as atmospheric air, carbon dioxide, nitrogen, and certain perfluorocarbons (PFC), may be used to inflate the implant and can act as a low or variable rate spring in series with the native fluidic circuit of the urinary tract. The implant can take many forms including a sphere, some examples of which will be outlined below.

In some embodiments, the implant can include an outer surface that defines a container within the outer surface. The implant may also include a valve that can allow for the addition or removal of substances from the container.

Additional embodiments of an implantable device are described in U.S. Pat. No. 6,682,473, incorporated by reference herein. See for example, FIGS. 5, 5A, 7A-C, 8A-E, 13-25, and 27-31, and the accompanying discussion, including at columns 9-12, 13-14, 17-20, and 21-24. See also the similar disclosure from U.S. Pat. No. 6,976,950, incorporated by reference herein, as well as, FIGS. 32A-33C, 36-38, 47A-C, 49 and the accompanying discussion, including at columns 15-18, 30-35, and 39-40.

U.S. Patent Application Publication No. 2010/0222802, incorporated by reference herein discloses still additional embodiments of implantable devices. See for example, FIGS. 5-5N, 8A-8B, 10A, 11C, 23A-23H, 34A-35D, 37A-37B, 38A-51C, and the accompanying discussion, including paragraphs [0127]-[0152], [0167]-[0168], [0174], [0177], [0233]-[0242], [0354]-[0438], and [0466]-[0475].

Figure 99B:
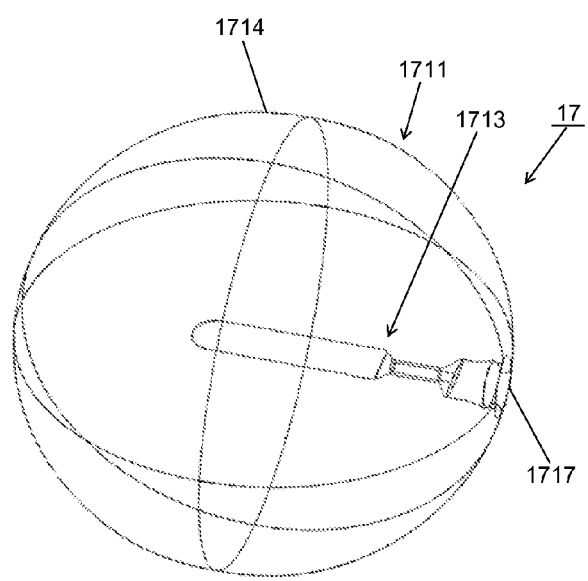
Figure 99C:
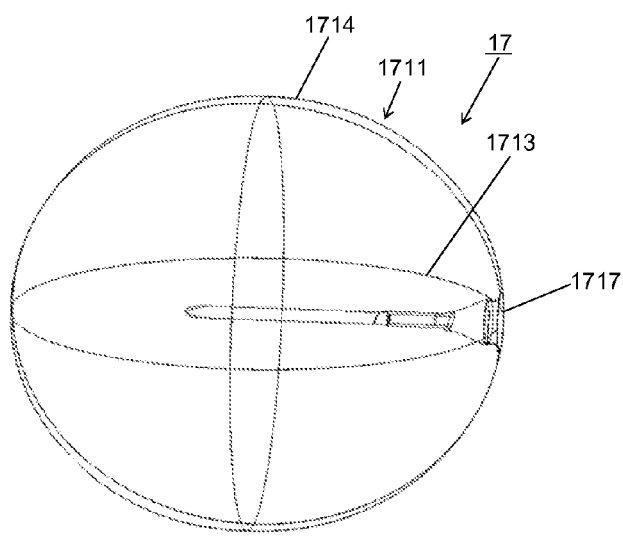

Referring now to FIGS. 99(a) through 100, implant or pressure-attenuating device 17 may comprise an inflatable cell 1711 and a valve 1713. The valve 1713 can serve to regulate the flow of fluid into and out of cell 1711. Cell 1711 may be made of an elastomeric material. When inflated, cell 1711 may comprise a generally spherical bulb portion 1714 and an inverted tubular tail portion 1717 extending into bulb portion 1714, tail portion 1717 terminating in an opening 1719 (FIG. 100). An area of increased wall thickness or retaining feature 1715 may be disposed on bulb portion 1714 opposite to tail portion 1717. The retaining feature 1715 can be a portion of the balloon that is used to retain the balloon into the window of the delivery system. The retaining feature 1715 can be an area of the cell 1711 that is the same or higher wall thickness than adjacent areas of the cell 1711, or a member that is more rigid than the cell 1711, which can be integral to or adhered to the cell 1711, as an example. In the present embodiment, cell 1711 may be made of a sufficiently transparent material to permit the contents housed by cell 1711 to be seen.

Cell 1711 may be seamless and may be substantially arcuate, with the only exception being tail portion 1717, which is inverted and to which valve 1713 can be welded or otherwise attached. To minimize the potential for encrustation, to maximize patient tolerability, or for other reasons, it is preferable that over 95% of the external surface area of cell 1711 be continuously arcuate and that less than 5% of the surface area of cell 1711 not be arcuate. More preferably, over 97% of the external surface area of cell 1711 is continuously arcuate and less than 3% of the external surface area is not arcuate. Even more preferably, over 99% of the external surface area of cell 1711 is continuously arcuate and less than 1% of the surface area is not arcuate.

For example, one embodiment of cell 1711 has an overall surface area of 4,586 sq. mm. The external surface area of the continuously arcuate portion of cell 1711 is 4,575 sq. mm. The ratio of continuously arcuate surface area to non-arcuate surface area for this embodiment is 401:1. This ratio is preferably from about 100:1 to 1500:1 and more preferably from about 400:1 to 600:1. The diameter of tail portion 1717 in the embodiment above is 0.15 inch, and the diameter of bulb portion 1714 is 1.58 inches. The ratio of the diameter of bulb portion 1714 to the diameter of tail portion 1717 is 10.53:1. This ratio is preferably between about 6:1 and 20:1 and more preferably greater than about 8:1. Without limitation to any particularly theory or embodiment, it is believed that such a ratio may serve to keep tail portion 1717 inverted within bulb portion 1714.

Valve 1713, which is also shown in FIG. 101, may be formed from a pair of matching, appropriately shaped, flat sheets of elastomeric material. The pair of matching flat sheets may be heat-sealed to one another along their respective sides to form a pair of seams 1720-1 and 1720-2 and may also be molded so as to define a proximal section 1721, an intermediate section 1723, and a distal section 1725. Proximal section 1721 may be generally flat or generally frusto-conical in shape and may include outer surfaces 1721-1 and 1721-2 that may be fixedly mounted within opening 1719 of cell 1711 (FIG. 100) by a flat weld (where proximal section 1721 is flat) or by a circumferential weld (where proximal section 1721 is frusto-conical.) Proximal section 1721 may include an end surface 1722, which may be a surface or mating surface, intended to interface the distal end 1527 of push-off member 1521, thereby allowing push-off member 1521 to push device 17 off distal end 1477 of inflation tube 1471. In one embodiment, this surface 1722 is a 90 degree flat surface. Other surfaces, such as a concave or convex surface that interacts with the distal end of push-off member 1521. The shape of the distal end of the pushoff member 1521 may be flat, concave, convex, or a shape that permits interaction with the end surface 1722. Intermediate section 1723 may be generally cylindrical and may be reduced in inner diameter and in outer diameter as compared to proximal section 1721. Moreover, intermediate section 1723 may be reduced in inner diameter as compared to the outer diameter of inflation tube 1471 and may include an inner side surface 1724 that may be used to make a stretch interference fit with inflation tube 1471 so as to seal against inflation tube 1471 or to prop open valve 1713, which will close upon release, thereby enabling cell 1711 to be inflated under high pressure with minimal leaking. For example, where the outer diameter of inflation tube 1471 may be in the range of about 0.001-5.00 inch, preferably about 0.005-0.50 inch, more preferably about 0.010-0.125 inch, the inner diameter of intermediate section 1723 may be correspondingly smaller, for example, in the range of about 0.0005-4.900 inch, preferably about 0.001-0.49 inch, more preferably about 0.005-0.120 inch. Moreover, the thickness of intermediate section 1723 may be in the range of about 0.0001-2.00 inch, preferably about 0.001-0.24 inch, more preferably about 0.005-0.050 inch. In certain applications, the nominal pressure exerted on the self sealing valve 1725 is relatively low, below 3 psi. Therefore the surface area of the contact area of the two surfaces must be sufficient to resist flow during use. This is accomplished with a structure 1725 that has a width typically less than 1', more preferably less than 0.5 inches, and more preferably less than 0.25 inches. To maintain valve function, the length of the structure 1725 is greater than the width of structure 1725, more preferably the length is greater than 1.5 times the width of the structure 1725, and more preferably greater than two times the width of the structure 1725. Distal section 1725 may be a generally elongated, flattened structure that is self-sealing (i.e., biased, independently of its environment, towards a closed state) and that has a distal end 1727 through which fluid inputted to valve 1713 in the manner discussed below may exit valve 1713 to occupy the space defined by cell 1711. Preferably, distal section 1725 is made sufficiently long to minimize the escape of fluid from within cell 1711 through valve 1713.

Figure 102:
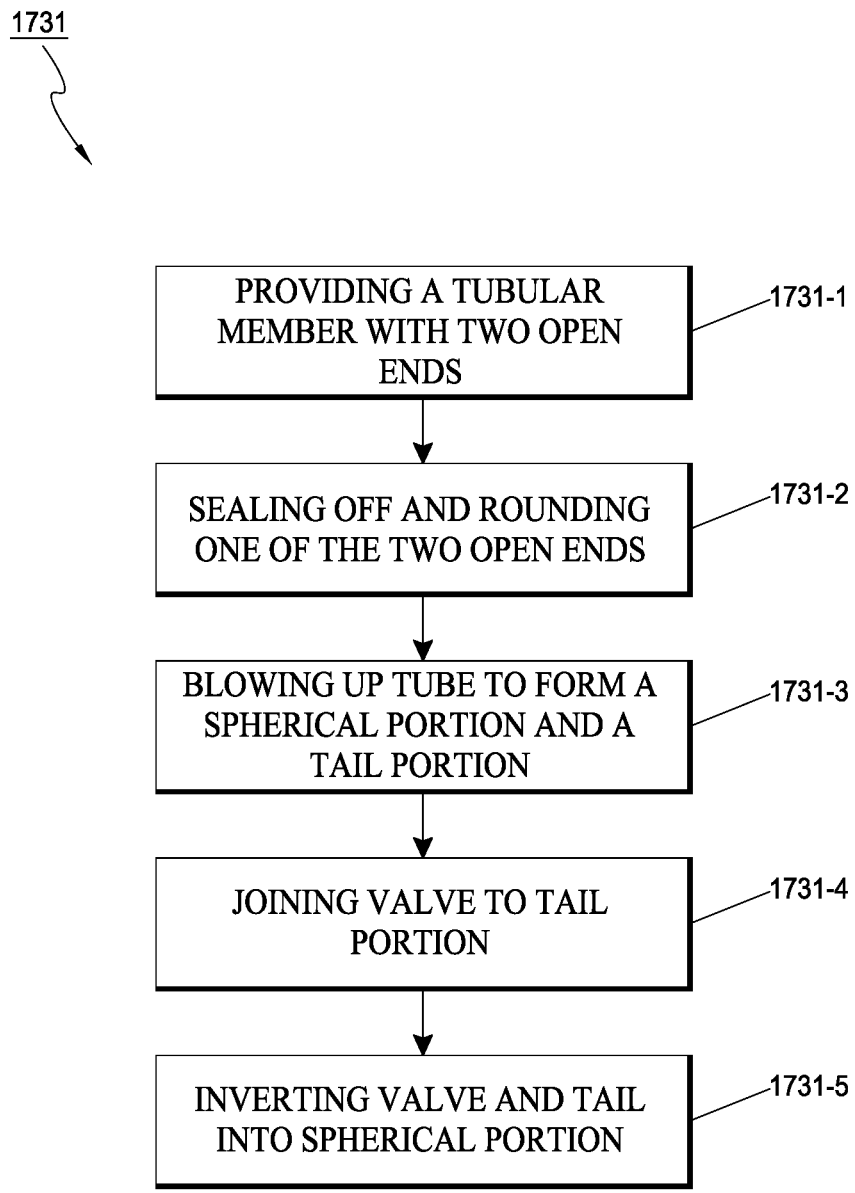
FIG. 102 is a flowchart, schematically illustrating one method of manufacturing the pressure-attenuating device of FIGS. 99(a) through 99(c)
Figure 103A:
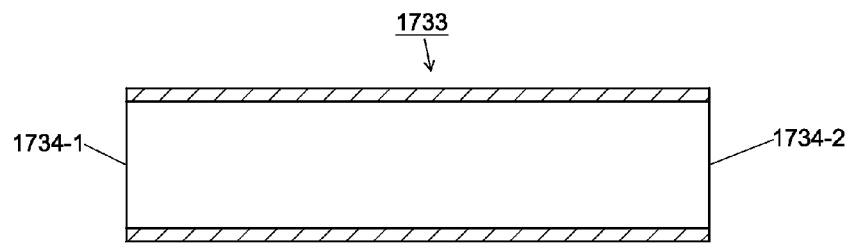
FIGS. 103(a) through 103(e) are section views, illustrating parts of certain steps of the method shown in FIG. 102.
Figure 103B:
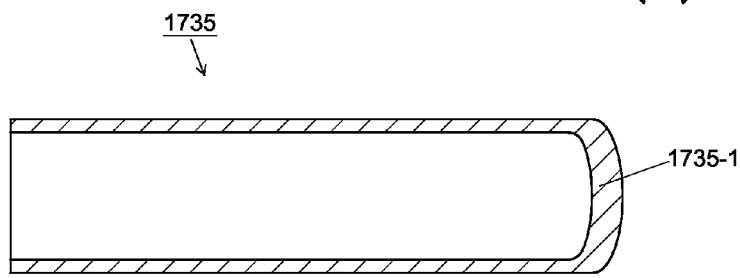
Figure 103C:
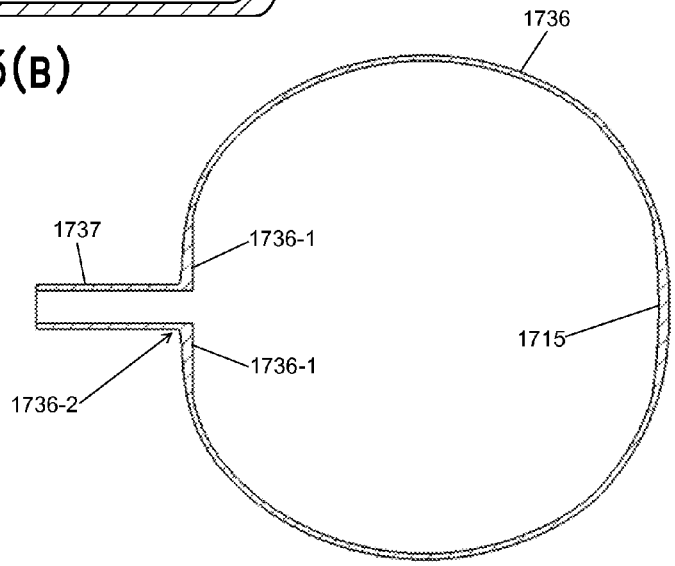
Figure 103D:
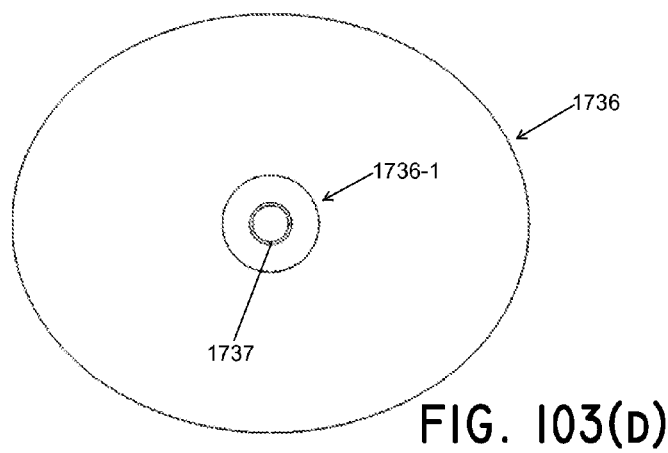

Referring now to FIG. 102, there is shown a flowchart, schematically depicting one possible method 1731 for making device 17. Method 1731 may begin with a step 1731-1 of providing a tubular member, which may be, for example, an extruded tube 1733 of elastomeric material having a pair of open ends 1734-1 and 1734-2 (see FIG. 103(*a*)). Method 1731 may continue with a step 1731-2 of closing off end 1734-2 to form a tube 1735 having a closed end 1735-1 (see FIG. 103(*b*)). Method 1731 may then continue with a step 1731-3 of blowing up or expanding tube 1735 to form a generally spherical portion 1736 and a generally cylindrical tail portion 1737 (see FIG. 103(*c*)). (Step 1731-3 may further include pulling on the closed end 1735-1 during said expansion of tube 1735.) Method 1731 may then continue with a step 1731-4 of inserting valve 1713 into tail portion 1737 and joining, such as by either a circumferential weld or a flat weld, proximal section 1721 to tail portion 1737 (see FIG. 103(*e*)). Method 1731 may then conclude with a step 1731-5 of inverting the combination of valve 1713 and tail portion 1737 into generally spherical portion 1736, thereby forming device 17. In some embodiments, to prevent the valve 1713 and tail portion 1737 from reversing this inverting step 1731-5 during use, the valve and tail portion may be anchored to the balloon wall in any method known in the art including but not limited to use of an adhesive or welding the distal end of the valve to the balloon wall, for example. A preferred embodiment is to fabricate the balloon to provide increase resistance to the reversal of inverting step 1731-5 with the following features: 1) An increase in wall thickness or stiffness on the balloon near the area of the balloon where the tail protrudes. For example, a circumferential increase in balloon thickness 1736-1 that measures more than two times the diameter of the tail, and more preferably more than 1.5 times the diameter of the tail and more preferably more than one times the diameter of the tail, and this circumferential wall thickness is less than 0.075 inches and more preferably less than 0.050 inches and more preferably less than 0.025 inches, and/or 2) a wall thickness of the tail 1737 that is at least one times the wall thickness of the balloon 1736, more preferably at least 1.5 times the wall thickness of the balloon 1736, more preferably at least two times the wall thickness of the balloon 1736, more preferably at least three times the wall thickness of the balloon 1763, and/or 3) a balloon with a measured angle between the wall of the balloon near the tail opening and the tail 1736-2 of at least 45 degrees, more preferable greater than 70 degrees, more preferable greater than 80 degrees, and more preferable approaching 90 degrees, and/or 4) a measured radius where the tail 1737 interfaces with balloon 1736 of less than 0.5 inches, more preferably less than 0.1 inches, more preferably less than 0.075 inches and more preferably less than 0.035 and preferably 0.015 inches. Preferably, device 17 is dimensioned so that spherical portion 1736, when expanded, has a diameter that is approximately 6-20 times the diameter of the entry port defined by the interface of spherical portion 1736 and inverted tail portion 1737. In one embodiment, the shape, thickness and material of closed end 1735-1 forms the integral retaining member 1715 in the wall of the balloon.

Cell 1711 may alternatively be made using a dip process that is common in the industry. For example, Brash et al., "Development of block copolyether-urethane intra-aortic balloons and other medical devices," *Journal of Biomedical Research*, 7(4):313-34 (1973), which is incorporated herein by reference, describe a manufacturing process that can be used to manufacture cell 1711. A mandrel is formed from expendable wax, and then dipped using commonly known balloon dipping methods to form a balloon. Upon cure of the balloon material, the wax is melted and removed, resulting in the desired balloon.

One advantageous feature of device 17 is that it may be devoid of seams on its exterior surface. The absence of such seams may be desirable since such seams may rub up against and cause irritation with the bladder or other anatomical structure in which device 17 is positioned. In addition, such seams may become encrusted, over time, with biological sediment from the anatomical structure in which device 17 is positioned, which encrustation may exacerbate such irritation or may otherwise be regarded as unhygienic or undesirable.

Delivery and Expansion of Implant

Figure 104:
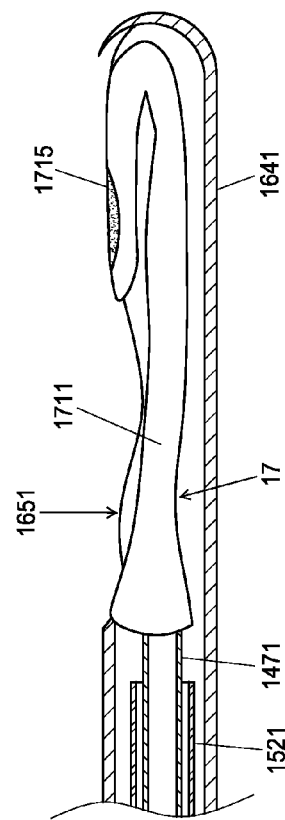
FIG. 104 is a fragmentary side view, partly in section, showing the pressure-attenuating device of FIGS. 99(a) through 99(c) stored in a deflated, folded state within the window catheter of the delivery device of FIGS. 78(a) and 78(b)
Figure 103E:
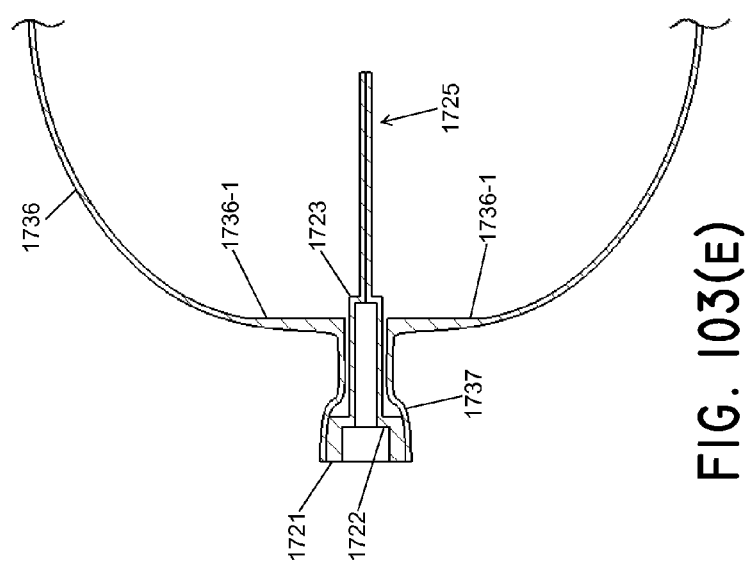

As noted above, device 17 may be delivered to an anatomical structure in a compacted or deflated state and, after being delivered to the anatomical structure, may be inflated and deployed. Preferably, the delivery of device 17 to the anatomical structure in a deflated state is accomplished by positioning device 17 in its deflated state within window catheter 1641, with distal end 1477 of inflation tube 1471 sealed against intermediate section 1723 of valve 1713 in the manner discussed above. As seen in FIG. 104, cell 1711 may be folded within catheter 1641 in a manner complementary to the shape of window 1651 so as to maximize the likelihood that device 17 may be retained within catheter 1641 by window 1651 prior to being inflated and may be released through window 1651 once inflated.

Figure 105:
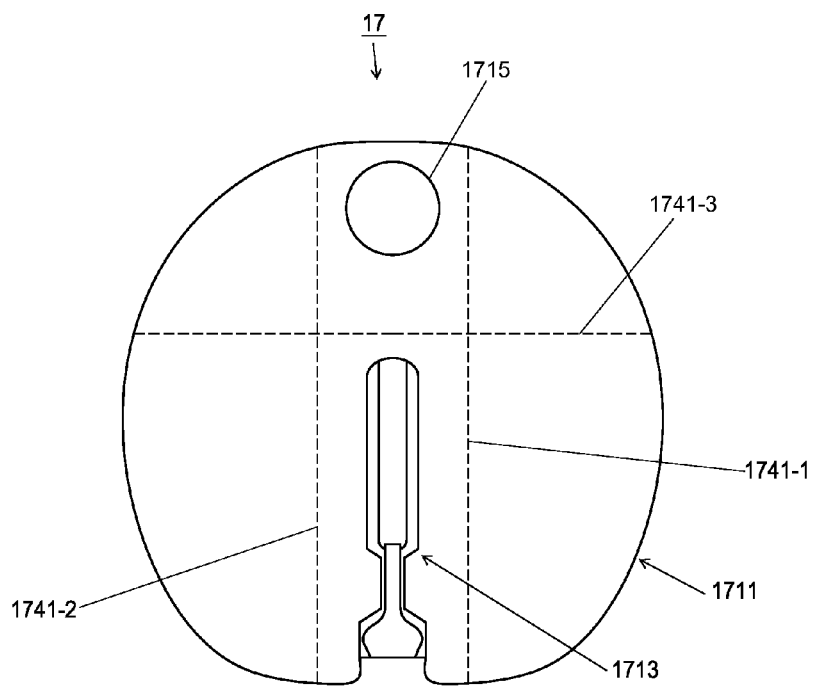
FIG. 105 is a top view of the pressure-attenuating device of FIGS. 99(a) through 99(c), the pressure-attenuating device being shown in a deflated, flattened state prior to being folded.

Referring now to FIG. 105, device 17 is shown in a deflated, flattened state with internal retention member 1715 on the lower layer of the balloon prior to being folded. A plurality of imaginary fold lines 1741-1, 1741-2, and 1741-3 are shown on cell 1711 to depict where cell 1711 may be folded. According to one embodiment of the invention, cell 1711 may first be folded about line 1741-1, then about line 1741-2, and then about line 1741-3. Alternatively, cell 1711 may be folded about line 1741-2, then about line 1741-1, and then about line 1741-3. When device 17 is inflated, cell 1711 may unfold in an order opposite to the order in which it had previously been folded. In an alternate embodiment, the balloon includes an integral retention member 1715, which is on top of the balloon when folded along line 1741-1 described above. The integral retention member may be circular, rectangular, oval or any shape so long as it is sufficiently wide to extend beyond the opening in the window, more preferably greater than 1.5 times the opening in the window, more preferably two times the opening in the window. This dimension permits the retention member to be tucked under the catheter on one or more sides of the window when the folded balloon is secured in the catheter.

It is to be understood that, although device 17 has been described herein as being inflatable, device 17 could be expandable in ways other than by inflation. For example, device 17 could be self-expandable, for instance, by virtue of being made of a shape-memory material.

Referring now to FIG. 106, there is shown a top view of one embodiment of a sterilizable kit comprising certain components of system 11, the sterilizable kit being represented generally by reference numeral 1751.

Kit 1751 may comprise a sheet of support material 1753, which may be a sheet of cardboard or a similarly suitable support material. Kit 1751 may further comprise a sealed pouch 1755 surrounding support material 1753, pouch 1755 defining a sealed cavity 1757. Pouch 1755 may be made of a transparent material, such as one or more transparent polymer sheets. Kit 1751 may further comprise the components of delivery device 15, excluding syringe 1671 (which syringe 1671 may be separately sterilized, for example, through heat-sterilization), the components of delivery device 15 nearly being fully assembled, except that syringe 1671 is not present and that syringe 1691 is not attached to the remaining components of delivery device 15. Syringe 1691 may be disposed within cavity 1757 and may be mounted on support material 1753, and the remainder of delivery device 15 may be disposed within cavity 1757 and may be mounted on support material 1753 at a distance from syringe 1691. Syringe 1691 may be opened to draw in a volume of air corresponding to the volume of air one wishes to dispense therefrom into device 17. Although not visible in FIG. 106, kit 1751 may further comprise pressure-attenuating device 17, which may be loaded within window catheter 1641 of delivery device 15 and may be coupled to inflation tube 1741 in the manner described above. Kit 1751 may further comprise a removable protective sleeve 1759, which may be inserted over catheter 1641 to ensure retention of device 17 within catheter 1641 during shipping and/or storage. (Sleeve 1759 is removed from catheter 1641 prior to use; alternatively, sleeve 1759 may be replaced with cover 1703, which may be retained for use in the manner described above.) All of the components of kit 1751 are made of a material that may be sterilizable by a suitable sterilization technique, such as gamma radiation.

An advantageous feature of kit 1751 is that the air contained within syringe 1691 may become sterilized during the sterilization procedure applied to kit 1751. In this manner, one may minimize the introduction of air into device 17 that may contain undesirable microorganisms. For similar reasons, microbial filters may alternatively or additionally be appropriately positioned within fluid connector 1423 and/or check valves 1441 and 1443.

Figure 107:
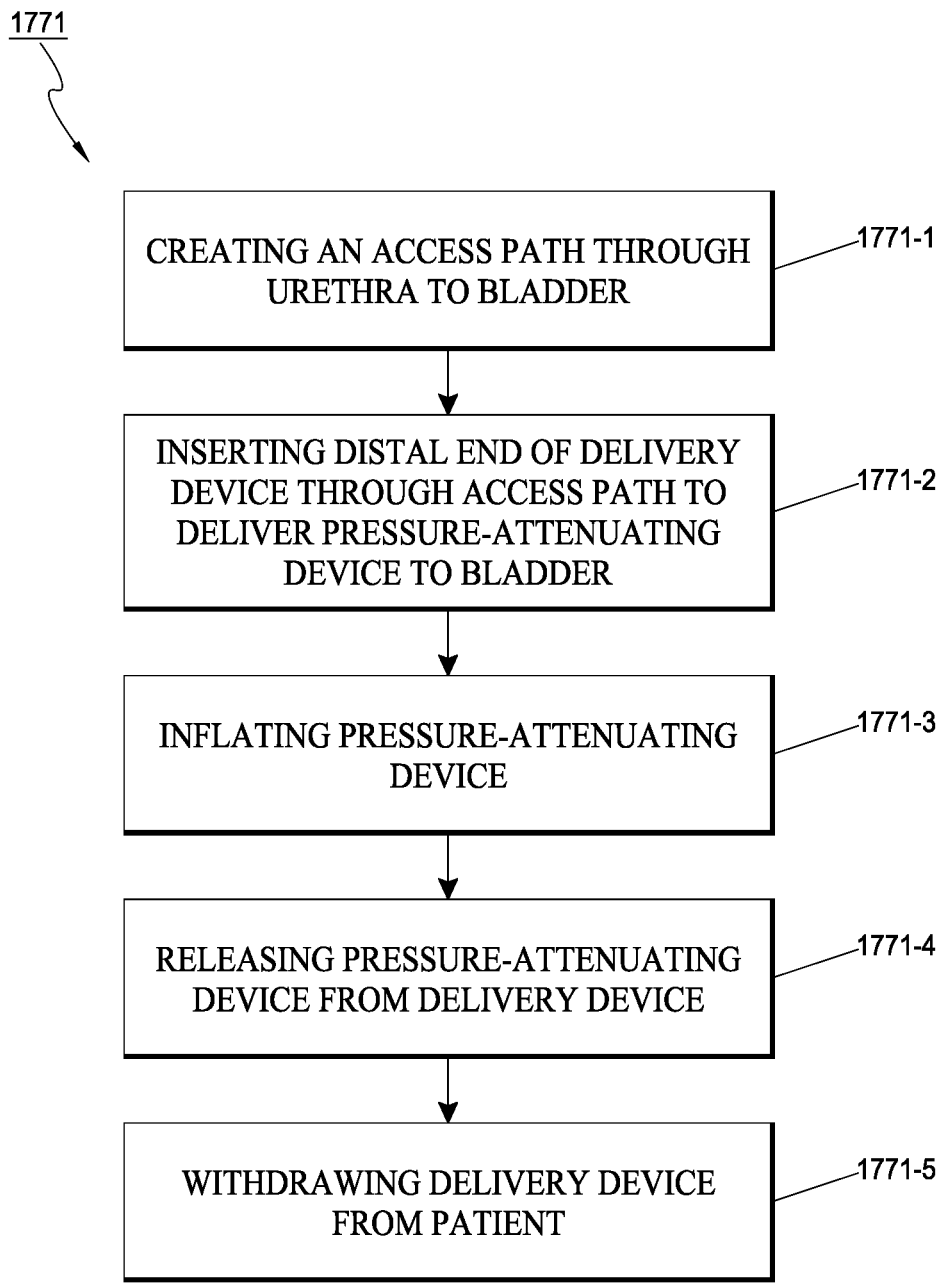
FIG. 107 is a flowchart, schematically illustrating one method of implanting the pressure-attenuating device of FIGS. 99(a) through 99(c) in a patient.
Figure 108A:
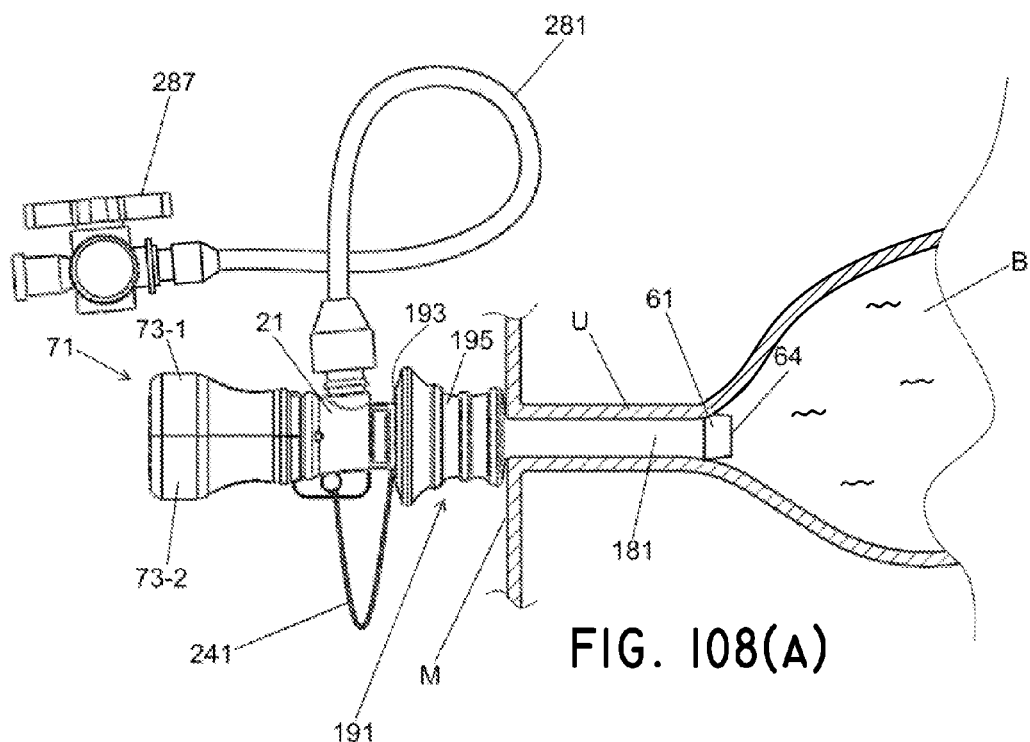
FIGS. 108(a) through 108(d) are fragmentary side views, partly in section, illustrating parts of certain steps of the method shown in FIG. 107.
Figure 108B:
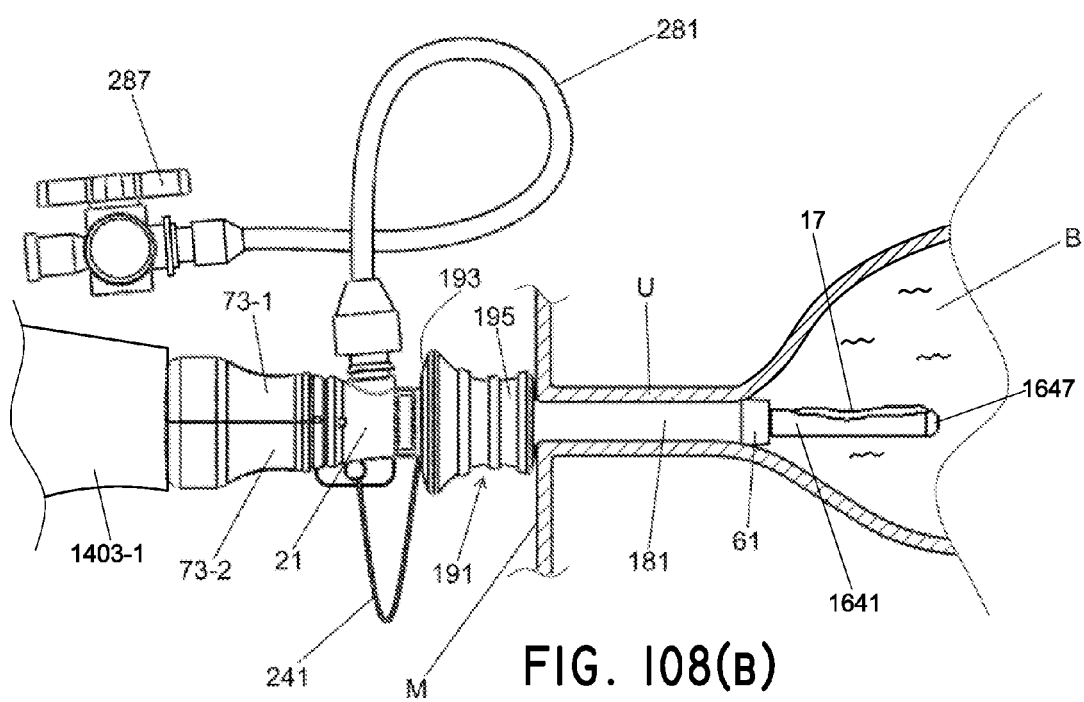
Figure 108C:
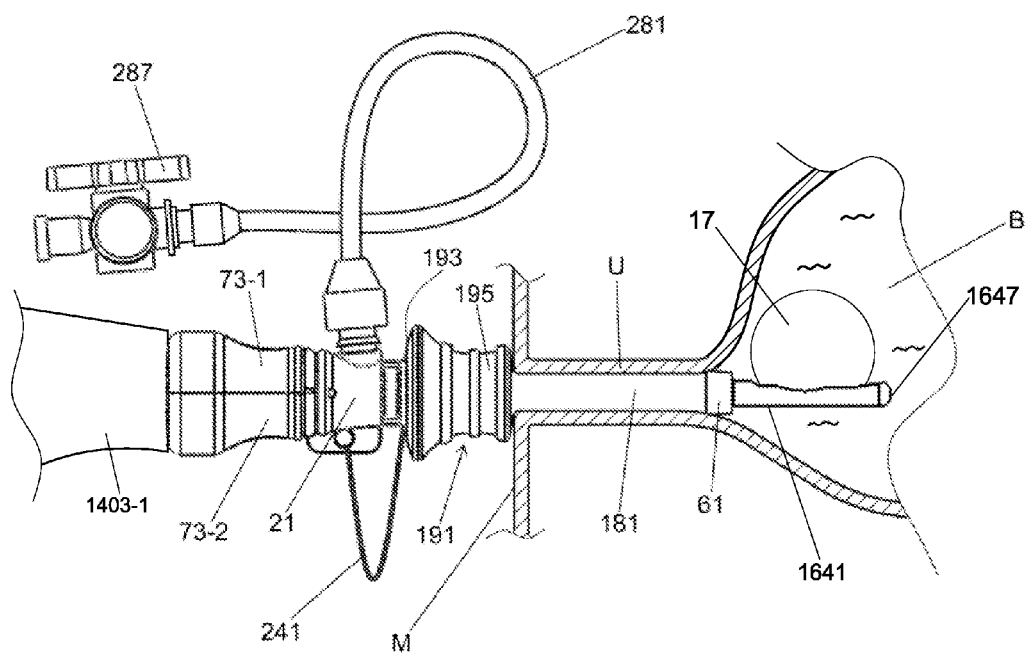
Figure 108D:
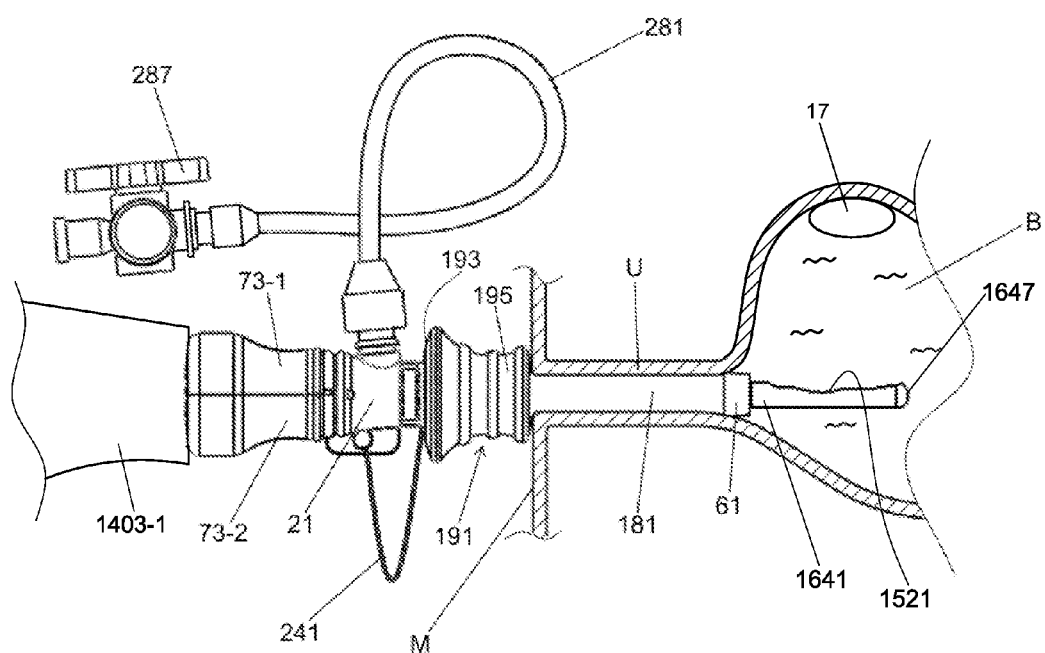

Referring now to FIG. 107, there is shown a flowchart, schematically depicting one possible method 1771 of implanting pressure-attenuating device 17 in an anatomical structure of a patient, such as a bladder. Method 1771 may begin with a step 1771-1 of installing an access device in a patient in any of the manners discussed above. Where, for example, access device 13 is used to provide transurethral access to the bladder, said installing step may comprise inserting distal end 135 of obturator 131, covered by sleeve 181, through the urethra and into the bladder and then removing obturator 131, whereby an access path extending across the urethra and into the bladder may be created (see FIG. 108(*a*)). Method 1771 may then continue with a step 1771-2 of inserting a distal end of a delivery device through the access device and into the anatomical structure of a patient. This may be done by inserting distal end 1647 of delivery device 15 through the remaining installed portion of access device 13 and into the bladder of the patient (see FIG. 108(*b*)). (Prior to insertion of delivery device 15 into access device 13, pressure-attenuating device 17 may be loaded into delivery device 15 in the manner discussed above.)

Method 1771 may then continue with a step 1771-3 of inflating pressure-attenuating device 17 (see FIG. 108(*c*)). Said inflating step may be effected by fully depressing piston 1679 to dispense first fluid medium 1677 from first syringe 1671 (FIG. 94) into pressure-attenuating device 17 and then by fully depressing piston 1697 to dispense second fluid medium 1695 (FIG. 95) from second syringe 1691 into pressure-attenuating device 17. (It may be preferred to dispense first fluid medium 1677 into device 17 before dispensing second fluid medium 1695 into device 17 where first fluid medium 1677 is a liquid and second fluid medium 1695 is a gas since a gas may be useful in flushing a liquid from delivery device 15 into device 17; however, such inflation may alternatively be achieved by dispensing second fluid medium 1695 before first fluid medium 1677 or by simultaneously dispensing first fluid medium 1677 and second fluid medium 1695.) Method 1771 may then continue with a step 1771-4 of releasing pressure-attenuating device 17 from delivery device 15 (see FIG. 108(*d*)), thereby allowing device 17 to float freely in the bladder or other anatomical structure. Said releasing step may be affected by deactivating safety 1591 and then by squeezing trigger 1541, thereby causing push-off member 1521 to slide distally until push-off member 1521 pushes device 17 off of distal end 1477 of inflation tube 1471. Method 1771 may then proceed with a step 1771-5 of withdrawing the delivery device from the access device. This may be done by withdrawing delivery device 15 from the remaining installed portion of access device 13 while holding the remaining installed portion of access device 13 stationary in the patient. (Access device 13 may thereafter be removed from the patient or may remain in the patient to provide a conduit through which observational, removal, or other devices may be inserted.)

Some of the advantageous features of using delivery device 15 to deliver pressure-attenuating device 17 are that, due to the orientation and placement of window 1651, there is a controlled deployment of pressure-attenuating device 17 away from the trigone of the patient and device 17 is kept away from the walls of the bladder while being inflated, such contact with the walls of the bladder possibly impeding the opening of valve 1713 to inflate device 17.

Referring back now to FIGS. 81(*a*) and 82(*b*), to assist an operator in properly using delivery device 15, one or both housing halves 1403-1 and 1403-2 may be imprinted with certain markings, indicating certain steps in the delivery sequence. For example, each of housing halves 1403-1 and 1403-2 may be imprinted with the following markings: marking 1781-1 comprising the number "1" and the text "Inject AirLoc" positioned proximate to opening 1417; marking 1781-2 comprising the number "2" and the text "Inject Air" positioned proximate to opening 1413; marking 1781-3 comprising the number "3" and the text "Release Balloon" positioned proximate to trigger 1541; and marking 1781-4 comprising the number "4" and the text "Hold Sheath Remove Tool" positioned proximate to opening 1419. As can be appreciated, markings 1781-1 through 1781-4 convey that syringe 1671 is to be emptied, followed by the emptying of syringe 1691, followed by the squeezing of trigger 1541, and followed by the removal of delivery device 15 from the remaining installed portion of access device 13. It is also to be noted that markings 1781-1 and 1781-4 can be positioned on housing halves 1403-1 and 1403-2 proximate to the related portions of delivery device 15, thereby reinforcing the connection between the step to be taken and the related physical structure of delivery device 15.

Removal

A removal device may be inserted through the passageway created by an access device. The removal device may be used to capture, to deflate and/or to remove the pressure-attenuating device. The removal device may also be used to view the inside of the anatomical structure, as well as the pressure-attenuating device. This viewing may be done during all or part of the capturing, deflating, and/or removing the pressure-attenuating device.

Certain additional embodiments of a removal device are described in U.S. Patent Application Publication No. 2010/0222802, incorporated by reference herein. See for example: FIGS. 19A-22B, 23H, and 24-29C and the accompanying discussion, including at paragraphs [0207]-[0274].

Embodiments of a removal device are also provided in U.S. Pat. No. 6,976,950, incorporated by reference herein. See for example: FIGS. 12, and 20-23, and the accompanying discussion, including at columns 18-21, and 25-26.

Referring now to FIGS. 109(a) through 109(d), removal device 19 according to certain embodiments is shown. The removal device 19 can include a pair of scissor-like handles, first member 1801 and second member 1803, that can be used to articulate a pair of jaws 1981 and 1983 as will be described below.

First member 1801 may be a unitary structure, preferably made of a hard, medical-grade polymer, polytetrafluoroethylene (PTFE)-coated (TEFLON®) aluminum, or a similarly suitable material. Member 1801 may be shaped to comprise an elongated arm portion 1805 having a transversely-extending ring portion 1807 disposed at one end thereof and having a longitudinally-extending, generally cylindrical portion 1809 disposed at the opposite end thereof. Ring portion 1807 may be appropriately dimensioned to receive a thumb of a user. Cylindrical portion 1809 may be shaped to include a bore 1811 extending longitudinally all the way from a proximal end 1813 to a distal end 1815 and may also be shaped to include a cavity 1817 extending longitudinally for a portion of the distance, but not entirely, from distal end 1815 towards proximal end 1813. Bore 1811 may be of comparatively greater diameter and cavity 1817 may be of comparatively lesser diameter.

Second member 1803 may be a unitary structure, preferably made of a hard, medical-grade polymer, polytetrafluoroethylene (PTFE)-coated (TEFLON®) aluminum, or a similarly suitable material. Member 1803 may be shaped to comprise an elongated arm portion 1821 having both a transversely-extending ring portion 1823 and a finger rest 1824 disposed at one end thereof and having a longitudinally-extending, generally cylindrical portion 1825 disposed at the opposite end thereof. Ring portion 1823 may be appropriately dimensioned to receive a finger of a user, such as a forefinger, and finger rest 1824 may be appropriately dimensioned to receive a finger of a user, such as the middle finger. Cylindrical portion 1825 may be shaped to include a bore 1827 of comparatively greater diameter extending longitudinally all the way from a proximal end 1829 to a distal end 1831 and a bore 1833 of comparatively lesser diameter extending longitudinally all the way from proximal end 1829 to distal end 1831. Bore 1827 and bore 1833 may have their axes generally aligned with bore 1811 and cavity 1817, respectively.

First member 1801 may be coupled to second member 1803 for pivotal movement relative thereto by a pin 1835 inserted through transverse openings 1837 and 1839 in first member 1801 and second member 1803, respectively. Pin 1835 may be held in openings 1837 and 1839 by having an end 1840 received within a cap 1841. In the above manner, first member 1801 may be regarded as a movable member pivotally mounted about pin 1835, and second member 1803 may be regarded as a stationary member.

Figure 110:
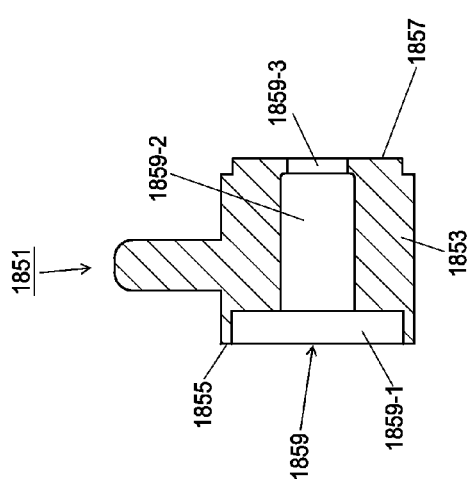

Removal device 19 may further comprise a scope connector 1851. Connector 1851, which is also shown separately in FIG. 110, may be a unitary structure, preferably made of a medical-grade stainless steel or a similarly suitable material. Connector 1851 may be a generally tubular member comprising a generally circular side wall 1853 defining a proximal end 1855, a distal end 1857, and a longitudinal channel 1859 extending all the way from proximal end 1855 to distal end 1857. Longitudinal channel 1859 may include a proximal portion 1859-1 of comparatively greater diameter, a distal portion 1859-2 of comparatively lesser diameter, and an intermediate portion 1859-3 intermediate in diameter to proximal portion 1859-1 and distal portion 1859-2.

Figure 111:
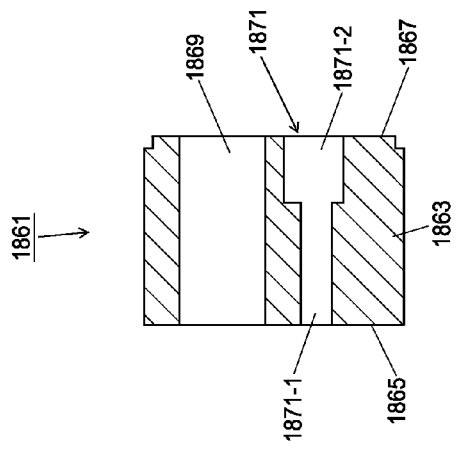
FIGS. 110 and 111 are respective section views of the scope connector and ring shown in FIG. 109(a)

Removal device 19 may further comprise a ring 1861. Ring 1861, which is also shown separately in FIG. 111, may be a unitary structure, preferably made of a medical-grade stainless steel or a similarly suitable material. Ring 1861, which may be fixedly coupled to member 1803, may be a generally tubular member comprising a generally circular side wall 1863 defining a proximal end 1865, a distal end 1867, and a pair of longitudinal bores 1869 and 1871, each of bores 1869 and 1871 extending all the way from proximal end 1865 to distal end 1867. Bore 1869 may be generally aligned with and comparable in diameter to bore 1827 of member 1803. Bore 1871 may be generally aligned with bore 1833 of member 1803 and may include a proximal portion 1871-1 of comparatively lesser diameter and a distal portion 1871-2 of comparatively greater diameter. Proximal portion 1871-1 may be comparable in diameter to bore 1833 of member 1803.

Figure 112:
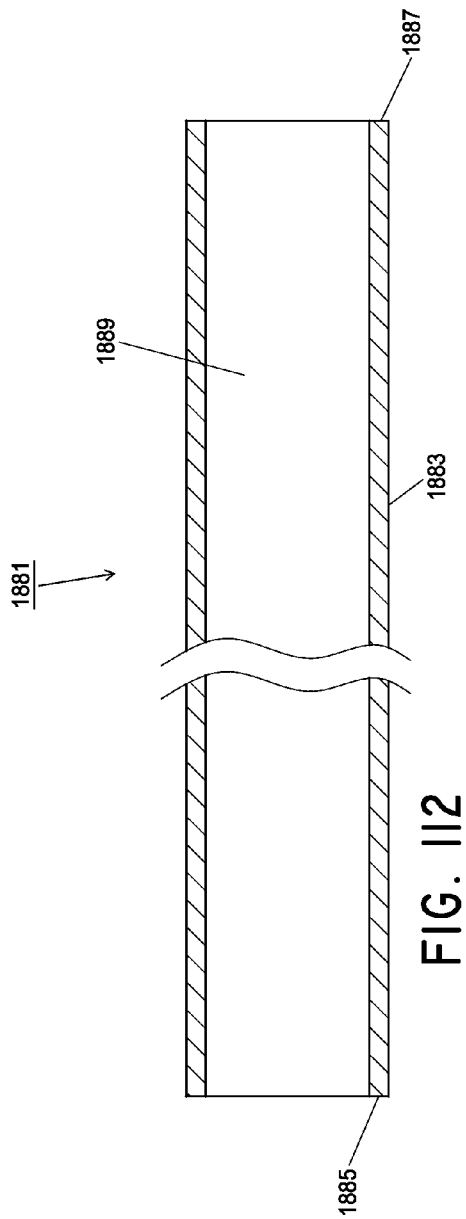

Removal device 19 may further comprise a scope guide 1881. Guide 1881, which is also shown separately in FIG. 112, may be a unitary structure, preferably made of a medical-grade stainless steel or a similarly suitable material. Guide 1881 may be a generally tubular member comprising a generally circular side wall 1883 defining a proximal end 1885, a distal end 1887, and a bore 1889, bore 1889 extending all the way from proximal end 1885 to distal end 1887. Proximal end 1885 of guide 1881 may be fixedly mounted within distal portion 1859-2 of scope connector 1851, with the remainder of guide 1881 extending distally through bore 1811 of member 1801, through bore 1827 of member 1803, and through bore 1869 of ring 1861. The length of guide 1881 passing through bore 1811 of first member 1801 may be slidable relative to first member 1801 whereas the lengths of guide 1881 passing through bore 1827 of member 1803 and through bore 1869 of ring 1861 may be fixed relative to member 1803 and ring 1861, respectively.

Removal device 19 may further comprise a cystoscope 1891. Cystoscope 1891, which is also shown separately in FIG. 113, may be a wide angle cystoscope. According to one embodiment, cystocope 1891 may have a field of view of approximately 30-150 degrees, preferably approximately 90-135 degrees, more preferably approximately 105-135 degrees, and more preferably approximately 115 degrees. According to another embodiment, cystoscope 1891 may have a field of view of approximately 180 degrees. Cystoscope 1891 may comprise an eyepiece portion 1893 and a barrel portion 1895. Eyepiece portion 1893 may comprise a distal end 1897 securely mountable within channel 1859 of connector 1851, and barrel portion 1895 may be appropriately dimensioned to extend distally from connector 1851 through member 1801, through member 1803, and through ring 1861 and to terminate proximate to the distal end 1887 of guide 1881. In this manner, cystoscope 1891 may be fixed relative to guide 1881.

Removal device 19 may further comprise a support 1901 (FIGS. 109(a)-109(b)). Support 1901 which is also shown separately in FIG. 114, may be a unitary structure, preferably made of a medical-grade stainless steel or a similarly suitable material. Support 1901 may be a generally tubular member comprising a generally circular side wall 1903 defining a proximal end 1905, a distal end 1907, and a bore 1909, bore 1909 extending all the way from proximal end 1905 to distal end 1907. Proximal end 1905 of support 1901 may be fixedly mounted within distal portion 1871-2 of ring 1861.

Removal device 19 may further comprise a bracket 1921 (FIGS. 109(a)-109(b)). Bracket 1921, which is also shown separately in FIG. 115, may be a unitary structure, preferably made of a medical-grade stainless steel or a similarly suitable material. Bracket 1921 may be shaped to include a proximal portion 1923 and a distal portion 1925. Proximal portion 1923 may be tubular and may be shaped to include a longitudinal channel 1927. Distal end 1907 of support 1901 may be fixedly mounted within channel 1927 of bracket 1921. Distal portion 1925 of bracket 1921 may be bifurcated and may include a top member 1929, a bottom member 1931, and a connecting member 1932, top member 1929 and bottom member 1931 being spaced apart and generally parallel to one another. Top member 1929 may include a transverse opening 1933. Connecting member 1932 may have a bore 1934 aligned with channel 1927.

Removal device 19 may further comprise a rod 1941 (FIG. 109(b)). Rod 1941, which is also shown separately in FIG. 116, may be a unitary structure, preferably made of a medical-grade stainless steel or a similarly suitable material. Rod 1941 may be a solid, rigid member shaped to include a proximal end 1943 and a distal end 1945. Rod 1941 may be appropriately dimensioned to be slidably mounted within support 1901, with proximal end 1943 being fixedly mounted within cavity 1817 of member 1801 and with distal end 1945 being adapted to slide back and forth through a distal end 1934-1 of bore 1934.

Removal device 19 may further comprise a connector 1951 (FIG. 109(b)). Connector 1951, which is also shown separately in FIG. 117, may be a unitary structure, preferably made of a medical-grade stainless steel or a similarly suitable material. Connector 1951 may be shaped to include a proximal portion 1953 and a distal portion 1955. Proximal portion 1953 may be tubular and may be shaped to include a channel 1954 extending longitudinally a portion of the way from a proximal end 1953-1 towards a distal end 1953-2. Distal end 1945 of rod 1941 may be fixedly mounted within channel 1954 of connector 1951, and proximal portion 1953 of connector 1951 may be appropriately dimensioned to slide back and forth within bracket 1921. Distal portion 1955 of connector 1951 may be generally flat and elongated and may be disposed in the space between top member 1929 and bottom member 1931 of bracket 1921. Distal portion 1955 of connector 1951 may be shaped to include a transverse opening 1957.

Figure 109C:
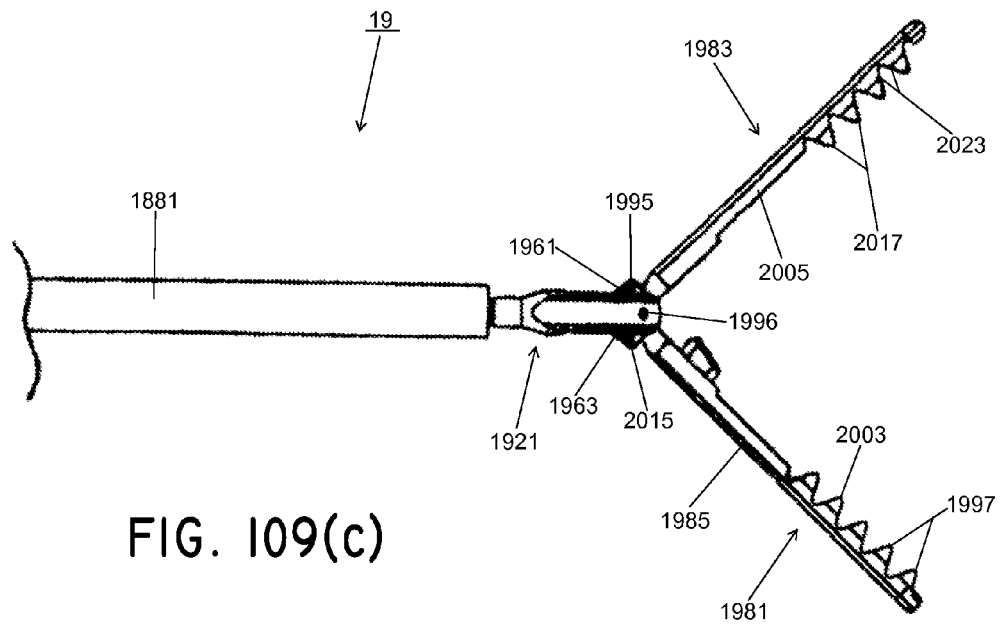
Figure 109D:
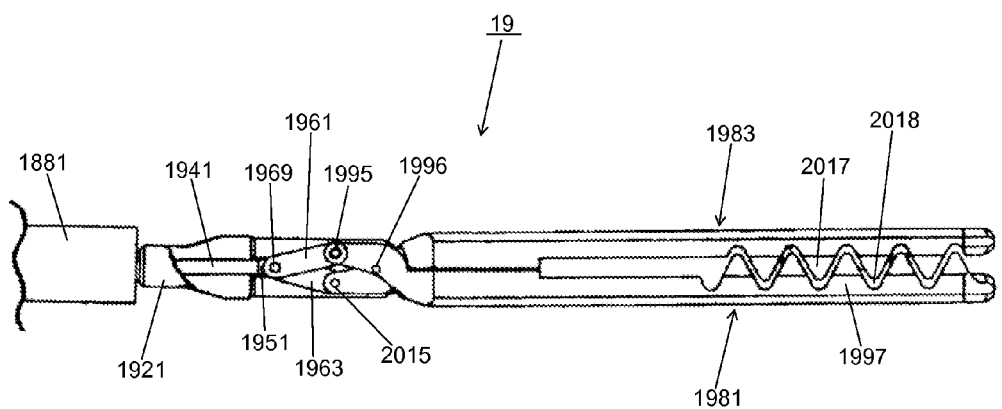

Removal device 19 may further comprise a pair of linking arms 1961 and 1963 (FIGS. 109(b)-109(d)). Arm 1961, which is also shown separately in FIG. 118, may be a unitary structure, preferably made of a medical-grade stainless steel or a similarly suitable material. Arm 1961 may be an elongated flat member shaped to include a first transverse opening 1965 proximate to a proximal end 1961-1 of arm 1961 and a second transverse opening 1967 proximate to a distal end 1961-2 of arm 1961. A pivot pin 1969 may be received within opening 1965 of arm 1961, as well as within opening 1957 of connector 1951, so as to pivotally couple arm 1961 to connector 1951. Arm 1963, which is also shown separately in FIG. 119, may be a unitary structure, preferably made of a medical-grade stainless steel or a similarly suitable material. Arm 1963 may be an elongated flat member shaped to include a first transverse opening 1971 proximate to a proximal end 1963-1 of arm 1963 and a second transverse opening 1973 proximate to a distal end 1963-2 of arm 1963. Pivot pin 1969 may additionally be received within opening 1971 of arm 1963 so as to pivotally couple arm 1963 both to arm 1961 and to connector 1951.

Figure 120A:
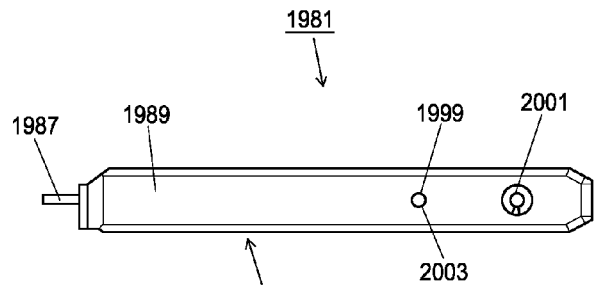
FIGS. 120(a) through 120(d) are left side, right side, top, and section views, respectively, of one of the jaws shown in FIG. 109(b)
Figure 120B:
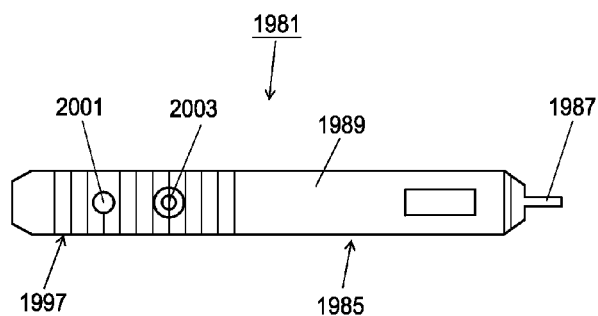
Figure 120C:
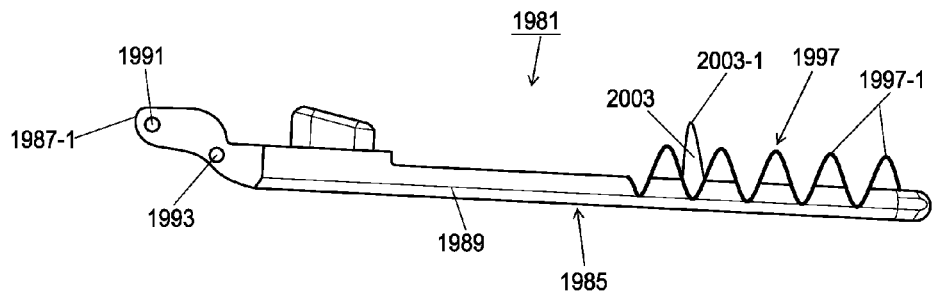
Figure 120D:
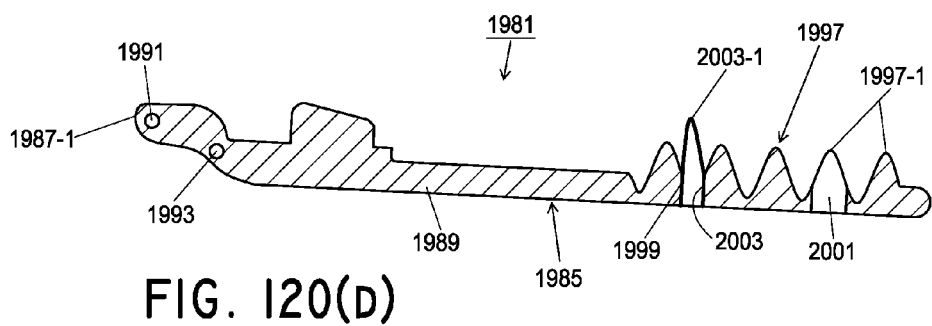
Figure 121A:
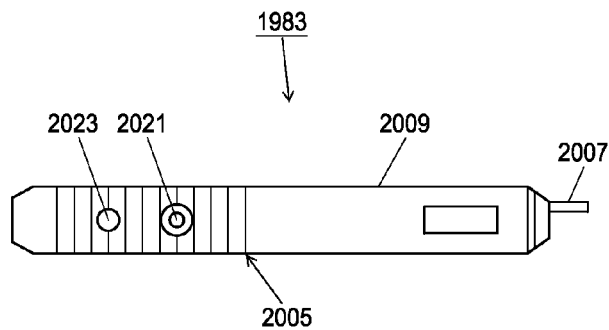
Figure 121B:
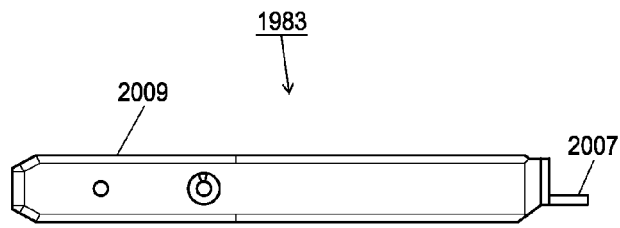
Figure 121C:
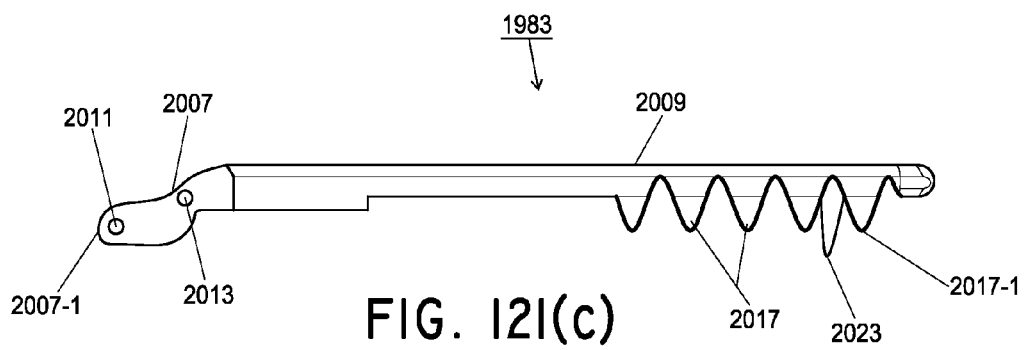
Figure 121D:
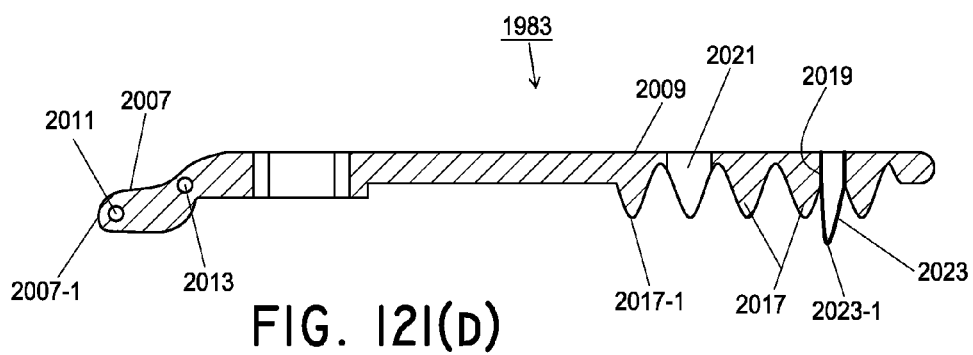

Removal device 19 may further comprise a pair of jaws 1981 and 1983 (FIGS. 109(a)-109(d)). The jaws can include corresponding teeth 1997, 2017 which can be used to grip or secure an implant. The jaws may also include one or more surface damaging or compromising structures. For example, the surface damaging structure 2003, 2023 can be a needle, knife, sharpened tooth, etc. In some embodiments, the surface damaging structure can be a canulated needle that can also serve to allow the media within in the implant to escape or otherwise be removed. In some embodiments, having the opening in the needle extend the entire length of the exposed needle structure permits the balloon to continue to deflate even when the needle has penetrated completely through the balloon. Additionally, the orientation of the sharp edge towards the distal end of the grasper has the advantage of preventing lacerating the balloon film during the tensile removal of the deflated or partially deflated balloon thru the sheath. Additionally, the proximity of the needle relative to adjacent teeth can improve the function of the removal system. Specifically, if the space between the tip of the needle and the tip of an adjacent tooth is between 0.05 and 10 times the difference in height between the tip of the needle and the tip of the adjacent tooth. This distance prevents the balloon from "tenting" over the needle and adjacent teeth without needle penetration of the balloon. An example of a larger distance between the tip of the needle and the tip of the adjacent tooth is shown in FIG. 120(e). Needle 2513-3 is taller than adjacent tooth 1997. The distance between the tip of the tooth 1997 and needle 2513-1 or 2513-3 is equal to or greater than the difference in distance between the height of needle 2513-1 or 2513-3 and the height of the adjacent tooth.

Jaw 1981, which is also shown separately in FIGS. 120(a) through 120(d), may comprise an elongated member 1985 (which may be, for example, approximately 1.55-2.5 inches in length), preferably made of a medical-grade stainless steel or a similarly suitable material. Member 1985 may be shaped to include a proximal portion 1987 and a distal portion 1989.

Proximal portion 1987, which may comprise a generally flat and arcuate arm, may be shaped to include a first transverse opening 1991 proximate to a proximal end 1987-1 of proximal portion 1987 and a second transverse opening 1993 spaced distally a short distance from first transverse opening 1991. A pivot pin 1995 may be received within opening 1991 of proximal portion 1987, as well as within opening 1967 of arm 1961, so as to pivotally couple jaw 1981 to arm 1961. A pivot pin 1996 may be received within opening 1993 of proximal portion 1987, as well as within opening 1933 of bracket 1921, so as to pivotally couple jaw 1981 to bracket 1921. Distal portion 1989 of member 1985 may be shaped to include a row of teeth 1997 facing towards jaw 1983, the row of teeth 1997 extending proximally from approximately the distal end of distal portion 1989. Each tooth 1997 may extend substantially across the width of distal portion 1989 and may have a height of, for example, approximately 1-10 mm, preferably approximately 5 mm. Each tooth 1997 may have a dulled peak 1997-1 that has a radius of, for example, 0.001-0.250 inch, preferably 0.005-0.050 inch, more preferably 0.010-0.25 inch. A first transverse opening 1999 may be provided in distal portion 1989 amongst teeth 1997, and a second transverse opening 2001 may be provided in distal portion 1989 amongst teeth 1997, first and second transverse openings 1999 and 2001 being spaced apart from one another by a short distance. A cannulated needle 2003 may be fixedly mounted in transverse opening 1999, needle 2003 having a sharpened end 2003-1 facing towards jaw 1983. Preferably, needle 2003 has a height that exceeds the height of teeth 1997 so that sharpened end 2003-1 extends beyond dulled peaks 1997-1. Needle 2003 may have an inner diameter of, for example, approximately 0.0005-0.500 inch, preferably approximately 0.005-0.250 inch, more preferably approximately 0.010-0.050 inch, and may have an outer diameter of, for example, approximately 0.001-0.750 inch, preferably approximately 0.010-0.300 inch, more preferably approximately 0.015-0.075 inch.

Jaw 1983, which is also shown separately in FIGS. 121(*a*) through 121(*d*), may comprise an elongated member 2005 (which may be, for example, approximately 1.55-2.5 inches in length), preferably made of a medical-grade stainless steel or a similarly suitable material. Member 2005 may be shaped to include a proximal portion 2007 and a distal portion 2009. Proximal portion 2007, which may comprise a generally flat and arcuate arm, may be shaped to include a first transverse opening 2011 proximate to a proximal end 2007-1 of proximal portion 2007 and a second transverse opening 2013 spaced distally a short distance from first transverse opening 2011. A pivot pin 2015 may be received within opening 2011 of proximal portion 2007, as well as within opening 1973 of arm 1963, so as to pivotally couple jaw 1983 to arm 1963. Pivot pin 1996 may be received within opening 2013 of proximal portion 2007, as well as within opening 1933 of bracket 1921, so as to pivotally couple jaw 1983 to bracket 1921. In this manner, proximal movement of rod 1941, which may be caused by pivotal movement of ring portion 1807 of member 1801 towards ring portion 1823 of member 1803, may cause arms 1961 and 1963 to pivot towards each other which, in turn, may cause jaws 1981 and 1983 to pivot towards each other. On the other hand, distal movement of rod 1941, which may be caused by pivotal movement of ring portion 1807 of member 1801 away from ring portion 1823 of member 1803, may cause arms 1961 and 1963 to pivot away from one another which, in turn, may cause jaws 1981 and 1983 to pivot away from one another. Jaws 1981 and 1983 may open to an angle of, for example, approximately 20-150 degrees.

Distal portion 2009 of member 2005 may be shaped to include a row of teeth 2017 facing towards jaw 1981. The row of teeth 2017 may be staggered relative to teeth 1997 so that the peaks 1997-1 of teeth 1997 may be aligned with the spaces between teeth 2017 when jaws 1981 and 1983 are closed and so that the peaks 2017-1 of teeth 2017 may be aligned with the spaces between teeth 1997 when jaws 1981 and 1983 are closed. Each tooth 2017 may extend substantially across the width of distal portion 2009 and may be shaped and dimensioned similarly to each of teeth 1997. A first transverse opening 2019 may be provided in distal portion 2009 amongst teeth 2017, and a second transverse opening 2021 may be provided in distal portion 2009 amongst teeth 2017. Opening 2019 may be appropriately positioned and appropriately dimensioned to receive cannulated needle 2003 of jaw 1981 when jaws 1981 and 1983 are closed. (By receiving the sharpened end 2003-1 of needle 2003, opening 2019 facilitates and promotes full closure of jaws 1981 and 1983 around an inflated device 17, as opposed to having needle 2003 be deflected from the compressed and inflated device 17.) Opening 2019 may have an inner diameter of, for example, approximately 0.002-0.100 inch, preferably 0.010-0.300 inch, more preferably 0.015-0.100 inch. Opening 2021 may be aligned with opening 2001 of jaw 1981 when jaws 1981 and 1983 are closed, and a cannulated needle 2023 may be fixedly mounted in opening 2021 so as to be receivable within opening 2001 of jaw 1981 when jaws 1981 and 1983 are closed. Cannulated needle 2023 may have a sharpened end 2023-1 facing towards jaw 1981, and needle 2023 and opening 2001 may be dimensioned similarly to needle 2003 and opening 2019, respectively.

Preferably, teeth 1997 and 2017 are dimensioned appropriately so that, when jaws 1981 and 1983 are closed, a small gap 2018 (seen best in FIG. 109(*d*)) is left between the respective rows of teeth 1997 and 2017 that enables device 17 to be trapped between teeth 1997 and 2017 while minimizing any tearing of device 17 by teeth 1997 and 2017. In this manner, device 17 may be securely held or gripped between teeth 1997 and 2017 while cannulated needles 2003 and 2023 puncture device 17. Moreover, because needles 2003 and 2023 are cannulated, the fluid contents of device 17 may be quickly evacuated from device 17 through needles 2003 and 2023 without having needles 2003 and 2023 plug the same puncture holes they create.

It is to be understood that, although cannulated needles 2003 and 2023 are described herein as being used to puncture device 17, other puncturing devices, such as, but not limited to, blades, scissors, pins, hooks, or the like, may alternatively or additionally be used.

In addition, it is to be understood that, although cannulated needles 2003 and 2023 are described herein as being oriented generally perpendicular to members 1985 and 2005, respectively, cannulated needles 2003 and 2023 need not be so oriented and may be oriented, for example, so that sharpened ends 2003-1 and 2023-1 are angled towards proximal portions 1987 and 2007, respectively.

Additionally, it is to be understood that, although both jaw 1981 and jaw 1983 are described herein as being movable, one could make one of jaws 1981 and 1983 stationary and the other of jaws 1981 and 1983 movable.

Referring now to FIG. 122, there is shown a flowchart, schematically depicting one possible method 2051 of using removal device 19 to remove an implanted pressure-attenuating device 17 from an anatomical structure of a patient, such as a bladder. Method 2051 may begin with a step 2051-1 of installing an access device in a patient in any of the manners discussed above. Where, for example, access device 13 is used to provide transurethral access to the bladder, said installing step may comprise inserting distal end 135 of obturator 131, which may be covered by sleeve 181, into the urethra, advancing obturator 131 and sheath 61 through the urethra and into the bladder, and then removing obturator 131, whereby an access path extending across the urethra and into the bladder may be created (see FIG. 123(*a*)). Method 2051 may then continue with a step 2051-2 of inserting the distal end of a removal device through the access device and into the anatomical structure of the patient. This can be done by inserting the distal end of removal device 19 through the remaining installed portion of access device 13 and into the bladder of the patient (see FIG. 123(*b*)). (In order to permit insertion of removal device 19 into access device 13, one may use one hand to pivot ring portion 1807 of member 1801 towards ring portion 1823 of member 1803 until jaws 1981 and 1983 close. After jaws 1981 and 1983 have been inserted completely through access device 13, jaws 1981 and 1983 may then be opened by pivoting ring portion 1807 away from ring portion 1823. Proper placement of the distal end of device 19 within the bladder may be confirmed by observation with scope 1891.)

Where the method 2051 is performed in the bladder, or other fluid filled structure, the method may then continue with a step 2051-3 of emptying the structure of liquid, such as through stopcock valve 287, until the inflated device comes into alignment with removal device. For example, urine can be removed from the bladder until the device 17 is aligned with opened jaws 1981 and 1983 as observed through scope 1891 (see FIG. 123(*c*)). Method 2051 may then continue with a step 2051-4 of engaging the inflated device with the removal device. This may also include deflating the inflated device. For example, the jaws 1981 and 1983 can close around device 17, causing device 17 to deflate over the next several seconds (see FIG. 123(*d*)). Method 2051 may then conclude with a step 2051-5 of withdrawing removal device, together with the deflated pressure-attenuating device from the anatomical structure through the access device. The implanted device 17 may be held between jaws 1981 and 1983 and may be removed through the remaining installed portion of access device 13 while the remaining installed portion of access device 13 is held stationary in the patient. If, for some reason, device 17 has not deflated completely as it is being withdrawn from the patient, the distal end 64 of sheath 61 may advantageously serve as a fulcrum to help to compress device 17 sufficiently for its facile withdrawal from the patient. (Access device 13 may thereafter be removed from the patient or may remain in the patient to provide a conduit through which observational, removal, or other devices may be inserted.)

Alternative embodiments to sheath 61 are shown in FIGS. 121 and 122 and are represented generally by reference numerals 2071 and 2081, respectively. Sheaths 2071 and 2081 may be similar in most respects to sheath 61, sheaths 2071 and 2081 differing principally from sheath 61 in that sheaths 2071 and 2081 may include distal ends 2073 and 2083, respectively. Distal ends 2073 and 2083 may be advantageous in increasing the contact surface area during removal of device 17 and in forcing device 17 in a certain direction during removal.

As can readily be appreciated, although removal device 19 is discussed above as being used for observation and removal of an implanted device 17, removal device 19 could alternatively be used solely for observation of an implanted device 17, for example, for observation of an implanted device 17 immediately after its implantation in a patient to confirm that device 17 has been implanted properly.

As can be seen from the above discussion, one desirable feature of removal device 19 is that removal device 19 may be operated with one hand.

Referring now to FIGS. 126(*a*), 126(*b*), and 127, there are shown various views of a first alternate embodiment of a removal device, the first alternate embodiment of the removal device being represented generally by reference numeral 2101.

Removal device 2101 may be similar in many respects to removal device 19. A principal difference between the two devices may be that, whereas removal device 19 may comprise jaws 1981 and 1983 comprising rows of teeth 1997 and 2017, respectively, that may be generally triangular in shape in side profile (i.e., when viewed from above device 19), removal device 2101 may comprise jaws 2102 and 2104 comprising rows of teeth 2103 and 2105, respectively, that may be generally rectangular in shape in side profile.

Removal device 2101 may be used in a similar fashion to removal device 19.

Referring now to FIGS. 128(*a*), 128(*b*), and 129(*a*), there are shown various views of a second alternate embodiment of a removal device, the first alternate embodiment of the removal device being represented generally by reference numeral 2151.

Removal device 2151 may be similar in many respects to removal device 19. A principal difference between the two devices may be that, whereas removal device 19 may comprise jaws 1981 and 1983 comprising rows of teeth 1997 and 2017, respectively, that may be generally triangular in shape in side profile (i.e., when viewed from above device 19), removal device 2151 may comprise jaws 2152 and 2154 comprising rows of teeth 2153 and 2155, respectively, that may be generally sinusoidal in shape in side profile.

Removal device 2151 may be used in a similar fashion to removal device 19.

Referring now to FIGS. 130, 131, and 132(*a*) through 132(*c*), there are shown various views of a third alternate embodiment of a removal device, the third alternate embodiment of the removal device being represented generally by reference numeral 2201.

Removal device 2201, which may be similar in many respects to removal device 19, may comprise a scissors-like handle 2203, a hub 2205, a sheath 2206, a cystoscope 2207, a pair of jaws 2209 and 2211, a plurality of cannulated needles 2212-1 through 2212-3, and a wire 2213.

Scissors-like handle 2203, which may be a unitary structure made of a hard, medical-grade polymer or a similarly suitable material, may comprise a first member 2215, a second member 2217, and a living hinge member 2219. First member 2215 may be shaped to comprise an elongated arm portion 2221. A transversely-extending ring portion 2223, which may be appropriately dimensioned to receive, for example, the thumb of a user, may be disposed at one end of arm portion 2221. Second member 2217 may be shaped to comprise an elongated arm portion 2227. A transversely-extending ring portion 2229, which may be appropriately dimensioned to receive, for example, the forefinger of a user, and a finger rest 2231, which may be appropriately dimensioned to receive, for example, the middle finger of a user, may be disposed at one end of arm portion 2227. The opposite end of arm portion 2227 may be fixedly secured to sheath 2206. First member 2215 may be coupled to second member 2217 for pivotal movement relative thereto by living hinge member 2219. In this manner, handle 2203 may be operated much like a pair of scissors, albeit with first member 2215 being regarded as a movable member and with second member 2217 being regarded as a stationary member. It is to be understood, however, that handle 2203 could be modified so that both first member 2215 and second member 2217 are movable.

Hub 2205 may be a unitary, tubular structure made of a hard, medical-grade polymer or a similarly suitable material, and sheath 2206 may also be a unitary, tubular structure made of a hard, medical-grade polymer or a similarly suitable material. Hub 2205 and sheath 2206 may be joined to another by welding, adhesive or other suitable means and may be arranged to be coaxial with one another, with hub 2205 having a comparatively larger diameter and with sheath 2206 having a comparatively smaller diameter. Each of hub 2205 and sheath 2206 may be appropriately dimensioned to coaxially receive cystoscope 2207. Hub 2205 and sheath 2206 may have a combined length such that, when cystoscope 2207 is fully inserted into hub 2205 and sheath 2206, a distal end 2235 of cystoscope 2207 may extend just distally beyond a distal end 2237 of sheath 2206.

Sheath 2206 may be circular in transverse cross-section, which may be advantageous in helping to form a tight seal, for example, with seal 125 of access device 13 or, for example, with seal 917 of access device 901.

Cystoscope 2207 may be identical in size, shape, construction, and function to cystoscope 1891 of removal device 19.

Jaws 2209 and 2211, which may be similar in certain respects to jaws 1981 and 1983 of removal device 19, may be elongated members each made of a medical-grade polymer or a similarly suitable material. Jaws 2209 and 2211 may be pivotally mounted on distal end 2237 of sheath 2206 so that they may be moved towards and away from each other. Sheath 2206 and jaws 2209 and 2211 may form a unitary structure, with jaw 2209 being coupled to sheath 2206 by a living hinge 2241 and with jaw 2211 being coupled to sheath 2206 by a living hinge 2243. Articulation of jaws 2209 and 2211 may be effected using wire 2213, which may include a first end 2251 fixedly coupled to a tab 2253 provided on jaw 2211 and a second end 2255 fixedly coupled to a tab 2257 provided on jaw 2209, with an intermediate portion of wire 2213 passing through sheath 2206 beneath cystoscope 2207 and being fixedly coupled to first member 2215 of handle 2203. In this manner, as first member 2215 may be pivoted towards second member 2217 in a counterclockwise direction indicated by arrow 2218 in FIG. 130, wire 2213 may be moved proximally in tensile fashion, thereby causing jaws 2209 and 2211 to be pivoted towards one another. Conversely, as first member 2215 may be pivoted away from second member 2217, wire 2213 may be moved distally, thereby causing jaws 2209 and 2211 to be pivoted away from one another. As seen best in FIG. 132(b), when device 2201 is viewed from the top, the left end of wire 2213, namely, end 2251, is secured to the right jaw, namely, jaw 2211, and the right end of wire 2213, namely, end 2255, is secured to the left jaw, namely, jaw 2209. It is believed that such an arrangement is advantageous in providing increased leverage for closing jaws 2209 and 2211.

Jaw 2209 may be shaped to include a post 2260 extending upwardly at a distal end 2263 of jaw 2209, and jaw 2211 may be similarly shaped to include a post 2262 extending upwardly at a distal end 2265 of jaw 2211. Posts 2260 and 2262 may be helpful in enabling an operator to visualize the distal end of device 2201, which may facilitate the capture of pressure-attenuating device 17 or the like.

Jaw 2209 may be further shaped to include a couplet of teeth 2261-1 and 2261-2. Teeth 2261-1 and 2261-2 may be disposed at an intermediate location between tab 2257 and post 2260 and may extend generally in the direction of jaw 2211. A transverse opening 2265, which may serve as a relief hole in the manner to become apparent below, may be provided in jaw 2209 between teeth 2261-1 and 2261-2.

Jaw 2211 may be further shaped to include a first couplet of teeth 2271-1 and 2271-2 and a second couplet of teeth 2273-1 and 2273-2, all of which may be disposed between tab 2253 and post 2262. More specifically, teeth 2271-1 and 2271-2 may be positioned so that, when jaws 2209 and 2211 are brought together, teeth 2271-1 and 2271-2 may be located at an intermediate position between tab 2257 and teeth 2261-1 and 2261-2, and teeth 2273-1 and 2273-2 may be positioned so that, when jaws 2209 and 2211 are brought together, teeth 2273-1 and 2273-2 may be located at an intermediate position between teeth 2261-1 and 2261-2 and post 2262. A transverse opening 2277 may be provided in jaw 2211 between teeth 2271-1 and 2271-2, and a transverse opening 2279 may be provided in jaw 2211 between teeth 2273-1 and 2273-2. Openings 2277 and 2279 may function as relief holes in the manner to become apparent below.

Cannulated needle 2212-1 may be fixedly mounted in a transverse opening 2281 provided in jaw 2211 and may be appropriately positioned and dimensioned to be insertable between teeth 2261-1 and 2261-2 when jaws 2209 and 2211 are brought together. In a corresponding fashion, cannulated needle 2212-2 may be fixedly mounted in a transverse opening 2283 provided in jaw 2209 and may be appropriately positioned and dimensioned to be insertable between teeth 2271-1 and 2271-2 when jaws 2209 and 2211 are brought together, and cannulated needle 2212-3 may be fixedly mounted in a transverse opening 2285 provided in jaw 2209 and may be appropriately positioned and dimensioned to be insertable between teeth 2273-1 and 2273-2 when jaws 2209 and 2211 are brought together. It is believed that the present arrangement of teeth and cannulated needles is advantageous in that the teeth may be particularly well-suited to keeping taut the pressure-attenuating device 17 or other object that is to be punctured by the cannulated needles.

Cannulated needles 2212-1 through 2212-3 may be beveled at their respective free ends, and the bevels may extend to a depth that approaches or even exceeds the depths of the teeth on opposing sides of the cannulated needle. A bevel that exceeds the depth of the teeth may be preferred as it may facilitate air loss from the pressure-attenuating device 17 or other object that has been captured and punctured by removal device 2201.

Removal device 2201 may be used in a similar fashion to removal device 19.

It should be understood that the numbers of cannulated needles and teeth disclosed in the present embodiment are merely illustrative and that such numbers may be increased, decreased or otherwise modified. It should also be understood that the size, shape and positioning of such needles and teeth may also be modified. It should further be understood that, although both jaw 2209 and jaw 2211 are described herein as being movable, one could make one of jaws 2209 and 2211 stationary and the other of jaws 2209 and 2211 movable.

As alluded to above, handle 2203, hub 2205, sheath 2206, and jaws 2209 and 2211 may easily be made at low cost using polymeric materials. In addition, needles 2212-1 through 2212-3, and wire 2213 may easily be made at low cost using metallic materials. Moreover, the assembly of removal device 2201 may be achieved economically. Consequently, after a single use of removal device 2201, cystoscope 2207 may be removed and the remainder of removal device 2201 may be disposed. Cystoscope 2207 may then be sterilized for reuse as part of a new removal device 2201. A benefit to making the majority of removal device 2201 single-use is that there is no depreciation in the performance of the device over time.

Alternatively, instead of making cystoscope 2207 removable from hub 2205 and sheath 2206 to enable its sterilization and re-use, one could replace one or more of the components of cystoscope 2207 with disposable, single-use components. For example, one could replace the rod lens of cystoscope 2207 with an optical fiber or similar material that is permanently mounted within hub 2205 and sheath 2206.

Referring now to FIGS. 133(a) through 133(c), 134, 135, 136(a), 136(b), 137(a), and 137(b), there are shown various views of a fourth alternate embodiment of a removal device, the fourth alternate embodiment of the removal device being represented generally by reference numeral 2501.

Removal device 2501 may be similar in many respects to removal device 2201. A difference between the two removal devices may be that removal device 2501 may be, in its entirety, a disposable single-use device. Removal device 2501 may comprise a cystoscope 2503, a handle assembly 2505, a jaw assembly 2507, a sheath 2509, a wire 2511, and a plurality of cannulated needles 2513-1 through 2513-3.

Cystoscope 2503, which may be made of suitable materials for a single-use, may comprise an optical fiber 2515, an eyepiece 2517, and a light guide 2519.

Handle assembly 2505, which is also shown separately in FIG. 138, may be a unitary structure shaped to comprise a hub 2521, a first member 2523, and a second member 2525. Hub 2521 may be generally tubular in shape and may be dimensioned for insertion therethrough of the distal end of cystoscope 2503. First member 2523 may be shaped to comprise an elongated arm portion 2527. A transversely-extending ring portion 2529, which may be appropriately dimensioned to receive, for example, the thumb of a user, may be disposed at one end of arm portion 2527. Second member 2525 may be shaped to comprise an elongated arm portion 2531. A transversely-extending ring portion 2533, which may be appropriately dimensioned to receive, for example, the forefinger of a user, and a finger rest 2535, which may be appropriately dimensioned to receive, for example, the middle finger of a user, may be disposed at one end of arm portion 2531. The opposite end of arm portion 2531 may be joined to hub 2521. First member 2523 may be coupled to second member 2525 for pivotal movement relative thereto by living hinge member 2537. In this manner, first member 2523 and second member 2525 may be operated much like a pair of scissors, albeit with first member 2523 being regarded as a movable member and with second member 2525 being regarded as a stationary member. It is to be understood, however, that handle assembly 2505 could be modified so that both first member 2523 and second member 2525 are movable.

Jaw assembly 2507, which is also shown separately in FIGS. 139(a) through 139(c), 140(a) and 140(b), may be a unitary structure shaped to comprise a hub 2541, a first jaw 2543, and a second jaw 2545. Hub 2541 may be generally tubular in shape and may be dimensioned to securely receive the distal end of sheath 2509. Jaw 2543, which may be identical to jaw 2209, may be joined to hub 2541 by a living hinge 2547. Jaw 2545, which may be identical to jaw 2211, may be joined to hub 2541 by a living hinge 2549.

Sheath 2509, which is also shown separately in FIGS. 141(a) and 141(b), may be identical to sheath 2206 and may be shaped to include a first longitudinal cavity 2561 and a second longitudinal cavity 2563. First longitudinal cavity 2561 may be appropriately dimensioned to receive, for example, optical fiber 2515 of cystoscope 2503. Second longitudinal cavity 2563 may be appropriately dimensioned to receive, for example, wire 2511. The outer surface of sheath 2509 is circumferential, allowing for sealing around the sheath when the removal tool is placed in an access device such as 13 and 1291 described herein. The circumferential surface of sheath 2509 is advantageous compared to the outer surface of 1881 and 1901 in removal device 19 described herein. The gap between 1881 and 1901 permits leakage around the valves such as 125 and 91 described herein.

Wire 2511, which is also shown separately in FIGS. 142(a), 142(b), 143, and 144, may be a unitary structure shaped to include a first leg 2571 and a second leg 2573. The proximal ends of first leg 2571 and second leg 2573 may jointly form a loop 2575, which may be secured to first member 2523 of handle assembly 2505. The distal end of first leg 2571 may form a hook 2577, which may be secured to second jaw 2545, and the distal end of second leg 2573 may form a hook 2579, which may be secured to first jaw 2543.

Cannulated needle 2513-1, which may be identical cannulated to needles 2513-2 and 2513-3, may be a unitary structure having the shape shown in FIGS. 145(a) and 145(b).

Additional alternate embodiments to removal device 19 may comprise, in addition to or instead of the cannulated needle, a scissor or similar structure built into jaws 1981 and 1983 to puncture device 17 as teeth 1997 and 2017 hold device 17 or a razor blade or scalpel on one jaw and a receiving slot in the other jaw.

With reference now to FIGS. 146-153 an embodiment of an inflatable cell compression test fixture 2601 is illustrated. The inflatable cell test fixture 2601 comprises a test vessel 2611, piston 2621, a centering disk 2625, a heater 2631, a base 2623, a bracket post 2629, and a heater bracket 2627. Various views of an embodiment of the test vessel 2611 are illustrated in FIGS. 147(a)-(d). Various views of an embodiment of the piston 2621 are illustrated in FIGS. 148(a)-(d). Various views of an embodiment of centering disk 2625 are illustrated in FIGS. 149(a)-(e). Various views of an embodiment of the base 2623 are illustrated in FIGS. 150(a)-(e). Various views of an embodiment of the bracket post 2629 are illustrated in FIGS. 151(a)-(d). Various views of an embodiment of the heater bracket 2627 are illustrated in FIGS. 152(a)-(d).

The inflatable cell compression test fixture 2601 is assembled (base 2623, post 2629 and bracket 2627 with fasteners) and loaded onto the base 2623 of a vertical tensile and compression testing machine, such as an Instron, MTS, Chatillon, etc. Such machines can measure and record force and deflection through a data acquisition system. Data can be recorded in some embodiments at a minimum rate of 25 Hz. Distilled water can be heated and maintained at 37° C.+/−1° C. (98° F.) for the duration of the test. The test can be performed indoors at an ambient room temperature of 21° C. (70° F.). In one embodiment the test fixture can have a load cell rated at 50 lbs, a cross head speed of 2 inches per minute, a minimum data acquisition rate of 25 Hz, and a minimum crosshead travel distance of 8 inches. The test fixture 2601 can be used perform burst tests, deflection/deformation tests, and cyclical compression tests on a test vessel 2605.

The burst, deformation, and cyclical tests can be used to evaluate various inflatable cell materials, configurations, and wall thicknesses. Force and deformation distance can be measured during testing. With specific reference to FIG. 153, the test fixture 2601 can be used to simulate the clinical experience. During testing, the test sample of the inflatable cell (i.e., balloon) 2605 resides in the test vessel 2611. The opening 2606 for the inverted tail portion of the test sample 2605 is shown. The test sample 2605 is oriented within the test vessel 2611 so that the opening 2606, or a portion of the opening, is not positioned adjacent the test vessel orifice 2612. Preferably, the opening 2606 is positioned so that the opening 2606 does not contact the orifice 2612, or a portion of thereof, during operation of the test procedure. Preferably, the test sample is oriented similar to configuration in FIG. 153, such that the opening 2606 is aligned on a plane that is substantially perpendicular to the direction of the force applied by the piston 2621. The test vessel has a substantially hemispherical-shaped portion with a first diameter 2613, in this embodiment the first diameter is 1.625 inches. The test vessel 2611 constrains the test sample's deformation in all directions except at the bottom where there is a circular orifice 2612. The circular orifice 2612 has a diameter 2617. In one embodiment the diameter of the orifice is 0.575 inches. As the piston 2621 compresses the test sample 2605, only the portion of the test sample 2605 that aligned with the circular orifice 2612 is able to deform. Deformation is measured by determining the distance the test sample extends through the orifice 2612. The configuration and testing parameters described herein help replicate usage of the test sample 2605 in patients. For example, the pressure applied by the piston 2621 substantially replicates the pressure applied in the bladder of a patient and the orifice 2612 is substantially the same as the size of the bladder neck and urethra. The specific steps for the burst, deformation, and cyclical tests are described below.

The burst test comprises the steps: (a) position the piston 2621 for testing on the test fixture 2601; (b) orient the test sample 2605, with the desired section to be tested pointing down, and adhere the test sample 2605 to the underside of the piston 2621; (c) zero the force on the load cell; (d) lower the test sample 2605 into the test vessel 2611 until the test sample 2605 is close to the bottom of the test vessel 2611; (e) set the testing speed to 2.0 inches/min and enable the data acquisition system to record force and deformation. Set the program to complete the test if the force drops 95% of the maximum recorded value, which is usually indicative of test sample failure.

The deflection/deformation test comprises the steps: (a) position the piston 2621 for testing on the test fixture 2601; (b) orient the test sample 2605, with the desired section to be tested pointing down, and adhere the test sample 2605 to the underside of the piston 2621; (c) zero the force on the load cell; (d) lower the test sample 2605 into the test vessel 2611 until the test sample 2605 is close to the bottom of the test vessel 2611; (e) set the cycle program and data acquisition system to record Force and Deflection. Set the following parameters: (i) crosshead speed to 2.0 inches/min; (ii) set point of 4.25 lbs; (iii) peak force dwell time of 0.5 seconds; (iv) 5 cycles. (f) Record the maximum deflection distance on the 3rd cycle.

The cyclical compression test comprises the steps: (a) position the piston 2621 for testing on the test fixture 2601; (b) orient the test sample 2605, with the desired section to be tested pointing down, and adhere the test sample 2605 to the underside of the piston 2621; (c) zero the force on the load cell; (d) lower the test sample 2605 into the test vessel 2611 until the test sample 2605 is close to the bottom of the test vessel 2611; (e) set the cycle program and data acquisition system to record Force and Deflection. Set the following parameters: (i) crosshead speed to 2.0 inches/min; (ii) set point of 4.25 lbs; (iii) peak force dwell time of 0.5 seconds; (iv) 50 cycles.

Deformation tests determined the distance the inflatable cell deforms through the opening 2612 in the test chamber at a force of 4.25 lbs. Burst tests determined the distance the inflatable cell deformed and the force required for the inflatable cell to burst. The cyclical test determined the number of cycles that the inflatable cell survives with a force of 4.25 lbs applied in cyclic loading. Based on evaluation of empirical test data with clinical experience the following characteristics of the inflatable cell were determined.

A table illustrating exemplary test data is shown in FIG. 154. The columns are associated with different embodiments of the inflatable cell. The table is divided into three sections, a top section, a middle section, and a bottom section. The top section provides the characteristics of each cell. For each inflatable cell, the material, manufacturing process, cell size, and the wall thickness is provided. The middle section provides the results of the deformation test, burst test, and cyclical compression test. For the deformation test, the results of the cell deformation are provided in millimeters. For the burst test, the results of the force at burst are provided in pounds, and the results of the cell deformation ("d at burst") are provided in millimeters. For the cyclical compression test, the results indicate whether the cell was intact (i.e., 100%) at the end of the test. The bottom section provides pressure and volume characteristics of the inflatable cells at pressures of 30 cmH$_2$O and 15 cmH$_2$O. For each cell, a base cell volume, cell volume at pressure (30 cmH$_2$O and 15 cmH$_2$O), and percentage change in volume from base cell volume to cell volume at pressure (30 cmH$_2$O and 15 cmH$_2$O) is provided.

In one embodiment, preferably, the inflatable cell has a burst force of greater than about 3 pounds, more preferably greater than about 4 pounds, more preferably greater than about 4.9 pounds, more preferably greater than about 6 pounds, more preferably greater than about 7 pounds, and more preferably greater than about 8 pounds. In one embodiment the preferred inflatable cell will deform less than about 20 millimeters, more preferably less than about 18 millimeters, more preferably less than about 15 millimeters, more preferably less than about 11 millimeters, more preferably less than about 10 millimeters, more preferably less than about 8 millimeters, and more preferably less than about 6 millimeters with an applied pressure of 4.25 pounds thru a hole in the chamber of 0.575 inches.

Preferably, the wall thickness of the inflatable cell is between about 0.0003 and about 0.005 inches, and preferably between 0.0009 and 0.0015. In some embodiments the cell wall thickness can be varied based on materials and manufacturing processes. In some embodiments the cell wall thickness is not homogenous and can be varied. In some embodiments, the wall thickness can be varied dependent upon geometric configurations of the cell. In some geometric configurations the cell can be configured so that different portions of the cell have different thicknesses and exhibit different properties based on how the cell is configured to be placed within the patient.

Preferably the inflatable cell is compliant, so that with a change in internal pressure, the volume of the inflatable cell increases. Preferably, as the inflatable cell experiences a pressure increase from zero to 15 cmH$_2$O, the cell volume increases at least 5%, more preferably the volume increases at least 10%, from the cell volume at zero pressure. Preferably, as the inflatable cell experiences a pressure increase from zero to 30 cmH$_2$O, the cell volume increases at least 10%, more preferably the cell volume increases at least 15%, from the cell volume at zero pressure.

Preferably the inflatable cell also has sufficient structure to maintain its shape and not deform into the bladder neck and urethra, and to provide a P$_{skin}$ tension to maintain inflatable cell inflation as described in U.S. Patent Application No. 2010/0222802. Preferably, as the inflatable cell experiences a pressure increase from zero to 15 cmH$_2$O, the cell volume increases no more than 80% and, more preferably, the cell volume increases no more than 50%, from the cell volume at zero pressure. Preferably, as the inflatable cell experiences a pressure increase from zero to 30 cmH$_2$O, the cell volume increases no more than 80% and, more preferably, the cell volume increases no more than 50%, from the cell volume at zero pressure.

FIGS. 155 through 158 show exemplary test data for embodiments of inflatable cells on pressure volume charts. Each chart identifies a material used for the embodiment of the inflatable cell. The charts show pressure on the vertical axis in units of cmH$_2$O. Volume is shown on the horizontal axis in milliliters. The charts help illustrate the characteristics of some embodiments of the inflatable cells. The inflatable cells can provide predictable expansion based on pressure. In some embodiments the inflatable cells can have a low deviation from linearity as a function of pressure and volume. In some embodiments, the deviation from linearity can be less than 10%, and in some embodiments less than 5%.

In some embodiments the inflatable cell can be a silicone, manufactured with a dip molding process, estane polyurethane, manufactured with a blow molded process or using welded sheets, and pelethane polyurethane, manufactured with a blow molded process.

Embodiments of inflatable cells have been described as having certain properties and characteristics as described in relation to specific test procedures. In some embodiments, the cell may be substantially homogeneous such that the entirety of the inflatable cell exhibits the properties. For example the cell wall thickness can be substantially homogenous over the surface of the cell. In some embodiments the cell wall thickness can vary throughout the cell. In some embodiments, a portion of the inflatable cell that is less than the entirety of the cell can exhibit the properties. For example a portion of the inflatable cell wall could exhibit the characteristics described.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the claims that follow.

Similarly, this method of disclosure, is not to be interpreted as reflecting an intention that any claim require more features than are expressly recited in that claim. Rather, as the following claims reflect, inventive aspects lie in a combination of fewer than all features of any single foregoing disclosed embodiment. Thus, the claims following the Detailed Description are hereby expressly incorporated into this Detailed Description, with each claim standing on its own as a separate embodiment.

What is claimed is:

1. A medical device, the medical device comprising:
an implantable inflatable cell having a wall comprising an external surface and an inverted tail portion;
the inverted tail portion being elongate and tubular with an inner diameter and positioned within the inflatable cell, the wall further comprising:
a first wall thickness of the external surface forming a circumferential band surrounding an end of the tail portion connected to the external surface, the circumferential band having a width equal to at least the inner diameter of the tail portion;
a second wall thickness of the external surface that is less than the first wall thickness; and
a third wall thickness of the inverted tail portion that is greater than the second wall thickness;
wherein the circumferential band is configured to help maintain the tail portion in an inverted position with respect to the external surface.

2. The medical device of claim 1, wherein less than 3% of the surface area of the inflatable cell is not continuously arcuate.

3. The medical device of claim 1, wherein less than 1% of the surface area of the inflatable cell is not continuously arcuate.

4. The medical device of claim 1, wherein the second wall thickness is between about 0.0001 and about 0.25 inches.

5. The medical device of claim 1, wherein the second wall thickness is between about 0.0003 and about 0.005 inches.

6. The medical device of claim 1, wherein the inflatable cell is made of one or more of silicone and polyurethane.

7. The medical device of claim 1, wherein the inflatable cell has an initial volume between about 10 cc and about 60 cc.

8. The medical device of claim 1, further comprising an inflation media comprising a gas.

9. The medical device of claim 1, wherein the third wall thickness of the inverted tail portion is at least 3 times greater than the second wall thickness.

10. The medical device of claim 1, further comprising a valve attached to the tail portion.

11. The medical device of claim 1, wherein the inverted tail portion is further inverted on itself.

12. The medical device of claim 1, wherein the width of the circumferential band is equal to at least 1.5 times the inner diameter of the tail portion.

13. The medical device of claim 1, wherein the width of the circumferential band is equal to at least 2 times the inner diameter of the tail portion.

14. A medical device, the medical device comprising an implantable inflatable cell, the inflatable cell comprising:
a wall comprising an external surface and a tail portion, the tail portion being elongate and tubular, the tail portion being in a folded state with two overlapping layers of material positioned completely within the inflatable cell; the wall further comprising:
a first wall thickness; and
a second wall thickness that is less than the first wall thickness; and
a valve positioned within and secured to the tail portion, the valve configured to allow or prevent access to an interior of the inflatable cell to inflate or deflate the cell.

15. The medical device of claim 14, wherein the ratio of continuously arcuate surface area to non-arcuate surface area for the external surface of the inflatable cell is between 400:1 to 600:1.

16. The medical device of claim 14, wherein the second wall thickness is between about 0.0001 and about 0.25 inches.

17. The medical device of claim 14, wherein the second wall thickness is between about 0.0003 and about 0.005 inches.

18. The medical device of claim 14, wherein the inflatable cell is made of one or more of silicone and polyurethane.

19. The medical device of claim 14, wherein the inflatable cell has an initial volume between about 0.1 cc and about 500 cc.

20. The medical device of claim 14, wherein the inflatable cell has an initial volume between about 1 cc and about 180 cc.

21. The medical device of claim 14, further comprising an inflation media comprising a gas.

22. The medical device of claim 14, wherein a wall thickness of the tail portion is greater than or equal to the second wall thickness.

23. The medical device of claim 22, wherein the first wall thickness forms a circumferential band surrounding an end of the tail portion connected to the external surface, the circumferential band having a width equal to at least an inner diameter of the tail portion.

24. The medical device of claim 23, wherein the width of the circumferential band is equal to at least 2 times the inner diameter of the tail portion.

25. The medical device of claim 14, wherein the valve is positioned completely within the inflatable cell.

26. The medical device of claim 14, wherein the valve is attached to the tail portion at one of layers the two overlapping layers of material.

27. A medical device, the medical device comprising an implantable inflatable cell, the inflatable cell comprising:
   a bulb portion having an external surface;
   a tail portion being elongate and tubular and positioned within the bulb portion, the tail portion extending from a first end at the bulb portion to a second end defining an opening the tail portion being inverted on itself such that the second end of the tail portion points towards the first end; and
   a valve attached to the tail portion, the valve configured to allow or prevent access to an interior of the inflatable cell to inflate or deflate the cell.

28. The medical device of claim 27, wherein the ratio of the diameter of the bulb portion to the tail portion is between 8:1 and 20.1.

29. The medical device of claim 27, wherein the inflatable cell has a wall thickness of between about 0.0001 and about 0.25 inches.

30. The medical device of claim 27, wherein the inflatable cell has a wall thickness of between about 0.0003 and about 0.005 inches.

31. The medical device of claim 27, wherein the inflatable cell is made of one or more of silicone and polyurethane.

32. The medical device of claim 27, wherein the inflatable cell has an initial volume between about 0.1 cc and about 500 cc.

33. The medical device of claim 27, wherein the inflatable cell has an initial volume between about 10 cc and about 60 cc.

34. The medical device of claim 27, further comprising an inflation media comprising a gas.

35. The medical device of claim 27, wherein the valve is attached to the second end of the tail portion.

36. The medical device of claim 27, wherein the bulb portion has a first wall thickness and a second wall thickness that is less than the first wall thickness.

37. The medical device of claim 36, wherein a wall thickness of the tail portion is greater than the second wall thickness of the bulb portion.

38. The medical device of claim 37, wherein the first wall thickness forms a circumferential band surrounding an end of the tail portion connected to the external surface of the bulb portion, the circumferential band having a width equal to at least an inner diameter of the tail portion.

39. The medical device of claim 38, wherein the width of the circumferential band is equal to at least 2 times the inner diameter of the tail portion.

* * * * *